(12) United States Patent
Gahman et al.

(10) Patent No.: US 7,825,256 B2
(45) Date of Patent: Nov. 2, 2010

(54) INDUCIBLE NITRIC OXIDE SYNTHASE DIMERIZATION INHIBITORS

(75) Inventors: Timothy C. Gahman, Encinitas, CA (US); Hengyuan Lang, San Diego, CA (US); Mark R. Herbert, San Diego, CA (US); Angelina M. Thayer, San Diego, CA (US); Christian A. Hassig, Mira Mesa, CA (US); Stewart A. Noble, San Diego, CA (US); Russell D. Cousins, San Diego, CA (US); Hui Zhuang, San Diego, CA (US); Christopher R. Santos, Encinitas, CA (US); Xiaohong Chen, San Diego, CA (US)

(73) Assignee: Kalypsys, Inc., San Diego, CA (US)

( * ) Notice: Subject to any disclaimer, the term of this patent is extended or adjusted under 35 U.S.C. 154(b) by 708 days.

(21) Appl. No.: 11/288,888

(22) Filed: Nov. 28, 2005

(65) Prior Publication Data
US 2006/0116515 A1 Jun. 1, 2006

Related U.S. Application Data

(60) Provisional application No. 60/672,001, filed on Apr. 14, 2005, provisional application No. 60/631,971, filed on Dec. 1, 2004.

(51) Int. Cl.
| | |
|---|---|
| C07D 417/04 | (2006.01) |
| C07D 417/14 | (2006.01) |
| C07D 401/14 | (2006.01) |
| C07D 403/04 | (2006.01) |
| C07D 403/14 | (2006.01) |
| A61K 31/4178 | (2006.01) |
| A61K 31/4196 | (2006.01) |
| A61K 31/433 | (2006.01) |
| A61P 19/02 | (2006.01) |

(52) U.S. Cl. .................................. 548/128; 514/361
(58) Field of Classification Search ............... 548/128; 514/361
See application file for complete search history.

(56) References Cited

U.S. PATENT DOCUMENTS

| 4,699,914 A | 10/1987 | Hiboll et al. |
| 5,874,452 A | 2/1999 | Anthony |
| 6,432,947 B1 | 8/2002 | Arnaiz et al. |
| 6,723,743 B1 | 4/2004 | Thurkauf et al. |
| 2003/0191279 A1 | 2/2003 | Goldstein et al. |
| 2003/0083269 A1 | 5/2003 | Brouillette et al. |
| 2004/0152699 A1 | 8/2004 | Arora et al. |

FOREIGN PATENT DOCUMENTS

| DE | 101 10750 A1 | 9/2002 |
| EP | 00123319 A2 | 10/1984 |
| WO | WO 96/39400 A1 | 12/1996 |
| WO | WO 97/45115 A1 | 12/1997 |
| WO | 9800430 A1 | 1/1998 |
| WO | WO 01/14371 A1 | 3/2001 |
| WO | WO 02/49993 A2 | 6/2002 |
| WO | WO 03/006456 A1 | 1/2003 |
| WO | WO 03/082205 A2 | 10/2003 |
| WO | WO 03/082829 A1 | 10/2003 |
| WO | WO 03/084524 A1 | 10/2003 |
| WO | WO 2004/019986 A1 | 3/2004 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cecil Textbook of Medicine, edited by Bennet, J.C., and Plum F., 20th edition, vol. 1, 1004-1010, 1996.*
Mocellin et al., Med, Res. Rev., 27(3), 317-352, 2007(PubMed Abstract provided).*
Ekmekcioqlu et al., Curr. Cancer Drug Targets, 5(2), 103-115, 2005 (PubMed Abstracts provided).*

* cited by examiner

Primary Examiner—Venkataraman Balasubramanian
(74) Attorney, Agent, or Firm—Dennis A. Bennett; Cynthia Hathaway

(57) ABSTRACT

The present invention relates to compounds and methods useful as inhibitors of nitric oxide synthase. Certain compounds of the subject invention have the following structural formula:

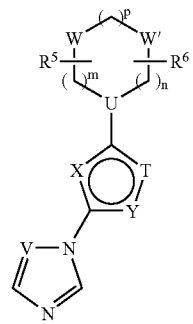

wherein T, X, and Y are independently selected from the group consisting of $CR^4$, N, $NR^4$, S, and O; U is selected from the group consisting of $CR^{10}$ and N; V is selected from the group consisting of $CR^4$ and N; W and W' are independently selected from the group consisting of $CH_2$, $CR^7R^8$, $NR^9$, O, N(O), $S(O)_q$ and C(O); n, m and p are independently an integer from 0 to 5; q is 0, 1, or 2; and other substituents are as defined herein. Other compounds of the subject invention have structural formulas as defined herein. Also disclosed herein are pharmaceutical compositions comprising the compounds of the subject invention.

20 Claims, No Drawings

INDUCIBLE NITRIC OXIDE SYNTHASE DIMERIZATION INHIBITORS

This application claims priority to U.S. provisional applications 60/672,001, filed Apr. 14, 2005, and 60/631,971 filed Dec. 1, 2004.

FIELD OF THE INVENTION

The present invention is directed to compounds that inhibit nitric oxide synthase, their synthesis, and their application as a pharmaceuticals for the treatment of disease.

BACKGROUND OF THE INVENTION

Nitric oxide (NO) is involved in the regulation of many physiological processes as well as the pathophysiology of a number of diseases. It is synthesized enzymatically from L-arginine in numerous tissues and cell types by three distinct isoforms of the enzyme NO synthase (NOS). Two of these isoforms, endothelial NOS (eNOS) and neuronal NOS (nNOS) are expressed in a constitutive manner and are calcium/calmodulin dependent. Endothelial NOS is expressed by endothelium and other cell types and is involved in cardiovascular homeostasis. Neuronal NOS is constitutively present in both the central and peripheral nervous system where NO acts a neurotransmitter. Under normal physiological conditions, these constitutive forms of NOS generate low, transient levels of NO in response to increases in intracellular calcium concentrations. These low levels of NO act to regulate blood pressure, platelet adhesion, gastrointestinal motility, bronchomotor tone and neurotransmission.

In contrast, the third isoform of NOS, inducible NOS (iNOS), a virtually calcium independent enzyme, is absent in resting cells, but is rapidly expressed in virtually all nucleated mammalian cells in response to stimuli such as endotoxins and/or cytokines. The inducible isoform is neither stimulated by calcium nor blocked by calmodulin antagonists. It contains several tightly bound co-factors, including FMN, FAD and tetrahydrobiopterin. The inducible isoform of nitric oxide synthase ($NOS_2$ or iNOS) is expressed in virtually all nucleated mammalian cells following exposure to inflammatory cytokines or lipopolysaccharide.

The enzyme iNOS synthase is a homodimer composed of 130 kDa subunits. Each subunit comprises an oxygenase domain and a reductase domain. Importantly, dimerization of the iNOS synthase is required for enzyme activity. If the dimerization mechanism is disrupted, the production of nitric oxide via inducible NOS enzyme is inhibited.

The presence of iNOS in macrophages and lung epithelial cells is significant. Once present, iNOS synthesizes 100-1000 times more NO than the constitutive enzymes synthesize and does so for prolonged periods. This excessive production of NO and resulting NO-derived metabolites (e.g., peroxynitrite) elicit cellular toxicity and tissue damage which contribute to the pathophysiology of a number of diseases, disorders and conditions.

Nitric oxide generated by the inducible form of NOS has also been implicated in the pathogenesis of inflammatory diseases. In experimental animals, hypotension induced by lipopolysaccharide or tumor necrosis factor alpha can be reversed by NOS inhibitors. Conditions which lead to cytokine-induced hypotension include septic shock, hemodialysis and interleukin therapy in cancer patients. An iNOS inhibitor has been shown to be effective in treating cytokine-induced hypotension, inflammatory bowel disease, cerebral ischemia, osteoarthritis, asthma and neuropathies such as diabetic neuropathy and post-herpetic neuralgia.

In addition, nitric oxide localized in high amounts in inflamed tissues has been shown to induce pain locally and to enhance central as well as peripheral stimuli. Because nitric oxide produced by an inflammatory response is thought to be synthesized by iNOS, the inhibition of iNOS dimerization produces both prophylactic and remedial analgesia in patients.

Hence, in situations where the overproduction of nitric oxide is deleterious, it would be advantageous to find a specific inhibitor of iNOS to reduce the production of NO. However, given the important physiological roles played by the constitutive NOS isoforms, it is essential that the inhibition of iNOS has the least possible effect on the activity of eNOS and nNOS.

SUMMARY OF THE INVENTION

Novel compounds and pharmaceutical compositions that inhibit dimerization of the inducible NOS synthase monomer have been found together with methods of synthesizing and using the compounds including methods for inhibiting or modulating nitric oxide synthesis and/or lowering nitric oxide levels in a patient by administering the compounds.

In one aspect, the invention provides compounds of the Formula I:

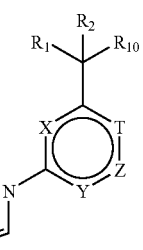

wherein:

T, V, X, and Y are independently selected from the group consisting of $CR^4$ and N;

Z is selected from the group consisting of $CR^3$ and N;

$R^1$ and $R^2$ are independently selected from the group consisting of hydrogen, halogen, optionally substituted alkyl, optionally substituted alkoxy, haloalkyl, haloalkoxy, optionally substituted aralkyl, optionally substituted aryl, optionally substituted heteroaryl, optionally substituted heteroaralkyl, optionally substituted alkene, optionally substituted alkyne, —(O)N($R^{11}$)$R^{12}$, —P(O)[N($R^{11}$)$R^{12}$]$_2$, —$SO_2$NHC(O)$R^{11}$, —N($R^{11}$)$SO_2R^{12}$, —$SO_2$N($R^{11}$)$R^{12}$, —$NSO_2$N($R^{11}$)$R^{12}$, —C(O)NHSO$_2R^{11}$, —CH=NOR$^{11}$, —OR$^{11}$, —S(O)$_t$—R$^{11}$, —N($R^{11}$)$R^{12}$, —N($R^{11}$)C(O)N($R^{12}$)$R^{13}$, —N($R^{11}$)C(O)OR$^{12}$, —N($R^{11}$)C(O)R$^{12}$, —[C($R^{14}$)$R^{15}$]$_r$—R$^{12}$, —[C($R^{14}$)$R^{15}$]$_r$—C(O)OR$^{11}$, —[C($R^{14}$)$R^{15}$]$_r$—C(O)OR$^{11}$]$_2$, —[C($R^{14}$)$R^{15}$]$_r$—C(O)N($R^{11}$)$R^{12}$, —[C($R^{14}$)$R^{15}$]$_9$—N($R^{11}$)$R^{12}$, [C($R^{14}$)$R^{15}$]$_r$—N($R^{11}$)—[C($R^{14}$)$R^{15}$]$_r R^{12}$, —[C($R^{14}$)$R^{15}$]$_r$—OR$^{11}$, —N($R^{11}$)—[C($R^{14}$)$R^{15}$]$_r$—R$^{12}$, —N($R^{11}$)C(O)N($R^{13}$)—[C($R^{14}$)$R^{15}$]$_r$—R$^{12}$, —C(O)—[C($R^{14}$)$R^{15}$]$_r$—N($R^{11}$)$R^{12}$, —N($R^{13}$)C(O)-L-($R^{11}$)$R^{12}$, —N($R^{11}$)—[C($R^{14}$)$R^{15}$]$_r$-L-$R^{12}$, —N($R^{11}$)C(O)N($R^{11}$)—[C($R^{14}$)$R^{15}$]$_r$-L-$R^{12}$, —[C($R^{14}$)$R^{15}$]$_r$-L-$R^{12}$, and -L-C(O)N($R^{11}$)$R^{12}$;

t is an integer from 0 to 2;

r is an integer from 0 to 5;

L is selected from the group consisting of an optionally substituted 3- to 7-membered carbocyclic group, an optionally substituted 3- to 7-membered heterocyclic group, an optionally substituted 6-membered aryl group, and an optionally substituted 6-membered heteroaryl group;

$R^3$, $R^4$, $R^{10}$, $R^{14}$, $R^{15}$, $R^{16}$, $R^{17}$, and $R^{18}$ are independently selected from the group consisting of hydrogen, halogen, optionally substituted alkyl, optionally substituted haloalkyl, haloalkoxy, optionally substituted aralkyl, optionally substituted aryl, optionally substituted heteroaryl, optionally substituted heteroaralkyl, optionally substituted alkene, optionally substituted alkyne; or $R^{14}$ and $R^{15}$ may together form a carbonyl, optionally substituted carbocycle or optionally substituted heterocycle; or $R^{14}$ and $R^{15}$ together may be null, forming an additional bond;

$R^{11}$, $R^{12}$, and $R^{13}$ are independently selected from the group consisting of hydrogen, halogen, optionally substituted alkyl, haloalkyl, haloalkoxy, optionally substituted aralkyl, optionally substituted aryl, optionally substituted heteroaryl, optionally substituted heteroaralkyl, optionally substituted alkene, optionally substituted alkyne, —$OR^{17}$, —$S(O)_t$—$R^{17}$, —$[C(R^{14})R^{15}]_r$—$C(O)OR^{17}$, —$[C(R^{14})R^{15}]_r$—$N(R^{17})R^{18}$, —$[C(R^{14})R^{15}]_r$—$N(R^{16})C(O)N(R^{17})R^{18}$, —$[C(R^{14})R^{15}]_r$—$N(R^{17})C(O)OR^{18}$, —$[C(R^{14})R^{15}]_r$—$R^{17}$, and —$[C(R^{14})R^{15}]_r$—$N(R^{17})C(O)R^{18}$; or $R^{11}$ or $R^{12}$ may be defined by a structure selected from the group consisting of

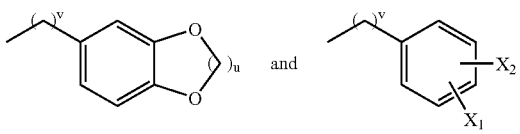

wherein:

u and v are independently an integer from 0 to 3; and $X^1$ and $X^2$ are independently selected from the group consisting of hydrogen, halogen, hydroxy, lower acyloxy, optionally substituted lower alkyl, optionally substituted lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides compounds of the Formula II:

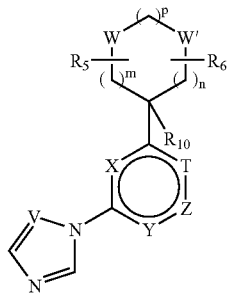

II wherein:

T, V, X, and Y are independently selected from the group consisting of $CR^4$ and N;

Z is from the group consisting of $CR^3$ and N;

W and W' are independently selected from the group consisting of $CH_2$, $CR^7R^8$, $NR^9$, O, N(O), $S(O)_q$ and C(O);

n, m and p are independently an integer from 0 to 5;

q is 0, 1, or 2;

$R^3$, $R^4$, $R^{10}$, $R^{14}$, $R^{15}$, $R^{16}$, $R^{17}$ and $R^{18}$ are independently selected from the group consisting of hydrogen, halogen, optionally substituted alkyl, optionally substituted haloalkyl, haloalkoxy, optionally substituted aralkyl, optionally substituted aryl, optionally substituted heteroaryl, optionally substituted heteroaralkyl, optionally substituted alkene, optionally substituted alkyne; or $R^{14}$ and $R^{15}$ may together form a carbonyl, optionally substituted carbocycle or optionally substituted heterocycle; or $R^{14}$ and $R^{15}$ together may be null, forming an additional bond;

$R^5$, $R^6$, $R^7$, $R^8$, and $R^9$ are independently selected from the group consisting of hydrogen, halogen, optionally substituted alkyl, optionally substituted alkoxy, haloalkyl, haloalkoxy, optionally substituted aralkyl, optionally substituted aryl, optionally substituted heteroaryl, optionally substituted heteroaralkyl, optionally substituted alkene, optionally substituted alkyne, —$(O)N(R^{11})R^{12}$, —$P(O)[N(R^{11})R^{12}]_2$, —$SO_2NHC(O)R^{11}$, —$N(R^{11})SO_2R^{12}$, —$SO_2N(R^{11})R^{12}$, —$NSO_2N(R^{11})R^{12}$, —$C(O)NHSO_2R^{11}$, —CH=$NOR^{11}$, —$OR^{11}$, —$S(O)_t$—$R^{11}$, —$N(R^{11})R^{12}$, —$N(R^{11})C(O)N(R^{12})R^{13}$, —$N(R^{11})C(O)OR^{12}$, —$N(R^{11})C(O)R^{12}$, —$[C(R^{14})R^{15}]_r$—$R^{12}$, —$[C(R^{14})R^{15}]_r$—$C(O)OR^{11}$, —$[C(R^{14})R^{15}]_r$—$[C(O)OR^{11}]_2$, —$[C(R^{14})R^{15}]_r$—$C(O)N(R^{11})R^{12}$, —$[C(R^{14})R^{15}]_r$—$N(R^{11})R^{12}$, —$[C(R^{14})R^{15}]_r$—$N(R^{11})$—$[C(R^{14})R^{15}]_r$—$R^{12}$, —$[C(R^{14})R^{15}]_r$—$OR^{11}$, —$N(R^{11})$—$[C(R^{14})R^{15}]_r$—$R^{12}$, —$N(R^{11})C(O)N(R^{13})$—$[C(R^{14})R^{15}]_r$—$R^2$, —$C(O)$—$[C(R^{14})R^{15}]_r$—$N(R^{11})R^{12}$, —$N(R^{13})C(O)$-L-$(R^{11})R^{12}$, —$N(R^{11})$—$[C(R^{14})R^{15}]_r$-L-$R^{12}$, —$N(R^{11})C(O)N(R^{11})$—$[C(R^{14})R^{15}]_r$-L-$R^{12}$, —$[C(R^{14})R^{15}]_r$-L-$R^{12}$, and -L-C(O) $N(R^{11})R^{12}$; or $R^5$ and $R^6$ together may form an optionally substituted aryl, optionally substituted heteroaryl, optionally substituted cycloalkyl, or optionally substituted heterocycloalkyl;

t is an integer from 0 to 2;

r is an integer from 0 to 5;

L is selected from the group consisting of an optionally substituted 3- to 7-membered carbocyclic group, an optionally substituted 3- to 7-membered heterocyclic group, an optionally substituted 6-membered aryl group, and an optionally substituted 6-membered heteroaryl group;

$R^{11}$, $R^{12}$, and $R^{13}$ are independently selected from the group consisting of hydrogen, halogen, optionally substituted alkyl, haloalkyl, haloalkoxy, optionally substituted aralkyl, optionally substituted aryl, optionally substituted heteroaryl, optionally substituted heteroaralkyl, optionally substituted alkene, optionally substituted alkyne, —$OR^{17}$, —S(O), $R^{17}$, —$[C(R^{14})R^{15}]_r$—$C(O)OR^{17}$, —$[C(R^{14})R^{15}]_r$—$N(R^{17})R^{18}$, —$[1C(R^4)R^{15}]_r$—$N(R^{16})C(O)N(R^{17})R^{18}$, —$[C(R^{14})R^{15}]_r$—$N(R^{17})C(O)OR^{18}$, —$[C(R^{14})R^{15}]_r$—$R^{17}$, and —$[C(R^{14})R^{15}]_r$—$N(R^{17})C(O)R^{18}$; or $R^{11}$ or $R^{12}$ may be defined by a structure selected from the group consisting of

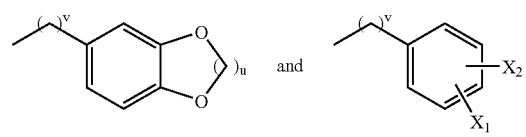

wherein:

u and v are independently an integer from 0 to 3; and $X^1$ and $X^2$ are independently selected from the group consisting of hydrogen, halogen, hydroxy, lower acyloxy, optionally substituted lower alkyl, optionally substituted lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides compounds of the Formula III:

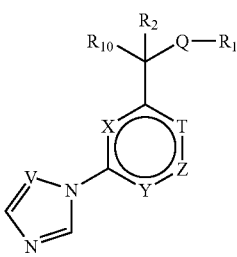

III wherein:

V, T, X, and Y are independently selected from the group consisting of $CR^4$ and N;

Q is selected from the group consisting of $NR^5$, O, and S;

Z is selected from the group consisting of $CR^3$ and N;

$R^1$ and $R^2$ are independently selected from the group consisting of hydrogen, halogen, optionally substituted alkyl, optionally substituted alkoxy, haloalkyl, haloalkoxy, optionally substituted aralkyl, optionally substituted aryl, optionally substituted heteroaryl, optionally substituted heteroaralkyl, optionally substituted alkene, optionally substituted alkyne, $-(O)N(R^{11})R^{12}$, $-P(O)[N(R^{11})R^{12}]_2$, $-SO_2NHC(O)R^{11}$, $-N(R^{11})SO_2R^{12}$, $-SO_2N(R^{11})R^{12}$, $-NSO_2N(R^{11})R^{12}$, $-C(O)NHSO_2R^{11}$, $-CH=NOR^{11}$, $-OR^{11}$, $-S(O)_t-R^{11}$, $-N(R^{11})R^{12}$, $-N(R^{11})C(O)N(R^{12})R^{13}$, $-N(R^{11})C(O)OR^{12}$, $-N(R^{11})C(O)R^{12}$, $-[C(R^{14})R^{15}]_r-R^{12}$, $-[C(R^{14})R^{15}]_r-C(O)OR^{11}$, $-[C(R^{14})R^{15}]_r-[C(O)OR^{11}]_2$, $-[C(R^{14})R^{15}]_r-C(O)N(R^{11})R^{12}$, $-[C(R^{14})R^{15}]_r-N(R^{11})R^{12}$, $-[C(R^{14})R^{15}]_r-N(R^{11})-[C(R^{14})R^{15}]_r-R^{12}$, $-[C(R^{14})R^{15}]_r-OR^{11}$, $-N(R^{11})-[C(R^{14})R^{15}]_r-R^{12}$, $-N(R^{11})C(O)N(R^{13})-[C(R^{14})R^{15}]_r-R^{12}$, $-C(O)-[C(R^{14})R^{15}]_t-N(R^{11})R^{12}$, $-N(R^{13})C(O)-L-(R^{11})R^{12}$, $-N(R^{11})-[C(R^{14})R^{15}]_r-L-R^{12}$, $-N(R^{11})C(O)N(R^{11})-[C(R^{14})R^{15}]_r-L-R^{12}$, $-[C(R^{14})R^{15}]_r-L-R^{12}$, $-[C(R^{14})R^{15}]_r-L-R^{12}$, and $-L-C(O)N(R^{11})R^{12}$; or $R^5$ and $R^6$ together may form an optionally substituted aryl, optionally substituted heteroaryl, optionally substituted cycloalkyl, or optionally substituted heterocycloalkyl;

t is an integer from 0 to 2;

r is an integer from 0 to 5;

L is selected from the group consisting of an optionally substituted 3- to 7-membered carbocyclic group, an optionally substituted 3- to 7-membered heterocyclic group, an optionally substituted 6-membered aryl group, and an optionally substituted 6-membered heteroaryl group;

$R^3$, $R^4$, $R^{10}$, $R^{14}$, $R^{15}$, $R^{16}$, $R^{17}$, and $R^{18}$ are independently selected from the group consisting of hydrogen, halogen, optionally substituted alkyl, optionally substituted haloalkyl, haloalkoxy, optionally substituted aralkyl, optionally substituted aryl, optionally substituted heteroaryl, optionally substituted heteroaralkyl, optionally substituted alkene, optionally substituted alkyne; or $R^{14}$ and $R^{15}$ may together form a carbonyl, optionally substituted carbocycle or optionally substituted heterocycle; or $R^{14}$ and $R^{15}$ together may be null, forming an additional bond;

$R^{11}$, $R^{12}$, and $R^{13}$ are independently selected from the group consisting of hydrogen, halogen, optionally substituted alkyl, haloalkyl, haloalkoxy, optionally substituted aralkyl, optionally substituted aryl, optionally substituted heteroaryl, optionally substituted heteroaralkyl, optionally substituted alkene, optionally substituted alkyne, $-OR^{17}$, $-S(O)_t-R^{17}$, $-[C(R^{14})R^{15}]_r-C(O)OR^{17}$, $-[C(R^{14})R^{15}]_r-N(R^{17})R^{18}$, $-[C(R^{14})R^{15}]_r-N(R^{16})C(O)N(R^{17})R^8$, $-[C(R^{14})R^{15}]_r-N(R^{17})C(O)OR^{18}$, $-[C(R^{14})R^{15}]_r-R^{17}$, and $-[C(R^{14})R^{15}]_r-N(R^{17})C(O)R^{18}$; or $R^{11}$ or $R^{12}$ may be defined by a structure selected from the group consisting of

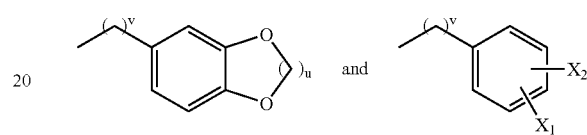

wherein:

u and v are independently an integer from 0 to 3; and

X1 and X2 are independently selected from the group consisting of hydrogen, halogen, hydroxy, lower acyloxy, optionally substituted lower alkyl, optionally substituted lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides compounds of the Formula IV:

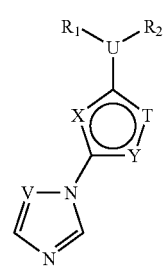

IV or a salt, ester, or prodrug thereof, wherein:

T, X, and Y are independently selected from the group consisting of $CR^4$, N, $NR^4$, S, and O;

U is $CR^{10}$ or N;

V is $CR^4$ or N;

$R^1$ and $R^2$ are independently selected from the group consisting of hydrogen, halogen, optionally substituted alkyl, optionally substituted alkoxy, haloalkyl, haloalkoxy, optionally substituted aralkyl, optionally substituted aryl, optionally substituted heteroaryl, optionally substituted heteroaralkyl, optionally substituted alkene, optionally substituted alkyne, $-(O)N(R^{11})R^{12}$, $-P(O)[N(R^{11})R^{12}]_2$, $-SO_2NHC(O)R^{11}$, $-N(R^{11})SO_2R^{12}$, $-SO_2N(R^{11})R^{12}$, $-NSO_2N(R^{11})R^{12}$, $-C(O)NHSO_2R^{12}$, $-CH=NOR^{11}$, $-OR^{11}$, $-S(O)_t-R^{11}$, $-N(R^{11})R^{12}$, $-N(R^{11})C(O)N(R^{12})R^{13}$, $-N(R^{11})C(O)OR^{12}$, $-N(R^{11})C(O)R^{12}$, $-[C(R^{14})R^{15}]_r-R^{12}$, $-[C(R^{14})$ $R^{15}]_r$—C(O)OR$^{11}$, —[C(R$^{14}$)R$^{15}]_r$—[C(O)OR$^{11}]_2$, —[C(R$^{14}$)R$^{15}]_r$—C(O)N(R$^{11}$)R$^{12}$, —[C(R$^{14}$)R$^{15}]_r$—N(R$^{11}$)R$^{12}$, —[C(R$^{14}$)R$^{15}]_r$—N(R$^{11}$)—[C(R$^{14}$)R$^{15}]_r$—R$^{12}$, —[C(R$^{14}$)R$^{15}]_r$—N(R$^{11}$)—C(O)N(R$^{11}$)R$^{12}$, —[C(R$^{14}$)R$^{15}]_r$—N(R$^{11}$)S(O)$_t$—C(O)N(R$^{11}$)R$^{12}$, —[C(R$^{14}$)R$^{15}]_r$—OR$^{11}$, —N(R$^{11}$)—[C(R$^{14}$)R$^{5}]_r$—R$^{12}$, —N(R$^{11}$)C(O)N(R$^{13}$)—[C(R$^{14}$)R$^{15}]_r$—R$^{12}$, —C(O)—[C(R$^{14}$)R$^{15}]_r$—N(R$^{11}$)R$^{12}$, —N(R$^{13}$)C(O)-L-(R$^{11}$)R$^{12}$, —N(R$^{11}$)—[C(R$^{14}$)R$^{15}]_r$-L-R$^{12}$, —N(R$^{11}$)C(O)N(R$^{11}$)—[C(R$^{14}$)R$^{15}]_r$-L-R$^{12}$, —[C(R$^{14}$)R$^{15}]_r$-L-R$^{12}$, and -L-C(O)N(R$^{11}$)R$^{12}$; or R$^5$ and R$^6$ together may form an optionally substituted aryl, optionally substituted heteroaryl, optionally substituted cycloalkyl, or optionally substituted heterocycloalkyl;

t is an integer from 0 to 2;

r is an integer from 0 to 5;

L is selected from the group consisting of an optionally substituted 3- to 7-membered carbocyclic group, an optionally substituted 3- to 7-membered heterocyclic group, an optionally substituted 6-membered aryl group, and an optionally substituted 6-membered heteroaryl group;

$R^4$, $R^{10}$, $R^{14}$, $R^{15}$, $R^{16}$, $R^{17}$, and $R^{18}$ are independently selected from the group consisting of hydrogen, halogen, optionally substituted alkyl, optionally substituted haloalkyl, haloalkoxy, optionally substituted aralkyl, optionally substituted aryl, optionally substituted heteroaryl, optionally substituted heteroaralkyl, optionally substituted alkene, optionally substituted alkyne; or $R^{14}$ and $R^{15}$ may together form a carbonyl, optionally substituted carbocycle or optionally substituted heterocycle; or $R^{14}$ and $R^{15}$ together may be null, forming an additional bond;

$R^{11}$, $R^{12}$, and $R^{13}$ are independently selected from the group consisting of hydrogen, halogen, optionally substituted alkyl, haloalkyl, haloalkoxy, optionally substituted aralkyl, optionally substituted aryl, optionally substituted heteroaryl, optionally substituted heteroaralkyl, optionally substituted alkene, optionally substituted alkyne, —OR$^{17}$, —S(O)$_t$—R$^{17}$, —[C(R$^{14}$)R$^{15}]_r$—C(O)OR$^{17}$, —[C(R$^{14}$)R$^{15}]_r$—N(R$^{17}$)R$^{18}$, —[C(R$^{14}$)R$^{15}]_r$—N(R$^{16}$)C(O)N(R$^{17}$)R$^{18}$, —[C(R$^{14}$)R$^{15}]_r$—N(R$^{17}$)C(O)OR$^{8}$, —[C(R$^{14}$)R$^{15}]_r$—R$^{17}$, and —[C(R$^{14}$)R$^{15}]_r$—N(R$^{17}$)C(O)R$^{18}$; or R$^{11}$ or R$^{12}$ may be defined by a structure selected from the group consisting of

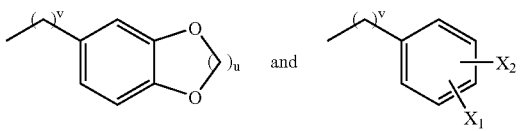

wherein:

u and v are independently an integer from 0 to 3; and $X^1$ and $X^2$ are independently selected from the group consisting of hydrogen, halogen, hydroxy, lower acyloxy, optionally substituted lower alkyl, optionally substituted lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides compounds of the Formula V:

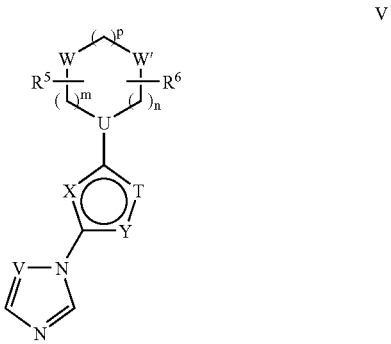

V wherein:

T, X, and Y are independently selected from the group consisting of CR$^4$, N, NR$^4$, S, and O;

U is selected from the group consisting of CR$^{10}$ and N;

V is selected from the group consisting of CR$^4$ and N;

W and W' are independently selected from the group consisting of CH$_2$, CR$^7$R$^8$, NR$^9$, O, N(O), S(O)$_q$, and C(O);

n, m and p are independently an integer from 0 to 5;

q is 0, 1, or 2;

$R^3$, $R^4$, $R^{10}$, $R^{14}$, $R^{15}$, $R^{16}$, $R^{17}$ and $R^{18}$ are independently selected from the group consisting of hydrogen, halogen, optionally substituted alkyl, optionally substituted haloalkyl, haloalkoxy, optionally substituted aralkyl, optionally substituted aryl, optionally substituted heteroaryl, optionally substituted heteroaralkyl, optionally substituted alkene, optionally substituted alkyne; or $R^{14}$ and $R^{15}$ may together form a carbonyl, optionally substituted carbocycle or optionally substituted heterocycle; or $R^{14}$ and $R^{15}$ together may be null, forming an additional bond;

$R^5$, $R^6$, $R^7$, $R^8$, and $R^9$ are independently selected from the group consisting of hydrogen, halogen, optionally substituted alkyl, optionally substituted alkoxy, haloalkyl, haloalkoxy, optionally substituted aralkyl, optionally substituted aryl, optionally substituted heteroaryl, optionally substituted heteroaralkyl, optionally substituted alkene, optionally substituted alkyne, —C(O)N(R$^{11}$)R$^{12}$, —P(O)[N(R$^{11}$)R$^{12}]_2$, —SO$_2$NHC(O)R$^{11}$, —N(R$^{11}$)SO$_2$R$^{12}$, —SO$_2$N(R$^{11}$)R$^{12}$, —NSO$_2$N(R$^{11}$)R$^{12}$, —C(O)NHSO$_2$R$^{11}$, —CH=NOR$^{11}$, —OR$^{11}$, —S(O)$_t$—R$^{11}$, —N(R$^{11}$)R$^{12}$, —N(R$^{11}$)C(O)N(R$^{12}$)R$^{13}$, —N(R$^{11}$)C(O)OR$^{12}$, —N(R$^{11}$)C(O)R$^{12}$, —[C(R$^{14}$)R$^{15}]_r$—R$^{12}$, —[C(R$^{14}$)R$^{15}]_r$—C(O)OR$^{11}$, —[C(R$^{14}$)R$^{15}]_r$—[C(O)OR$^{11}]_2$, —[C(R$^{14}$)R$^{15}]_r$—C(O)N(R$^{11}$)R$^{12}$, —[C(R$^{14}$)R$^{15}]_r$—N(R$^{11}$)R$^{12}$, —[C(R$^{14}$)R$^{15}]_r$—N(R$^{11}$)—[C(R$^{14}$)R$^{15}]_r$—R$^{12}$, —[C(R$^{14}$)R$^{15}]_r$—OR$^{11}$, —N(R$^{11}$)—[C(R$^{14}$)R$^{15}]_r$—R$^{12}$, —N(R$^{11}$)C(O)N(R$^{13}$)—[C(R$^{14}$)R$^{15}]_r$—R$^{12}$, —[C(R$^{14}$)R$^{15}]_r$—N(R$^{13}$)—C(O)N(R$^{11}$)R$^{12}$, —[C(R$^{14}$)R$^{15}]_r$—N(R$^{13}$)S(O)$_t$—C(O)N(R$^{11}$)R$^{12}$, —C(O)—[C(R$^{14}$)R$^{15}]_r$—N(R$^{11}$)R$^{12}$, —N(R$^{13}$)C(O)-L-(R$^{11}$)R$^{12}$, —N(R$^{11}$)—[C(R$^{14}$)R$^{15}]_r$-L-R$^{12}$, —N(R$^{11}$)C(O)N(R$^{11}$)—[C(R$^{14}$)R$^{15}]_r$-L-R$^{12}$, —[C(R$^{14}$)R$^{15}]_r$-L-R$^{12}$, and -L-C(O) N(R$^{11}$)R$^{12}$; or R$^5$ and R$^6$ together may form an optionally substituted aryl, optionally substituted heteroaryl, optionally substituted cycloalkyl, or optionally substituted heterocycloalkyl;

t is an integer from 0 to 2;

r is an integer from 0 to 5;

L is selected from the group consisting of an optionally substituted 3- to 7-membered carbocyclic group, an optionally substituted 3- to 7-membered heterocyclic group, an optionally substituted 6-membered aryl group, and an optionally substituted 6-membered heteroaryl group; and $R^{11}$, $R^{12}$, and $R^{13}$ are independently selected from the group consisting of hydrogen, halogen, optionally substituted alkyl, haloalkyl, haloalkoxy, optionally substituted aralkyl, optionally substituted aryl, optionally substituted heteroaryl, optionally substituted heteroaralkyl, optionally substituted alkene, optionally substituted alkyne, —$OR^{17}$, —$S(O)_t$—$R^{17}$, —$[C(R^{14})R^{15}]_r$—$C(O)OR^{17}$, —$[C(R^{14})R^{15}]_r$—$N(R^{17})R^{18}$, —$[C(R^{14})R^{15}]_r$—$N(R^{16})C(O)N(R^{17})R^{18}$, —$[C(R^{14})R^{15}]_r$—$N(R^{17})C(O)OR^{18}$, —$[C(R^{14})R^{15}]_r$—$R^{17}$, and —$[C(R^{14})R^{15}]_r$—$N(R^{17})C(O)R^{18}$; or $R^{11}$ or $R^{12}$ may be defined by a structure selected from the group consisting of

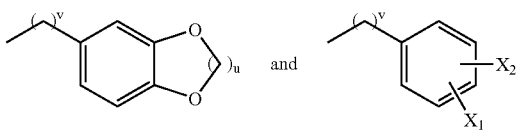

wherein:

u and v are independently an integer from 0 to 3; and $X^1$ and $X^2$ are independently selected from the group consisting of hydrogen, halogen, hydroxy, lower acyloxy, optionally substituted lower alkyl, optionally substituted lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

In a broad aspect, the subject invention provides for novel compounds, pharmaceutical compositions and methods of making and using the compounds and compositions. These compounds possess useful nitric oxide synthase inhibiting or modulating activity, and may be used in the treatment or prophylaxis of a disease or condition in which the synthesis or over-synthesis of nitric oxide forms a contributory part. These compounds can inhibit and/or modulate the inducible isoform of nitric oxide synthase over the constitutive isoforms of nitric oxide synthase.

DETAILED DESCRIPTION OF THE INVENTION

The invention provides for iNOS dimerization inhibitors of compounds of Formulas I, II, III, IV and IV as defined above.

The invention provides for compounds of Formula II wherein V is $CR^4$.

The invention provides for compounds of Formula II wherein Z is $CR^3$ and Y is N.

The invention provides for compounds of Formula II wherein T is $CR^4$.

The invention provides for compounds of Formula II wherein X is N.

The invention provides for compounds of Formula II wherein X is $CR^4$.

The invention provides for compounds of Formula II wherein T is N.

The invention provides for compounds of Formula II wherein X is N.

The invention provides for compounds of Formula II wherein:

$R^5$, $R^6$, $R^7$, $R^8$, and $R^9$ are independently selected from the group consisting of hydrogen, halogen, lower alkyl, haloalkyl, optionally substituted aralkyl, optionally substituted aryl, optionally substituted heteroaryl, lower alkene, lower alkyne, —$(O)N(R^{11})R^{12}$, —$P(O)[N(R^{11})R^{12}]_2$, —$SO_2NHC(O)R^{11}$, —$N(R^{11})SO_2R^{12}$, —$SO_2N(R^{11})H$, —$C(O)NHSO_2R^{11}$, —$CH=NOR^{11}$, —$OR^{11}$, —$S(O)_t$—$R^{11}$, —$N(R^{11})R^{12}$, —$N(R^{11})C(O)N(R^{12})R^{13}$, —$N(R^{11})C(O)OR^{12}$, —$N(R^{11})C(O)R^{12}$, —$[C(R^{14})R^{15}]_r$—$C(O)OR^{11}$, —$[C(R^{14})R^{15}]_r$—$[C(O)OR^{11}]_2$, —$[C(R^{14})R^{15}]_r$—$N(R^{11})R^{12}$, —$[C(R^{14})R^{15}]_r$—$C(O)N(R^{11})R^{12}$, —$N(R^{11})$—$[C(R^{14})R^{15}]_r$—$R^{12}$, —$N(R^{11})C(O)N(R^{12})$—$[C(R^{14})R^{15}]_r$—$R^{12}$, —$[C(R^{14})R^{15}]_r$—$R^{12}$, —$N(R^{11})$—$[C(R^{14})R^{15}]_r$-L-$R^{12}$, —$[C(R^{14})R^{15}]_r$-L-$R^{12}$ and —$N(R^{11})C(O)N(R^{12})R^{13}$—$[C(R^{14})R^{15}]_r$-L-$R^{12}$; or $R^5$ and $R^6$ together may form an optionally substituted aryl, optionally substituted heteroaryl, optionally substituted cycloalkyl, or optionally substituted heterocycloalkyl;

$R^3$, $R^4$, $R^{10}$, $R^{14}$, $R^{15}$, $R^{16}$, $R^{17}$ and $R^{18}$ are independently selected from the group consisting of hydrogen, halogen, lower alkyl, haloalkyl, optionally substituted aralkyl, optionally substituted aryl, optionally substituted heteroaryl, lower alkene, and lower alkyne; or $R^{14}$ and $R^{15}$ may together form a carbonyl, optionally substituted carbocycle or optionally substituted heterocycle; and $R^{11}$, $R^{12}$, and $R^{13}$ are independently selected from the group consisting of hydrogen, halo, lower alkyl, haloalkyl, optionally substituted aralkyl, optionally substituted aryl, optionally substituted heteroaralkyl, optionally substituted heteroaryl, lower alkene, and lower alkyne; or $R^{11}$ or $R^{12}$ may be defined by a structure selected from the group consisting of wherein:

u and v are independently an integer from 0 to 3; and $X^1$ and $X^2$ are independently selected from the group consisting of hydrogen, halogen, hydroxy, lower acyloxy, lower alkyl, lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

In certain embodiments, the invention further provides for compounds of Formula II wherein:

$R^7$, $R^8$, and $R^9$ are independently selected from the group consisting of hydrogen, halogen, lower alkyl, haloalkyl, optionally substituted aralkyl, optionally substituted aryl, optionally substituted heteroaryl, lower alkene, lower alkyne, —$N(R^{11})SO_2R^2$, —$SO_2N(R^{11})H$, —$OR^{11}$, —$S(O)_t$—$R^{11}$, —$N(R^{11})R^{12}$, —$N(R^{11})C(O)N(R^{12})R^{13}$, —$N(R^{11})C(O)R^{12}$, —$[C(R^{14})R^{15}]_r$—$N(R^{11})R^{12}$, —$[C(R^{14})R^{15}]_r$—$C(O)N(R^{12})$, —$N(R^{11})$—$[C(R^{14})R^{15}]_r$—$R^{12}$, —$N(R^{11})$—$[C(R^{14})R^{15}]_r$-L-$R^{12}$, —$[C(R^{14})R^{15}]_r$-L-$R^{12}$, and —$N(R^{11})C(O)N(R^{12})R^{13}$—$[C(R^{14})R^{15}]_r$-L-$R^{12}$; and $R^5$ and $R^6$ are independently selected from the group consisting of hydrogen, halo, lower alkyl, haloalkyl, optionally substituted aralkyl, optionally substituted aryl, optionally substituted heteroaryl, lower alkene, lower alkyne, —$N(R^{11})C(O)R^{12}$, —$[C(R^{14})R^{15}]_r$—$C(O)OR^{11}$, —$[C(R^{14})R^{15}]_r$—$N(R^{11})R^{12}$, —$[C(R^{14})R^{15}]_r$—$C(O)N(R^{11})R^{12}$, and —$N(R^{11})$—$[C(R^{14})R^{15}]_r$—$R^{12}$, or $R^5$ and $R^6$ together may form an optionally substituted aryl, optionally substituted heteroaryl, optionally substituted cycloalkyl, or optionally substituted heterocycloalkyl.

The invention provides for compounds of Formula II wherein $R^7$ and $R^9$ are independently selected from the group consisting of hydrogen, halogen, lower alkyl, haloalkyl, optionally substituted aralkyl, optionally substituted aryl, optionally substituted heteroaryl, lower alkene, lower alkyne, —N($R^{11}$)$SO_2R^{12}$, —$SO_2$N($R^{11}$)H, —O$R^{11}$, —S(O)$_r$—$R^{11}$, —N($R^{11}$)$R^{12}$, —N($R^{11}$)C(O)N($R^{12}$)$R^{13}$, —N($R^{11}$)C(O)$R^{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, and —N($R^{11}$)—[C($R^{14}$)$R^{15}$]$_r$—$R^{12}$. The invention provides for compounds of Formula II wherein W is $CH_2$ and W' is $NR^9$. The invention provides for compounds of Formula II wherein n, m, and p are each independently an integer from 0 to 2. The invention further provides for compounds of Formula II wherein $R^9$ is selected from the group consisting of —C(O)N($R^{11}$)$R^{12}$ and —[C($R^{14}$)$R^{15}$]$_r$—N($R^{11}$)$R^{12}$. The invention yet further provides for compounds of Formula II wherein $R^9$ is —[C($R^{14}$)$R^{15}$]$_r$—N($R^{11}$)$R^{12}$. The invention yet further provides for compounds of Formula II wherein r is 2.

The invention provides for compounds of Formula II wherein $R^{11}$ is selected from the group consisting of hydrogen and lower alkyl. The invention further provides for compounds of Formula II wherein $R^{11}$ is selected from the group consisting of hydrogen and methyl. The invention yet further provides for compounds of Formula II wherein $R^{11}$ is hydrogen.

The invention provides for compounds of Formula II wherein $R^{12}$ is defined by the following structural formula:

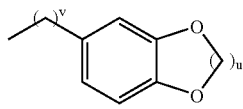

wherein u and v are independently an integer from 0 to 3. The invention further provides for compounds of Formula II wherein u and v are independently 1 or 2.

The invention provides for compounds of Formula II wherein p and m are 1 and n is 0.

The invention provides for compounds of Formula II wherein $R^{14}$ and $R^{15}$ are hydrogen.

The invention provides for compounds of Formula II wherein $R^4$, $R^5$, $R^6$ and $R^{10}$ are hydrogen.

The invention provides for compounds of Formula II wherein $R^3$ is methyl.

The invention provides for compounds of Formula II wherein u and v are each 1.

The invention provides for compounds of Formula II wherein T is $CR^4$ and X is N.

The invention provides for compounds of Formula IV wherein T and X are independently selected from the group consisting of $CR^4$ and N, and Y is selected from the group consisting of S and O.

The invention provides for compounds of Formula IV wherein T is selected from the group consisting of S and O, and X and Y independently are selected from the group consisting of $CR^4$ and N.

The invention provides for compounds of Formula IV wherein Y is N.

The invention provides for compounds of Formula IV wherein X is N.

The invention provides for compounds of Formula IV wherein T is S.

The invention provides for compounds of Formula IV wherein V is $CR^4$.

The invention provides for compounds of Formula IV wherein:

$R^1$ and $R^2$ are independently selected from the group consisting of hydrogen, halogen, lower alkyl, haloalkyl, optionally substituted aralkyl, optionally substituted aryl, optionally substituted heteroaryl, lower alkene, lower alkyne, —(O)N($R^{11}$)$R^{12}$, —P(O)[N($R^{11}$)$R^{12}$]$_2$, —$SO_2$NHC(O)$R^{11}$, —N($R^{11}$)$SO_2R^{12}$, —$SO_2$N($R^{11}$)H, —C(O)NHSO$_2R^{11}$, —CH=NO$R^{11}$, —O$R^{11}$, —S(O)$_r$—$R^{13}$, —N($R^{11}$)$R^{12}$, —N($R^{11}$)C(O)N($R^{12}$)$R^{13}$, —N($R^{11}$)C(O)O$R^{12}$, —N($R^{11}$)C(O)$R^{12}$, —[C($R^{14}$)$R^{15}$]$_r$—C(O)O$R^{11}$, —[C($R^{14}$)$R^{15}$]$_r$—[C(O)O$R^{11}$]$_{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, —N($R^{11}$)—[C($R^{14}$)$R^{15}$]$_r$—$R^{12}$, —N($R^{11}$)C(O)N($R^{12}$)—[C($R^{14}$)$R^{15}$]$_r$—$R^{12}$, —[C($R^{14}$)$R^{15}$]$_r$—$R^{12}$, —[C($R^{14}$)$R^{15}$]$_r$—N($R^{13}$—C(O)N($R^{11}$)$R^{12}$, —[C($R^{14}$)$R^{15}$]$_r$—N($R^{13}$)S(O)$_r$—C(O)N($R^{11}$)$R^{12}$, —N($R^{11}$)—[C($R^{14}$)$R^{15}$]$_r$-L-$R^{12}$, —[C($R^{14}$)$R^{15}$]$_r$-L-$R^{12}$ and —N($R^{11}$)C(O)N($R^{12}$)$R^{13}$—[C($R^{14}$)$R^{15}$]$_r$-L-$R^{12}$; or $R^5$ and $R^6$ together may form an optionally substituted aryl, optionally substituted heteroaryl, optionally substituted cycloalkyl, or optionally substituted heterocycloalkyl;

$R^4$, $R^{10}$, $R^{14}$, $R^{15}$, $R^{16}$, $R^{17}$ and $R^{18}$ are independently selected from the group consisting of hydrogen, halogen, lower alkyl, haloalkyl, optionally substituted aralkyl, optionally substituted aryl, optionally substituted heteroaryl, lower alkene, and lower alkyne; or $R^{14}$ and $R^{15}$ may together form a carbonyl, optionally substituted carbocycle or optionally substituted heterocycle; and $R^{11}$, $R^{12}$, and $R^{13}$ are independently selected from the group consisting of hydrogen, halo, lower alkyl, haloalkyl, optionally substituted aralkyl, optionally substituted aryl, optionally substituted heteroaralkyl, optionally substituted heteroaryl, lower alkene, and lower alkyne; or $R^{11}$ or $R^{12}$ may be defined by a structure selected from the group consisting of

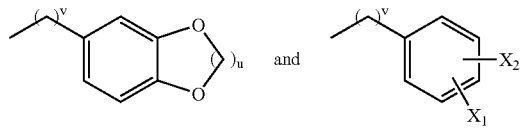

wherein:

u and v are independently an integer from 0 to 3; and $X^1$ and $X^2$ are independently selected from the group consisting of hydrogen, halogen, hydroxy, lower acyloxy, lower alkyl, lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides for compounds of Formula IV wherein:

$R^1$ is selected from the group consisting of hydrogen, halogen, lower alkyl, haloalkyl, optionally substituted aralkyl, optionally substituted aryl, optionally substituted heteroaryl, lower alkene, lower alkyne, —N($R^{11}$)$SO_2R^{12}$,—$SO_2$N($R^{11}$)H, —O$R^{11}$, —S(O)$_r$—$R^{11}$, —N($R^{11}$)$R^{12}$, —N($R^{11}$)C(O)N($R^{12}$)$R^{13}$, —N($R^{11}$)C(O)$R^{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, —N($R^{11}$)—[C($R^{14}$)$R^{15}$]$_r$—$R^{12}$, —N($R^{11}$)—[C($R^{14}$)$R^{15}$]$_r$-L-$R^{12}$, —[C($R^{14}$)$R^{15}$]$_r$-L-$R^{12}$, —N($R^{11}$)C(O)N($R^{12}$)$R^{13}$—[C($R^{14}$)$R^{15}$]$_r$-L-$R^{12}$, —[C($R^{14}$)$R^{15}$]$_r$—N($R^{13}$)—C(O)N($R^{11}$)$R^{12}$, and —[C($R^{14}$)$R^{15}$]$_r$—N($R^{13}$)S(O)$_r$—C(O)N($R^{11}$)$R^{12}$; and $R^2$ is selected from the group consisting of hydrogen, halo, lower alkyl, haloalkyl, optionally substituted aralkyl, optionally substituted aryl, optionally substituted heteroaryl, lower alkene, lower alkyne, $-N(R^{11})C(O)R^{12}$, $-[C(R^{14})R^{15}]_r-C(O)OR^{11}$, $-[C(R^{14})R^{15}]_r-N(R^{11})R^{12}$, $-[C(R^{14})R^{15}]_r-C(O)N(R^{11})R^{12}$, and $-N(R^{11})-[C(R^{24})R^{15}]_r-R^{12}$, The invention yet further provides for compounds of Formula IV wherein $R^1$ is selected from the group consisting of hydrogen, halogen, lower alkyl, haloalkyl, optionally substituted aralkyl, optionally substituted aryl, optionally substituted heteroaryl, lower alkene, lower alkyne, $-N(R^{11})SO_2R^{12}$, $-SO_2N(R^{11})H$, $-OR^{11}$, $-S(O)_r-R^{11}$, $-N(R^{11})R^{12}$, $-N(R^{11})C(O)N(R^{12})R^{13}$, $-N(R^{11})C(O)R^{12}$, $-[C(R^{14})R^{15}]_r-N(R^{11})R^{12}$, $-[C(R^{14})R^{15}]_r-C(O)N(R^{11})R^{12}$, $-N(R^{11})-[C(R^{14})R^{15}]_r-R^{12}$, $-[C(R^{14})R^{15}]_r-N(R^{13})-C(O)N(R^{11})R^{12}$, and $-[C(R^{14})R^{15}]_r-N(R^{13})S(O)_r-C(O)N(R^{11})R^{12}$.

The invention provides for compounds of Formula IV wherein U is N.

The invention provides for compounds of Formula IV wherein $R^1$ is selected form the group consisting of $-[C(R^{14})R^{15}]_r-N(R^{11})R^{12}$, $-[C(R^{14})R^{15}]_r-C(O)N(R^{11})R^{12}$, $-[C(R^{14})R^{15}]_r-N(R^{13})-C(O)N(R^{11})R^{12}$, and $-[C(R^{14})R^{15}]_r-N(R^{13})S(O)_r-C(O)N(R^{11})R^{12}$.

The invention provides for compounds of Formula IV wherein $R^{12}$ is selected from the group consisting of $NH_2$ and heteroaryl, or is defined by one of the following structural formulae:

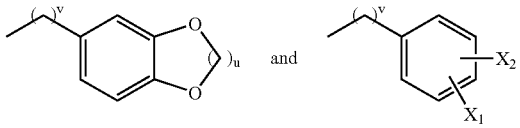

wherein:
u and v are independently an integer from 0 to 3; and
$X^1$ and $X^2$ are independently selected from the group consisting of hydrogen, halogen, hydroxy, lower acyloxy, lower alkyl, lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides for compounds of Formula IV wherein $X_1$ and $X_2$ are independently selected from the group consisting of hydrogen, halogen, hydroxy, lower alkyl, lower alkoxy, lower haloalkyl, lower haloalkoxy, and lower perhaloalkyl.

The invention provides for compounds of Formula IV wherein $R^9$ is $-[C(R^{14})R^{15}]_r-N(R^{11})R^{12}$.

The invention provides for compounds of Formula IV wherein $R^{12}$ is defined by the following structural formula:

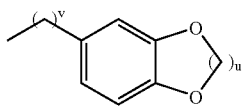

and u and v are independently 1 or 2.

The invention provides for compounds of Formula IV wherein $R^{14}$ and $R^{15}$ are both hydrogen.

The invention provides for compounds of Formula IV wherein $R^2$ is selected from the group consisting of hydrogen and lower alkyl.

The invention provides for compounds of Formula IV wherein $R^{11}$ is hydrogen or methyl.

The invention provides for compounds of Formula IV wherein $R^2$ is methyl.

The invention provides for compounds of Formula IV wherein $R^{10}$, $R^{11}$, and $R^4$ are hydrogen, and u and v are 1.

The invention provides for compounds of Formula IV wherein Y and X are N, T is S, and V is $CR^4$.

The invention provides for compounds of Formula IV wherein T and X are independently selected from the group consisting of $CR^4$ and N, and Y is selected from the group consisting of S and O.

The invention provides for compounds of Formula IV wherein T is selected from the group consisting of S and O, and X and Y are independently selected from the group consisting of $CR^4$ and N.

The invention provides for compounds of Formula V wherein Y is N.

The invention provides for compounds of Formula V wherein X is N.

The invention provides for compounds of Formula V wherein T is S.

The invention provides for compounds of Formula V wherein V is $CR^4$.

The invention provides for compounds of Formula V wherein Y is $CR^4$.

The invention provides for compounds of Formula V wherein:

$R^5$, $R^6$, $R^7$, $R^8$, and $R^9$ are independently selected from the group consisting of hydrogen, halogen, lower alkyl, haloalkyl, optionally substituted aralkyl, optionally substituted aryl, optionally substituted heteroaryl, lower alkene, lower alkyne, $-C(O)N(R^{11})R^{12}$, $-P(O)[N(R^{11})R^{12}]_2$, $-SO_2NHC(O)R_{11}$, $-N(R^{11})SO_2R^{12}$, $-SO_2N(R^{11})H$, $-C(O)NHSO_2R^{11}$, $-CH=NOR^{11}$, $-OR^{11}$, $-S(O)_r-R^{11}$, $-N(R^{11})R^{12}$, $-N(R^{11})C(O)N(R^{12})R^{13}$, $-N(R^{11})C(O)OR^{12}$, $-N(R^{11})C(O)R^{12}$, $-[C(R^{14})R^{15}]_r-C(O)OR^{11}$, $-[C(R^{14})R^{15}]_r-[C(O)OR^{11}]_{12}$, $-[C(R^{14})R^{15}]_r-N(R^{11})R^{12}$, $-[C(R^{14})R^{15}]_r-C(O)N(R^{11})R^{12}$, $-N(R^{11})-[C(R^{14})R^{15}]_r-R^{12}$, $-N(R^{11})C(O)N(R^{12})-[C(R^{14})R^{15}]_r-R^{12}$, $-[C(R^{14})R^{15}]_r-R^{12}$, $-N(R^{11})-[C(R^{14})R^{15}]_r-L-R^{12}$, $-[C(R^{14})R^{15}]_r-L-R^{12}$ and $-N(R^{11})C(O)N(R^{12})R^{13}-[C(R^{14})R^{15}]_r-L-R^{12}$; or $R^5$ and $R^6$ together may form an optionally substituted aryl, optionally substituted heteroaryl, optionally substituted cycloalkyl, or optionally substituted heterocycloalkyl;

$R^3$, $R^4$, $R^{10}$, $R^{14}$, $R^{15}$, $R^{16}$, $R^{17}$ and $R^{18}$ are independently selected from the group consisting of hydrogen, halogen, lower alkyl, haloalkyl, optionally substituted aralkyl, optionally substituted aryl, optionally substituted heteroaryl, lower alkene, and lower alkyne; or $R^{14}$ and $R^{15}$ may together form a carbonyl, optionally substituted carbocycle or optionally substituted heterocycle; and $R^{11}$, $R^{12}$, and $R^{13}$ are independently selected from the group consisting of hydrogen, halo, lower alkyl, haloalkyl, optionally substituted aralkyl, optionally substituted aryl, optionally substituted heteroaralkyl, optionally substituted heteroaryl, lower alkene, and lower alkyne; or $R^{11}$ or $R^{12}$ may be defined by a structure selected from the group consisting of

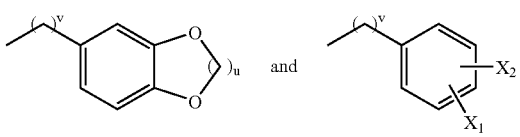

wherein:

u and v are independently an integer from 0 to 3; and $X^1$ and $X^2$ are independently selected from the group consisting of hydrogen, halogen, hydroxy, lower acyloxy, lower alkyl, lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

The invention further provides for compounds of Formula V wherein:

$R^7$, $R^8$, and $R^9$ are independently selected from the group consisting of hydrogen, halogen, lower alkyl, haloalkyl, optionally substituted aralkyl, optionally substituted aryl, optionally substituted heteroaryl, lower alkene, lower alkyne, —C(O)N($R^{11}$)$R^{12}$, —[C($R^{14}$)$R^{15}$]$_r$—N($R^{11}$)$R^{12}$, —N($R^{11}$)SO$_2$$R^{12}$, —SO$_2$N($R^{11}$)H, —O$R^{11}$, —S(O)$_r$—$R^{11}$, —N($R^{11}$)$R^{12}$, —N($R^{11}$)C(O)N($R^{12}$)$R^{13}$, —N($R^{11}$)C(O)$R^{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, —N($R^{11}$)—[C($R^{14}$)$R^{15}$]$_r$—$R^{12}$, —N($R^{11}$)—[C($R^{14}$)$R^{15}$]$_r$-L-$R^{12}$, —[C($R^{14}$)$R^{15}$]$_r$-L-$R^{12}$ and —N($R^{11}$)C(O)N($R^{12}$)$R^{13}$—[C($R^{14}$)$R^{15}$]$_r$-L-$R^{12}$; and $R^5$ and $R^6$ are independently selected from the group consisting of hydrogen, halo, lower alkyl, haloalkyl, optionally substituted aralkyl, optionally substituted aryl, optionally substituted heteroaryl, lower alkene, lower alkyne, —O$R^{11}$, —S(O)$_r$—$R^{11}$, —N($R^{11}$)$R^{12}$, —N($R^{11}$)C(O)$R^{12}$, —[C($R^{14}$)$R^{15}$]$_r$—C(O)O$R^{11}$, —[C($R^{14}$)$R^{15}$]$_r$—N($R^{11}$)$R^{12}$, —[C($R^{14}$)$R^{15}$]$_r$—C(O)N($R^{11}$)$R^{12}$, and —N($R^{11}$)—[C($R^{14}$)$R^{15}$]$_r$—$R^{12}$, or $R^5$ and $R^6$ together may form an optionally substituted aryl, optionally substituted heteroaryl, optionally substituted cycloalkyl, or optionally substituted heterocycloalkyl.

The invention yet further provides for compounds of Formula V wherein $R^7$ and $R^9$ are independently selected from the group consisting of hydrogen, halogen, lower alkyl, haloalkyl, optionally substituted aralkyl, optionally substituted aryl, optionally substituted heteroaryl, lower alkene, lower alkyne, —N($R^{11}$)SO$_2$$R^{12}$, —SO$_2$N($R^{11}$)H, —O$R^{11}$, —S(O)$_r$—$R^{11}$, —N($R^{11}$)$R^{12}$, —N($R^{11}$)C(O)N($R^{12}$)$R^{13}$, —N($R^{11}$)C(O)$R^{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, and —N($R^{11}$)—[C($R^{14}$)$R^{15}$]$_r$—$R^{12}$.

The invention provides for compounds of Formula V wherein $R^{12}$ is defined by the following structural formula:

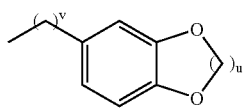

wherein u and v are independently an integer from 0 to 3. The invention further provides for compounds of Formula V wherein u and v are independently 1 or 2.

The invention provides for compounds of Formula V wherein $R^{11}$ is selected from the group consisting of hydrogen and lower alkyl. The invention further provides for compounds of Formula V wherein $R^{11}$ is selected from the group consisting of hydrogen and methyl. The invention yet further provides for compounds of Formula V wherein $R^3$ is methyl.

The invention provides for compounds of Formula V wherein U is N, W is CH$_2$, and W' is CR$^7$R$^8$.

The invention provides for compounds of Formula V wherein U is CR$^4$, W is CH$_2$, and W' is NR$^9$.

The invention provides for compounds of Formula V wherein n, m, and p are each independently an integer from 0 to 2.

The invention further provides for compounds of Formula V wherein $R^8$ is selected from the group consisting of —C(O)N($R^{11}$)$R^{12}$ and —[C($R^{14}$)$R^{15}$]$_r$—N($R^{11}$)$R^{12}$.

The invention provides for compounds of Formula V wherein $R^{14}$ and $R^{15}$ are hydrogen.

The invention provides for compounds of Formula V wherein r is 1 to 3.

The invention provides for compounds of Formula V wherein $R^7$ is hydrogen.

The invention provides for compounds of Formula V wherein $R^5$ is selected from the group consisting of hydrogen, —O$R^{11}$, —S(O), —$R^{11}$, and —N($R^{11}$)$R^{12}$.

The invention provides for compounds of Formula V wherein $R^{11}$ is hydrogen or methyl.

The invention provides for compounds of Formula V wherein $R^2$ is defined by the following structural formula:

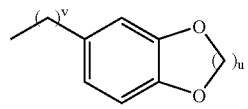

and u and v are independently 1 or 2.

The invention provides for compounds of Formula V wherein $R^4$ and $R^6$ and are hydrogen.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxylmethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Compounds of the present invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Gels for topical or transdermal administration of compounds of the subject invention may comprise, generally, a mixture of volatile solvents, nonvolatile solvents, and water. The volatile solvent component of the buffered solvent system may preferably include lower (C1-C6) alkyl alcohols, lower alkyl glycols and lower glycol polymers. More preferably, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. Preferably, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess will result in a lack of bioavailability due to poor release of drug from solvent mixture. The buffer component of the buffered solvent system may be selected from any buffer commonly used in the art; preferably, water is used. The preferred ratio of ingredients is about 20% of the non-volatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as siliceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds of the subject invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, amide, prodrug, or solvate) in combination with another therapeutic agent. By way of example only, if one of the side effects experienced by a patient upon receiving one of the compounds herein is hypertension, then it may be appropriate to administer an antihypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention with: a) corticosteroids including betamethasone dipropionate (augmented and nonaugemented), betamethasone valerate, clobetasol propionate, diflorasone diacetate, halobetasol propionate, amcinonide, dexosimethasone, fluocinolone acetononide, fluocinonide, halocinonide, clocortalone pivalate, dexosimetasone, and flurandrenalide; b) non-steroidal anti-inflammatory drugs including diclofenac, ketoprofen, and piroxicam; c) muscle relaxants and combinations thereof with other agents, including cyclobenzaprine, baclofen, cyclobenzaprine/lidocaine, baclofen/cyclobenzaprine, and cyclobenzaprine/lidocaine/ketoprofen; d) anesthetics and combinations thereof with other agents, including lidocaine, lidocaine/deoxy-D-glucose (an antiviral), prilocaine, and EMLA Cream [Eutectic Mixture of Local Anesthetics (lidocaine 2.5% and prilocaine 2.5%; an emulsion in which the oil phase is a eutectic mixture of lidocaine and prilocaine in a ratio of 1:1 by weight. This eutectic mixture has a melting point below room temperature and therefore both local anesthetics exist as a liquid oil rather then as crystals)]; e) expectorants and combinations thereof with other agents, including guaifenesin and guaifenesin/ketoprofen/cyclobenzaprine; f) antidepressants including tricyclic antidepressants (e.g., amitryptiline, doxepin, desipramine, imipramine, amoxapine, clomipramine, nortriptyline, and protriptyline), selective serotonin/norepinephrine reuptake inhibitors including (e.g., duloxetine and mirtazepine), and selective norepinephrine reuptake inhibitors (e.g., nisoxetine, maprotiline, and reboxetine), selective serotonin reuptake inhibitors (e.g., fluoxetine and fluvoxamine); g) anticonvulsants and combinations thereof, including gabapentin, carbamazepine, felbamate, lamotrigine, topiramate, tiagabine, oxcarbazepine, carbamezipine, zonisamide, mexiletine, gabapentin/clonidine, gabapentin/carbamazepine, and carbamazepine/cyclobenzaprine; h) antihypertensives including clonidine; i) opioids including loperamide, tramadol, morphine, fentanyl, oxycodone, levorphanol, and butorphanol; j) topical counter-irritants including menthol, oil of wintergreen, camphor, eucalyptus oil and turpentine oil; k) topical cannabinoids including selective and non-selective CB1/CB2 ligands; and other agents, such as capsaicin.

In any case, the multiple therapeutic agents (at least one of which is a compound of any of Formulas I to V, described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Compounds of the subject invention are useful in treating nitric oxide synthase-mediated disease, disorders and conditions, and are particularly suitable as inhibitors of nitric oxide synthase dimerization. The compounds of the present invention are useful to treat patients with neuropathy or inflammatory pain such as reflex sympathetic dystrophy/causalgia (nerve injury), peripheral neuropathy (including diabetic neuropathy), intractable cancer pain, complex regional pain syndrome, and entrapment neuropathy (carpel tunnel syndrome). The compounds are also useful in the treatment of pain associated with acute herpes zoster (shingles), pos-therepetic neuralgia (PHN), and associated pain syndromes such as ocular pain. The compounds are further useful as analgesics in the treatment of pain such as surgical analgesia, or as an antipyretic for the treatment of fever. Pain indications include, but are not limited to, post-surgical pain for various surgical procedures including post-cardiac surgery, dental pain/dental extraction, pain resulting from cancer, muscular pain, mastalgia, pain resulting from dermal injuries, lower back pain, headaches of various etiologies, including migraine, and the like. The compounds are also useful for the treatment of pain-related disorders such as tactile allodynia and hyperalgesia. The pain may be somatogenic (either nociceptive or neuropathic), acute and/or chronic. The nitric oxide dimerization inhibitors of the subject invention are also useful in conditions where NSAIDs, morphine or fentanyl opiates and/or other opioid analgesics would traditionally be administered.

Furthermore, the compounds of the subject invention can be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the compounds and methods of the present invention are useful in the treatment or prevention of drug withdrawal symptoms, for example treatment or prevention of symptoms of withdrawal from opiate, alcohol, or tobacco addiction.

In addition, the compounds of the subject invention can be used to treat insulin resistance and other metabolic disorders such as atherosclerosis that are typically associated with an exaggerated inflammatory signaling.

The present invention encompasses therapeutic methods using novel selective iNOS inhibitors to treat or prevent respiratory disease or conditions, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchioectasis cystic fibrosis, pigeon fancier's disease, farmer's lung, acute respiratory distress syndrome, pneumonia, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus and hypoxia.

Other disorders or conditions which can be advantageously treated by the compounds of the present invention include inflammation. The compounds of the present invention are useful as anti-inflammatory agents with the additional benefit of having significantly less harmful side effects. The compounds are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds are also useful in treating osteoporosis and other related bone disorders. These compounds can also be used to treat gastrointestinal conditions such as reflux esophagitis, diarrhea, inflammatory bowel disease, Crohn's disease, gastritis, irritable bowel syndrome and ulcerative colitis. The compounds may also be used in the treatment of pulmonary inflammation, such as that associated with viral infections and cystic fibrosis. In addition, compounds of invention are also useful in organ transplant patients either alone or in combination with conventional immunomodulators. Yet further, the compounds of the invention are useful in the treatment of pruritis and vitaligo.

The compounds of the present invention are also useful in treating tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, swelling occurring after injury, ischemias including myocardial ischemia, cardiovascular ischemia, and ischemia secondary to cardiac arrest, and the like.

The compounds of the subject invention are also be useful for the treatment of certain diseases and disorders of the nervous system. Central nervous system disorders in which nitric oxide inhibition is useful include cortical dementias including Alzheimer's disease, central nervous system damage resulting from stroke, ischemias including cerebral ischemia, thrombotic stroke and global ischemia (for example, secondary to cardiac arrest), and trauma. Neurodegenerative disorders in which nitric oxide inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and AIDS-related dementia, cachexia, Sydenham's chorea, Huntington's disease, Parkinson's Disease, amyotrophic lateral sclerosis (ALS), Korsakoffs disease, imbecility relating to a cerebral vessel disorder, sleeping disorders, schizophrenia, depression, depression or other symptoms associated with Premenstrual Syndrome (PMS), and anxiety.

Furthermore, the compounds of the present invention are also useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy. These compounds can also be used to treat allergic rhinitis, respiratory distress syndrome, endotoxin shock syndrome, and atherosclerosis.

Still other disorders or conditions advantageously treated by the compounds of the subject invention include the prevention or treatment of cancer, such as colorectal cancer, and cancer of the breast, lung, prostate, bladder, cervix and skin. Compounds of the invention may be used in the treatment and prevention of neoplasias including but not limited to brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

The compounds of the subject invention can be used in the treatment of ophthalmic diseases, such as glaucoma, retinal ganglion degeneration, occular ischemia, retinitis, retinopathies, uveitis, ocular photophobia, and of inflammation and pain associated with acute injury to the eye tissue. Specifically, the compounds can be used to treat glaucomatous retinopathy and/or diabetic retinopathy. The compounds can also be used to treat post-operative inflammation or pain as from ophthalmic surgery such as cataract surgery and refractive surgery.

Moreover, compounds of the subject invention may be used in the treatment of menstrual cramps, dysmenorrhea, premature labor, tendonitis, bursitis, skin-related conditions such as psoriasis, eczema, burns, sunburn, dermatitis, pancreatitis, hepatitis, and the like. Other conditions in which the compounds of the subject invention provides an advantage in inhibiting nitric oxide inhibition include diabetes (type I or type II), congestive heart failure, myocarditis, atherosclerosis, and aortic aneurysm.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds of the subject invention may also be used to prevent tissue damage when therapeutically combined with antibacterial or antiviral agents.

Besides being useful for human treatment, these compounds are also useful for veterinary treatment of companion animals, exotic animals and farm animals, including mammals, rodents, and the like. More preferred animals include horses, dogs, and cats.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. Examples of acyl groups include formyl, alkanoyl and aroyl radicals.

The term "acylamino" embraces an amino radical substituted with an acyl group. An example of an "acylamino" radical is acetylamino (CH$_3$C(O)NH—).

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkoxyalkoxy," as used herein, alone or in combination, refers to one or more alkoxy groups attached to the parent molecular moiety through another alkoxy group. Examples include ethoxyethoxy, methoxypropoxyethoxy, ethoxypentoxyethoxyethoxy and the like.

The term "alkoxyalkyl," as used herein, alone or in combination, refers to an alkoxy group attached to the parent molecular moiety through an alkyl group. The term "alkoxyalkyl" also embraces alkoxyalkyl groups having one or more alkoxy groups attached to the alkyl group, that is, to form monoalkoxyalkyl and dialkoxyalkyl groups.

The term "alkoxycarbonyl," as used herein, alone or in combination, refers to an alkoxy group attached to the parent molecular moiety through a carbonyl group. Examples of such "alkoxycarbonyl" groups include methoxycarbonyl, ethoxycarbonyl, propoxycarbonyl, butoxycarbonyl and hexyloxycarbonyl.

The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—).

The term "alkylamino," as used herein, alone or in combination, refers to an amino group attached to the parent molecular moiety through an alkyl group.

The term "alkylaminocarbonyl" as used herein, alone or in combination, refers to an alkylamino group attached to the parent molecular moiety through a carbonyl group. Examples of such radicals include N-methylaminocarbonyl and N,N-dimethylcarbonyl.

The term "alkylcarbonyl" and "alkanoyl," as used herein, alone or in combination, refers to an alkyl group attached to the parent molecular moiety through a carbonyl group. Examples of such groups include methylcarbonyl and ethylcarbonyl.

The term "alkylidene," as used herein, alone or in combination, refers to an alkenyl group in which one carbon atom of the carbon-carbon double bond belongs to the moiety to which the alkenyl group is attached.

The term "alkylsulfinyl," as used herein, alone or in combination, refers to an alkyl group attached to the parent molecular moiety through a sulfinyl group. Examples of alkylsulfinyl groups include methylsulfinyl, ethylsulfinyl, butylsulfinyl and hexylsulfinyl.

The term "alkylsulfonyl," as used herein, alone or in combination, refers to an alkyl group attached to the parent molecular moiety through a sulfonyl group. Examples of alkylsulfinyl groups include methanesulfonyl, ethanesulfonyl, tert-butanesulfonyl, and the like.

The term "alkylthio," as used herein, alone or in combination, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethoxyethylthio and the like.

The term "alkylthioalkyl" embraces alkylthio radicals attached to an alkyl radical. Alkylthioalkyl radicals include "lower alkylthioalkyl" radicals having alkyl radicals of one to six carbon atoms and an alkylthio radical as described above. Examples of such radicals include methylthiomethyl.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl, and the like.

The term "amido," as used herein, alone or in combination, refers to an amino group as described below attached to the parent molecular moiety through a carbonyl group. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein.

The term "amino," as used herein, alone or in combination, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxy-alkyl, nitro, and oxo.

The term "aminoalkyl," as used herein, alone or in combination, refers to an amino group attached to the parent molecular moiety through an alkyl group. Examples include aminomethyl, aminoethyl and aminobutyl. The term "alkylamino" denotes amino groups which have been substituted with one or two alkyl radicals. Suitable "alkylamino" groups may be mono- or dialkylated, forming groups such as, for example, N-methylamino, N-ethylamino, N,N-dimethylamino, N,N-diethylamino and the like.

The terms "aminocarbonyl" and "carbamoyl," as used herein, alone or in combination, refer to an amino-substituted carbonyl group, wherein the amino group can be a primary or secondary amino group containing substituents selected from alkyl, aryl, aralkyl, cycloalkyl, cycloalkylalkyl radicals and the like.

The term "aminocarbonylalkyl," as used herein, alone or in combination, refers to an aminocarbonyl radical attached to an alkyl radical, as described above. An example of such radicals is aminocarbonylmethyl. The term "amidino" denotes an —C(NH)NH$_2$ radical. The term "cyanoamidino" denotes an —C(N—CN)NH$_2$ radical.

The term "aralkenyl" or "arylalkenyl," as used herein, alone or in combination, refers to an aryl group attached to the parent molecular moiety through an alkenyl group.

The term "aralkoxy" or "arylalkoxy," as used herein, alone or in combination, refers to an aryl group attached to the parent molecular moiety through an alkoxy group.

The term "aralkyl" or "arylalkyl," as used herein, alone or in combination, refers to an aryl group attached to the parent molecular moiety through an alkyl group.

The term "aralkylamino" or "arylalkylamino," as used herein, alone or in combination, refers to an arylalkyl group attached to the parent molecular moiety through a nitrogen atom, wherein the nitrogen atom is substituted with hydrogen.

The term "aralkylidene" or "arylalkylidene," as used herein, alone or in combination, refers to an aryl group attached to the parent molecular moiety through an alkylidene group.

The term "aralkylthio" or "arylalkylthio," as used herein, alone or in combination, refers to an arylalkyl group attached to the parent molecular moiety through a sulfur atom.

The term "aralkynyl" or "arylalkynyl," as used herein, alone or in combination, refers to an aryl group attached to the parent molecular moiety through an alkynyl group.

The term "aralkoxycarbonyl," as used herein, alone or in combination, refers to a radical of the formula aralkyl-O—C (O) in which the term "aralkyl," has the significance given above. Examples of an aralkoxycarbonyl radical are benzyloxycarbonyl (Z or Cbz) and 4-methoxyphenylmethoxycarbonyl (MOS).

The term "aralkanoyl," as used herein, alone or in combination, refers to an acyl radical derived from an aryl-substituted alkanecarboxylic acid such as benzoyl, phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" refers to an acyl radical derived from an arylcarboxylic acid, "aryl" having the meaning given below. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylamino" as used herein, alone or in combination, refers to an aryl group attached to the parent moiety through an amino group, such as methylamino, N-phenylamino, and the like.

The terms "arylcarbonyl" and "aroyl," as used herein, alone or in combination, refer to an aryl group attached to the parent molecular moiety through a carbonyl group.

The term "aryloxy," as used herein, alone or in combination, refers to an aryl group attached to the parent molecular moiety through an oxygen atom.

The term "arylsulfonyl," as used herein, alone or in combination, refers to an aryl group attached to the parent molecular moiety through a sulfonyl group.

The term "arylthio," as used herein, alone or in combination, refers to an aryl group attached to the parent molecular moiety through a sulfur atom.

The terms "carboxy" or "carboxyl", whether used alone or with other terms, such as "carboxyalkyl", denotes —$CO_2H$.

The terms "benzo" and "benz," as used herein, alone or in combination, refer to the divalent radical $C_6H_4$= derived from benzene. Examples include benzothiophene and benzimidazole.

The term "O-carbamyl" as used herein, alone or in combination, refers to a —OC(O)NR, group—with R as defined herein.

The term "N-carbamyl" as used herein, alone or in combination, refers to a ROC(O)NH— group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multi-centered) saturated or partially unsaturated type. The latter type of isomer is exemplified in general by bicyclo[2,2,2] octane, bicyclo[2,2,2]octane, bicyclo[1,1,1]pentane, camphor and bicyclo[3,2,1]octane term "cycloalkyl" embraces radicals having three to ten carbon atoms, such as cyclopropyl cyclobutyl, cyclopentyl, cyclohexyl and cycloheptyl.

The term "ester," as used herein, alone or in combination, refers to a carbonyl group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CFH—), difluoromethylene (—$CF_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl," as used herein, alone or in combination, refers to 3 to 7 membered, preferably 5 to 7 membered, unsaturated heterocyclic rings wherein at least one atom is selected from the group consisting of O, S, and N. Heteroaryl groups are exemplified by: unsaturated 3 to 7 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.]tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic groups containing an oxygen atom, for example, pyranyl, furyl, etc.; unsaturated 3 to 6-membered heteromonocyclic groups containing a sulfur atom, for example, thienyl, etc.; unsaturated 3- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic groups containing 1 to 2 oxygen atoms and 1 to 3 nitrogen atoms [e.g. benzoxazolyl, benzoxadiazolyl, etc.]; unsaturated 3 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] and isothiazolyl; unsaturated condensed heterocyclic groups containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like.

The term "heteroaralkenyl" or "heteroarylalkenyl," as used herein, alone or in combination, refers to a heteroaryl group attached to the parent molecular moiety through an alkenyl group.

The term "heteroaralkoxy" or "heteroarylalkoxy," as used herein, alone or in combination, refers to a heteroaryl group attached to the parent molecular moiety through an alkoxy group.

The term "heteroalkyl" or "heteroarylalkyl," as used herein, alone or in combination, refers to a heteroaryl group attached to the parent molecular moiety through an alkyl group.

The term "heteroaralkylidene" or "heteroarylalkylidene," as used herein, alone or in combination, refers to a heteroaryl group attached to the parent molecular moiety through an alkylidene group.

The term "heteroaryloxy," as used herein, alone or in combination, refers to a heteroaryl group attached to the parent molecular moiety through an oxygen atom.

The term "heteroarylsulfonyl," as used herein, alone or in combination, refers to a heteroaryl group attached to the parent molecular moiety through a sulfonyl group.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkenyl," as used herein, alone or in combination, refers to a heterocycle group attached to the parent molecular moiety through an alkenyl group.

The term "heterocycloalkoxy," as used herein, alone or in combination, refers to a heterocycle group attached to the parent molecular group through an oxygen atom.

The term "heterocycloalkyl," as used herein, alone or in combination, refers to an alkyl radical as defined above in which at least one hydrogen atom is replaced by a heterocyclo radical as defined above, such as pyrrolidinylmethyl, tetrahydrothienylmethyl, pyridylmethyl and the like.

The term "heterocycloalkylidene," as used herein, alone or in combination, refers to a heterocycle group attached to the parent molecular moiety through an alkylidene group.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl" as used herein, alone or in combination, refers to a linear or branched alkyl group having one to about ten carbon atoms any one of which may be substituted with one or more hydroxyl radicals. Examples of such radicals include hydroxylmethyl, hydroxyethyl, hydroxypropyl, hydroxybutyl and hydroxyhexyl.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptoalkyl" as used herein, alone or in combination, refers to an R'SR— group, where R and R' are as defined herein.

The term "mercaptomercaptyl" as used herein, alone or in combination, refers to a RSR'S— group, where R is as defined herein.

The term "mercaptyl" as used herein, alone or in combination, refers to an RS— group, where R is as defined herein.

The term "null" refers to a lone electron pair.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "oxo" as used herein, alone or in combination, refers to a doubly bonded oxygen.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S and —S—.

The term "sulfinyl," as used herein, alone or in combination, refers to —S(O)—.

The term "sulfonyl," as used herein, alone or in combination, refers to —SO$_2$—.

The term "N-sulfonamido" refers to a RS(=O)$_2$NH— group with R as defined herein.

The term "S-sulfonamido" refers to a —S(=O)$_2$NR$_2$, group, with R as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thioether," as used herein, alone or in combination, refers to a thio group bridging two moieties linked at carbon atoms.

The term "thiol," as used herein, alone or in combination, refers to an —SH group.

The term "thiocarbonyl," as used herein, when alone includes thioformyl —C(S)H and in combination is a —C(S) group.

The term "N-thiocarbamyl" refers to an ROC(S)NH— group, with R as defined herein.

The term "O-thiocarbamyl" refers to a —OC(S)NR, group with R as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, or mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "optionally substituted" means the anteceding group may be substituted or unsubstituted. When substituted, the substituents of an "optionally substituted" group may include, without limitation, one or more substituents independently selected from the following groups or designated subsets thereof, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, N$_3$, NHCH$_3$, N(CH$_3$)$_2$, SH, SCH$_3$, C(O)CH$_3$, CO$_2$CH$_3$, CO$_2$H, C(O)NH$_2$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH2CH$_3$), fully substituted (e.g., —CF$_2$CF$_3$), monosubstituted (e.g., —CH$_2$CH$_2$F) substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended.

The term R or the term R', appearing by itself and without a number designation, unless otherwise defined, refers to an optionally substituted moiety selected from the group consisting of alkyl, cycloalkyl, heteroalkyl, aryl, heteroaryl and heterocycloalkyl. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence.

The term "bond" refers to a covalent linkage between two atoms, or two moieties when the atoms joined by the bond are considered to be part of larger substructure. A bond may be single, double, or triple unless otherwise specified.

The term "prodrug" refers to a compound that is made more active in vivo. The present compounds can also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the combined amount of active ingredients in the combination therapy. This combined amount will achieve the goal of reducing or eliminating the hyperlipidemic condition.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "therapeutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methanesulfonate, naphthalenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The compounds of the present invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question.

Several compounds of the invention, enumerated in the Examples below, were prepared as various salts, and the present invention provides for these salts. There exist a variety of techniques well-known in the art for preparing salts, and the present invention contemplates these methods without limitation. Two protocols, described below, were employed in an initial screen of approximately 24 acids for their suitability in preparation of salts.

Under one protocol, experiments were carried out in a 96-well, polypropylene-bottomed microplate. 50 μL aliquots of an approximately 40 mg/mL stock solution of N'-benzo[1,3]dioxol-5-ylmethyl-N-(3-imidazol-1-yl-[1,2,4]thiadiazol-5-yl)-N-methyl-propane-1,3-diamine in methanol were added to the wells of the microplate, which was centrivapped for about 2 minutes to remove the excess methanol leaving approximately 2 mg of compound free base. 15 μL of methanol was added to each well, followed by 55.9 μL of a 0.1M solution of a given carboxylic acid in methanol, and the plate was allowed to evaporate overnight. 50 μL portions of either methanol, 95:5/ethanol:H$_2$0, isopropranol, and methylene chloride were then added. The microplate was sealed and maintained at approximately 55° C. for approximately 3 hours and cooled to ambient temperature. The solvent was subsequently allowed to evaporate in a fume hood. The samples were then recovered and examined using standard techniques known in the art. It is expected that a screen performed with N'-(3-imidazol-1-yl-[1,2,4]thiadiazol-5-yl)-N'-thiazol-2-ylmethyl-propane-1,3-diamine would yield similar results.

Under another protocol, microscale experiments were carried out individually, and generally involved preparation of a solution containing equimolar amounts of benzo[1,3]dioxol-5-ylmethyl-{2-[2-(2-imidazol-1-yl-6-methyl-pyrimidin-4-yl)-pyrrolidin-1-yl]-ethyl}-amine (from a 125 mg/mL stock solution in methanol, or an oily residue thereof) and acid in a suitable solvent (methanol, acetonitrile, tetrahydrofuran, ethyl acetate, methyl tert-butyl ether (MTBE), toluene, and mixtures thereof), followed by addition of a suitable second solvent or antisolvent to facilitate precipitation, and/or evaporation (slow, fast, or flash), optionally accompanied by sonication. In the slow and fast evaporation modes, the sample vial was covered with aluminum foil pierced with one small or large (respectively) hole and allowed to evaporate slowly at ambient temperature; in the flash evaporation mode, the vial was covered with aluminum foil pierced with one large hole and allowed to evaporate quickly at ambient temperature, then rotovapped. Solids were recovered after various lengths of time, from immediately to three days after precipitation and/or evaporation, and characterized by techniques known in the art. It is expected that a screen performed with N'-(3-imidazol-1-yl-[1,2,4]thiadiazol-5-yl)-N'-thiazol-2-ylmethyl-propane-1,3-diamine would yield similar results.

A number of acids common to both screens resulted in samples of particular interest as salts suitable to the compounds of the present invention. Thus, preferred salts include hydrochloride, hydrobromide, acetate, adipate, p-toluenesulfonate, glycolate, oxalate, fumarate, and phosphonate salts of a compound of the present invention. Particularly preferred salts include hydrochloride, hydrobromide, acetate, and adipate salts of a compound of the present invention. The present invention provides for N'-(3-imidazol-1-yl-[1,2,4]thiadiazol-5-yl)-N'-thiazol-2-ylmethyl-propane-1,3-diamine hydrochloride, N'-(3-imidazol-1-yl-[1,2,4]thiadiazol-5-yl)-N'-thiazol-2-ylmethyl-propane-1,3-diamine hydrobromide, N'-(3-imidazol-1-yl-[1,2,4]thiadiazol-5-yl)-N'-thiazol-2-ylmethyl-propane-1,3-diamine acetate, N'-(3-imidazol-1-yl-[1,2,4]thiadiazol-5-yl)-N'-thiazol-2-ylmethyl-propane-1,3-diamine adipate, N'-benzo[1,3]dioxol-5-ylmethyl-N-(3-imidazol-1-yl-[1,2,4]thiadiazol-5-yl)-N-methyl-propane-1,3-diamine hydrochloride, N'-(3-imidazol-1-yl-[1,2,4]thiadiazol-5-yl)-N'-thiazol-2-ylmethyl-propane-1,3-diamine p-toluenesulfonate, N'-(3-imidazol-1-yl-[1,2,4]thiadiazol-5-yl)-N'-thiazol-2-ylmethyl-propane-1,3-diamine glycolate, benzo[1,3]dioxol-5-ylmethyl-{2-[2-(2-imidazol-1-yl-6-methyl-pyrimidin-4-yl)-pyrrolidin-1-yl]-ethyl}-amine hydrochloride, N'-(3-imidazol-1-yl-[1,2,4]thiadiazol-5-yl)-N'-thiazol-2-ylmethyl-propane-1,3-diamine oxalate, N'-(3-imidazol-1-yl-[1,2,4]thiadiazol-5-yl)-N'-thiazol-2-ylmethyl-propane-1,3-diamine fumarate, and N'-(3-imidazol-1-yl-[1,2,4]thiadiazol-5-yl)-N'-thiazol-2-ylmethyl-propane-1,3-diamine phosphonate salts.

All references, patents or applications, U.S. or foreign, cited in the application are hereby incorporated by reference as if written herein.

The following schemes can be used to practice the present invention.

General Synthetic Methods For Preparing Compounds

Examples 2, 6-12, 15-22, 30-36, 46-63, 79-88, 101-106, 127-128 and 145 can be synthesized using the following general synthetic procedure set forth in Scheme I.

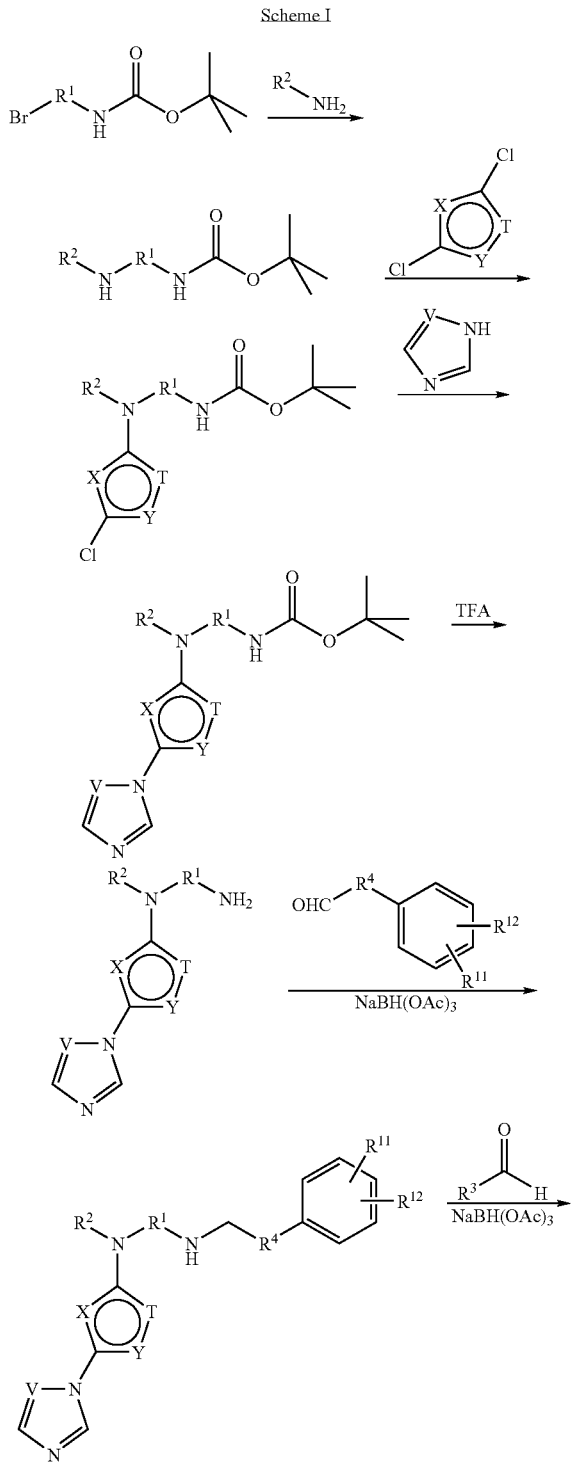

Scheme I

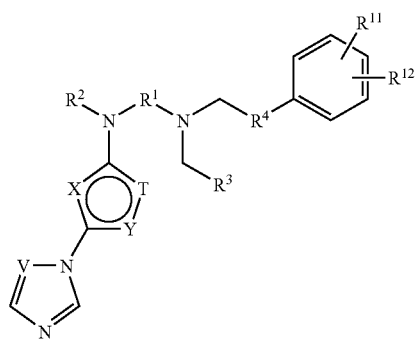
Examples 1, 38, 43-45, 64-65, 68, 97-100, 121 and 130-131 can be synthesized using the following general synthetic procedure set forth in Scheme II.
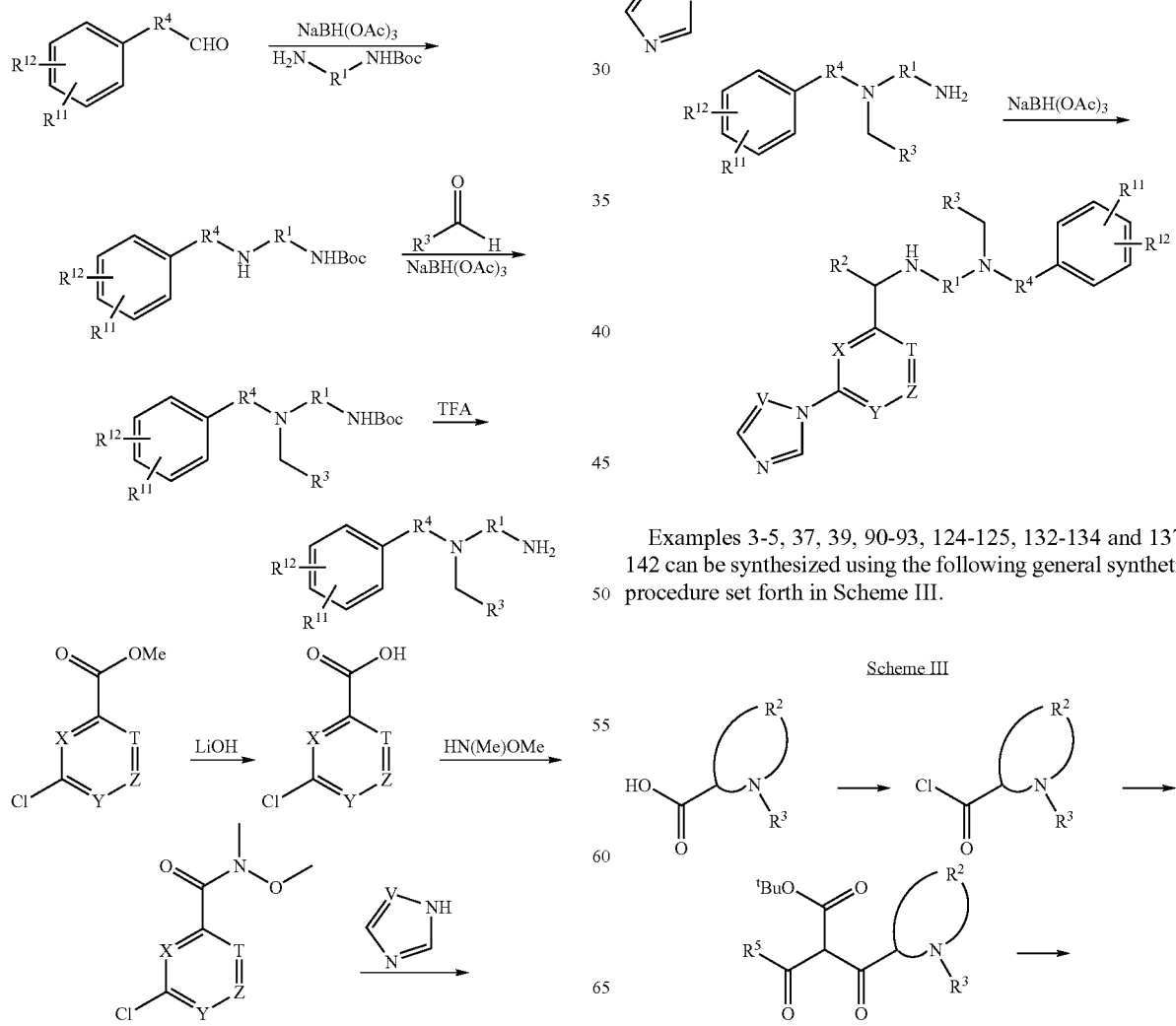
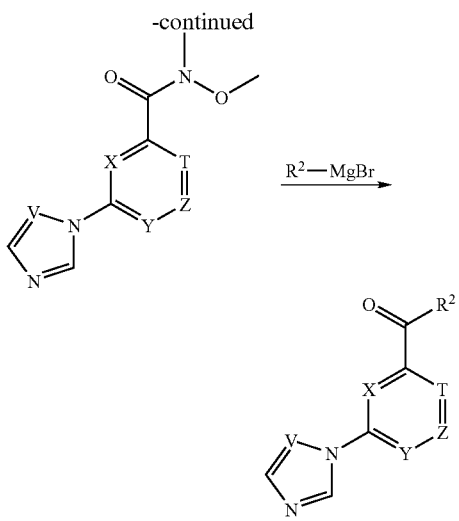
Examples 3-5, 37, 39, 90-93, 124-125, 132-134 and 137-142 can be synthesized using the following general synthetic procedure set forth in Scheme III.
Scheme III
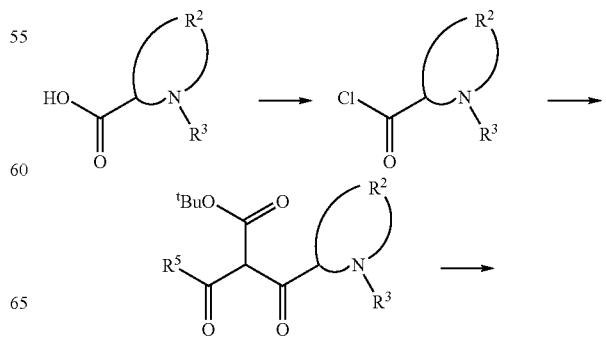

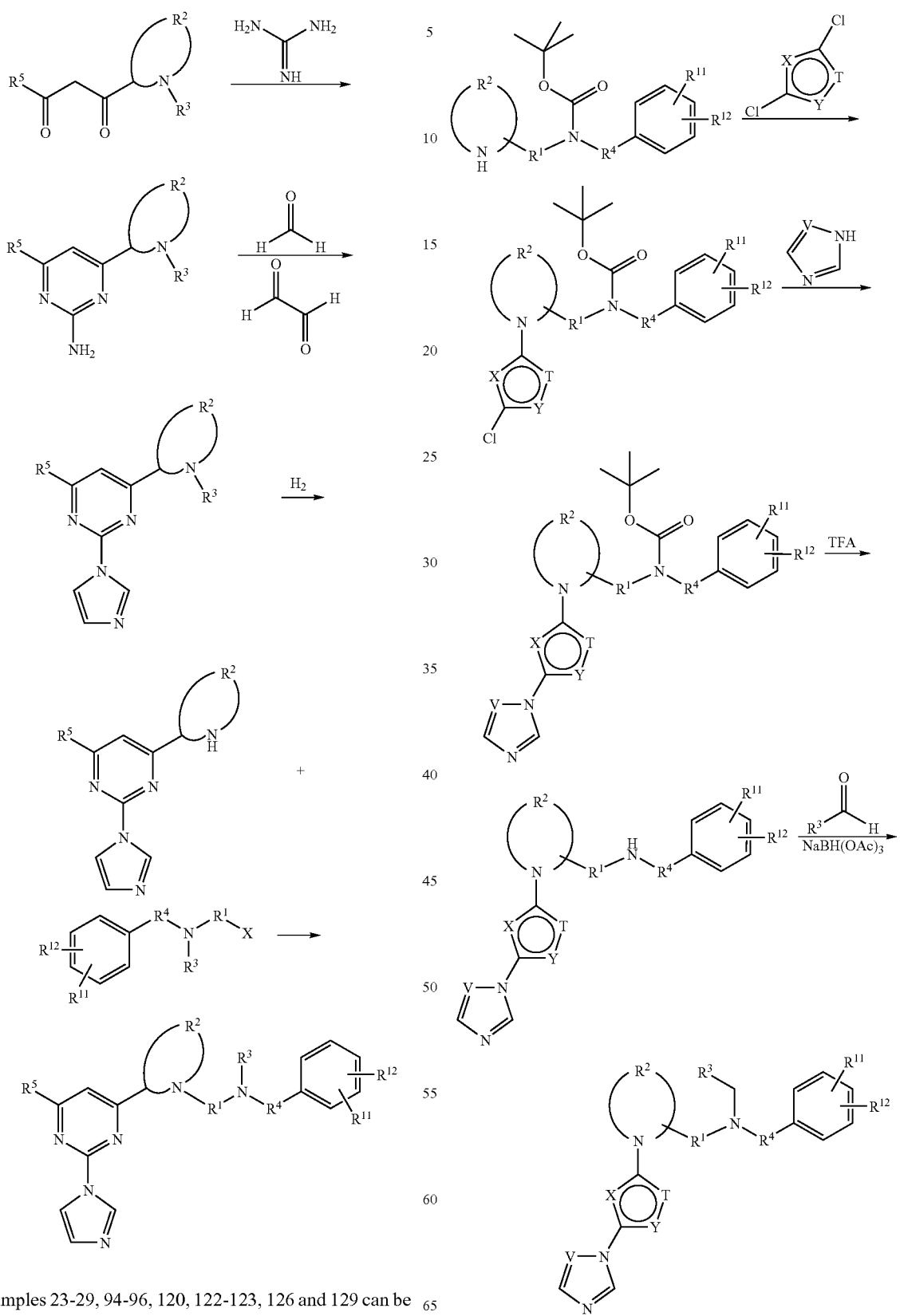
Examples 23-29, 94-96, 120, 122-123, 126 and 129 can be synthesized using the following general synthetic procedure set forth in Scheme IV.

Examples 135 and 136 can be synthesized using the following general synthetic procedure set forth in Scheme V.
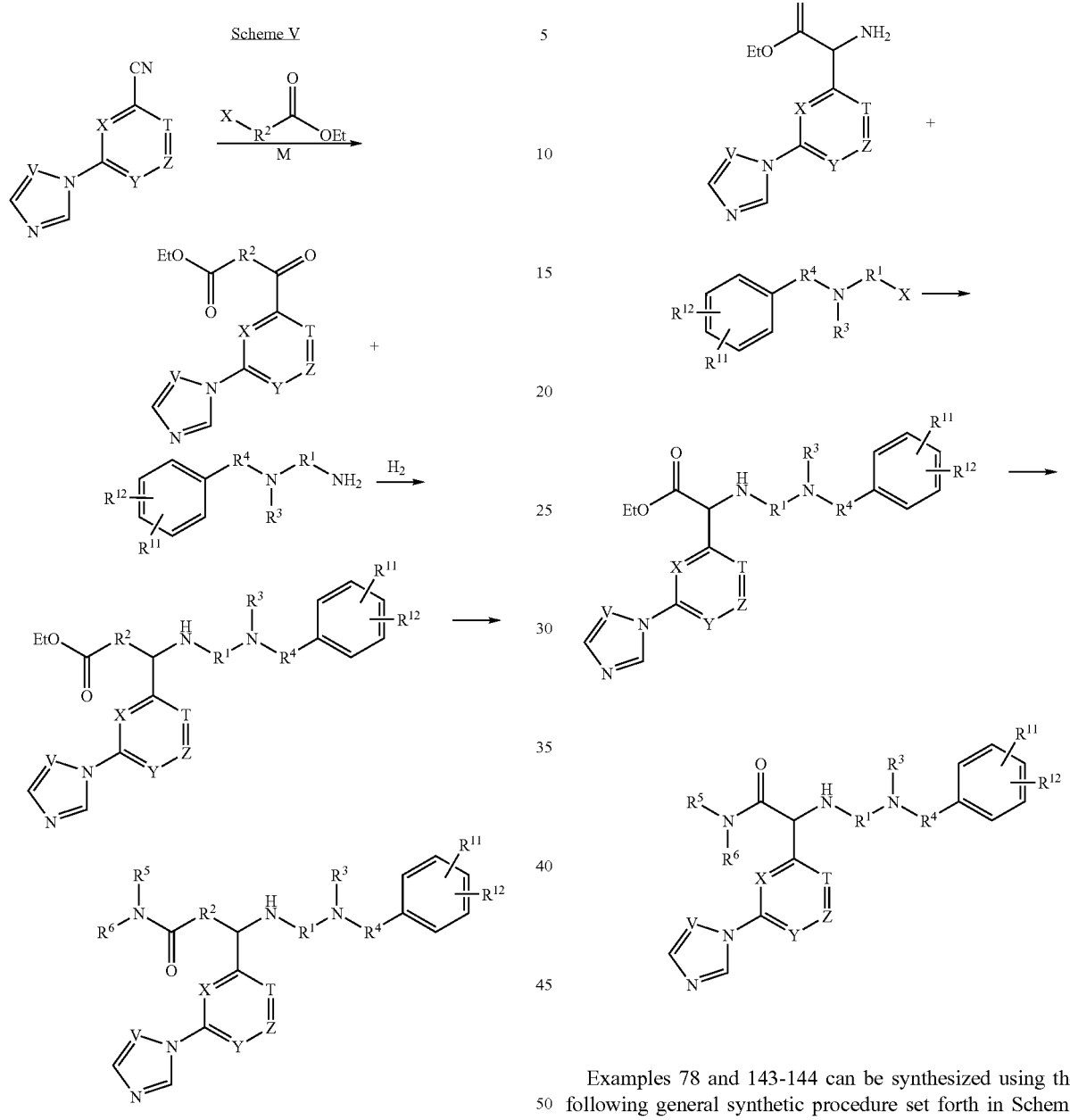
Examples 41 and 42 can be synthesized using the following general synthetic procedure set forth in Scheme VI.
Examples 78 and 143-144 can be synthesized using the following general synthetic procedure set forth in Scheme VII.
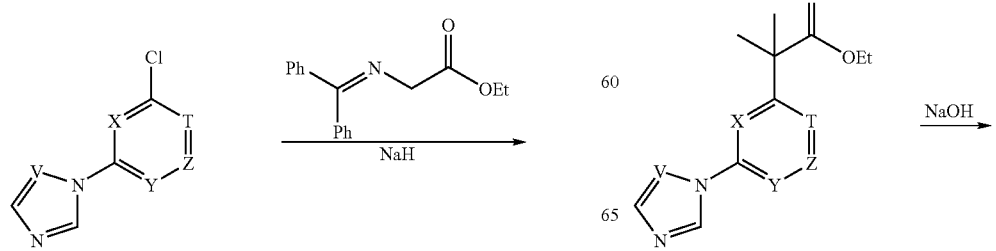

-continued
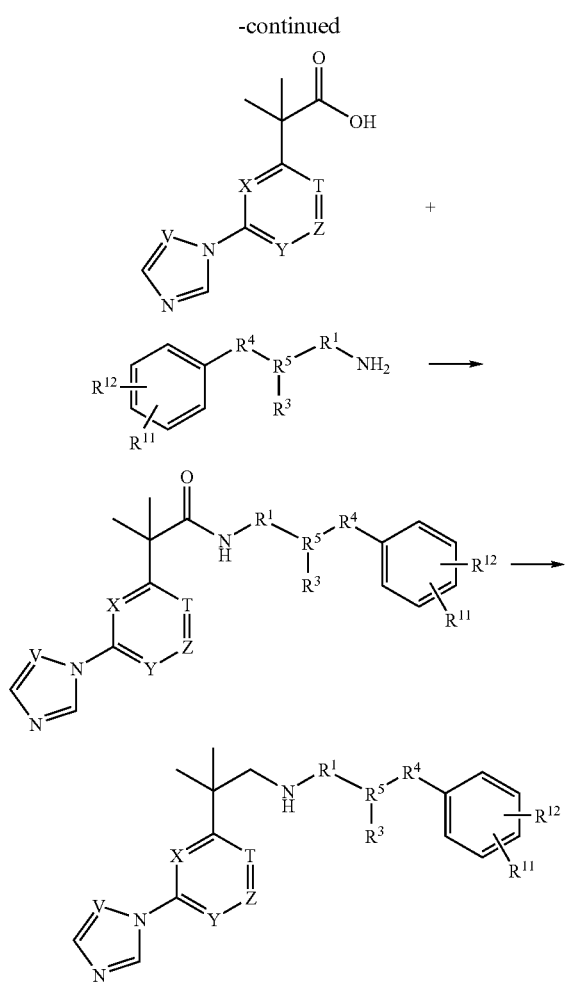
Examples 74 and 75 can be synthesized using the following general synthetic procedure set forth in Scheme VIII.
Scheme VIII
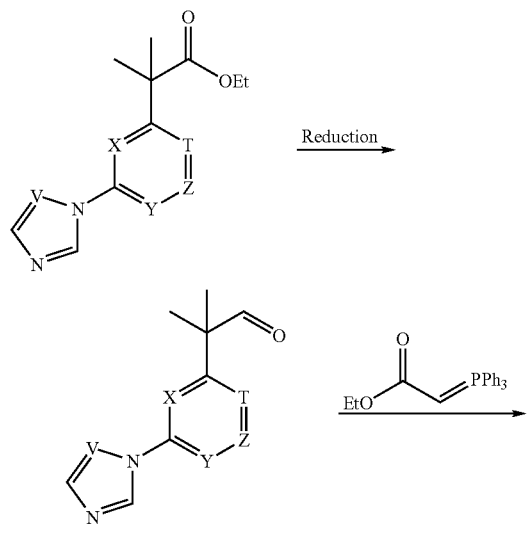
-continued
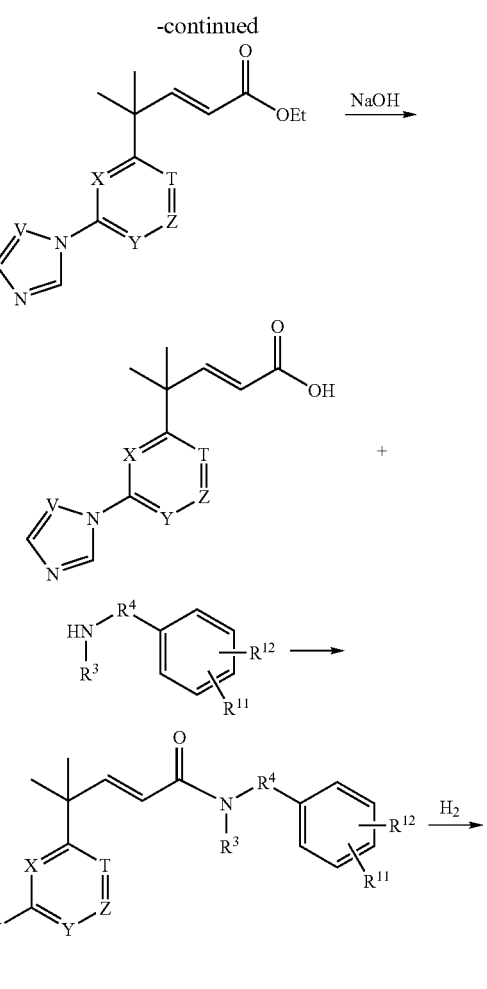
Example 76 can be synthesized using the following general synthetic procedure set forth in Scheme IX.
Scheme IX
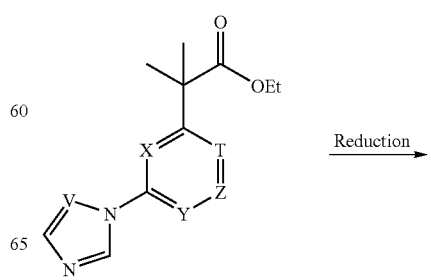

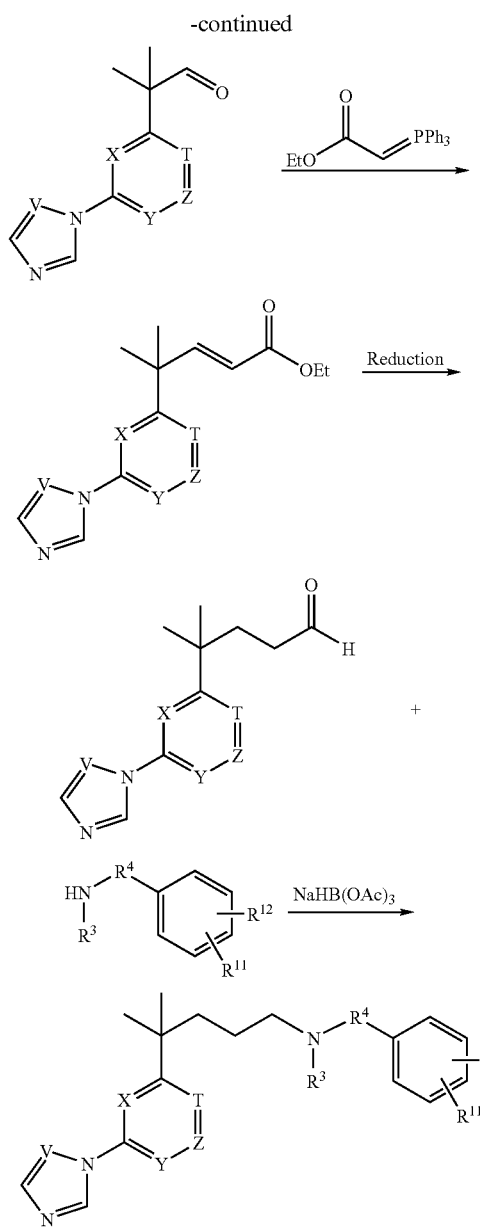
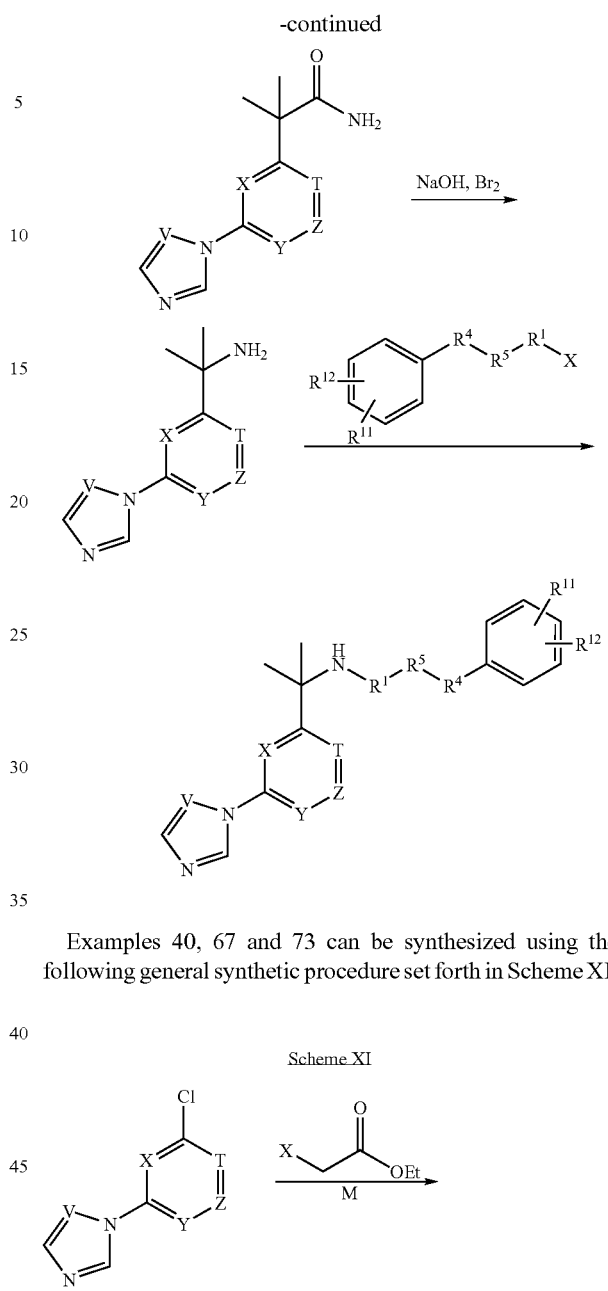
Examples 40, 67 and 73 can be synthesized using the following general synthetic procedure set forth in Scheme XI.
Example 77 can be synthesized using the following general synthetic procedure set forth in Scheme X.
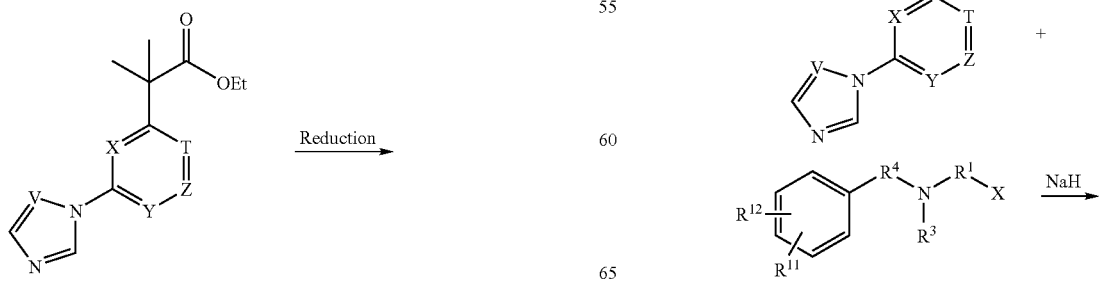

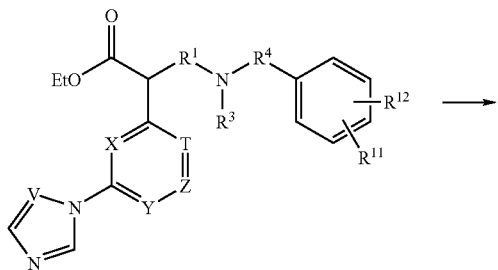
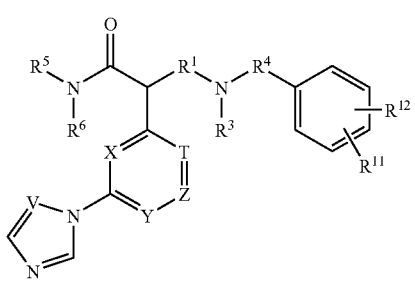
Examples 13-14 and 69-71 can be synthesized using the following general synthetic procedure set forth in Scheme XII.
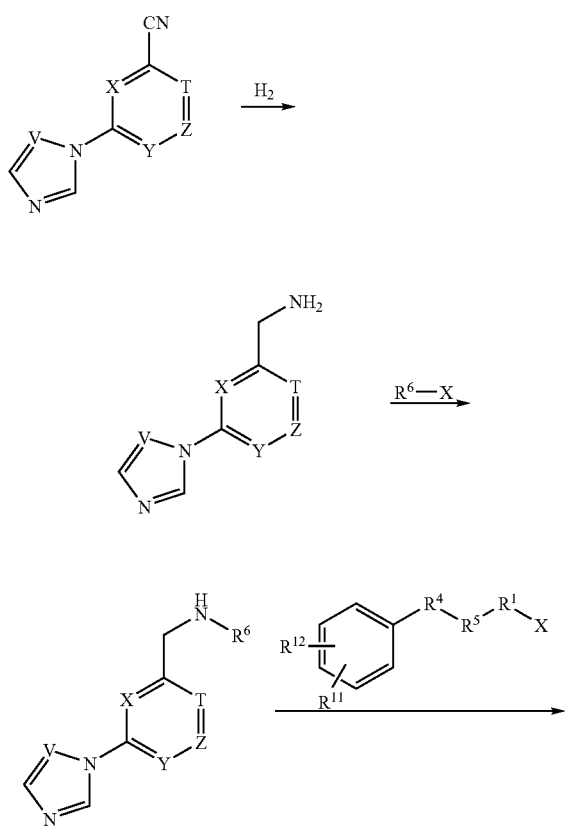
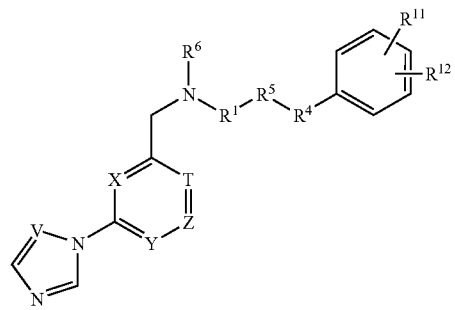
Examples 107-119 can be synthesized using the following general synthetic procedure set forth in Scheme XIII.
Scheme XIII
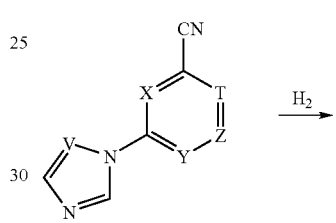
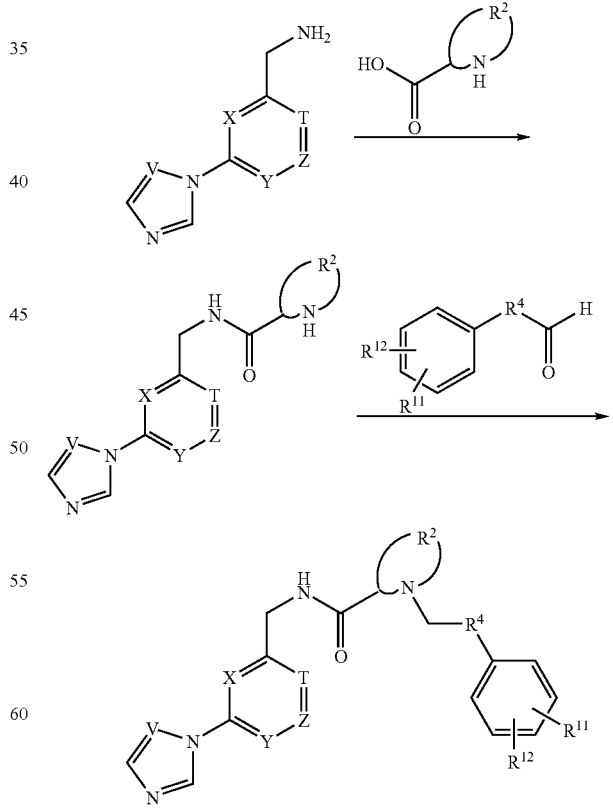
Examples 89 can be synthesized using the following general synthetic procedure set forth in Scheme XIV.

Scheme XIV

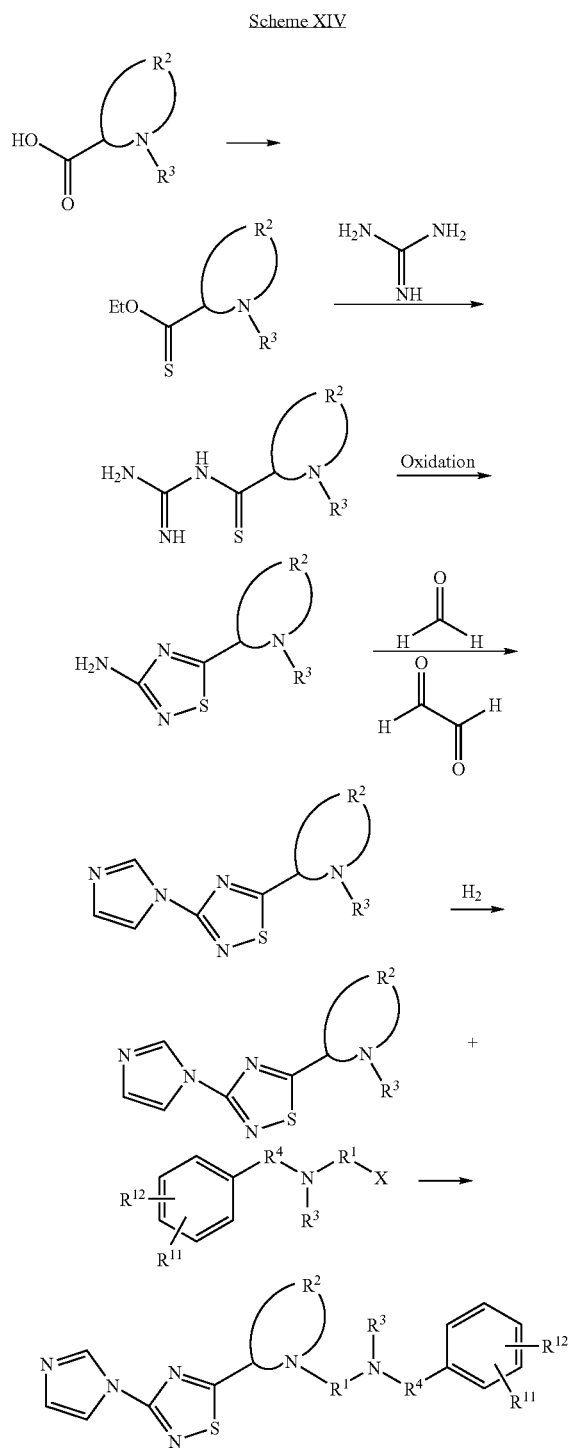

R groups in Schemes I through XIV above are for convenience only, and are intended to represent variability at different positions in the context of a general synthetic scheme, and are not intended to correspond to those defined in Formulas I through V. Likewise, the moiety represented in the Schemes above by a benzyl group substituted with $R^{11}$ and $R^{12}$ should be understood to represent any generic moiety, cyclic or not, heteroatom-containing or not, that one of skill in the art might contemplate as appropriate in such a position. It is consistent for the sake of convenience only in the Schemes above. For a comprehensive description of structural formulas and allowed groups at various positions provided for by the present invention, see the summary of the invention and detailed description of the invention, above. The invention is further illustrated by the following examples.

Example 1

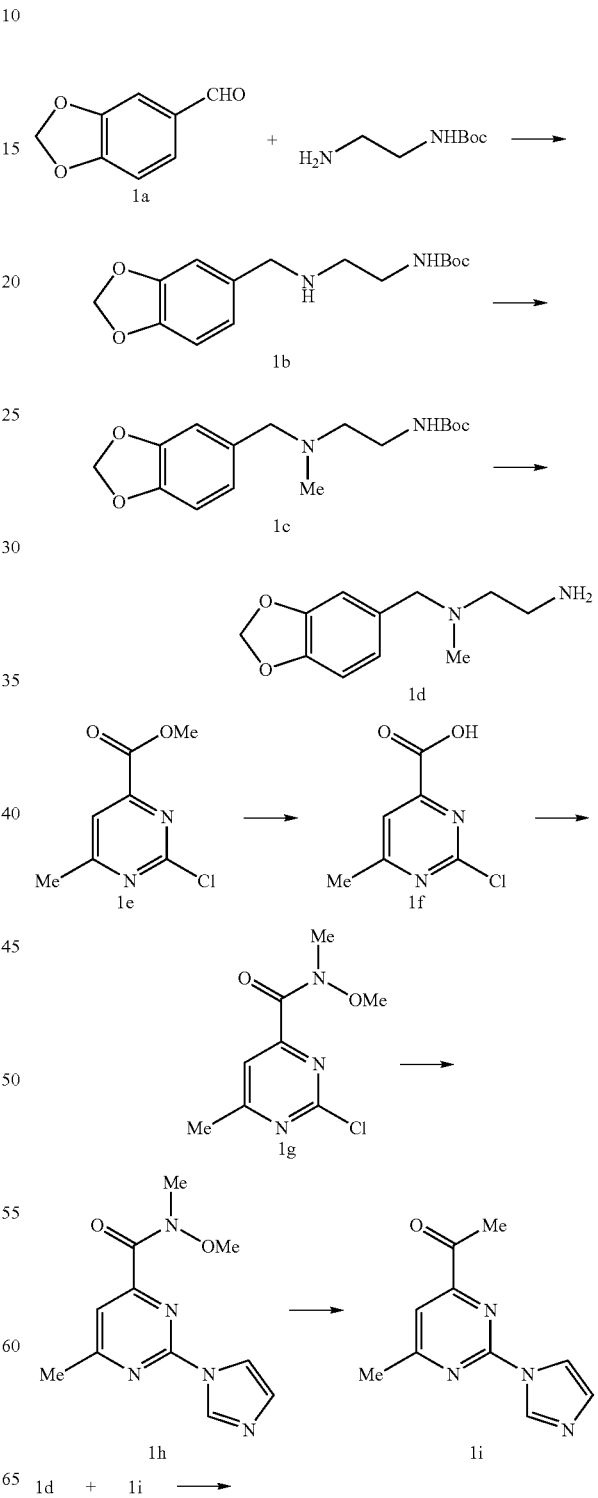

-continued

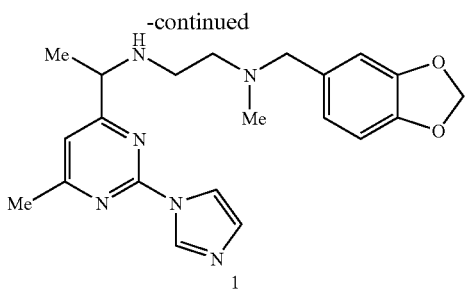

1

Step 1

Preparation of compound 1b: {2-[(Benzo[1,3]dioxol-5-ylmethyl)-amino]-ethyl}-carbamic acid tert-butyl ester A solution of piperonal (5.00 g, 33.3 mmol) and tert-butyl N-(2-aminoethylcarbamate (5.00 g, 31.2 mmol) in dry dioxane (70 mL) and AcOH (10 mL) was heated at 80° C. for 2 h. The solvent was evaporated prior to sequential addition of anhydrous THF (50 mL), MeOH (20 mL) and sodium triacetoxyborohydride (15.8 g, 74.5 mmol). The mixture was stirred for an additional 30 min then the solvent was removed under vacuum. NaOH solution (20% aqueous, w/w) was added to make the solution basic (pH 9), and the solution was extracted with EtOAc (150 mL). When the extracts were washed with brine, a precipitate formed in the funnel. It was filtered and dried to give 7.50 g (82%) of {2-[(benzo[1,3]dioxol-5-ylmethyl)-amino]-ethyl}-carbamic acid tert-butyl ester as a white solid.

Step 2

Preparation of compound 1c: [2-(Benzo[1,3]dioxol-5-ylmethyl-methyl-amino)-ethyl]-carbamic acid tert-butyl ester To a mixture of 1b (10.0 g, 34.0 mmol) in MeOH (80 mL), was added 37 wt % formaldehyde in H$_2$O (9 mL), glacial AcOH (14 mL) and NaBH$_3$CN (5.00 g, 79.6 mmol). The solution was stirred at r.t. for 20 min and the solvent was evaporated. NaOH solution (20% aqueous, w/w) was added to make the solution basic (pH 9). The solution was extracted with ethyl acetate (2×150 mL), dried over Na$_2$SO$_4$. Evaporation of the solvent gave 8.00 g (76%) of [2-(benzo[1,3]dioxol-5-ylmethyl-methyl-amino)-ethyl]-carbamic acid tert-butyl ester as a colorless oil. [M+H]$^+$ 309.07.

Step 3

Preparation of compound 1d: N-1-Benzo[1,3]dioxol-5-ylmethyl-N-1-methyl-ethane-1,2-diamine A solution of 1c (8.00 g, 25.9 mmol) in TFA/DCM (50%, 40 mL) was stirred at r.t. for 20 min. The solvent was evaporated and a NaOH solution (1M, 30 mL) was added to make the mixture basic (pH 9). The solution was extracted with ethyl acetate (2×100 mL), dried over Na$_2$SO$_4$, filtered and concentrated under reduced pressure to afford 5.05 g (94%) of N-1-benzo[1,3]dioxol-5-ylmethyl-N-1-methyl-ethane-1,2-diamine as a clear oil. [M+H]$^+$ 209.09.

Step 4

Preparation of compound 1f: 2-Chloro-6-methyl-pyrimidine-4-carboxylic acid

To a solution of NaOH (960 mg, 24 mmol) in water (70 mL) and THF (5 mL) at r.t. was added ester 1e (3.7 g, 20 mmol). The solution was stirred for 2 h and conc. hydrochloride acid (2.5 mL) was added. The solution was then extracted with ethyl acetate (2×150 mL), dried over Na$_2$SO$_4$, filtered and concentrated to give 3.4 g (99%) of 2-chloro-6-methyl-pyrimidine-4-carboxylic acid as a white solid.

Step 5

Preparation of compound 1g: 2-Chloro-6-methylpyrimidine-4-carboxylic acid-O,N-dimethylamide Triethylamine (42 mL, 0.30 mol) was added dropwise (15 minutes) to a stirred solution of 2-chloro-6-methylpyrimidine-4-carboxylic acid (33 g, 0.19 mol), 3-hydroxybenzotriazole hydrate (28 g, 0.21 mol), 1-(3-dimethylaminopropyl)-3-ethylcarbodiimide hydrochloride (40 g, 0.21 mol), O,N-dimethylamine hydrochloride (20 g, 0.21 mol) and N,N-dimethylformamide (400 mL) under nitrogen with sufficient cooling (ice-water bath) to keep the internal temperature below 26° C. After the addition was complete, the mixture was stirred at room temperature for 20 minutes. It was then partitioned between ethyl acetate (400 mL) and water (500 mL). The aqueous phase was extracted with ethyl acetate (3×400 mL). The combined organic extracts were washed with water (3×400 mL), dried over magnesium sulfate and concentrated under vacuum. The residue was purified by silica gel chromatography (hexanes to 1:2 hexanes/EtOAc) to give 23 g (56%) of 2-chloro-6-methylpyrimidine-4-carboxylic acid-O,N-dimethylamide as a yellow oil. [M+H]$^+$ 216.03, 217.98.

Step 6

Preparation of compound 1h: 2-Imidazol-1-yl-6-methyl-pyrimidine-4-carboxylic acid methoxy-methyl-amide 2-Chloro-6-methylpyrimidine-4-carboxylic acid-O,N-dimethylamide (1.70 g, 7.88 mmol) was added all at once to a solution of imidazole (1.70 g, 18.9 mmol) and DMSO (15 mL) at rt under an atmosphere of nitrogen. The reaction mixture was stirred for 1 h prior to addition of water (40 mL). The solution was extracted with ethyl acetate (3×150 mL), washed with brine and dried over Na$_2$SO$_4$. Evaporation of the solvent gave 1.40 g (72%) of 2-imidazol-1-yl-6-methyl-pyrimidine-4-carboxylic acid methoxy-methyl-amide as a white solid. [M+H]$^+$ 248.04; $^1$H-NMR (400 MHz, CD$_3$OD) δ 8.65 (s, 1H), 7.92 (s, 1H), 7.26 (s, 1H), 7.18 (s, 1H), 3.80 (s, 3H), 3.40 (s, 3H), 2.63 (s, 3H).

Step 7

Preparation of compound 1i: 1-(2-Imidazol-1-yl-6-methyl-pyrimidin-4-yl)-ethanone To a solution of 2-imidazol-1-yl-6-methyl-pyrimidine-4-carboxylic acid methoxy-methyl-amide (162 mg, 0.800 mmol) in THF (10 mL) at 0° C. was added MeMgBr (0.8 mL, 3M in Et$_2$O, 2.40 mmol). The solution was warmed to rt and stirred for 20 min. Water was added and the mixture was extracted with ethyl acetate, washed with brine and dried over Na$_2$SO$_4$. Evaporation of the solvent gave 143 mg (88%) of 1-(2-imidazol-1-yl-6-methyl-pyrimidin-4-yl)-ethanone as a yellow solid. [M+H]$^+$ 203.17.

Step 8

Preparation of compound 1: N-Benzo[1,3]dioxol-5-ylmethyl-N'-[1-(2-imidazol-1-yl-6-methyl-pyrimidin-4-yl)-ethyl]-N-methyl-propane-1,3-diamine A solution of 1d (1.85 g, 8.90 mmol) and 1i (1.09 g, 5.40 mmol) in dry dioxane (20 mL) with a catalytic amount of TsOH (110 mg) was heated at 65-70° C. under nitrogen for 4 h. The reaction was then cooled to r.t. and dry THF (25 mL) and NaBH$_3$CN (2.50 g, 25.7 mmol) were added. The reaction mixture was stirred for an additional 1 h prior to addition of water. The solution was extracted with ethyl acetate (2×200 mL), washed with brine and dried over Na$_2$SO$_4$. Evaporation of the solvent and purification by column chromatography (EtOAc to 1:3 EtOAc: MeOH) gave 580 mg (27%) of N-benzo[1,3]dioxol-5-ylmethyl-N'-[1-(2-imidazol-1-yl-6-methyl-pyrimidin-4-yl)-ethyl]-N-methyl-propane-1,3-diamine as a clear oil. [M+H]$^+$ 395.06; $^1$H-NMR (400 MHz, CD$_3$OD) δ 8.72 (s, 1H), 8.04 (s, 1H), 7.29 (s, 1H), 7.12 (s, 1H), 6.78 (s, 1H), 6.77 (m, 2H). 5.94 (s, 2H), 3.93 (q, 1H), 3.57 (m, 2H), 3.38 (m, 2H), 2.73 (m, 2H), 2.60 (s, 3H), 2.27 (s, 3H), 1.47 (d, 3H); $^{13}$C-NMR (100 MHz, CD$_3$OD) δ 173.5, 170.8, 154.2, 147.9, 147.3, 136.0, 130.5, 129.0 122.7, 116.9, 116.3, 109.3, 107.6, 101.1, 61.5, 57.6, 55.0, 43.6, 40.9, 23.0, 20.3.

Example 2

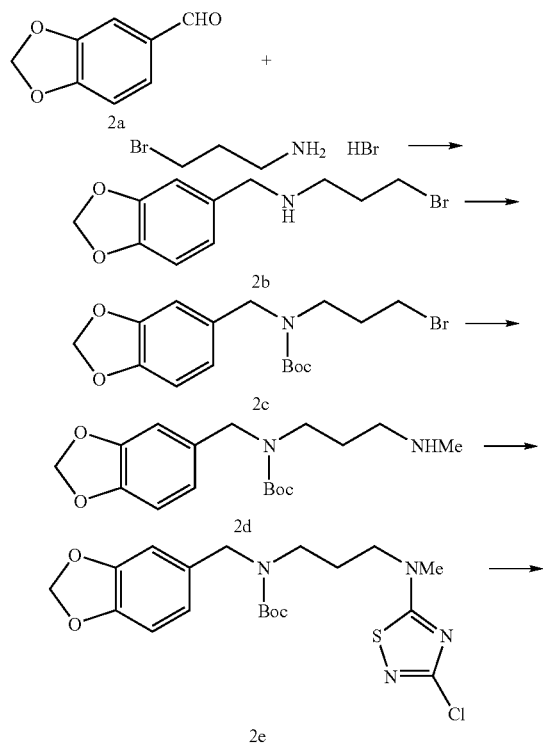

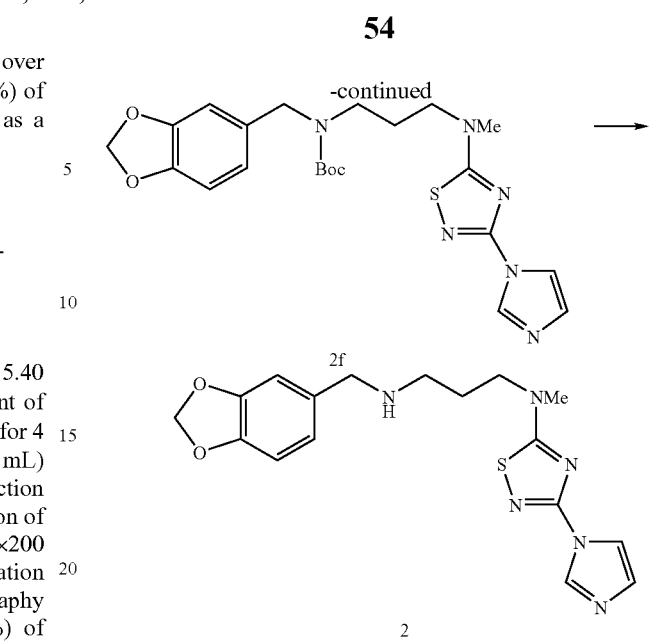

Step 1

Preparation of compound 2b: Benzo[1,3]dioxol-5-ylmethyl-(3-bromo-propyl)-amine

3-Bromopropyl-1-amine hydrobromide (65.6 g, 300 mmol) was slurried with CHCl$_3$ (1.50 L) under an atmosphere of nitrogen. Triethylamine (44.0 mL, 315 mmol) was added all at once to the well stirred suspension. The mixture was stirred at ambient temperature for 30 minutes. Piperonal (45.0 g, 300 mmol) and MgSO$_4$ (75 g) were added sequentially and the suspension was stirred at ambient temperature for 20 h. The slurry was filtered and concentrated to a white suspension. The suspension was titurated with Et$_2$O (1 L), TEA-HBr salts removed via filtration, and the clear filtrate concentrated to afford imine (80.7 g, quant) as a clear oil. Imine (80.7 g, 300 mmol) was diluted in dry ethanol (600 mL) and acetic acid (50 mL) to afford a clear yellow solution which was cooled to 0° C. NaHB(OAc)$_3$ (191 g, 900 mmol) was added to a vented reaction mixture portionwise (10 g portions over 1 h). The ice-bath was removed and the solution allowed to warm to rt over a 1 h period. The mixture was concentrated to a white slurry, diluted with ice-water (1 L) to afford a clear solution, cooled to 0° C. and quenched with a solution of K$_2$CO$_3$ (150 g in 1 L). Brine (1 L) was then added to the partial white suspension causing mass precipitation of the product. The product was filtered, washed with water (1 L) and Et$_2$O (1 L) and dried overnight under vacuum to afford 67.8 g (84%) of benzo[1,3]dioxol-5-ylmethyl-(3-bromo-propyl)-amine as a white solid. [M+H]$^+$ 271.90, 273.94; $^1$H-NMR (400 MHz, DMSO) δ 7.25 (s, 1H), 7.04 (d, 1H), 6.96 (d, 1H), 6.05 (s, 2H), 4.04 (s, 2H), 3.61 (t, 2H), 2.94 (t, 2H), 2.24 (t, 2H); $^{13}$C-NMR (100 MHz, DMSO) δ 148.1, 147.7, 126.1, 124.6, 110.8, 108.7, 101.8, 50.1, 45.2, 31.9, 29.1.

Step 2

Preparation of compound 2c: Benzo[1,3]dioxol-5-ylmethyl-(3-bromo-propyl)-carbamic acid tert-butyl ester To a mixture of benzo[1,3]dioxol-5-ylmethyl-(3-bromo-propyl)-amine (10.0 g, 36.8 mmol) and di-tert-butyl dicarbonate (9.00 g, 41.2 mmol) in THF (80 mL) and MeOH (80 mL) was added triethylamine (15 mL). The solution was then stirred for 30 min at r.t. The solvent was evaporated and ethyl acetate (20 mL) and diethyl ether (20 mL) was added. The white solid formed was filtered off. The filtrate was dried and chromatographed (1:10 EtOAc: Hexane) to give 11.5 g (84%) of benzo[1,3]dioxol-5-ylmethyl-(3-bromo-propyl)-carbamic acid tert-butyl ester as a clear oil.

Step 3

Preparation of compound 2d: Benzo[1,3]dioxol-5-ylmethyl-(3-methylamino-propyl)-carbamic acid tert-butyl ester Benzo[1,3]dioxol-5-ylmethyl-(3-bromo-propyl)-carbamic acid tert-butyl ester (23.0 g, 61.8 mmol) was diluted in methylamine (2.00M in THF, 300 mL, 600 mmol) at rt under an atmosphere of nitrogen and stirred at ambient temperature for 16 h. The solvent was evaporated and saturated sodium carbonate solution was added. The solution was extracted with ethyl acetate (2×150 mL), dried over $Na_2SO_4$, filtered and concentrated under reduced pressure to give 18.2 g (91%) of benzo[1,3]dioxol-5-ylmethyl-(3-methylamino-propyl)-carbamic acid tert-butyl ester as a clear oil. $[M+H]^+$ 323.09.

Step 4

Preparation of compound 2e: Benzo[1,3]dioxol-5-ylmethyl-{3-[(3-chloro-[1,2,4]thiadiazol-5-yl)-methyl-amino]-propyl}-carbamic acid tert-butyl ester A solution of benzo[1,3]dioxol-5-ylmethyl-(3-methylamino-propyl)-carbamic acid tert-butyl ester (10 g, 46 mmol), 3,5-dichloro-1,2,4-thiadiazole (7.1 g, 46 mmol), DMSO (20 mL) and TEA (20 mL) was stirred at r.t. for 20 min. Water (150 mL) was added and the solution was extracted with ethyl acetate (2×150 mL), washed with brine and dried over $Na_2SO_4$. Evaporation of the solvent gave 14 g (69%) of benzo[1,3]dioxol-5-ylmethyl-{3-[(3-chloro-[1,2,4]thiadiazol-5-yl)-methyl-amino]-propyl}-carbamic acid tert-butyl ester as a clear gum. The product was used directly in the next step. $^1$H-NMR (400 MHz, $CD_3OD$) δ 6.77 (m, 3H), 5.96 (s, 2H), 4.35 (s, 2H), 3.4-3.0 (m, 6H), 1.84 (br s, 3H), 1.50 (s, 9H).

Step 5

Preparation of compound 2f: Benzol[1,3]dioxol-5-ylmethyl-{3-[(3-imidazol-1-yl-[1,2,4]thiadiazol-5-yl)-methyl-amino]-propyl}-carbamic acid tert-butyl ester To a solution of imidazole (10.0 g, 111 mmol) in DMSO (50 mL) was added sodium hydride (60% dispersion on mineral oil, 4.00 g, 100 mmol). The resultant solution was added directly to benzo[1,3]dioxol-5-ylmethyl-{3-[(3-chloro-[1,2,4]thiadiazol-5-yl)-methyl-amino]-propyl}-carbonic acid tert-butyl ester (15.8 g, 33.3 mmol). The solution was heated at 85° C. for 12 h. Water was added and the solution was extracted with ethyl acetate (2×200 mL), washed with brine and dried over $Na_2SO_4$. Evaporation of the solvent gave a residue which was purified by column chromatography (1:1 hexane:EtOAc) to afford 10.6 g (67%) of benzo[1,3]dioxol-5-ylmethyl-{3-[(3-imidazol-1-yl-[1,2,4]thiadiazol-5-yl)-methyl-amino]-propyl}-carbamic acid tert-butyl ester as a colorless oil. $[M+H]^+$ 473.06; $^1$H-NMR (400 MHz, $CD_3OD$) δ 8.32 (s, 1H), 7.68 (s, 1H), 7.12 (s, 1H), 6.62-6.80 (m, 3H), 5.96 (s, 2H), 4.38 (s, 2H), 3.0-3.6 (m, 6H), 1.88 (br s, 3H), 1.52 (s, 9H).

Step 6

Preparation of compound 2: N'-Benzo[1,3]dioxol-5-ylmethyl-N-(3-imidazol-1-yl-[1,2,4]thiadiazol-5-yl)-N-methyl-propane-1,3-diamine A solution of benzo[1,3]dioxol-5-ylmethyl-{3-[(3-imidazol-1-yl-[1,2,4]thiadiazol-5-yl)-methyl-amino]-propyl}-carbamic acid tert-butyl ester (10.6 g, 22.4 mmol) in TFA/DCM (50%, 70 mL) was stirred at room temperature for 30 min. The solvent was evaporated and a saturated solution of potassium carbonate (50 mL) was added to make it basic (pH 9). The solution was extracted with ethyl acetate (2×200 mL), washed with brine and dried over $Na_2SO_4$. Evaporation of the solvent gave 8.30 g (99%) of N'-benzo[1,3]dioxol-5-ylmethyl-N-(3-imidazol-1-yl-[1,2,4]thiadiazol-5-yl)-N-methyl-propane-1,3-diamine as a colorless oil. $[M+H]^+$ 373.26; $^1$H-NMR (400 MHz, $CD_3OD$) δ 8.28 (s, 1H), 7.63 (s, 1H), 7.07 (s, 1H), 6.79 (s, 1H), 6.72 (s, 2H), 5.92 (s, 2H), 3.67 (s, 3H), 3.60 (br s, 1H), 3.10 (br s, 2H), 2.66 (t, 2H), 2.0 (br s, 2H), 1.87 (q, 2H); $^{13}$C-NMR (100 MHz, $CD_3OD$) δ 184.3, 156.7, 147.7, 146.6, 136.4, 133.8, 129.9, 121.2, 117.1, 108.6, 108.1, 100.9, 53.7, 45.7, 27.1.

Example 3

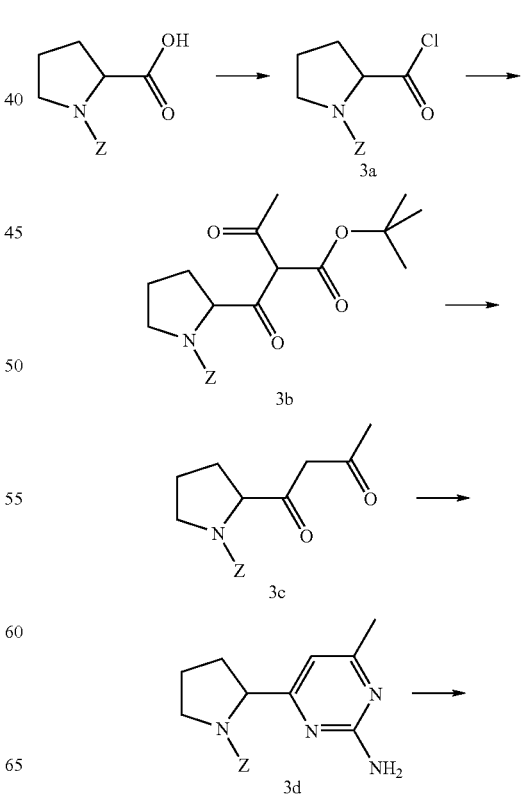

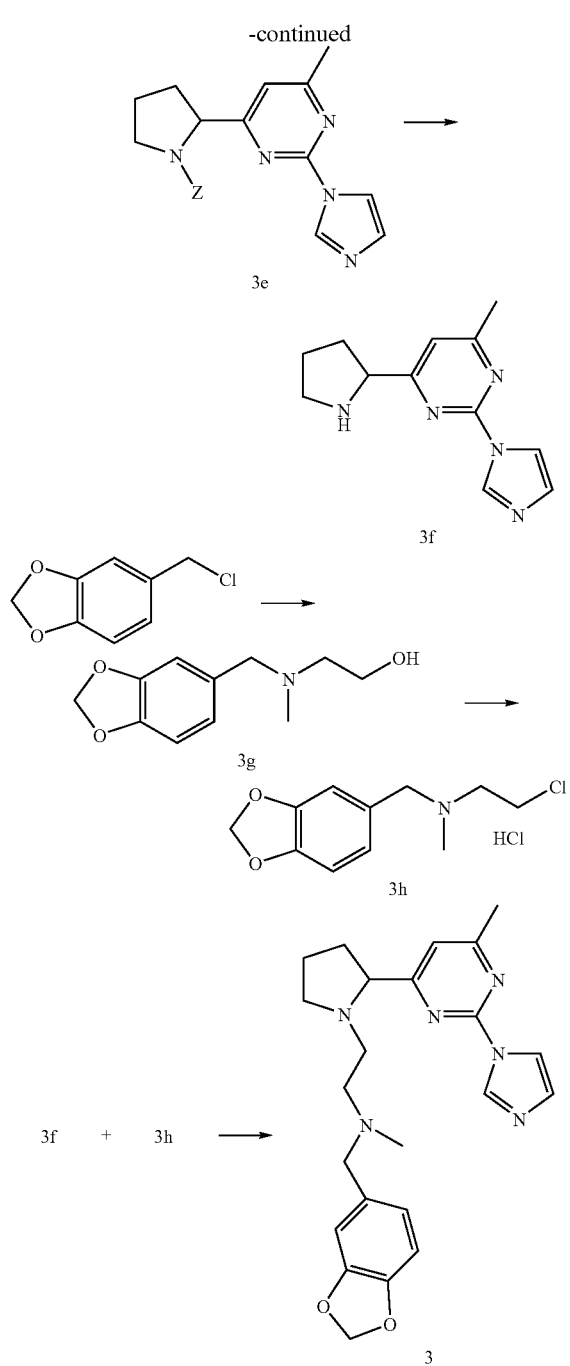

Step 1

Preparation of compound 3a:
2-Chlorocarbonyl-pyrrolidine-1-carboxylic acid benzyl ester Oxalyl chloride (1.21 mL, 14.0 mmol) was added dropwise (15 minutes) to a 0° C. solution of N-carbobenzyloxy-D,L-proline (2.50 g, 10.0 mmol), dimethylformamide (1 drop, cat.) and methylene chloride (anhydrous, 25 mL) under a nitrogen atmosphere. The mixture was removed from the ice-bath and stirred at ambient temperature for 1 h. The reaction mixture was concentrated to afford 2.63 g (98%) of 2-chlorocarbonyl-pyrrolidine-1-carboxylic acid benzyl ester as an orange oil. The product was used directly in subsequent steps.

Step 2

Preparation of compound 3b: 2-(2-tert-Butoxycarbonyl-3-oxo-butyryl)-pyrrolidine-1-carboxylic acid benzyl ester A solution of tert-butylacetoacetate (7.90 g, 50.0 mmol) in anhydrous THF (50 mL) was cooled to 4° C. (ice-water bath) prior to dropwise addition of methylmagnesium chloride (16.3 mL of a 3.00M solution in THF, 50.0 mmol) at such a rate that the temperature did not exceed 10° C. After the addition was complete the cooling bath was removed. When the temperature reached 15° C., 2-chlorocarbonyl-pyrrolidine-1-carboxylic acid benzyl ester (6.60 g, 25.0 mmol) was added dropwise over 1 h then warmed to rt and stirred for 12 h. The reaction was quenched with saturated aqueous $NH_4Cl$ (30 mL). The organic layer was separated from the solid residues and concentrated under vacuum to give 9.74 g (quant.) of 2-(2-tert-butoxycarbonyl-3-oxo-butyryl)-pyrrolidine-1-carboxylic acid benzyl ester as a yellow oil. The product was used directly in the subsequent step without further purification.

Step 3

Preparation of compound 3c:
2-(3-Oxo-butyryl)-pyrrolidine-1-carboxylic acid benzyl ester 2-(2-tert-Butoxycarbonyl-3-oxo-butyryl)-pyrrolidine-1-carboxylic acid benzyl ester (9.74 g, 25.0 mmol) was dissolved toluene (40 mL) and was washed with 1N HCl (2×50 mL). To the resulting solution was added p-toluenesulfonic acid monohydrate (1.00 g, 5.00 mmol) and the solution was heated under nitrogen to 80° C. for 4 hours. The dark mixture was allowed to cool and was washed with water (3×100 mL). The organic layer was concentrated to give 6.87 g (95%) of 2-(3-oxo-butyryl)-pyrrolidine-1-carboxylic acid benzyl ester as an amber oil. The product was used directly in the subsequent step without further purification. $[M+H]^+$ 290.03.

Step 4

Preparation of compound 3d: 2-(2-Amino-6-methyl-pyrimidin-4-yl)-pyrrolidine-1-carboxylic acid benzyl ester Sodium (550 mg, 25.0 mmol) was added portionwise to a stirred solution of anhydrous ethanol (30 mL) under nitrogen at room temperature. When all the sodium had dissolved, to the solution was added a solution of guanidine hydrochloride (2.28 g, 25.0 mmol) in ethanol (20 mL). The resulting mixture was stirred for 20 minutes. The precipitated sodium chloride was removed by filtration and to the clear filtrate was added 2-(3-oxo-butyryl)-pyrrolidine-1-carboxylic acid benzyl ester (6.87 g, 23.7 mmol). The flask was then fitted with a Dean-Stark Tube and 20 mL of distillate was removed as the solution was heated to reflux under nitrogen for 12 h. The mixture was allowed to cool to room temperature, then was gradually cooled to −5° C. The resulting solid was collected by filtration and air dried to give 3.37 g (46%) of 2-(2-amino-6-methyl-pyrimidin-4-yl)-pyrrolidine-1-carboxylic acid benzyl ester as cream colored crystals. $[M+H]^+$ 312.88.

Step 5

Preparation of compound 3e: 2-(2-Imidazol-1-yl-6-methyl-pyrimidin-4-yl)-pyrrolidine-1-carboxylic acid benzyl ester 2-(2-Amino-6-methyl-pyrimidin-4-yl)-pyrrolidine-1-carboxylic acid benzyl ester (2.65 g, 8.48 mmol) was diluted in dioxane (31.2 mL) and water (4.24 mL) at ambient temperature. The pH was adjusted to 2 with $H_3PO_4$ (470 µL) resulting in a yellow suspension. Glyoxal (40 wt % in water, 1.23 g, 8.48 mmol), paraformaldehyde (254 mg, 8.48 mmol) and water (8.48 mL) were added and the suspension was heated to 80° C. Saturated $NH_4Cl$ (453 mg, 8.48 mmol in 2.4 mL of $H_2O$) was added dropwise to the clear yellow solution at 80° C. prior to heating at 100° C. for a period of 2 h. The clear dark red solution was cooled to rt and bought to pH 12 with 4M NaOH then extracted with ethyl acetate. The combined organics were washed with brine, dried over $MgSO_4$, filtered and concentrated. The crude residue was ran through a plug of $SiO_2$ and eluted with 5:1 ethyl acetate/hexanes to afford 1.98 g (64%) of 2-(2-imidazol-1-yl-6-methyl-pyrimidin-4-yl)-pyrrolidine-1-carboxylic acid benzyl ester as a white solid. $[M+H]^+$ 363.78.

Step 6

Preparation of compound 3f: 2-Imidazol-1-yl-4-methyl-6-pyrrolidin-2-yl-pyrimidine 10% Pd/C (12 mg) was added to a solution of 2-(2-imidazol-1-yl-6-methyl-pyrimidin-4-yl)-pyrrolidine-1-carboxylic acid benzyl ester (112 mg, 0.308 mmol) and ethanol (3 mL) at rt. The reaction was vacuum purged with $N_2$ then stirred under a balloon of $H_2$ for 4 h. The reaction mixture was filtered through celite and concentrated. Column chromatography (10 g, DCM to 20% MeOH/DCM) afforded 63 mg (89%) of 2-imidazol-1-yl-4-methyl-6-pyrrolidin-2-yl-pyrimidine. $[M+H]^+$ 230.16; $^1$H-NMR (400 MHz, $CD_3OD$) δ 8.74 (s, 1H), 8.05 (s, 1H), 7.31 (s, 1H), 7.14 (s, 1H), 4.95 (s, 2H), 4.25 (t, 1H), 3.25 (m, 1H), 3.05 (m, 1H), 2.59 (s, 3H), 2.35 (m, 1H), 1.90 (m, 2H); $^{13}$C-NMR (100 MHz, $CD_3OD$) δ 173.4, 170.4, 153.9, 136.0, 128.9, 116.8, 116.0, 62.1, 46.5, 32.7, 25.3, 22.7.

Step 7

Preparation of compound 3g: 2-(Benzo[1,3]dioxol-5-ylmethyl-methyl-amino)-ethanol 2-(Methylamino)ethanol (22.0 g, 290 mmol) is added all at once to a stirred solution of 3,4-methylenedioxybenzyl chloride (25.0 g, 147 mmol) in DCM (45 mL) at −78° C. under nitrogen. The solution is stirred for 15 minutes at −78° C. then allowed to warm to room temperature overnight (16 h). The reaction is quenched with 1.2 M NaOH (100 mL), washed twice with water, dried of $MgSO_4$, and filtered. Concentration under reduced pressure afforded 25.3 g (83%) of 2-(benzo[1,3]dioxol-5-ylmethyl-methyl-amino)-ethanol as a clear oil which was suitable for use in the next step.

Step 8

Preparation of compound 3h: Benzo[1,3]dioxol-5-ylmethyl-(2-chloro-ethyl)-methyl-amine hydrochloride salt Thionyl chloride (60 mL) is added dropwise over 30 minutes to a 0° C. solution of 2-(benzo[1,3]dioxol-5-ylmethyl-methyl-amino)-ethanol (22.2 g, 110 mmol) in DCM (250 mL) under nitrogen. The ice bath is removed, and the solution is stirred at room temperature overnight (16 h). The white slurry is concentrated under reduced pressure, diluted with brine (150 mL) and ethyl acetate (200 mL), and the precipitate is collected via vacuum filtration. The solid is washed with ethyl acetate and dried overnight under vacuum to afford 26.5 g (91%) of benzo[1,3]dioxol-5-ylmethyl-(2-chloro-ethyl)-methyl-amine hydrochloride as a white powder.

Step 9

Preparation of compound 3: Benzo[1,3]dioxol-5-ylmethyl-{2-[2-(2-imidazol-1-yl-6-methyl-pyrimidin-4-yl)-pyrrolidin-1-yl]-ethyl}-amine A solution of 2-imidazol-1-yl-4-methyl-6-pyrrolidin-2-yl-pyrimidine (2.1 g, 9.2 mmol) in DMF (15 mL) was added all at once to a stirred mixture of benzo[1,3]dioxol-5-ylmethyl-(2-chloro-ethyl)-methyl-amine hydrochloride salt (2.2 g, 8.1 mmol), DMF (10 mL) and diisopropylethylamine (2.5 mL) at ambient temperature under nitrogen. A catalytic amount of potassium iodide (340 mg, 2.0 mmol) is then added. The mixture is heated to 80° C. for 3 h. The solution is then cooled to room temperature, quenched into 200 mL of 1N dibasic potassium phosphate solution (pH 9), and extracted with ethyl acetate. The combined organics are dried over $MgSO_4$, filtered and concentrated to a red residue. Purification via silica gel column chromatography (DCM to 4:1 DCM/MeOH) gave 2.0 g (52%) of benzo[1,3]dioxol-5-ylmethyl-{2-[2-(2-imidazol-1-yl-6-methyl-pyrimidin-4-yl)-pyrrolidin-1-yl]-ethyl}-amine as a red oil. $[M+H]^+$ 421.30; $^1$H-NMR (400 MHz, $CDCl_3$) δ 8.60 (s, 1H), 7.89 (s, 1H), 7.30 (s, 1H), 7.10 (s, 1H), 6.78 (s, 1H), 6.67 (m, 2 H), 5.88 (s, 2H), 3.52 (t, 1H, J=6.8 Hz), 3.6 (m, 3H), 2.77 (m, 1H), 2.2-2.6 (m, 8H), 1.62-1.95 (m, 3H). $^{13}$C-NMR (100 MHz, $CDCl_3$) δ 175.7, 169.6, 154.0, 147.6, 146.5, 136.2, 132.8, 130.1, 121.9, 116.6, 115.0, 109.2, 107.8, 100.8, 69.8, 62.3, 56.0, 54.3, 53.1, 42.5, 33.2, 24.2, 23.4.

Example 4

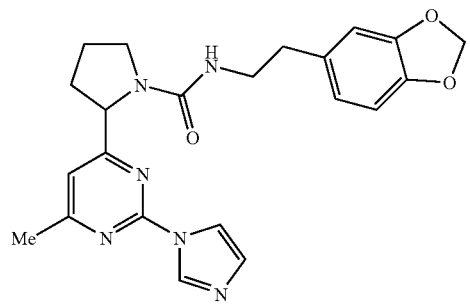

4

Preparation of compound 4: 2-(2-Imidazol-1-yl-6-methyl-pyrimidin-4-yl)-pyrrolidine-1-carboxylic acid (2-benzo[1,3]dioxol-5-yl-ethyl)-amide A solution of 2-imidazol-1-yl-4-methyl-6-pyrrolidin-2-yl-pyrimidine (21.8 mg, 0.095 mmol), 3,4-methylenedioxyphenethyl isocyanate (29 mg, 0.151 mmol) and triethylamine (0.4 mL) in anhydrous THF (1.5 mL) was reacted for 10 min. Water was added and the solution was extracted with ethyl acetate (2×3 mL), washed with brine and dried over Na₂SO₄. Evaporation of the solvent and purification by TLC plate gave 36 mg (90%) of 2-(2-imidazol-1-yl-6-methyl-pyrimidin-4-yl)-pyrrolidine-1-carboxylic acid (2-benzo[1,3]dioxol-5-yl-ethyl)-amide as a white solid. [M+H]⁺ 421.15; ¹H-NMR (400 MHz, CD₃OD) δ 8.65 (s, 1H), 7.99 (s, 1H), 7.14 (s, 1H), 7.11 (s, 1H), 6.65 (m, 3H), 5.88 (s, 2H), 4.98 (m, 1H), 3.62 (m, 1H), 3.55 (m, 1H), 3.34 (m, 2H), 2.69 (m, 2H), 2.56 (s, 3H), 2.41 (m, 1H), 2.03 (m, 3H); ¹³C-NMR (100 MHz, CD₃OD) δ 173.9, 170.3, 166.5, 157.7, 147.6, 145.9, 133.2, 128.9, 121.3, 115.0, 108.6, 107.6, 106.9, 61.4, 46.4, 41.8, 35.7, 32.4, 23.3, 22.8.

Example 5

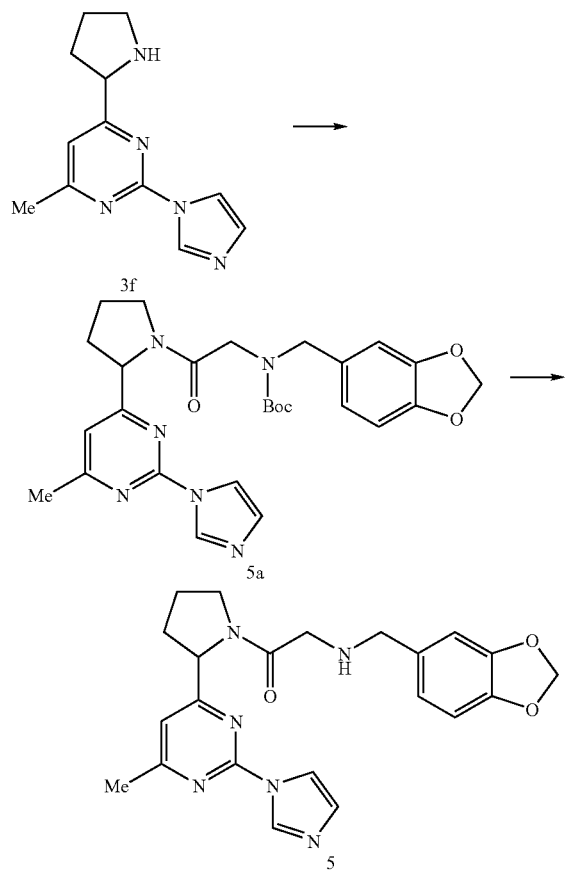

Step 1

Preparation of compound 3f: 2-Imidazol-1-yl-4-methyl-6-pyrrolidin-2-yl-pyrimidine was prepared following the procedures described in preparation of compound 3f in Example 3

Step 2

Preparation of compound 5: 2-(2-Imidazol-1-yl-6-methyl-pyrimidin-4-yl)-pyrrolidine-1-carboxylic acid (benzo[1,3]dioxol-5-ylmethyl)-amide A solution of 4b (21.0 mg, 0.092 mmol), N-Boc-[(benzo[1,3]dioxaol-5-ylmethyl)amino]acetic acid (39 mg, 0.126 mmol), 1-ethyl-3-(3-dimethylaminopropyl)carbodiimide hydrochloride (28 mg, 0.146 mmol) and 1-hydroxybenzotriazole (20 mg, 0.148 mmol) in dry DMF (1.5 mL) was stirred for 30 min. Water was added and the solution was extracted with ethyl acetate (2×10 mL), washed with brine and dried over Na₂SO₄. Evaporation of the solvent and purification by TLC plate gave the desired product 5a (48 mg). A solution of 5a in TFA (0.5 mL) and DCM (0.5 mL) was stirred for 20 min. The solvent was evaporated and sat. aqueous sodium carbonate solution was added. Then the solution was extracted with ethyl acetate (2×5 mL), washed with brine and dried over Na₂SO₄. Evaporation of the solvent gave the desired product 5 (25 mg). [M+H]⁺ 421.07; ¹H-NMR (400 MHz, CD₃OD) δ 8.67 (s, 1H), 8.00 (s, 1H), 7.23 (s, 1H), 6.86 (s, 1H), 6.78 (m, 2H), 6.53 (s, 1H), 5.93 (s, 1H), 3.83 (m, 1H), 3.70-3.50 (m, 6H), 3.34 (s, 1H), 2.58 (s, 3H), 2.50-1.90 (m, 4H).

Example 6

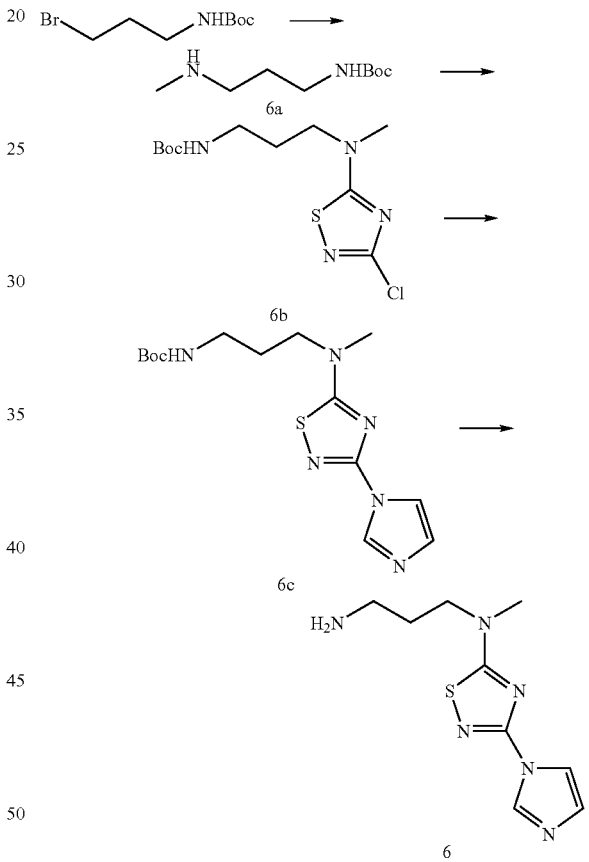

Step 1

Preparation of compound 6a:
(3-Methylamino-propyl)-carbamic acid tert-butyl ester (3-Bromo-propyl)-carbamic acid tert-butyl ester (11.2 g, 47.0 mmol) was combined with 2.0 M Methylamine in THF (100 mL, 200 mmol) and was stirred at room temperature for 4 h. After this period, a precipitate formed in the solution. The solution was filtered and concentrated under reduced pressure to yield 7.58 g (86%) of (3-methylamino-propyl)-carbamic acid tert-butyl ester as a clear oil. [M+H]⁺ 188.94.

Step 2

Preparation of compound 6b: {3-[(3-Chloro-[1,2,4]thiadiazol-5-yl)-methyl-amino]-propyl}-carbamic acid tert-butyl ester (3-Methylamino-propyl)-carbamic acid tert-butyl ester (7.00 g, 36.8 mmol) and 3,5-dichloro-[1,2,4]thiadiazole (4.75 g, 30.7 mmol) were dissolved in DMSO (150 mL). Finally, triethylamine (3 mL) was added and the reaction mixture was stirred at room temperature for 24 h. After this period, brine (100 mL) was poured into the reaction vessel and the mixture was transferred to a separatory funnel. The resulting layer was extracted with DCM (3×300 mL). The DCM layer was then dried over anhydrous $Na_2SO_4$. The crude product was purified using flash silica chromatography (DCM to 9:1 DCM/MeOH) to afford 6.5 g (69%) of {3-[(3-chloro-[1,2,4]thiadiazol-5-yl)-methyl-amino]-propyl}-carbamic acid tert-butyl ester as a clear oil. $[M+H]^+$ 307.40.

Step 3

Preparation of compound 6c: {3-[(3-Imidazol-1-yl-[1,2,4]thiadiazol-5-yl)-methyl-amino]-propyl}-carbamic acid tert-butyl ester {3-[(3-Chloro-[1,2,4]thiadiazol-5-yl)-methyl-amino]-propyl}-carbamic acid tert-butyl ester (6.50 g, 21.2 mmol) was combined with imidazole (7.20 g, 105 mmol) and dissolved in DMSO (100 mL). Next, the sodium hydride (833 mg of a 60% dispersion on mineral oil, 57.8 mmol) was added the reaction mixture was stirred at 60° C. overnight. After this period, brine was added to the reaction mixture and it was transferred to a separatory funnel. The product was extracted with copious DCM and the organic layer was dried over anhydrous $Na_2SO_4$. The crude material was purified by flash silica chromatography (Hex to 1:4 Hex/EtOAc) to yield 6.78 g (94%) of {3-[(3-imidazol-1-yl-[1,2,4]thiadiazol-5-yl)-methyl-amino]-propyl}-carbamic acid tert-butyl ester as a clear oil. $[M+H]^+$ 339.10.

Step 4

Preparation of compound 6: N-1-(3-Imidazol-1-yl-[1,2,4]thiadiazol-5-yl)-N-1-methyl-propane-1,3-diamine {3-[(3-Imidazol-1-yl-[1,2,4]thiadiazol-5-yl)-methyl-amino]-propyl}-carbamic acid ester (450 mg, 1.33 mmol) was dissolved in DCM (2 mL), followed by addition of TFA (2 mL). The mixture was stirred at room temperature for 2 hours. After this time, the mixture was dried under $N_2$ gas. The residue was dissolved in DCM and washed with 1M NaOH (2×25 mL). The organic layer was partitioned from the aqueous layer, dried over anhydrous $Na_2SO_4$ and concentrated under vacuum. This residue was purified by flash silica chromatography (DCM to 9:1 DCM/MeOH) to yield 303 mg (96%) of N-1-(3-imidazol-1-yl-[1,2,4]thiadiazol-5-yl)-N-1-methyl-propane-1,3-diamine as a white solid. $[M+H]^+$ 239.08.

Example 7

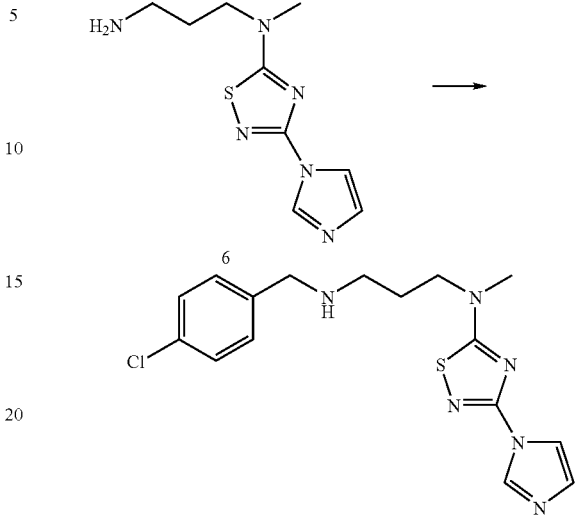

Preparation of compound 7: N'-(4-Chloro-benzyl)-N-(3-imidazol-1-yl-[1,2,4]thiadiazol-5-yl)-N-methyl-propane-1,3-diamine N-1-(3-Imidazol-1-yl-[1,2,4]thiadiazol-5-yl)-N-1-methyl-propane-1,3-diamine (150 mg, 0.64 mmol) and 4-chloro-benzaldehyde (90 mg, 0.64 mmol) were dissolved in anhydrous ethanol (2 mL) and glacial acetic acid (150 μL). The reaction mixture was stirred at 60° C. overnight. After this time, the reaction mixture was concentrated down under vacuum and ethanol (2 mL) was added. The solution was cooled to 0° C. and sodium triacetoxyborohydride (270 mg, 1.3 mmol) was added. The reaction was stirred at room temperature overnight. After this time, the solution was concentrated down under vacuum and the residue was dissolved in DCM and washed with sat. $NaHCO_3$ (2×25 mL). The organic layer was dried over $Na_2SO_4$ and concentrated under vacuum. The crude product was purified by flash silica chromatography (DCM to 1:19 MeOH/DCM) to yield 37 mg (16%) of 7 as a clear, glassy oil. $[M+H]^+$ 363.00; $^1$H NMR (400 MHz, $CDCl_3$) δ 8.30 (d, 1H), 7.64 (s, 1H), 7.25 (q, 4H), 7.09 (d, 1H) 3.75 (s, 2H), 3.62 (t, 2H), 3.12 (s, 3H), 2.68 (t, 2H), 1.86 (q, 2H), 1.78 (s, 1H).

Example 8

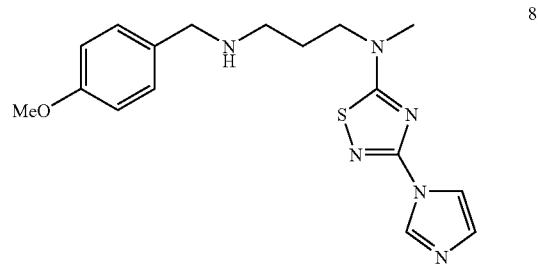

Preparation of compound 8: N-(3-Imidazol-1-yl-[1,2,4]thiadiazol-5-yl)-N'-(4-methoxy-benzyl)-N-methyl-propane-1,3-diamine was prepared following the procedures described in preparation of Example 7 using 4-methoxybenzaldehyde. [M+H]+ 360.40; 1H NMR (400 MHz, CDCl3) δ 8.35 (s, 1H), 7.67 (s, 1H), 7.25 (d, 2H), 7.13 (s, 1H) 6.86 (d, 2H), 3.82 (s, 1H) 3.79 (s, 2H), 3.52 (d, 2H), 3.12 (s, 1H), 3.12-2.73 (m, 2H), 2.07 (s, 3H), 2.07-1.96 (m, 2H).

Example 9

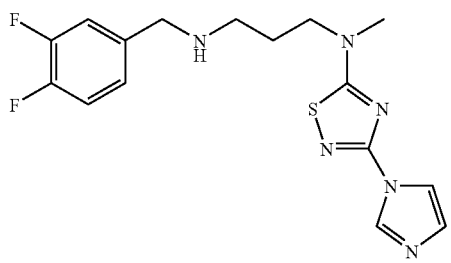

9

Preparation of compound 9: N'-(3,4-Difluro-benzyl)-N-(3-imidazol-1-yl-[1,2,4]thiadiazol-5-yl)-N-methyl-propane-1,3-diamine was prepared following the procedures described in preparation of Example 7 using 3,4-difluoro-benzaldehyde. [M+H]+ 365.01; 1H NMR (400 MHz, CDCl3) δ 8.31 (s, 1H), 7.65 (d, 1H), 7.18-7.01 (m, 4H), 3.74 (s, 2H) 3.70-3.49 (m, 2H) 3.14 (s, 3H), 2.70-2.67 (t, 2H), 1.93-1.87 (m, 2H)

Example 10

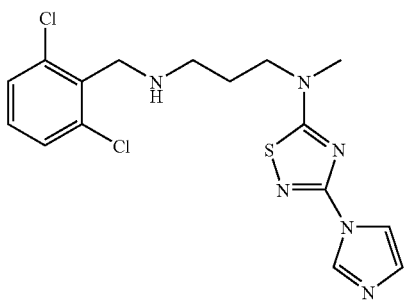

10

Preparation of compound 10: N'-(2,6-Dichloro-benzyl)-N-(3-imidazol-1-yl-[1,2,4]thiadiazol-5-yl)-N-methyl-propane-1,3-diamine was prepared following the procedures described in preparation of Example 7 using 2,6-dichloro-benzaldehyde. [M+H]+ 398.90; 1H NMR (400 MHz, CDCl3) δ 9.31 (s, 1H), 7.93 (s, 1H), 7.44 (s, 1H), 7.36-7.28 (m, 3H) 4.15 (s, 2H), 3.79 (s, 1H), 3.22-3.18 (t, 2H), 3.12 (s, 2H), 2.68 (s, 3H), 2.30-2.27 (m, 2H).

Example 11

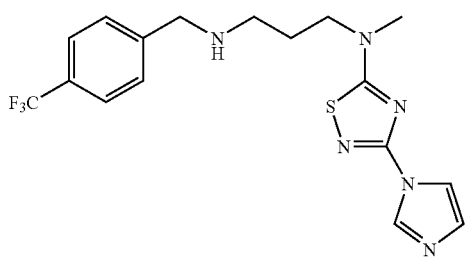

11

Preparation of compound 11: N-(3-Imidazol-1-yl-[1,2,4]thiadiazol-5-yl)-N-methyl-N'-(4-trifluoromethyl-benzyl)-propane-1,3-diamine was prepared following the procedures described in preparation of Example 7 using 4-trifluoromethyl-benzaldehyde. [M+H]+ 396.70; 1H NMR (400 MHz, CDCl3) δ 9.49 (s, 1H), 7.93 (s, 1H), 7.60 (s, 4H), 7.39 (s, 1H) 4.23 (s, 2H), 3.80 (br s, 1H), 3.51 (s, 2H), 3.12-3.09 (m, 2H), 2.68 (s, 3H), 2.20-2.14 (m, 2H).

Example 12

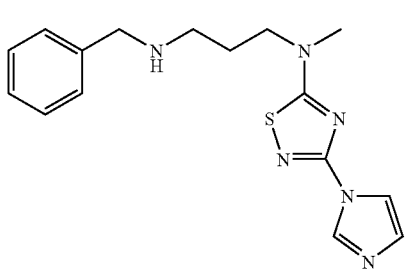

12

Preparation of compound 12: N'-Benzyl-N-(3-imidazol-1-yl-[1,2,4]thiadiazol-5-yl)-N-methyl-propane-1,3-diamine was prepared following the procedures described in preparation of Example 7 using benzaldehyde. [M+H]+ 329.20; 1H NMR (400 MHz, CDCl3) δ 8.32 (s, 1H), 7.67 (s, 1H), 7.35-7.28 (m, 5H), 7.12-7.11 (d, 1H), 3.80 (s, 2H), 3.52 (m, 2H), 3.15 (s, 3H), 2.74-2.71 (t, 2H), 1.93-1.90 (m, 2H), 1.66 (s, 1H).

Example 13

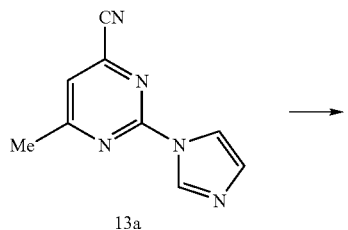

13a

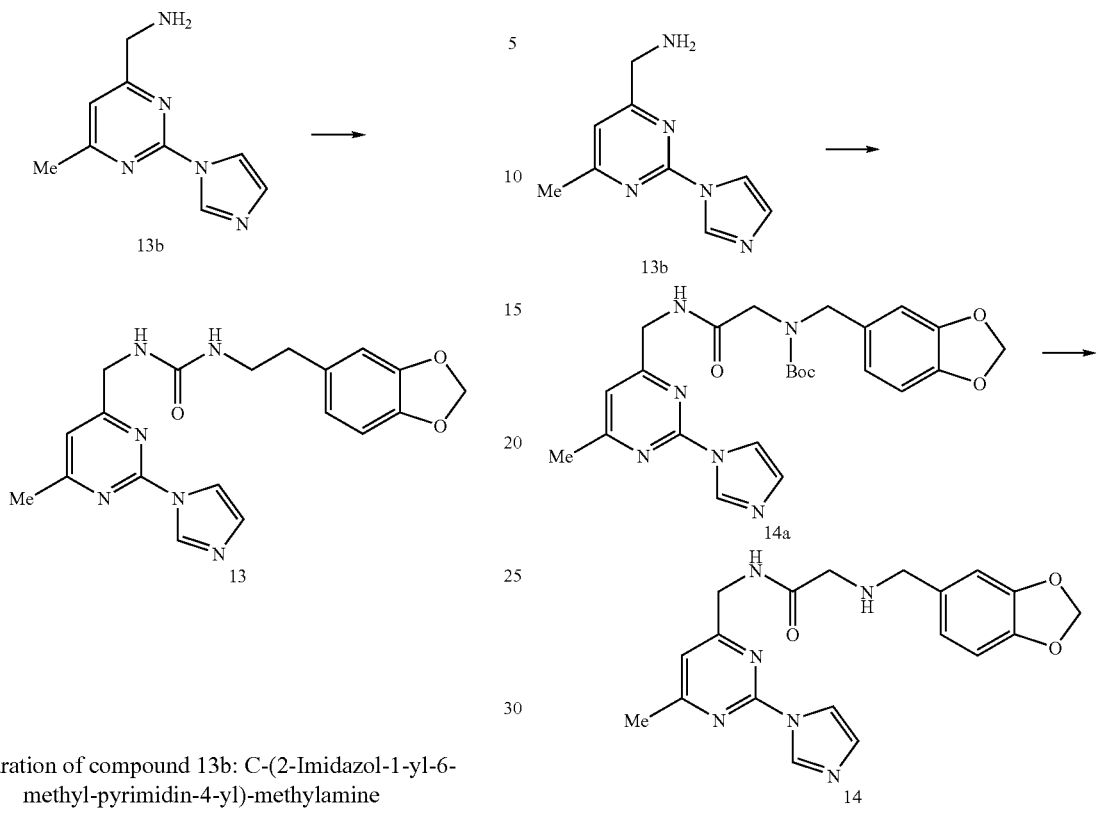

Example 14

Step 1

Preparation of compound 13b: C-(2-Imidazol-1-yl-6-methyl-pyrimidin-4-yl)-methylamine To a solution of 13a (1.0 g, 5.4 mmol) in dichloromethane (40 mL) was added diisobutylaluminum hydride (15 mL, 1M in toluene, 15 mmol) at r.t. The solution was stirred for 1 h and brine was added. The solution was extracted with ethyl acetate (2×200 mL), washed with brine and dried over $Na_2SO_4$. Evaporation of the solvent and purification by column chromatography (10:1 EtOAc/MeOH to MeOH) gave 0.12 g (11%) of 13b as an oil. $[M+H]^+$ 190.10.

Step 2

Preparation of compound 13: 1-(2-Benzo[1,3]dioxol-5-yl-ethyl)-3-(2-imidazol-1-yl-6-methyl-pyrimidin-4-ylmethyl)-urea A solution of 13b (46 mg, 0.24 mmol), 3,4-methylenedioxyphenethyl isocyanate (46 mg, 0.24 mmol) and triethylamine (0.5 mL) in dry THF (1.5 mL) was reacted for 10 min at r.t. Water was added and the solution was extracted with ethyl acetate (2×3 mL), washed with brine and dried over $Na_2SO_4$. Evaporation of the solvent and purification by preparatory TLC gave 42 mg (46%) of 13 as a white solid. $[M+H]^+$ 381.13; $^1$H-NMR (400 MHz, $CD_3OD$) δ 8.70 (s, 1H), 8.03 (s, 1H), 7.19 (s, 1H), 7.15 (s, 1H), 6.73 (m, 3H), 5.91 (s, 2H), 4.43 (s, 2H), 3.38 (t, 2H), 2.74 (t, 2H), 2.58 (s, 3H).

Step 1

Preparation of compound 14a: Benzo[1,3]dioxol-5-ylmethyl-{[(2-imidazol-1-yl-6-methyl-pyrimidin-4-ylmethyl)-carbamoyl]-methyl}-carbamic acid tert-butyl ester A solution of 13b (55 mg, 0.29 mmol), N-Boc-[(benzo[1,3]dioxaol-5-ylmethyl)amino]acetic acid (84 mg, 0.27 mmol), 1-ethyl-3-(3-dimethylaminopropyl)carbodiimide hydrochloride (80 mg, 0.42 mmol) and 1-hydroxybenzotriazole (40 mg, 0.30 mmol) in dry DMF (1.5 mL) was stirred for 20 min. Water was added and the solution was extracted with ethyl acetate (2×10 mL), washed with brine and dried over $Na_2SO_4$. Evaporation of the solvent and purification by preparatory TLC gave 70 mg (54%) of 14a. $[M+H]^+$ 481.07.

Step 2

Preparation of compound 14: 1-Benzo[1,3]dioxol-5-ylmethyl-3-(2-imidazol-1-yl-6-methyl-pyrimidin-4-ylmethyl)-urea A solution of 14a (70 mg, 0.15 mmol) in TFA/DCM (1 mL, 50%) was stirred at r.t. for 20 min. The solvent was evaporated and sat. aqueous sodium carbonate solution was added. The solution was extracted with ethyl acetate (2×5 mL), washed with brine and dried over $Na_2SO_4$. Evaporation of the solvent gave 56 mg (98%) of 14. $[M+H]^+$ 381.04; $^1$H-NMR (400 MHz, $CDCl_3$) δ 8.61 (s, 1H), 8.20 (br s, 1H), 7.87 (s, 1H), 7.13 (s, 1H), 6.98 (s, 1H), 6.75 (s, 3H), 5.93 (s, 2H), 4.55 (d, 2H), 3.75 (s, 2H), 3.41 (s, 2H), 2.55 (s, 1H).

Example 15

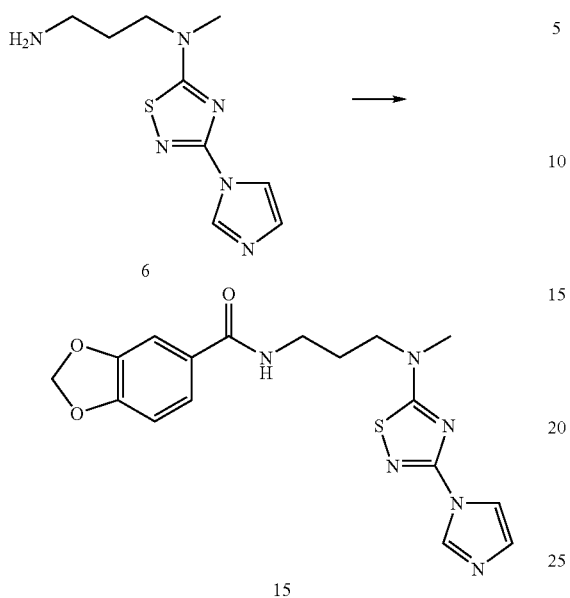

Preparation of compound 15: N'-Benzo[1,3]dioxol-5-ylmethyl-N-(3-imidazol-1-yl-[1,2,4]thiadiazol-5-yl)-N-methyl-propane-1,3-diamine N-1-(3-Imidazol-1-yl-[1,2,4]thiadiazol-5-yl)-N-1-methyl-propane-1,3-diamine (150 mg, 0.63 mmol) was dissolved in DCE (4 mL), followed by addition of piperonyloyl chloride (140 mg, 0.76 mmol). Finally, the DIEA (130 µL, 0.76 mmol) was added and the reaction was stirred at room temperature overnight. After this time, the reaction was dried under $N_2$ gas. The residue was dissolved in DCM and washed with copious sat. aq. $NaHCO_3$. The organic layer was partitioned from the aqueous phase and dried over $MgSO_4$. The crude material was concentrated under vacuum and purified by preparative HPLC to afford 102.1 mg (42%) of 15. $[M+H]^+$ 387.03; $^1$H NMR (400 MHz, CDCl3) δ 13.0 (s, 1H), 9.25 (s, 1H), 7.82 (d, 1H), 7.40 (d, 1H) 7.25 (d, 1H), 7.20 (s, 1H), 6.78 (d, 1H), 6.01 (s, 2H), 3.48 (s, 2H), 3.15 (s, 2H), 3.12 (bs, 2H), 2.65 (s, 3H), 2.05 (in, 2H).

Example 16

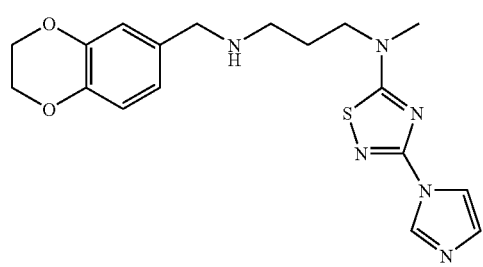

Preparation of compound 16: N'-(2,3-Dihydro-benzo[1,4]dioxin-6-ylmethyl)-N-(3-imidazol-1-yl-[1,2,4]thiadiazol-5-yl)-N-methyl-propane-1,3-diamine was prepared following the procedures described in preparation of Example 7 using 2,3-dihydro-benzo[1,4]dioxine-6-carbaldehyde. $[M+H]^+$ 386.86; $^1$H-NMR (400 MHz, CDCl$_3$) δ 8.30 (s, 1H), 7.64 (s, 1H), 7.27 (s, 1H), 7.08 (s, 1H), 6.79 (d, 1H), 6.75 (d, 1H), 4.24 (s, 4H), 3.67 (s, 3H), 2.67 (t, 2H), 1.87 (t, 4H).

Example 17

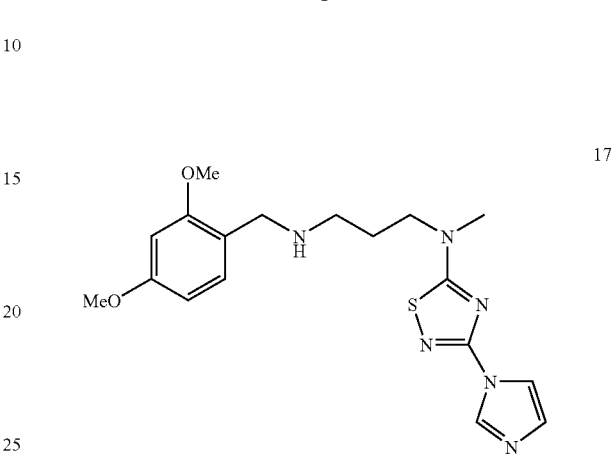

Preparation of compound 17: N'-(2,4-Dimethoxy-benzyl)-N-(3-imidazol-1-yl-[1,2,4]thiadiazol-5-yl)-N-methyl-propane-1,3-diamine was prepared following the procedures described in preparation of Example 7 using 2,4-dimethoxy-benzaldehyde. $[M+H]^+$ 389.01; $^1$H-NMR (400 MHz, CDCl$_3$) δ 8.30 (s, 1H), 7.64 (s, 1H), 7.08 (t, 2H), 6.43 (d, 1H), 6.40 (d, 1H), 3.81 (s, 6H), 3.74 (s, 2H), 3.12 (bs, 3H), 2.68 (t, 2H), 2.45 (bs, 2H), 1.92 (t, 2H).

Example 18

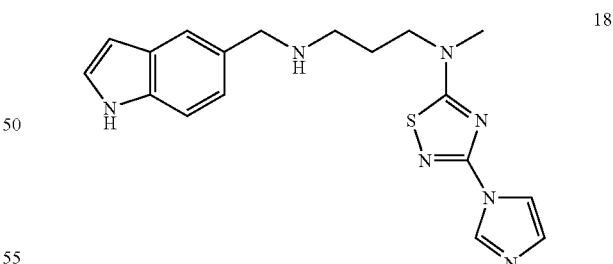

Preparation of compound 18: N-(3-Imidazol-1-yl-[1,2,4]thiadiazol-5-yl)-N'-(1H-indol-5-ylmethyl)-N-methyl-propane-1,3-diamine was prepared following the procedures described in preparation of Example 7 using 1H-indole-5-carbaldehyde. $[M+H]^+$ 368.04; $^1$H-NMR (400 MHz, CDCl$_3$) δ 8.30 (s, 1H), 7.63 (s, 1H), 7.59 (s, 1H), 7.38 (d, 1H), 7.22 (d, 1H), 7.18 (d, 1H), 7.08 (s, 1H), 6.52 (d, 1H), 3.94 (s, 2H), 3.18 (bs, 3H), 2.78 (t, 2H), 1.98 (t, 2H).

Example 19

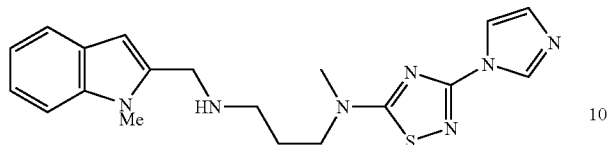

Preparation of compound 19: N-(3-Imidazol-1-yl-[1,2,4]thiadiazol-5-yl)-N-methyl-N'-(1-methyl-1H-indol-2-ylmethyl)-propane-1,3-diamine was prepared following the procedures described in preparation of Example 7 using 1-methyl-1H-indole-2-carbaldehyde. [M+H]$^+$ 382.07; $^1$H-NMR (400 MHz, CDCl$_3$) δ 8.34 (s, 1H), 7.65 (s, 1H), 7.60 (d, 1H), 7.33 (d, 1H), 7.24 (t, 1H), 7.13 (t, 1H), 6.41 (s, 1H), 3.98 (s, 2H), 3.80 (s, 2H), 3.24 (bs, 3H), 2.78 (t, 2H), 1.92 (t, 2H).

Example 20

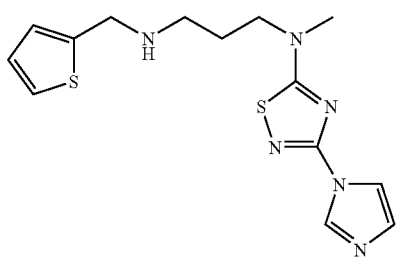

Preparation of compound 20: N-(3-Imidazol-1-yl-[1,2,4]thiadiazol-5-yl)-N-methyl-N'-thiophen-2-ylmethyl-propane-1,3-diamine was prepared following the procedures described in preparation of Example 7 using thiophene-2-carbaldehyde. [M+H]$^+$ 335.11; $^1$H-NMR (400 MHz, CDCl$_3$) δ 8.32 (s, 1H), 7.67 (s, 1H), 7.22 (dd, 1H), 7.11 (t, 1H), 6.97 (dd, 1H), 6.92 (s, 1H), 4.01 (s, 2H), 3.62 (bs, 2H), 3.08 (bs, 3H), 2.78 (t, 2H), 1.90 (t, 2H).

Example 21

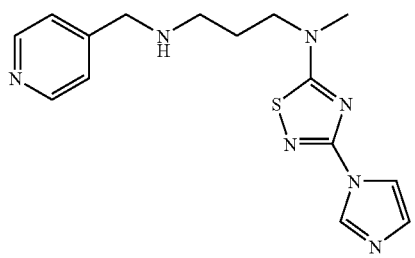

Preparation of compound 21: N-(3-Imidazol-1-yl-[1,2,4]thiadiazol-5-yl)-N-methyl-N'-pyridin-4-ylmethyl-propane-1,3-diamine was prepared following the procedures described in preparation of Example 7 using pyridine-4-carbaldehyde. [M+H]$^+$ 330.05; $^1$H-NMR (400 MHz, CDCl$_3$) δ 8.60-8.52 (m, 2H), 8.32 (s, 1H), 7.66 (d, 1H), 7.36-7.25 (m, 2H), 7.08 (d, 1H), 4.80 (s, 3H), 3.82 (m, 2H), 3.20 (s, 1H), 2.65 (t, 2H), 1.95 (m, 2H), 1.05 (m, 2H).

Example 22

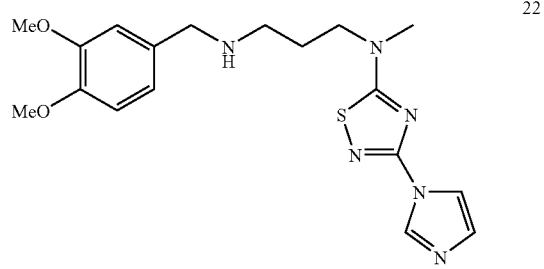

Preparation of compound 22: N'-(3,4-Dimethoxy-benzyl)-N-(3-imidazol-1-yl-[1,2,4]thiadiazol-5-yl)-N-methyl-propane-1,3-diamine was prepared following the procedures described in preparation of Example 7 using 3,4-dimethoxy-benzaldehyde. [M+H]$^+$ 389.02; $^1$H-NMR (400 MHz, CDCl$_3$) δ 8.33 (s, 1H), 7.66 (d, 1H), 7.30 (s, 1H), 7.11 (d, 1H), 6.91 (d, 1H), 6.83 (d, 1H), 3.90 (s, 3H), 3.88 (s, 3H), 3.76 (s, 2H), 3.15 (bs, 3H), 2.73 (t, 2H), 1.94 (t, 2H).

Example 23

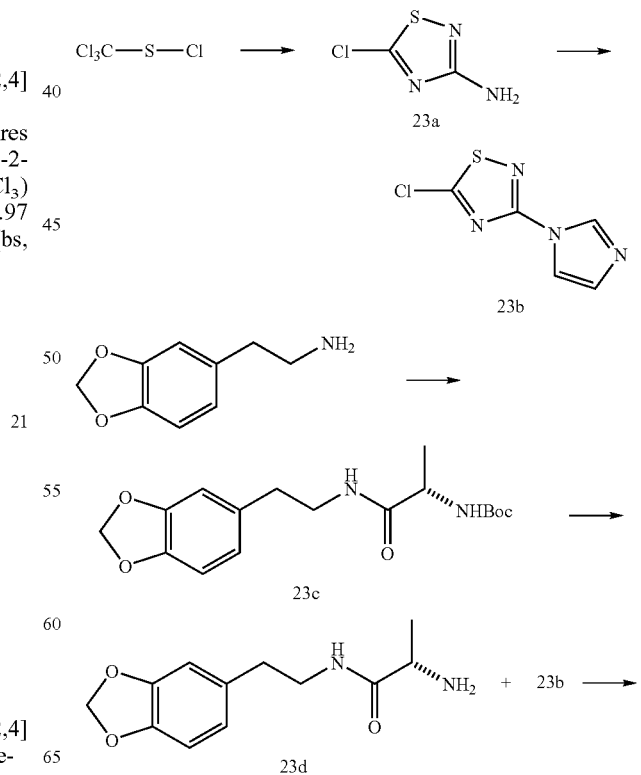

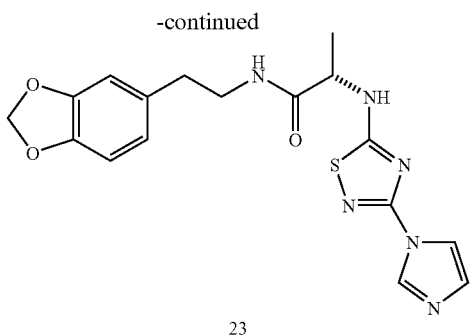

23

Step 1

Preparation of compound 23a: 5-Chloro-[1,2,4]thiadiazol-3-ylamine

Trichloromethanesulfonyl chloride (20.0 g, 107 mmol) and guanidine hydrochloride were added to a −10° C. solution of DCM (200 mL). Next, a solution of NaOH (43 g, 1.08 mmol) in water (43 mL) was added dropwise to the reaction while maintaining the temperature between −10° C. to −20° C. An orange precipitate formed upon addition of the NaOH solution. The reaction was stirred for 3 hours at −10° C. The reaction was allowed to equilibrate to room temperature while stirring overnight. The mixture was filtered through celite and the resulting filtrate was transferred to a separatory funnel. The organic layer was partitioned from the aqueous layer. The aqueous layer was back extracted with DCM (100 mL). The organic layers were combined, dried over Na$_2$SO$_4$ and concentrated. The crude material was purified by flash chromatography (DCM to 9:1 DCM/MeOH) to afford 2.15 g (4%) of 5-chloro-[1,2,4]thiadiazol-3-ylamine.

Step 2

Preparation of compound 23b: 5-Chloro-3-imidazol-1-yl-[1,2,4]thiadiazole

5-Chloro-[1,2,4]thiadiazol-3-ylamine (1.00 g, 7.40 mmol) and glyoxal 40% wt (5.35 g, 92.0 mmol) were dissolved in ethanol (100 mL). The solution was stirred at 80° C. for 4 hours. Ammonium chloride (1.97 g, 37.0 mmol), formaldehyde (2.97 g, 37.0 mmol) and phosphoric acid (2.97 g, 30.0 mmol) were added to the solution and stirred overnight. The reaction was concentrated down under vacuo and redissolved in water (50 mL). The solution was extracted with ethyl acetate (2×50 mL). The aqueous layer was neutralized with 1M NaOH, extracted with ethyl acetate (2×50 mL), dried over MgSO$_4$ and concentrated under vacuo to afford 200 mg (20%) of 5-chloro-3-imidazol-1-yl-[1,2,4]thiadiazole. $^1$H-NMR (400 MHz, CDCl$_3$) δ 8.84 (s, 1H), 7.75 (d, 1H), 7.22 (d, 1H).

Step 3

Preparation of compound 23c: (S)—[1-(2-Benzo[1,3]dioxol-5-yl-ethylcarbamoyl)-ethyl]-carbamic acid tert-butyl ester Boc-Ala-OH (222 mg, 1.20 mmol) was dissolved in DCE (4 mL), followed by addition of CDI (209 mg, 1.20 mmol). The mixture was stirred at room temperature for 30 min. 3,4-Methylenedioxyphenethylamine hydrochloride (240 mg, 1.20 mmol) and TEA (2.4 mmol) were added and the reaction was stirred at room temperature under Nitrogen for 16 hours. Next, the reaction mixture was concentrated under reduced pressure and the residue was dissolved in DCM and transferred to a separatory funnel and washed with saturated NaHCO$_3$ (aq). The organic layer was dried with Na$_2$SO$_4$ and concentrated down. The crude material was purified by flash chromatography (DCM to 9:1 DCM/MeOH) to yield 350 mg (88%) of (S)—[1-(2-benzo[1,3]dioxol-5-yl-ethylcarbamoyl)-ethyl]-carbamic acid tert-butyl ester. [M+H]$^+$ 337.05.

Step 4

Preparation of compound 23d: (S)-2-Amino-N-(2-benzo[1,3]dioxol-5-yl-ethyl)-propionamide

[1-(2-Benzo[1,3]dioxol-5-yl-ethylcarbamoyl)-ethyl]-carbamic acid tert-butyl ester (350 mg, 1.04 mmol) was dissolved in TFA:DCM (1:1, 4 mL) and allowed to stir at room temperature for 2 h. After this time, the solution was concentrated down under N$_2$ gas and dissolved in DCM. The solution was washed several times with 1M NaOH (aq). The organic layer was dried with Na$_2$SO$_4$ and concentrated down under N$_2$. The crude material was purified by flash chromatography (DCM to 9:1 DCM/MeOH) to afford 189 mg (77% yield) of (S)-2-amino-N-(2-benzo[1,3]dioxol-5-yl-ethyl)-propionamide. [M+H]$^+$ 237.10.

Step 5

Preparation of compound 23: (S)—N-(2-Benzo[1,3]dioxol-5-yl-ethyl)-2-(3-imidazol-1-yl-[1,2,4]thiadiazol-5-ylamino)-propionamide 2-Amino-N-(2-benzo[1,3]dioxol-5-yl-ethyl)-propionamide (190 mg, 0.80 mmol) was dissolved in DMSO (2 mL) followed by addition of Example 23b (74 mg, 0.40 mmol) and TEA (0.8 mmol). The reaction mixture was stirred at room temperature for 16 hours. After this time, reaction was stopped and transferred to a separatory funnel. Brine was added and the product was extracted into ethyl acetate. The ethyl acetate was dried over Na$_2$SO$_4$ and concentrated to afford the crude material. This material was then purified by flash chromatography (DCM to 9:1 DCM/MeOH) to yield 77 mg (50%). [M+H]$^+$ 386.94; $^1$H-NMR (400 MHz, CD$_3$OD) δ 8.36 (s, 1H), 7.77 (s, 1H), 7.11 (s, 1H), 6.68 (s, 1H), 6.61 (d, 2H), 5.86 (dd, 2H), 3.47 (t, 2H), 2.75 (t, 2H), 1.46 (d, 3H).

Example 24

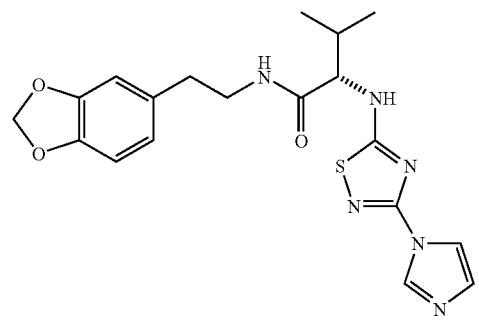

24

Preparation of compound 24: (S)—N-(2-Benzo[1,3]dioxol-5-yl-ethyl)-2-(3-imidazol-1-yl-[1,2,4]thiadiazol-5- ylamino)-3-methyl-butyramide was prepared following the procedures described in preparation of Example 23 using Boc-Val-OH. [M+H]+ 414.98. ¹H-NMR (400 MHz, CDCl₃) δ 8.52 (s, 1H), 7.72 (s, 1H) 7.00 (s, 1H), 6.62 (d, 1H), 6.58 (d, 1H), 5.98 (s, 1H), 5.91 (dd, 2H), 3.51 (t, 2H), 2.79 (t, 2H), 1.03 (d, 6H), 1.00 (d, 1H), 0.80 (d, 1H).

Example 25

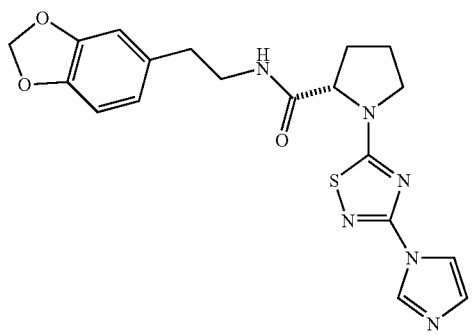

Preparation of compound 25: (S)-1-(3-Imidazol-1-yl-[1,2,4]thiadiazol-5-yl)-pyrrolidine-2-carboxylic acid (2-benzo[1,3]dioxol-5-yl-ethyl)-amide was prepared following the procedures described in preparation of Example 23 using Boc-Pro-OH. [M+H]+ 412.98; ¹H-NMR (400 MHz, CDCl₃) δ 8.19 (s, 1H), 7.59 (s, 1H), 7.04 (s, 1H), 6.54 (d, 1H), 6.53 (s, 1H), 6.43 (d, 1H), 5.93 (dd, 2H), 3.58 (m, 1H), 3.45 (t, 2H), 2.70 (t, 2H), 2.42 (t, 2H), 2.20 (m, 4H).

Example 26

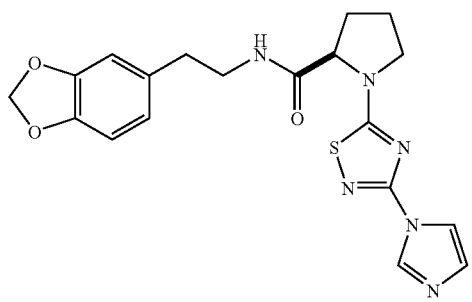

Preparation of compound 26: (R)-1-(3-Imidazol-1-yl-[1,2,4]thiadiazol-5-yl)-piperidine-2-carboxylic acid (2-benzo[1,3]dioxol-5-yl-ethyl)-amide was prepared following the procedures described in preparation of Example 23 using (R)-(+)-N-Boc-2-piperidine carboxylic acid. [M+H]+ 426.56; ¹H-NMR (400 MHz, CDCl₃) δ 8.23 (s, 1H), 7.59 (s, 1H), 7.01 (s, 1H), 6.59 (d, 1H), 6.58 (s, 1H), 6.45 (d, 1H), 5.84 (dd, 2H), 3.52 (m, 2H), 3.51 (t, 1H), 3.43 (t, 2H), 2.70 (t, 2H), 1.58-1.80 (m, 6H).

Example 27

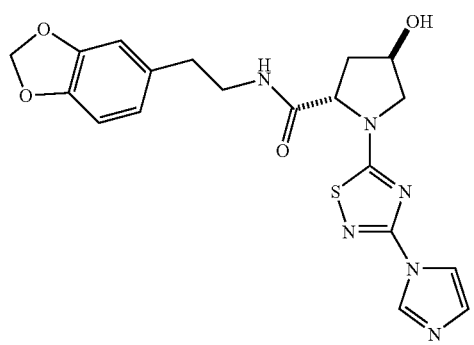

Preparation of compound 27: (2S,4R)-4-Hydroxy-1-(3-imidazol-1-yl-[1,2,4]thiadiazol-5-yl)-pyrrolidine-2-carboxylic acid (2-benzo[1,3]dioxol-5-yl-ethyl)amide was prepared following the procedures described in preparation of Example 23 using trans-N-t-Boc-4-hydroxy-D-proline. [M+H]+ 428.75; ¹H-NMR (400 MHz, CDCl₃) δ 9.35 (s, 1H), 7.81 (s, 1H), 7.40 (s, 1H), 6.59 (s, 1H), 6.51 (s, 1H), 6.58 (d, 1H), 5.82 (dd, 2H), 3.68 (m, 1H), 3.44 (m, 2H), 3.42 (t, 2H), 2.70 (t, 2H) 2.50 (d, 1H), 2.31 (m, 2H).

Example 28

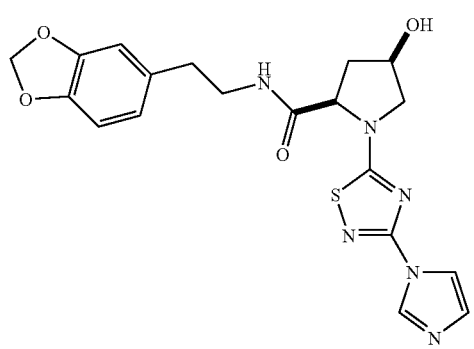

Preparation of compound 28: (2R,4R)-4-Hydroxy-1-(3-imidazol-1-yl-[1,2,4]thiadiazol-5-yl)-pyrrolidine-2-carboxylic acid (2-benzo[1,3]dioxol-5-yl-ethyl)-amide was prepared following the procedures described in preparation of Example 23 using cis-N-t-Boc-4-hydroxy-D-proline. [M+H]+ 428.91; ¹H-NMR (400 MHz, CDCl₃) δ 9.35 (s, 1H), 7.81 (s, 1H), 7.40 (s, 1H), 6.59 (s, 1H), 6.58 (s, 1H), 6.51 (d, 1H), 5.82 (dd, 2H), 3.68 (m, 1H), 3.44 (m, 2H), 3.42 (t, 2H), 2.70 (t, 2H) 2.50 (d, 1H), 2.31 (m, 2H).

Example 29

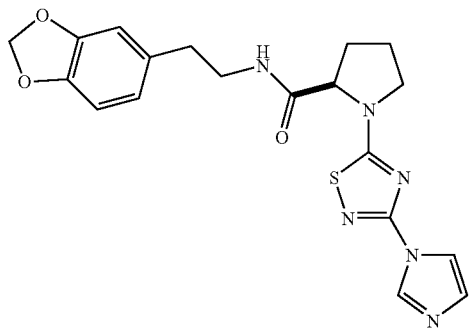

Preparation of compound 29: (R)-1-(3-Imidazol-1-yl-[1,2,4]thiadiazol-5-yl)pyrrolidine-2-carboxylic acid (2-benzo[1,3]dioxol-5-yl-ethyl)-amide was prepared following the procedures described in preparation of Example 23 using Boc-D-pro-OH. [M+H]+ 412.93; 1H-NMR (400 MHz, CDCl3) δ 8.19 (s, 1H), 7.59 (s, 1H), 7.04 (s, 1H), 6.54 (d, 1H), 6.53 (s, 1H), 6.43 (d, 1H), 5.93 (dd, 2H), 3.58 (m, 1H), 3.45 (t, 2H), 2.70 (t, 2H), 2.42 (t, 2H), 2.20 (m, 4H).

Example 30

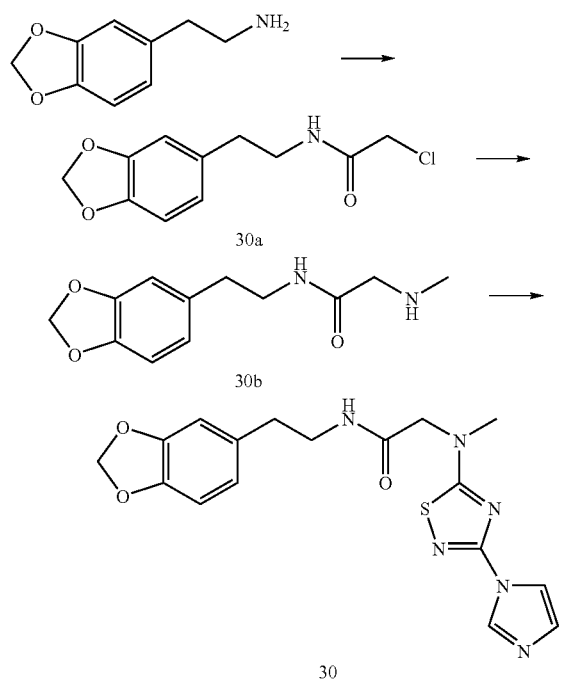

Step 1

Preparation of compound 30a: N-(2-Benzo[1,3]dioxol-5-yl-ethyl)-2-chloro-acetamide 3,4-Methylenedioxyphenethylamine hydrochloride (101 mg, 0.5 mmol) was dissolved in DCE (2 mL) and TEA (70 µL). Next, chloroacetyl chloride (48 µL, 0.6 mmol) was added and the reaction was allowed to stir at room temperature for 16 hours. After this time, the solution was concentrated down under N2. The residue was redissolved in DCM, washed with sat. NaHCO3 (aq) and dried over Na2SO4. The crude residue was purified by Prep-LCMS to afford 32 mg (27%) of N-(2-benzo[1,3]dioxol-5-yl-ethyl)-2-chloro-acetamide. 1H-NMR (400 MHz, CDCl3) δ 6.75-6.62 (m, 3H), 5.92 (s, 2H), 4.01 (s, 2H), 3.52-3.47 (m, 2H), 2.79-2.72 (t, 2H).

Step 2

Preparation of compound 30b: N-(2-Benzo[1,3]dioxol-5-yl-ethyl)-2-methylamino-acetamide N-(2-Benzo[1,3]dioxol-5-yl-ethyl)-2-chloro-acetamide (32 mg, 0.13 mmol) was dissolved in methylamine in anhydrous ethanol (33% by wt., 5 mL). The solution was allowed to stir at room temperature for 16 hours. After this time, the solution was concentrated down under N2 gas. The crude material was purified by prep-LCMS to afford 21 mg (68%) of N-(2-benzo[1,3]dioxol-5-yl-ethyl)-2-methylamino-acetamide. 1H-NMR (400 MHz, CD3OD) δ 6.73-6.65 (m, 3H), 5.89 (s, 2H), 3.46-3.39 (t, 2H), 3.31-3.29 (m, 2H), 2.74-2.70 (t, 2H), 2.35 (s, 3H).

Step 3

Preparation of compound 30: N-(2-Benzo[1,3]dioxol-5-yl-ethyl)-2-[(3-imidazol-1-yl-[1,2,4]thiadiamol-5-yl)-methyl-amino]-acetamide was prepared following the procedures described in preparation of Example 23 in Step 3. [M+H]+ 386.84; 1H NMR (400 MHz, CDCl3) δ 8.24 (s, 1H), 7.62 (d, 1H), 7.12 (d, 1H), 6.62-6.48 (m, 3H), 6.00 (s, 1H), 5.82 (s, 2H), 4.18 (s, 2H), 3.45 (m, 2H), 3.12 (s, 3H), 2.65 (m, 2H).

Example 31

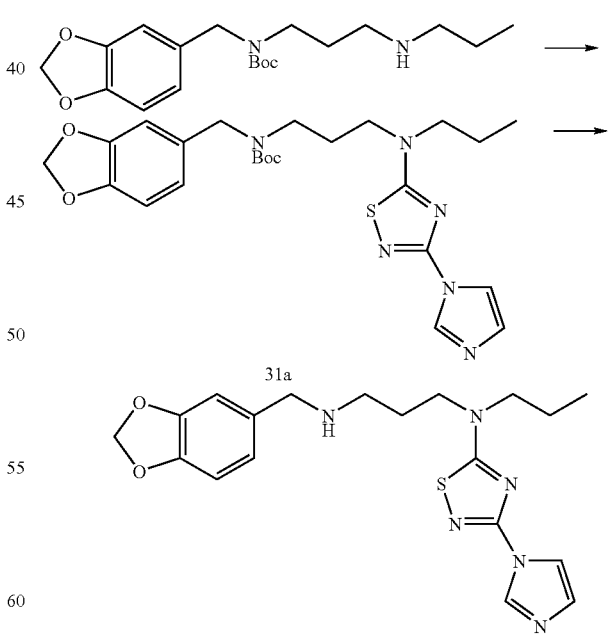

Step 1

Preparation of compound 31a: Benzo[1,3]dioxol-5-ylmethyl-{3-[(3-imidazol-1-yl-[1,2,4]thiadiazol-5-yl)-propylamino]-propyl}-carbamic acid tert-butyl ester was prepared following the procedures described in preparation of Example 30 in Step 3 using benzo[1,3]dioxol-5-ylmethyl-(3-propylamino-propyl)-carbamic acid tert-butyl ester.

Step 2

Preparation of compound 31: N'-Benzo[1,3]dioxol-5-ylmethyl-N-(3-imidazol-1-yl-[1,2,4]thiadiazol-5-yl)-N-propyl-propane-1,3-diamine was prepared following the procedures described in preparation of Example 23 in Step 2. [M+H]$^+$ 400.90; $^1$H-NMR (400 MHz, CDCl$_3$) δ 8.28 (s, 1H), 7.62 (s, 1H), 7.04 (d, 1H), 6.80 (d, 1H), 5.92 (s, 2H), 3.64 (s, 2H), 2.64 (t, 2H), 1.88 (t, 3H), 1.71 (q, 2H), 1.60 (m, 2H), 0.99 (t, 4H).

Example 32

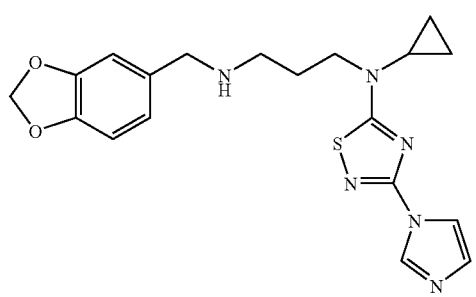

Preparation of compound 32: N'-Benzo[1,3]dioxol-5-ylmethyl-N-cyclopropyl-N-(3-imidazol-1-yl-[1,2,4]thiadiazol-5-yl)-propane-1,3-diamine was prepared following the procedures described in preparation of Example 31 using benzo[1,3]dioxol-5-ylmethyl-(3-cyclopropylamino-propyl)-carbamic acid tert-butyl ester. [M+H]$^+$ 407.10; $^1$H-NMR (400 MHz, CDCl$_3$) δ 8.26 (s, 1H), 7.62 (s, 1H), 7.07 (s, 1H), 7.79 (s, 1H), 6.70 (t, 2H), 5.93 (s, 2H), 3.74 (t, 2H), 3.63 (s, 2H), 2.72 (quin, 1H), 2.65 (2, t), 1.93 (td, 2H), 1.29 (t, 2H), 0.92 (m, 2H).

Example 33

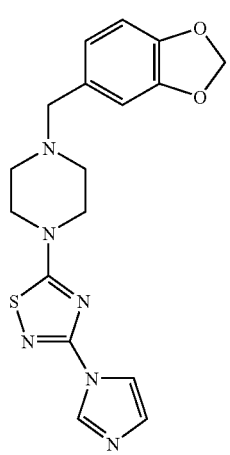

Preparation of compound 33: 1-Benzo[1,3]dioxol-5-ylmethyl-4-(3-imidazol-1-yl-[1,2,4]thiadiazo-5-yl)-piperazine was prepared following the procedures described in preparation of Example 23 in Step 1 using 1-benzo[1,3]dioxol-5-ylmethyl-piperazine. [M+H]$^+$ 370.96; $^1$H-NMR (400 MHz, CDCl$_3$) δ 8.30 (s, 1H), 7.65 (d, 1H), 7.09 (d, 1H), 6.87 (s, 1H), 6.75 (d, 2H), 5.97 (s, 2H), 3.57 (bs, 4H), 2.57 (t, 4H), 1.95 (s, 2H).

Example 34

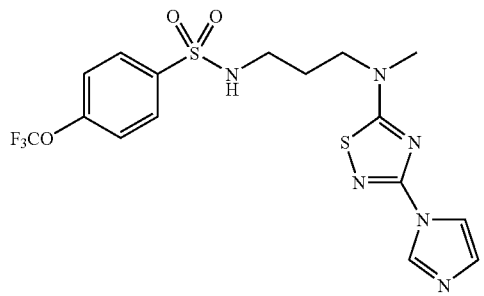

Preparation of compound 34: N-{3-[(3-Imidazol-1-yl-[1,2,4]thiadiazol-5-yl)-methyl-amino]-propyl}-4-trifluoromethoxy-benzenesulfonamide N-1-(3-Imidazol-1-yl-[1,2,4]thiadiazole-5-yl)-N-1-methyl-propane-1,3-diamine (100 mg, 0.43 mmol) was dissolved in DCE (1 mL). Next, 4-(trifluoromethoxy)-benzenesulfonyl chloride (146 µL, 0.86 mmol) and DIEA (150 µL) were added. The reaction was stirred at room temperature for 16 hours. After this time, the solution was concentrated down under N$_2$. The residue was dissolved in DCM and transferred to a separatory funnel. The organic layer was washed with sat. NaHCO$_3$ (aq) and dried over Na$_2$SO$_4$. The organic layer was concentrated under vacuum to afford the crude product. The crude material was purified by preparatory LCMS to afford 34 mg (32%) of N-{3-[(3-imidazol-1-yl-[1,2,4]thiadiazol-5-yl)-methyl-amino]-propyl}-4-trifluoromethoxy-benzenesulfonamide. [M+H]$^+$ 462.83; $^1$H-NMR (400 MHz, CDCl$_3$) δ 9.38 (bs, 1H), 8.01 (d, 1H), 7.91 (d, 2H), 7.43 (s, 1H), 7.36 (d, 2H), 3.30 (s, 3H), 3.08 (t, 2H), 2.00 (t, 2H).

Example 35

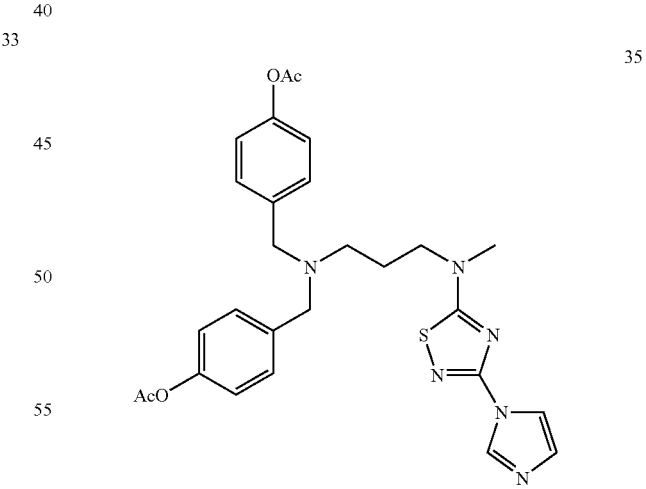

Preparation of compound 35: Acetic acid 4-[((4-acetoxy-benzyl)-{3-[(3-imidazol-1-yl-[1,2,4]thiadiazol-5-yl)-methyl-amino]-propyl}-amino)-methyl]-phenyl ester 4-Acetoxybenzaldehyde (80 mg, 0.49 mmol) and 6 (120 mg, 0.50 mmol) were heated at 80° C. in THF (2 mL) with catalytical amount of p-toluenesulfonic acid (15 mg, 0.09 mmol) for 0.5 h. The solution was cooled to room temperature and glacial acetic acid (0.3 mL) and sodium triacetoxyborohydride (800 mg, 3.8 mmol) was added. The mixture was stirred overnight. Most of the solvent was evaporated under reduced pressure and sat. aqueous sodium carbonate solution was added to make the solution basic (pH 9). The solution was extracted with ethyl acetate, washed with brine and dried over $Na_2SO_4$. Evaporation of solvent and separation by column gave 26 mg (10%) of acetic acid 4-[((4-acetoxy-benzyl)-{3-[(3-imidazol-1-yl-[1,2,4]thiadiazol-5-yl)-methyl-amino]-propyl}-amino)-methyl]-phenyl ester. $[M+H]^+$ 536.32; $^1$H-NMR (400 MHz, $CDCl_3$) δ 8.27 (s, 1H), 7.60 (s, 1H), 7.35 (d, 4H), 7.02 (m, 5H), 3.55 (s, 4H), 3.42 (br s, 2H), 2.95 (br s, 2H), 2.48 (t, 2H), 2.29 (s, 6H), 1.83 (t, 2H).

Example 36

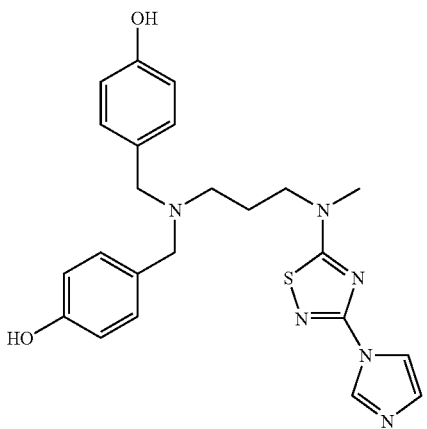

36

Preparation of compound 36: N-(3-Imidazol-1-yl-[1,2,4]thiadiazol-5-yl)-N',N'-bis-(4-hydroxy-benzyl)-N-methyl-propane-1,3-diamine was prepared following the procedures described in preparation of Example 35. $[M+H]^+$ 450.99; $^1$H-NMR (400 MHz, $CD_3OD$) δ 8.28 (s, 1H), 7.65 (s, 1H), 7.10 (d, 4H), 7.03 (s, 1H), 6.72 (d, 4H), 3.36 (m, 7H), 2.95 (br s, 2H), 2.38 (m, 2H), 1.77 (m, 2H).

Example 37

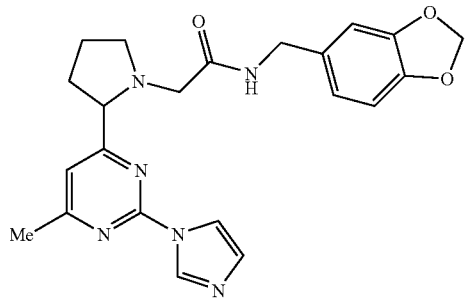

37

Preparation of compound 37: N-Benzo[1,3]dioxol-5-ylmethyl-2-[2-(2-imidazol-1-yl-6-methyl-pyrimidin-4-yl)-pyrrolidin-1-yl]-acetamide A solution of 3f (4 mg, 0.02 mmol) and N-benzo[1,3]dioxol-5-ylmethyl-2-chloro-acetamide (4 mg, 0.02 mmol) in DMF (0.5 mL) and TEA (0.2 mL) was heated at 60° C. for 20 h. Water was added and the mixture was extracted with ethyl acetate, washed with brine and dried over $Na_2SO_4$. Evaporation of the solvent gave the residue which was purified by TLC plate to give 5 mg (60%) of N-benzo[1,3]dioxol-5-ylmethyl-2-[2-(2-imidazol-1-yl-6-methyl-pyrimidin-4-yl)-pyrrolidin-1-yl]-acetamide. $[M+H]^+$ 421.09.

Example 38

Step 1

Preparation of compound 38a: Benzo[1,3]dioxol-5-ylmethyl-{1-(2-imidazol-1-yl-6-methyl-pyrimidin-4-yl)-ethylamino]-ethyl}-carbamic acid tert-butyl ester A solution of 1i (0.28 g, 1.4 mmol) and (2-amino-ethyl)-benzo[1,3]dioxol-5-ylmethyl-carbamic acid tert-butyl ester (0.40 g, 1.4 mmol) in dry benzene (6 mL) and THF (3 mL) with catalytic amount of p-toluenesulfonic acid was heated at 65-70° C. for 4 h then cooled to r.t and stirred for 12 h under nitrogen. MeOH (3 mL) and $NaHB(OAc)_3$ (1.8 g, 8.5 mmol) were added and the reaction was stirred for 4 hour. Water was added and the solution was extracted with ethyl acetate (100 mL×2), washed with brine and dried over $Na_2SO_4$. Evaporation of the solvent and purification by column chromatography gave 155 mg (23%) of benzo[1,3]dioxol-5-ylmethyl-{2-

[1-(2-imidazol-1-yl-6-methyl-pyrimidin-4-yl)-ethylamino]-ethyl}-carbamic acid tert-butyl ester as a clear oil. [M+H]+ 481.00.

Step 2

Preparation of compound 38: N-Benzo[1,3]dioxol-5-ylmethyl-N'-[1-(2-imidazol-1-yl-6-methyl-pyrimidin-4-yl)-ethyl]-ethane-1,2-diamine A solution of benzo[1,3]dioxol-5-ylmethyl-{2-[1-(2-imidazol-1-yl-6-methyl-pyrimidin-4-yl)-ethylamino]-ethyl}-carbamic acid tert-butyl ester (155 mg, 0.320 mmol) in DCM/TFA (50%, 5 mL) was stirred for 0.5 h. The solvent was evaporated and sat. aqueous $K_2CO_3$ solution was added. The mixture was extracted with ethyl acetate, washed with brine and dried over $Na_2SO_4$. Evaporation of the solvent gave 110 mg (90%) of N-benzo[1,3]dioxol-5-ylmethyl-N'-[1-(2-imidazol-1-yl-6-methyl-pyrimidin-4-yl)-ethyl]-ethane-1,2-diamine as a red oil. [M+H]+ 380.96; 1H-NMR (400 MHz, $CDCl_3$) δ 8.59 (s, 1H), 7.87 (s, 1H), 7.09 (s, 1H), 7.05 (s, 1H), 6.79 (s, 1H), 6.71 (s, 2H), 5.90 (s, 2H), 3.74 (q, 1H), 3.66 (s, 2H), 2.70-2.50 (m, 6H), 2.2 (br s, 2H), 1.37 (d, 3H); 13C-NMR (100 MHz, $CDCl_3$) δ 175.6, 170.0, 154.6, 147.9, 146.8, 136.4, 134.2, 130.5, 121.4, 116.8, 115.6, 108.8, 108.3, 101.1, 58.8, 53.8, 48.9, 47.4, 24.4, 22.4.

Example 39 rolidin-1-yl]-ethyl}-carbamic acid tert-butyl ester was prepared following the procedures described in the preparation of Example 3 using 3f.

Step 2

Preparation of compound 39: Benzo[1,3]dioxol-5-ylmethyl-{2-[2-(2-imidazol-1-yl-6-methyl-pyrimidin-4-yl)-pyrrolidin-1-yl]-ethyl}-amine was prepared following the procedures described in the preparation of Example 38 in Step 2. [M+H]+ 406.97; 1H-NMR (400 MHz, $CDCl_3$) δ 8.54 (s, 1H), 7.83 (s, 1H), 7.49 (s, 1H), 7.04 (s, 1H), 6.71 (s, 1H), 6.64 (m, 2H), 5.85 (s, 2H), 3.60-3.20 (m, 5H), 2.80-2.20 (m, 9H), 1.90-1.60 (m, 2H); 13C-NMR (100 MHz, $CDCl_3$) δ 175.6, 170.0, 154.2, 147.9, 146.8, 136.4, 133.7, 130.2, 121.4, 116.9, 115.4, 108.7, 108.2, 101.1, 69.9, 54.6, 54.2, 53.7, 50.2, 47.6, 33.6, 24.4, 23.7.

Example 40

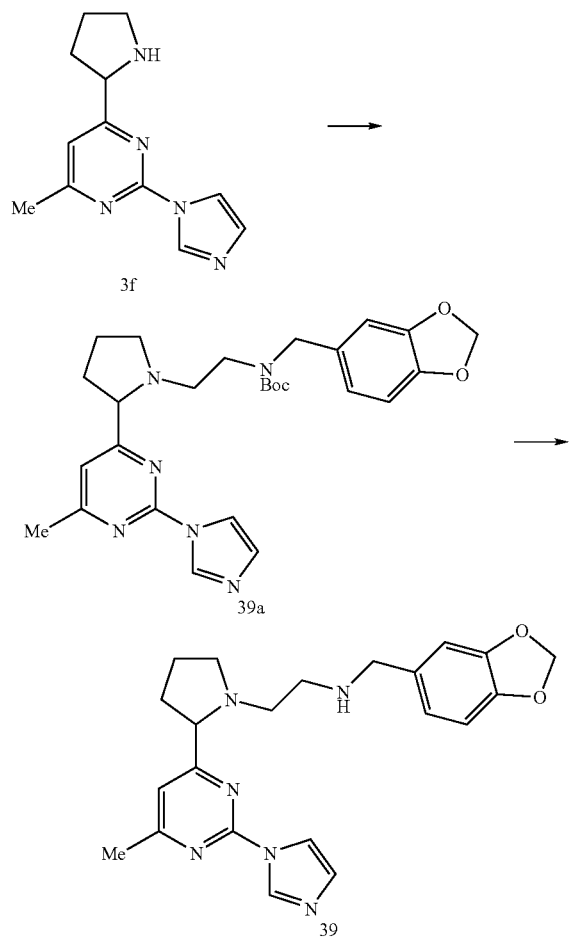

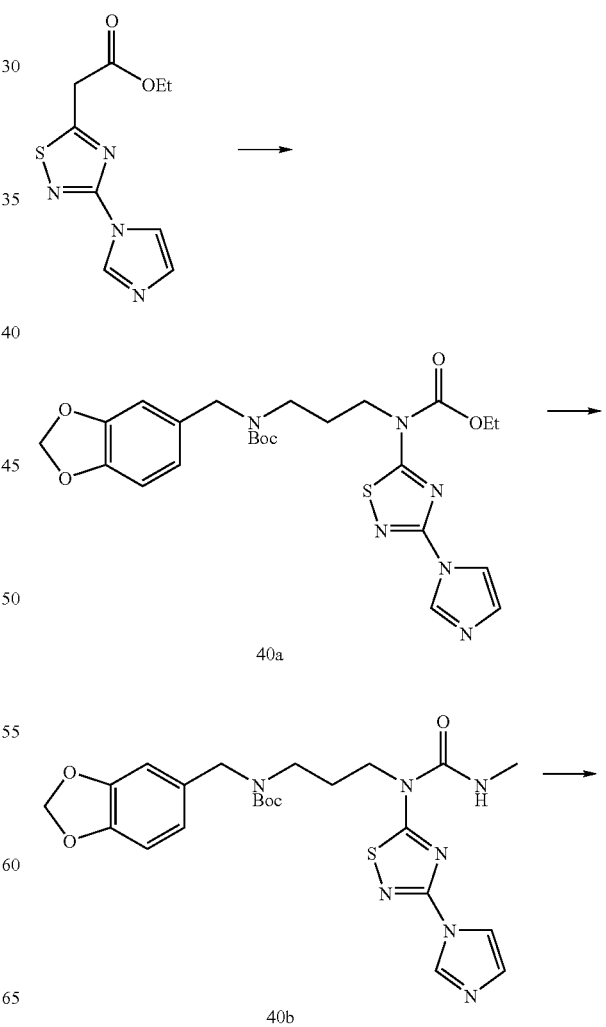

Step 1
Preparation of compound 39a: Benzo[1,3]dioxol-5-ylmethyl-{2-[2-(2-imidazol-1-yl-6-methyl-pyrimidin-4-yl)-pyr-

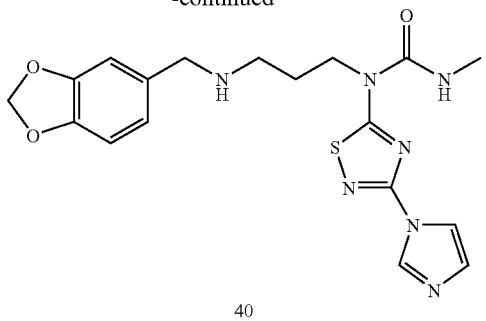

Step 1

Preparation of compound 40a: 5-(Benzo[1,3]dioxol-5-ylmethyl-tert-butoxycarbonyl-amino)-2-(3-imidazol-1-yl-[1,2,4]thiadiazol-5-yl)-pentanoic acid ethyl ester To a solution of (3-imidazol-1-yl-[1,2,4]thiadiazol-5-yl)-acetic acid ethyl ester (240 mg, 1.0 mmol) in DMSO (2 mL) was added NaH (70 mg of a 60% dispersion on mineral oil, 1.8 mmol) and benzo[1,3]dioxol-5-ylmethyl-(3-bromo-propyl)-carbamic acid tert-butyl ester (370 mg, 1.0 mmol) subsequently. The solution was stirred for 2 h at 60° C. Water (4 mL) was added and the solution was extracted with ethyl acetate, washed with brine and dried over $Na_2SO_4$. Evaporation of the solvent gave a residue which was purified by column chromatography to afford 370 mg (70%) of 5-(benzo[1,3]dioxol-5-ylmethyl-tert-butoxycarbonyl-amino)-2-(3-imidazol-1-yl-[1,2,4]thiadiazol-5-yl)-pentanoic acid ethyl ester as a red oil.

Step 2

Preparation of compound 40b: 5-(Benzo[1,3]dioxol-5-ylmethyl-tert-butoxycarbonyl-amino)-2-(3-imidazol-1-yl-[1,2,4]thiadiazol-5-yl)-pentanoic acid ethyl ester A solution of 5-(benzo[1,3]dioxol-5-ylmethyl-tert-butoxycarbonyl-amino)-2-(3-imidazol-1-yl-[1,2,4]thiadiazol-5-yl)-pentanoic acid ethyl ester (150 mg, 0.28 mmol) in methylamine/ethanol (33 wt %, 10 mL) was heated to 95° C. in a microwave reactor for 90 min. The solvent was evaporated and the residue was purified by preparatory TLC to give 86 mg (60%) of 5-(benzo[1,3]dioxol-5-ylmethyl-tert-butoxycarbonyl-amino)-2-(3-imidazol-1-yl-[1,2,4]thiadiazol-5-yl)-pentanoic acid ethyl ester. $[M+H]^+$ 515.05.

Step 3

Preparation of compound 40: 5-[(Benzo[1,3]dioxol-5-ylmethyl)-amino]-2-(3-imidazol-1-yl-[1,2,4]thiadiazol-5-yl)-pentanoic acid methylamide was prepared following the procedures described in the preparation of Example 38 in Step 2. $[M+H]^+$ 415.03; $^1$H-NMR (400 MHz, $CD_3OD$) 8.48 (s, 1H), 7.84 (s, 1H), 7.13 (s, 1H), 6.80 (s, 1H), 6.70 (m, 2H), 5.89 (s, 2H), 3.59 (s, 2H), 3.30 (m, 1H), 2.80 (s, 3H), 2.54 (t, 2H), 2.05-1.98 (m, 2H), 1.62-1.50 (m, 2H); $^{13}$C-NMR (100 MHz, $CD_3OD$) δ 172.5, 158.9, 148.0, 147.0, 136.4, 133.2, 129.2, 129.0, 121.7, 117.7, 108.6, 107.8, 101.1, 52.9, 33.5, 26.1, 25.4.

Example 41

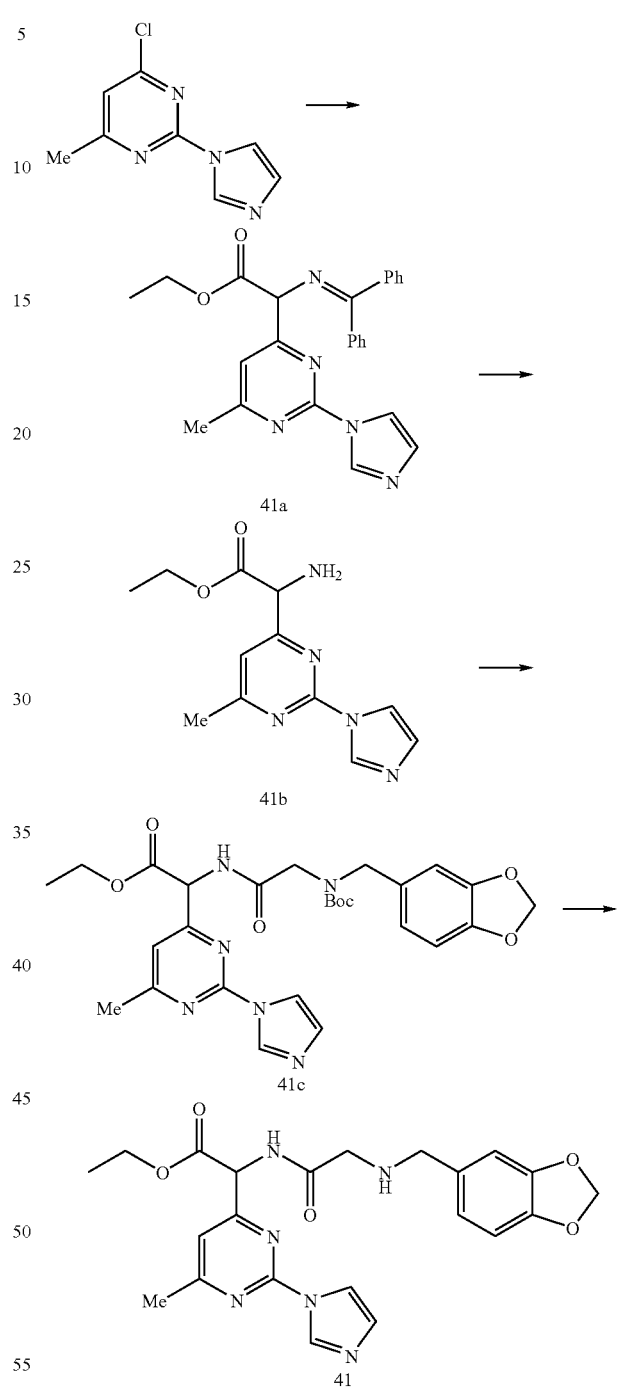

Step 1

Preparation of compound 41a: (Benzhydrylidene-amino)-(2-imidazol-1-yl-6-methyl-pyrimidin-4-yl)-acetic acid ethyl ester To a solution of (benzhydrylidene-amino)-acetic acid ethyl ester (2.67 g, 10.0 mmol) in DMSO (50 mL) was added NaH (600 mg of a 60% dispersion on mineral oil, 15.0 mmol)

slowly at r.t. under nitrogen and the mixture was stirred for 5 min. Then a solution of 4-chloro-2-imidazol-1-yl-6-methyl-pyrimidine (1.95 g, 10.0 mmol) in DMSO (15 mL) was added and the reaction mixture stirred at r.t overnight. Water was added and the solution was extracted with ethyl acetate, washed with brine and dried over Na₂SO₄. Evaporation of the solvent gave residue which was purified by column chromatography to give 1.30 g (31%) of (benzhydrylidene-amino)-(2-imidazol-1-yl-6-methyl-pyrimidin-4-yl)-acetic acid ethyl ester. [M+H]⁺ 426.18.

Step 2

Preparation of compound 41b: Amino-(2-imidazol-1-yl-6-methyl-pyrimidin-4-yl)-acetic acid ethyl ester A solution of (benzhydrylidene-amino)-(2-imidazol-1-yl-6-methyl-pyrimidin-4-yl)-acetic acid ethyl ester (460 mg, 1.10 mmol) in THF (4 mL), water (3 mL) and hydrochloride acid (1 mL, 37%) was stirred at r.t for 0.5 h. The saturated K₂CO₃ solution was added to make the solution basic (pH 9). The mixture was extracted with ethyl acetate (2×100 mL), washed with brine and dried over Na₂SO₄. Evaporation of the solvent and purification by column chromatography gave 200 mg (70%) of amino-(2-imidazol-1-yl-6-methyl-pyrimidin-4-yl)-acetic acid ethyl ester. [M+H]⁺ 262.64.

Step 3

Preparation of compound 41c: [2-(Benzo[1,3]dioxol-5-yl-methyl-tert-butoxycarbonyl-amino)-acetylamino]-(2-imidazol-1-yl-6-methyl-pyrimidin-4-yl)-acetic acid ethyl ester was prepared following the procedures described in the preparation of Example 14a.

Step 4

Preparation of compound 41: {2-[(Benzo[1,3]dioxol-5-yl-methyl)-amino]-acetylamino}-(2-imidazol-1-yl-6-methyl-pyrimidin-4-yl)-acetic acid ethyl ester was prepared following the procedures described in the preparation of Example 38 in Step 2. [M+H]⁺ 453.01; ¹H-NMR (400 MHz, CDCl₃) δ 8.66 (d, 1H), 8.51 (s, 1H), 7.18 (s, 1H), 7.06 (s, 1H), 6.72 (s, 1H), 6.70 (m, 2H), 5.86 (s, 2H), 5.64 (d, 1H), 4.20 (m, 2H) 3.70 (q, 2H), 3.34 (m, 2H), 2.53 (s, 3H), 1.20 (t, 3H); ¹³C-NMR (100 MHz, CDCl₃) δ 171.9, 171.1, 168.4, 164.9, 154.5, 148.0, 147.0, 136.4, 133.3, 130.7, 121.6, 117.5, 116.8, 108.8, 108.4, 101.2, 62.7, 56.5, 53.9, 51.8, 24.4, 14.3.

Example 42

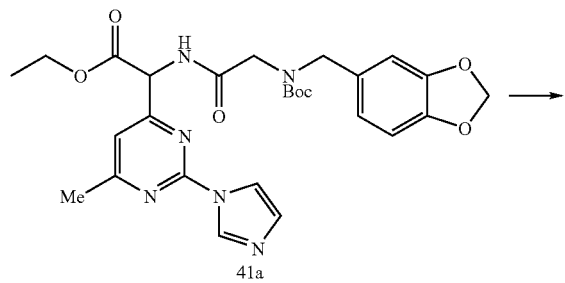

41a

-continued

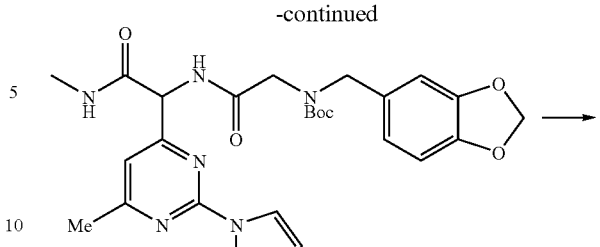

42b

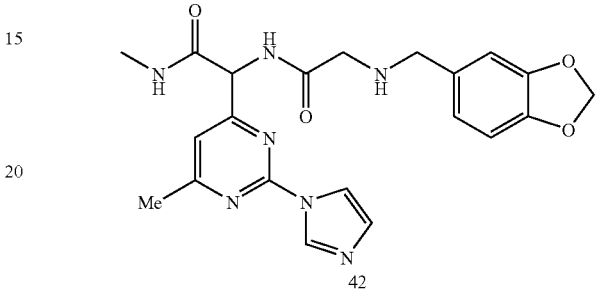

42

Step 1

Preparation of compound 42a: Benzo[1,3]dioxol-5-ylm-ethyl-({[(2-imidazol-1-yl-6-methyl-pyrimidin-4-yl)-methyl-carbamoyl-methyl]-carbamoyl}-methyl)-carbamic acid tert-butyl ester was prepared following the procedures described in the preparation of Example 40 in Step 2.

Step 2

Preparation of compound 42: 2-{2-[(Benzo[1,3]dioxol-5-ylmethyl)-amino]-acetylamino}-2-(2-imidazol-1-yl-6-methyl-pyrimidin-4-yl)-N-methyl-acetamide was prepared following the procedures described in the preparation of Example 38 in Step 2. [M+H]⁺ 437.98; ¹H-NMR (400 MHz, (CDCl₃) 8.86 (d, 1H), 8.57 (s, 1H), 7.81 (s, 1H), 7.09 (s, 1H), 7.06 (s, 1H), 6.83 (s, 1H), 6.71 (m, 2H), 5.91 (s, 2H), 5.50 (d, 1H), 3.73 (m, 2H), 3.40 (m, 2H), 2.78 (s, 3H), 2.50 (s, 3H); ¹³C-NMR (100 MHz, CDCl₃) δ 172.6, 171.0, 167.8, 166.3, 154.1, 148.1, 147.1, 136.4, 133.2, 130.6, 121.7, 116.8, 115.6, 108.9, 108.4, 101.2, 57.5, 54.1, 51.9, 26.9, 24.5.

Example 43

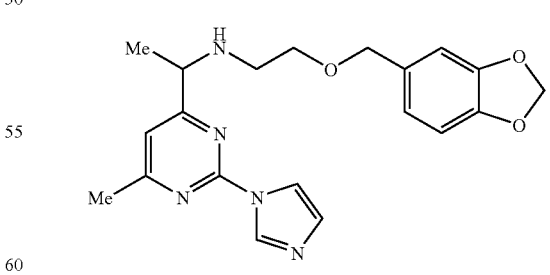

43

Preparation of compound 43: [2-(Benzo[1,3]dioxol-5-yl-methoxy)-ethyl]-[1-(2-imidazol-1-yl-6-methyl-pyrimidin-4-yl)-ethyl]-amine was prepared following the procedures described in the preparation of Example 38 in Step 1 using 1i and 2-(benzo[1,3]dioxol-5-ylmethoxy)-ethylamine. [M+H]⁺ 382.89; ¹H NMR (400 MHz, d₆-DMSO) δ 8.55 (s, 1H), 7.91

(d, 1H), 7.47 (s, 1H), 7.37 (s, 1H), 7.11 (d, 1H), 6.87-6.75 (m, 2H), 5.99 (s, 2H), 4.68 (q, 1H), 4.33 (s, 2H), 3.44 (t, 2H), 2.64 (t, 2H), 2.45 (s, 2H), 1.42 (d, 3H).

Example 44

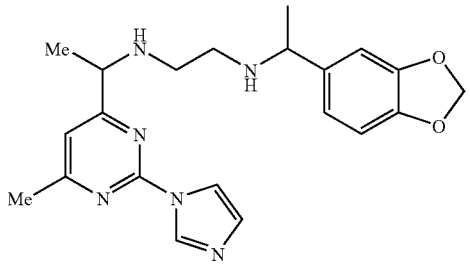

44

Preparation of compound 44: N-(1-Benzo[1,3]dioxol-5-yl-ethyl)-N'-[1-(2-imidazol-1-yl-6-methyl-pyrimidin-4-yl)-ethyl]-ethane-1,2-diamine 3,4-(Methylenedioxy)acetophenone (95.0 mg, 577 μmol) and (2-amino-ethyl)-[1-(2-imidazol-1-yl-6-methyl-pyrimidin-4-yl)-ethyl]-carbamic acid tert-butyl ester (200 mg, 577 μmol) were heated to 70° C. in 1,4-dioxane (4 mL) under a nitrogen atmosphere for 16 h. The reaction was then cooled to r.t. and NaHB(OAc)$_3$ (367 mg, 1.73 mmol) was added. After stirring for an additional hour, water was added and the solution was extracted with ethyl acetate (2×50 mL), washed with brine and dried over Na$_2$SO$_4$. Evaporation of the solvent gave a yellow residue which was dissolved in TFA/DCM (1:1, 5 mL) and stirred at room temperature for 30 min. The solvent was evaporated to afford an orange residue. The crude product was diluted with EtOAc (50 mL), washed with 1M NaOH (50 mL), brine (50 mL), dried over Na$_2$SO$_4$, filtered and concentrated to an oil. Purification was achieved using column chromatography (CH$_2$Cl$_2$ to 4:1 CH$_2$Cl$_2$/MeOH) to afford 198 mg (87%) of N-(1-benzo[1,3]dioxol-5-yl-ethyl)-N'-[1-(2-imidazol-1-yl-6-methyl-pyrimidin-4-yl)-ethyl]-ethane-1,2-diamine as a clear glass. [M+H]$^+$ 395.05; $^1$H NMR (400 MHz, CD$_3$OD) δ 8.87 (s, 1H), 8.09 (s, 1H), 7.42 (s, 1H), 7.36 (s, 1H), 7.00 (d, 1H), 6.91 (dd, 1H), 6.78 (dd, 1H), 5.96 (s, 2H), 4.30 (q, 1H), 3.57 (m, 2H), 3.38 (q, 1H), 2.73 (m, 4H), 2.60 (s, 3H), 1.60 (d, 3H), 1.48 (d, 3H).

Example 45

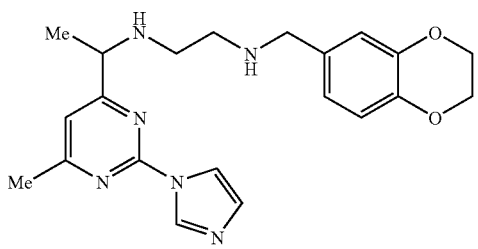

45

Preparation of compound 45: N-(2,3-Dihydro-benzo[1,4]dioxin-6-ylmethyl)-N'-[1-(2-imidazol-1-yl-6-methyl-pyrimidin-4-yl)-ethyl]-ethane-1,2-diamine was prepared following the procedures described in the preparation of Example 44 using 1,4-benzodioxane-6-carboxaldehyde. [M+H]$^+$ 395.10; $^1$H NMR (400 MHz, d$_6$-DMSO) δ 8.60 (s, 1H), 7.96 (s, 1H), 7.40 (s, 1H), 7.14 (s, 1H), 6.86 (s, 1H), 6.79 (m, 2H), 4.22 (s, 4H), 3.75 (q, 1H), 3.66 (s, 2H), 3.36 (br s, 2H), 2.63-2.58 (m, 4H), 2.54 (s, 3H), 1.31 (d, 3H).

Example 46

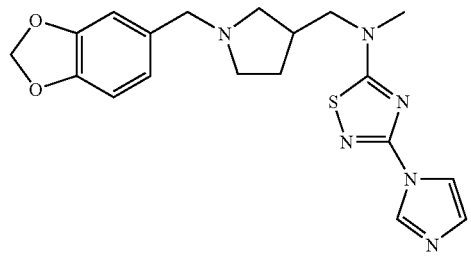

46

Preparation of compound 46: (1-Benzo[1,3]dioxol-5-ylmethyl-pyrrolidin-3-ylmethyl)-(3-imidazol-1-yl-[1,2,4]thiadiazol-5-yl)-methyl-amine was prepared following the procedures described in the preparation of Example 23 in Step 3 using (1-benzo[1,3]dioxol-5-ylmethyl-pyrrolidin-3-ylmethyl)-methyl-amine and 5-chloro-3-imidazol-1-yl-[1,2,4]thiadiazole. [M+H]$^+$ 398.99; $^1$H NMR (400 MHz, CDCl$_3$) δ 8.28 (s, 1H), 7.63 (s, 1H), 7.06 (s, 1H), 6.81 (s, 1H), 6.70-6.67 (m, 2H), 5.89 (s, 2H), 3.14 (s, 2H), 2.92 (s, 2H), 2.90 (m, 2H), 2.65-2.47 (m, 2H), 2.58 (s, 3H), 2.00 (m, 2H), 1.72 (m, 1H).

Example 47

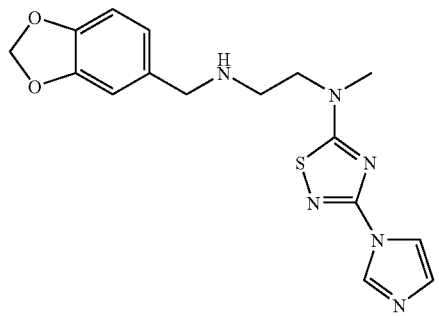

47

Preparation of compound 47: N'-Benzo[1,3]dioxol-5-ylmethyl-N-(3-imidazol-1-yl-[1,2,4]thiadiazol-5-yl)-N-methyl-ethane-1,2-diamine A solution of benzo[1,3]dioxol-5-ylmethyl-(2-methylamino-ethyl)-carbamic acid tert-butyl ester (200 mg, 649 μmol), 5-chloro-3-imidazol-1-yl-[1,2,4]thiadiazole (121 mg, 649 μmol) and TEA (181 μL, 1.30 mmol) in DMSO (6 mL) was stirred at r.t. for 21 h. Water (50 mL) was added and the solution was extracted with ethyl acetate (2×25 mL), washed with brine, dried over Na$_2$SO$_4$, filtered and concentrated to a clear oil. The crude residue was dissolved in TFA/DCM (1:1, 4 mL) and stirred at room temperature for 30 min. The solvent was evaporated to afford an orange oil. The crude product was diluted with EtOAc (50 mL), washed with 1M NaOH (50 mL), brine (50 mL), dried over Na$_2$SO$_4$, filtered and concentrated to an oil. Purification was achieved using column chromatography (CH$_2$Cl$_2$ to 4:1 CH$_2$Cl$_2$/MeOH) to afford 21.3 mg (9%) of N'-benzo[1,3]dioxol-5-ylmethyl-N-(3-imidazol-1-yl-[1,2,4]thiadiazol-5-yl)-N-methyl-ethane-1,2-diamine as a white solid. [M+H]$^+$ 358.92; $^1$H NMR (400 MHz, CDCl$_3$) δ 8.30 (s, 1H), 7.64 (s, 1H), 7.07 (s, 1H), 6.81 (s, 1H), 6.73 (m, 2H), 5.92 (s, 2H), 3.76 (s, 3H), 3.65 (br s, 1H), 3.14 (m, 4H), 2.95 (t, 2H).

Example 48

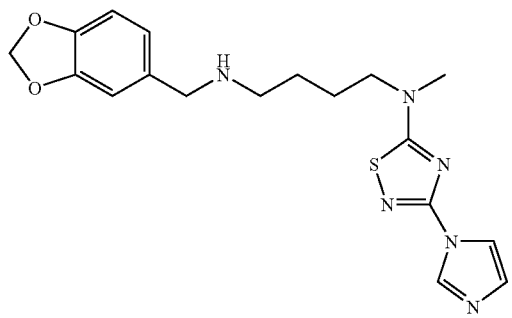

Preparation of compound 48: N'-Benzo[1,3]dioxol-5-ylmethyl-N-(3-imidazol-1-yl-[1,2,4]thiadiazol-5-yl)-N-methyl-butane-1,4-diamine was prepared following the procedures described in the preparation of Example 47 using benzo[1,3]dioxol-5-ylmethyl-(4-methylamino-butyl)-carbamic acid tert-butyl ester. [M+H]$^{30}$ 386.90; $^1$H NMR (400 MHz d$_6$-DMSO) δ 8.34 (s, 1H), 7.75 (s, 1H), 7.11 (s, 1H), 6.93 (s, 1H), 6.86-6.78 (m, 2H), 6.00 (s, 2H), 3.63 (s, 3H), 3.36 (s, 2H) 3.20-3.05 (m, 5H), 1.72 (dtt, 2H), 1.49 (tt, 2H).

Example 49

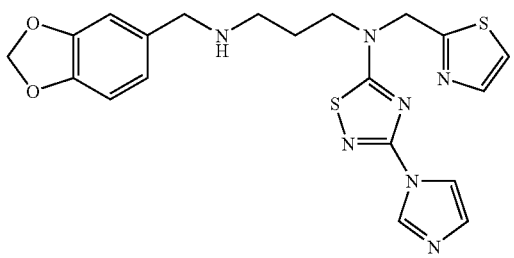

Preparation of compound 49: N'-Benzo[1,3]dioxol-5-ylmethyl-N-(3-imidazol-1-yl-[1,2,4]thiadiazol-5-yl)-N-thiazol-2-ylmethyl-propane-1,3-diamine was prepared following the procedures described in the preparation of Example 47 using benzo[1,3]diox-5-ylmethyl-{3-[(thiazol-2-ylmethyl)-amino]-propyl}-carbamic acid tert-butyl ester. [m+H]$^+$ 455.87; $^1$H NMR (400 MHz, CDCl$_3$) δ 8.33 (s, 1H), 7.74 (d, 1H), 7.66 (s, 1H), 7.33 (d, 1H), 7.09 (s, 1H), 6.83 (s, 1H), 6.73 (m, 2H), 5.92 (s, 2H), 5.03 (br s, 2H), 3.70 (s, 2H), 3.68 (br s, 1H), 3.61 (m, 2H), 2.68 (t, 2H), 1.95 (m, 2H).

Example 50

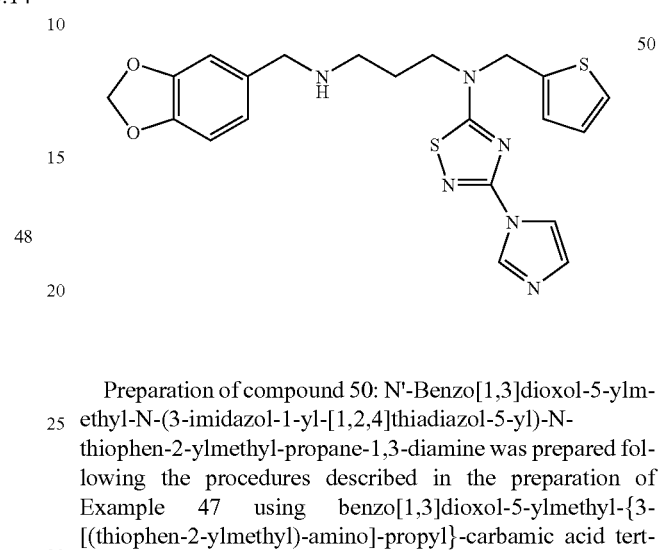

Preparation of compound 50: N'-Benzo[1,3]dioxol-5-ylmethyl-N-(3-imidazol-1-yl-[1,2,4]thiadiazol-5-yl)-N-thiophen-2-ylmethyl-propane-1,3-diamine was prepared following the procedures described in the preparation of Example 47 using benzo[1,3]dioxol-5-ylmethyl-{3-[(thiophen-2-ylmethyl)-amino]-propyl}-carbamic acid tert-butyl ester. [M+H]$^+$ 455.27; $^1$H NMR (400 MHz, CDCl$_3$) δ 8.34 (s, 1H), 7.67 (s, 1H), 7.28 (d, 1H), 7.09 (s, 1H), 7.07 (d, 1H), 6.97 (dd, 1H) 6.86 (s, 1H), 6.78-6.72 (m, 2H), 5.92 (s, 2H), 4.83 (s, 2H), 3.72 (s, 2H), 3.57 (m, 2H) 2.72 (t, 2H), 1.96 (m, 2H).

Example 51

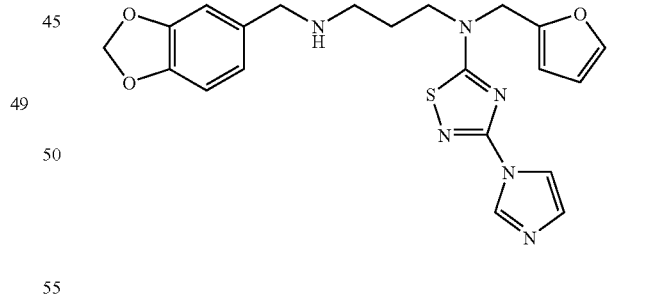

Preparation of compound 51: N'-Benzo[1,3]dioxol-5-ylmethyl-N-furan-2-ylmethyl-N-(3-imidazol-1-yl-[1,2,4]thiadiazol-5-yl)-propane-1,3-diamine was prepared following the procedures described in the preparation of Example 47 using benzo[1,3]dioxol-5-ylmethyl-{3-[(furan-2-ylmethyl)-amino]-propyl}-carbamic acid tert-butyl ester. [M+H]$^+$ 439.40; $^1$H NMR (400 MHz, CDCl$_3$) δ 8.31 (s, 1H), 7.64 (s, 1H), 7.39 (d, 1H), 7.08 (s, 1H), 6.85 (s, 1H), 6.75-6.72 (m, 2H), 6.39-6.34 (m, 2H), 5.93 (s, 2H), 4.60 (s, 2H), 3.73 (s, 2H), 3.61 (s, 2H), 2.70 (t, 2H), 1.95 (m, 2H).

Example 52

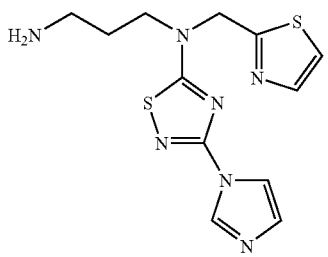

52

Preparation of compound 52: N'-(3-Imidazol-1-yl-[1,2,4]thiadiazol-5-yl)-N'-thiazol-2-ylmethyl-propane-1,3-diamine was prepared following the procedures described in the preparation of Example 47 using {3-[(thiazol-2-ylmethyl)-amino]-propyl}-carbamic acid tert-butyl ester. [M+H]$^+$ 321.94; $^1$H NMR (400 MHz, CDCl$_3$) δ 7.85 (s, 1H), 7.81 (d, 1H), 7.46 (s, 1H), 7.41 (d, 1H), 7.31 (s, 1H), 4.78 (s, 2H), 4.27 (br s, 1H), 3.72 (t, 2H), 3.49 (t, 2H), 3.09 (br s, 1H), 2.20 (m, 2H).

Example 53

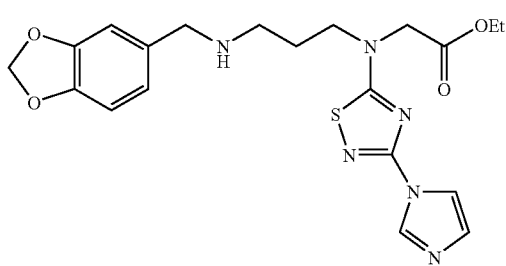

53

Preparation of compound 53: [{3-[(Benzo[1,3]dioxol-5-ylmethyl)-amino]-propyl}-(3-imidazol-1-yl-[1,2,4]thiadiazol-5-yl)-amino]-acetic acid ethyl ester was prepared following the procedures described in the preparation of Example 47 using [3-(benzo[1,3]dioxol-5-ylmethyl-tert-butoxycarbonyl-amino)-propylamino]-acetic acid ethyl ester. [M+H]$^+$ 444.95; $^1$H NMR (400 MHz, CDCl$_3$) δ 8.27 (s, 1H), 7.63 (s, 1H), 7.09 (s, 1H), 6.81 (s, 1H), 6.74 (m, 2H), 5.94 (s, 2H), 4.27 (br s, 2H), 4.24 (q, 2H), 3.71 (s, 2H), 3.56 (br s, 2H), 2.74 (t, 2H), 1.90 (m, 2H), 1.30 (t, 3H).

Example 54

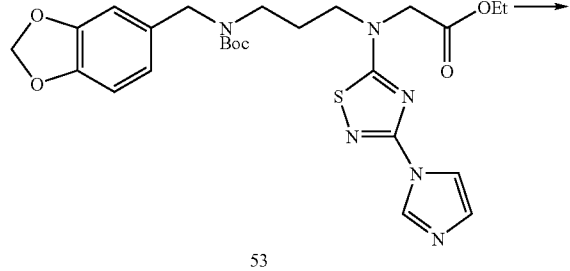

53

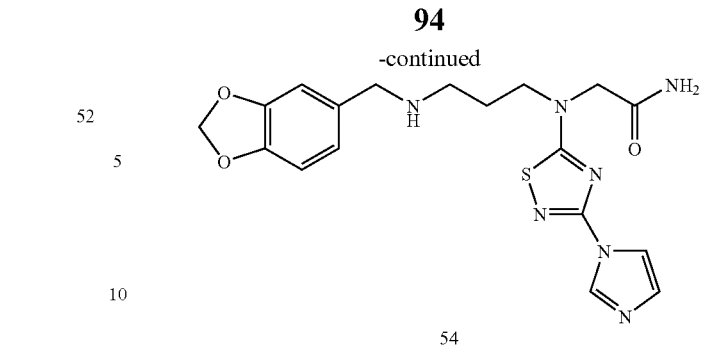

54

Preparation of compound 54: 2-[{3-[(Benzo[1,3]dioxol-5-ylmethyl)-amino]-propyl}-(3-imidazol-1-yl-[1,2,4]thiadiazol-5-yl)-amino]-acetamide A mixture of [[3-(benzo[1,3]dioxol-5-ylmethyl-tert-butoxycarbonyl-amino)-propyl]-(3-imidazol-1-yl-[1,2,4]thiadiazol-5-yl)-amino]-acetic acid ethyl ester from Step 1 (115 mg, 211 μmol) and a 2.0 M solution NH$_3$ in MeOH (10 mL) was stirred at r.t. for 24 h. The reaction mixture was concentrated to a yellow oil. The crude residue was dissolved in TFA/DCM (1:1, 3 mL) and stirred at room temperature for 30 min. The solvent was evaporated to afford an orange oil. The crude product was diluted with EtOAc (50 mL), washed with 1M NaOH (50 mL), brine (50 mL), dried over Na$_2$SO$_4$, filtered and concentrated to an oil. Purification was achieved using column chromatography (CH$_2$Cl$_2$ to 4:1 CH$_2$Cl$_2$/MeOH) to afford 53 mg (60%) of 2-[{3-[(benzo[1,3]dioxol-5-ylmethyl)-amino]-propyl}-(3-imidazol-1-yl-[1,2,4]thiadiazol-5-yl)-amino]-acetamide as a white solid. [M+H]$^+$ 415.97; $^1$H NMR (400 MHz, d$_6$-DMSO) δ 8.29 (s, 1H), 7.72 (s, 1H), 7.63 (br s, 1H), 7.28 (br s, 1H), 7.09 (s, 1H), 6.92 (s, 1H), 6.82 (m, 2H), 5.98 (s, 2H), 4.20 (br s, 1H), 3.60 (s, 2H), 3.33 (s, 2H), 2.54 (m, 4H), 1.80 (m, 2H).

Example 55

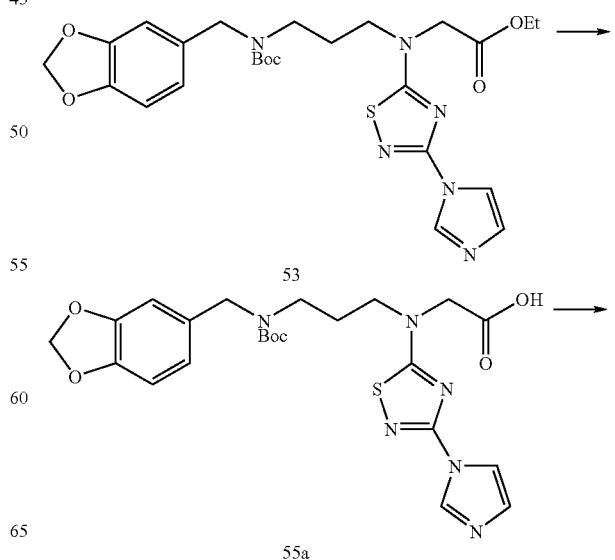

53

55a

-continued

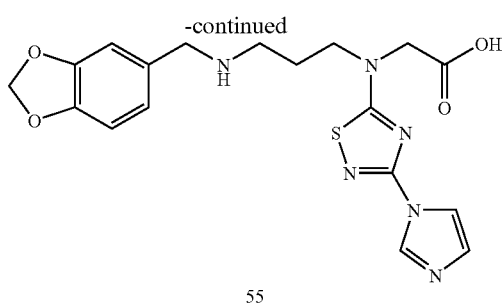

55

Step 1

Preparation of compound 55a: [[3-(Benzo[1,3]dioxol-5-ylmethyl-tert-butoxycarbonyl-amino)-propyl]-(3-imidazol-1-yl-[1,2,4]thiadiazol-5-yl)-amino]-acetic acid A solution of [[3-(benzo[1,3]dioxol-5-ylmethyl-tert-butoxycarbonyl-amino)-propyl]-(3-imidazol-1-yl-[1,2,4]thiadiazol-5-yl)-amino]-acetic acid ethyl ester (489 mg, 898 μmol), 1.0M aqueous LiOH (1.35 mL, 1.35 mmol) and THF (10 mL) was stirred at r.t. for 18 h. The reaction mixture was concentrated under reduced pressure to afford a white solid. EtOAc (100 mL) was added and the solution was washed with 1.0M aqueous HCl (50 mL), brine (50 mL), dried over $Na_2SO_4$, filtered and concentrated to a white solid. Obtained was 452 mg (97%) of [[3-(benzo[1,3]dioxol-5-ylmethyl-tert-butoxycarbonyl-amino)-propyl]-(3-imidazol-1-yl-[1,2,4]thiadiazol-5-yl)-amino]-acetic acid. [M+H]$^+$ 517.01.

Step 2

Preparation of compound 55: [{3-[(Benzo[1,3]dioxol-5-ylmethyl)-amino]-propyl}-(3-imidazol-1-yl-[1,2,4]thiadiazol-5-yl)-amino]-acetic acid

[[3-(Benzo[1,3]dioxol-5-ylmethyl-tert-butoxycarbonyl-amino)-propyl]-(3-imidazol-1-yl-[1,2,4]thiadiazol-5-yl)-amino]-acetic acid (70 mg, 140 μmol) was dissolved in TFA/DCM (1:1, 2 mL) and stirred at room temperature for 30 min. $SiO_2$ (3 g) was added and the solvent was evaporated to afford a white slurry. Purification was achieved using column chromatography ($CH_2Cl_2$ to 4:1 $CH_2Cl_2$/MeOH) to afford 58 mg (99%) of [{3-[(benzo[1,3]dioxol-5-ylmethyl)-amino]-propyl}-(3-imidazol-1-yl-[1,2,4]thiadiazol-5-yl)-amino]-acetic acid as a white solid. [M+H]$^+$ 416.92; $^1$H NMR (400 MHz, $d_6$-DMSO) δ 9.05 (s, 1H), 8.79 (br s, 1H), 8.00 (s, 1H), 7.49 (s, 1H), 7.06 (s, 1H), 6.97 (m, 2H), 6.06 (s, 2H), 4.39 (br s, 2H), 4.26 (s, 2H), 3.66 (m, 2H), 3.00 (m, 2H), 2.01 (m, 2H).

Example 56

56

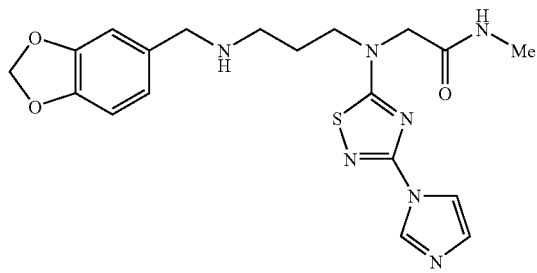

Preparation of compound 56: 2-[{3-[(Benzo[1,3]dioxol-5-ylmethyl)-amino]-propyl}-(3-imidazol-1-yl-[1,2,4]thiadiazol-5-yl)-amino]-N-methyl-acetamide BOP-Cl (170 mg, 686 μmol) was added all at once to a solution [[3-(benzo[1,3]dioxol-5-ylmethyl-tert-butoxycarbonyl-amino)-propyl]-(3-imidazol-1-yl-[1,2,4]thiadiazol-5-yl)-amino]-acetic acid (177 mg, 343 μmol) and DCM (3 mL) and stirred at room temperature for 30 min prior to addition of a 2.0M solution of $MeNH_2$ in THF (686 μL, 1.37 mmol). The reaction mixture stirred at r.t. for an additional 20 h prior to loading directly onto a $SiO_2$ column (EtOAc to 9:1 EtOAc/MeOH) to afford a white solid (120 mg). The white solid was dissolved in TFA/DCM (1:1, 3 mL) and stirred at room temperature for 30 min. The solvent was evaporated to afford an orange solid. The crude product was diluted with EtOAc (50 mL), washed with 1M NaOH (50 mL), brine (50 mL), dried over $Na_2SO_4$, filtered and concentrated to an oil.

Purification was achieved using column chromatography ($CH_2Cl_2$ to 4:1 $CH_2Cl_2$/MeOH) to afford 89 mg (60%) of 2-[{3-[(benzo[1,3]dioxol-5-ylmethyl)-amino]-propyl}-(3-imidazol-1-yl-[1,2,4]thiadiazol-5-yl)-amino]-N-methyl-acetamide as a white solid. [M+H]$^+$ 429.99; $^1$H NMR (400 MHz, $d_6$-DMSO) δ 8.31 (s, 1H), 8.00 (brs, 1H), 7.72 (s, 1H), 7.10 (s, 1H), 6.93 (s, 1H), 6.82 (m, 2H), 5.99 (s, 2H), 3.98 (s, 2H), 3.64 (br s, 2H), 3.19 (t, 2H), 2.99 (s, 3H), 2.88 (t, 2H), 2.54 (br s, 1H), 1.84 (m, 2H).

Example 57

57

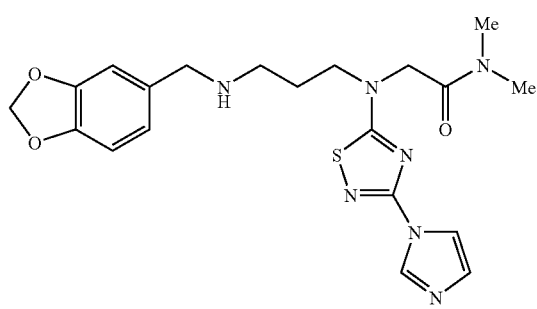

Preparation of compound 57: 2-[{3-[(Benzo[1,3]dioxol-5-ylmethyl)-amino]-propyl}-(3-imidazol-1-yl-[1,2,4]thiadiazol-5-yl)-amino]-N,N-dimethyl-acetamide was prepared following the procedures described in the preparation of Example 56 using [[3-(benzo[1,3]dioxol-5-ylmethyl-tert-butoxycarbonyl-amino)-propyl]-(3-imidazol-1-yl-[1,2,4]thiadiazol-5-yl)-amino]-acetic acid and $Me_2NH$. [M+H]$^+$ 443.99; $^1$H NMR (400 MHz, $d_6$-DMSO) δ 8.34 (s, 1H), 7.75 (s, 1H), 7.12 (s, 1H), 6.99 (s, 1H), 6.87 (m, 2H), 6.03 (s, 2H), 4.51 (br s, 1H), 3.78 (br s, 2H), 3.38 (br s, 2H), 3.05 (s, 3H), 2.89 (s, 3H), 2.75 (m, 2H), 2.53 (m, 2H), 1.89 (m, 2H).

Example 58

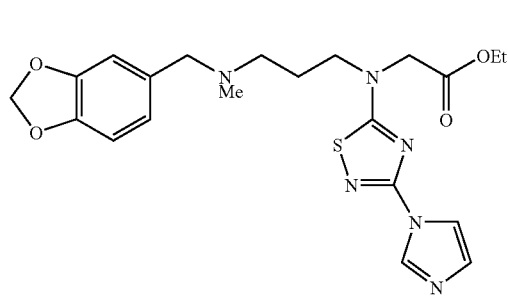

Preparation of compound 58: [[3-(Benzo[1,3]dioxol-5-yl-methyl-methyl-amino)-propyl]-(3-imidazol-1-yl-[1,2,4]thiadiazol-5-yl)-amino]-acetic acid ethyl ester was prepared following the procedures described in the preparation of Example 54 using [3-(benzo[1,3]dioxol-5-ylmethyl-methyl-amino)-propylamino]-acetic acid ethyl ester. [M+H]$^+$ 458.98; $^1$H NMR (400 MHz, CDCl$_3$) δ 8.26 (s, 1H), 7.63 (s, 1H), 7.07 (s, 1H), 6.82 (s, 1H), 6.73 (m, 2H), 5.93 (s, 2H), 4.28 (s, 2H), 4.23 (q, 2H), 3.52 (s, 2H), 3.43 (m, 2H), 2.46 (t, 2H), 2.21 (s, 3H), 1.91 (m, 2H), 1.29 (t, 3H).

Example 59

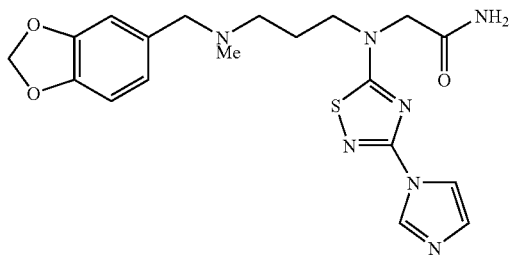

Preparation of compound 59: 2-[[3-(Benzo[1,3]dioxol-5-ylmethyl-methyl-amino)-propyl]-(3-imidazol-1-yl-[1,2,4]thiadiazol-5-yl)-amino]-acetamide was prepared following the procedures described in the preparation of Example 56 using [[3-(benzo[1,3]dioxol-5-ylmethyl-methyl-amino)-propyl]-(3-imidazol-1-yl-[1,2,4]thiadiazol-5-yl)-amino]-acetic acid ethyl ester and NH$_3$. [M+H]$^+$ 429.87; $^1$H NMR (400 MHz, d$_6$-DMSO) δ 8.24 (s, 1H), 7.68 (s, 1H), 7.54 (br s, 1H), 7.18 (br s, 1H), 7.06 (s, 1H), 6.86-6.70 (m, 3H), 5.98 (s, 2H), 3.45-3.35 (m, 4H), 3.31 (s, 2H), 2.36 (m, 2H), 2.10 (s, 3H), 1.72 (m, 2H).

Example 60

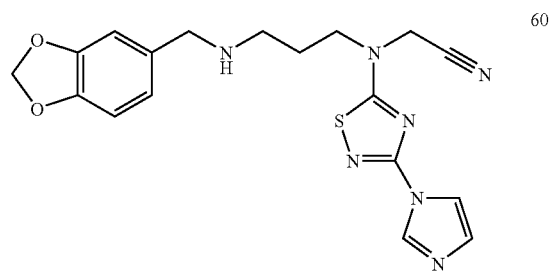

Preparation of compound 60: [{3-[(Benzo[1,3]dioxol-5-ylmethyl)-amino]-propyl}-(3-imidazol-1-yl-[1,2,4]thiadiazol-5-yl)-amino]-acetonitrile was prepared following the procedures described in the preparation of Example 47 using benzo[1,3]dioxol-5-ylmethyl-[3-(cyanomethyl-amino)-propyl]-carbamic acid tert-butyl ester. [M+H]$^+$ 397.90; $^1$H NMR (400 MHz, CDCl$_3$) δ 8.32 (s, 1H), 7.67 (s, 1H), 7.11 (s, 1H), 6.81 (s, 1H), 6.80-6.73 (m, 2H), 5.94 (s, 2H), 4.58 (s, 2H), 3.69 (s, 2H), 3.60 (t, 2H), 2.72 (t, 2H), 1.92 (tt, 2H).

Example 61

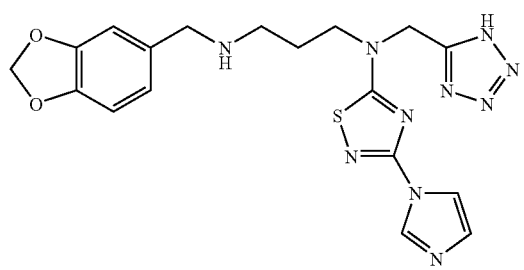

Preparation of compound 61: N'-Benzo[1,3]dioxol-5-ylmethyl-N-(3-imidazol-1-yl-[1,2,4]thiadiazol-5-yl)-N-(1H-tetrazol-5-ylmethyl)-propane-1,3-diamine A solution of [{3-[(benzo[1,3]dioxol-5-ylmethyl)-amino]-propyl}-(3-imidazol-1-yl-[1,2,4]thiadiazol-5-yl)-amino]-acetonitrile (37 mg, 91 μmol), sodium azide (12 mg, 184 μmol) and zinc (II) bromide (10 mg, 46 μmol) in 2:1H$_2$O/$^i$PrOH (1 mL) was heated to 150° C. for 24 h. The reaction mixture was cooled to r.t. prior to loading directly onto a SiO$_2$ column (CH$_2$Cl$_2$ to 4:1 CH$_2$Cl$_2$/MeOH) to afford 14 mg (35%) of N'-benzo[1,3]dioxol-5-ylmethyl-N-(3-imidazol-1-yl-[1,2,4]thiadiazol-5-yl)-N-(1H-tetrazol-5-ylmethyl)-propane-1,3-diamine as a white solid. [M+H]$^+$ 441.01; $^1$H NMR (400 MHz, CD$_3$OD) δ 8.35 (s, 1H), 7.74 (s, 1H), 7.07 (s, 1H), 6.85-6.74 (m, 3H), 5.92 (s, 2H), 4.43 (s, 2H), 4.06 (s, 2H), 3.81 (br s, 2H), 3.31 (t, 2H), 3.06 (t, 2H), 2.17 (tt, 2H).

Example 62

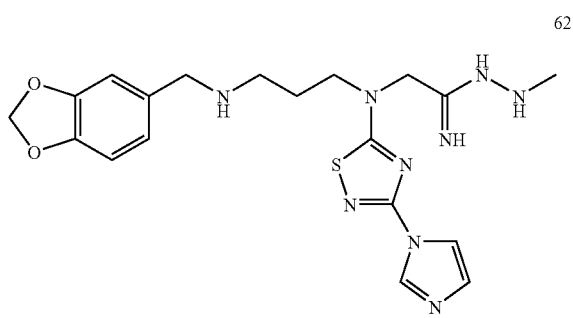

Preparation of compound 62: 2-[{3-[(Benzo[1,3] dioxol-5-ylmethyl)-amino]-propyl}-(3-imidazol-1-yl-[1,2,4]thiadiazol-5-yl)-amino]-acetamidine N'-methyl-hydrazide Methylhydrazine (37 μL, 700 μmol) was added all at once a solution of [{3-[(benzo[1,3]dioxol-5-ylmethyl)-amino]-propyl}-(3-imidazol-1-yl-[1,2,4]thiadiazol-5-yl)-amino]-acetonitrile (27 mg 70 μmol) in EtOH (500 μL) at r.t. The reaction mixture stirred at r.t. for 19 h prior to concentrating to a white solid. The residue was purified using column chromatography (CH$_2$Cl$_2$ to 4:1 CH$_2$Cl$_2$/MeOH) to afford 14 mg (45%) of 2-[{3-[(benzo[1,3]dioxol-5-ylmethyl)-amino]-propyl}-(3-imidazol-1,2,4]thiadiazol-5-yl)-amino]-acetamidine N'-methyl-hydrazide as a white solid. [M+H]$^+$ 444.53; $^1$H NMR (400 MHz, CD$_3$OD) δ 8.34 (s, 1H), 7.73 (s, 1H), 7.07 (s, 1H), 6.83 (s, 1H), 6.77-6.72 (m, 2H), 5.88 (s, 2H), 4.23 (br s, 2H), 3.70 (d, 3H), 3.68 (s, 2H), 3.61 (s, 2H), 3.30 (s, 2H), 2.72 (m, 2H), 1.96 (tt, 2H).

Example 63

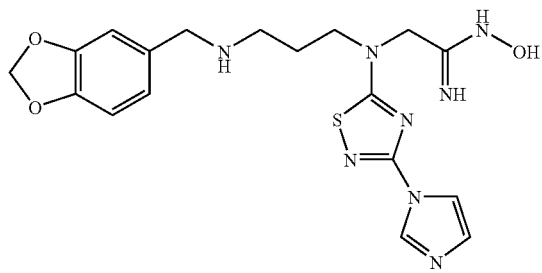

Preparation of compound 63: 2-[{3-[(Benzo[1,3] dioxol-5-ylmethyl)-amino]-propyl}-(3-imidazol-1-yl-[1,2,4]thiadiazol-5-yl)-amino]-N-hydroxy-acetamidine Hydroxylamine (1.0 mL of a 50 wt % in H$_2$O, 15 mmol) was added all at once a solution of [{3-[(benzo[1,3]dioxol-5-ylmethyl)-amino]-propyl}-(3-imidazol-1-yl-[1,2,4]thiadiazol-5-yl)-amino]-acetonitrile (30 mg, 75 μmol) in MeOH (1.0 mL) at r.t. The reaction mixture stirred at r.t. for 30 h prior to concentrating to a white solid. The residue was purified using column chromatography (CH$_2$Cl$_2$ to 4:1 CH$_2$Cl$_2$/MeOH) to afford 7.0 mg (22%) of 2-[{3-[(benzo[1,3]dioxol-5-ylmethyl)-amino]-propyl}-(3-imidazol-1-yl-[1,2,4]thiadiazol-5-yl)-amino]-N-hydroxy-acetamidine as a white solid. [M+H]$^+$ 430.91; $^1$H NMR (400 MHz, CD$_3$OD) δ 8.39 (s, 1H), 7.79 (s, 1H), 7.76 (s, 1H), 7.07 (s, 1H), 6.82 (s, 1H), 6.76-6.70 (m, 2H), 5.89 (s, 2H), 4.19 (s, 2H), 3.65 (s, 2H), 3.58 (m, 2H), 2.63 (t, 2H), 1.94 (tt, 2H).

Example 64

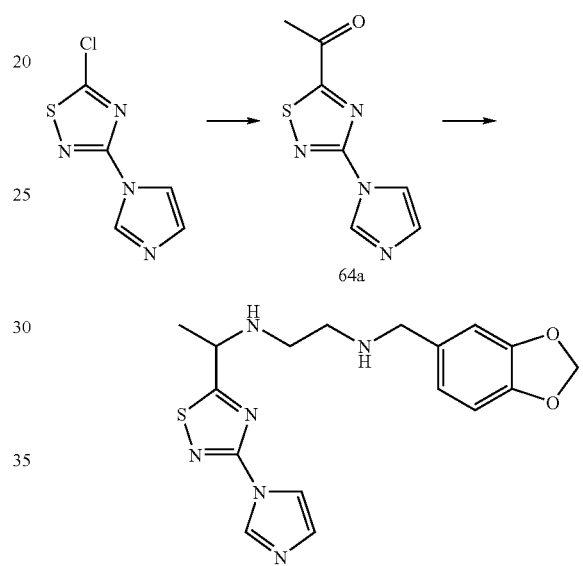

Step 1

Preparation of compound 64a: 1-(3-Imidazol-1-yl-[1,2,4]thiadiazol-5-yl)-ethanone A catalytic amount of dichloropalladium(II)bis(triphenylphosphine) (189 mg, 268 μmol) was added to a solution of 5-chloro-3-imidazol-1-yl-[1,2,4]thiadiazole (500 mg, 2.68 mmol) and tributyl-(1-ethoxy-vinyl)-stannane (904 μL, 2.68 mmol) in DMF (10 mL) under a nitrogen atmosphere at r.t. prior to heating at 65-70° C. for 21 h. The reaction was then cooled to r.t., H$_2$O (70 mL) was added, filtered through celite, and washed with EtOAc (200 mL). The organic layer was separated, dried over Na$_2$SO$_4$, filtered and concentrated to a yellow residue. The yellow residue was diluted with a 5:1 mixture of 5N HCl/THF (48 mL) and stirred at r.t. for a period of 2 hours prior to concentrating to a white residue. The crude product was diluted with EtOAc (100 mL), washed with 1M NaOH (75 mL), brine (75 mL), dried over Na$_2$SO$_4$, filtered and concentrated to a white solid. Purification was achieved using column chromatography (CH$_2$Cl$_2$ to 9:1 CH$_2$Cl$_2$/MeOH) to afford 398 mg (77%) of 1-(3-imidazol-1-yl-[1,2,4]thiadiazol-5-yl)-ethanone as a white solid. [M+H]$^+$ 195.35.

Step 2

Preparation of compound 64: N-Benzo[1,3]dioxol-5-ylmethyl-N'-[1-(3-imidazol-1-yl-[1,2,4]thiadiazol-5-yl)-ethyl]-ethane-1,2-diamine A catalytic amount of TsOH (20 mg) was added to a solution of 1-(3-imidazol-1-yl-[1,2,4]thiadiazol-5-yl)-ethanone obtained from Step 1 (233 mg, 1.20 mmol) and (2-aminoethyl)-benzo[1,3]dioxol-5-ylmethyl-carbamic acid tert-butyl ester (565 mg, 1.92 mmol) in 1,4-dioxane (10 mL) under a nitrogen atmosphere at r.t. prior to heating at 65-70° C. for 4 h. The reaction was then cooled to r.t. and NaHB(OAc)$_3$ (763 mg, 3.60 mmol) was added. After stirring for an additional hour, water was added and the solution was extracted with ethyl acetate (2×70 mL), washed with brine and dried over Na$_2$SO$_4$. Evaporation of the solvent gave a yellow residue which was dissolved in TFA/DCM (1:1, 6 mL) and stirred at room temperature for 30 min. The solvent was evaporated to afford a yellow solid. The crude product was diluted with EtOAc (100 mL), washed with 1M NaOH (50 mL), brine (50 mL), dried over Na$_2$SO$_4$, filtered and concentrated to an orange solid. Purification was achieved using column chromatography (CH$_2$Cl$_2$ to 4:1 CH$_2$Cl$_2$/MeOH) to afford 31 mg (7%) of N-benzo[1,3]dioxol-5-ylmethyl-N'-[1-(3-imidazol-1-yl-[1,2,4]thiadiazol-5-yl)-ethyl]-ethane-1,2-diamine as a white solid. [M+H]$^+$ 372.97; $^1$H NMR (400 MHz, CDCl$_3$) δ 8.40 (s, 1H), 7.74 (s, 1H), 7.13 (s, 1H), 6.84 (s, 1H), 6.76 (m, 2H), 5.93 (s, 2H), 4.12 (q, 1H), 3.73 (d, 2H), 2.91-2.77 (m, 4H), 2.19 (br s, 2H), 1.54 (d, 3H).

Example 65

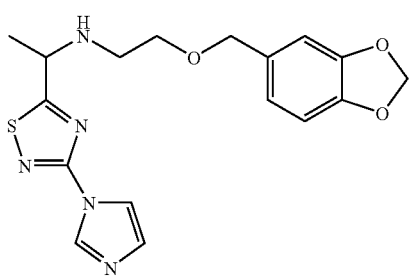

Preparation of compound 65: [2-(Benzo[1,3]dioxol-5-ylmethoxy)-ethyl]-[1-(3-imidazol-1-yl-[1,2,4]thiadiazol-5-yl)-ethyl]-amine was prepared following the procedures described in the preparation of Example 64 in Step 2 using 2-(benzo[1,3]dioxol-5-ylmethoxy)-ethylamine. [M+H]$^+$ 373.90; $^1$H NMR (400 MHz, CDCl$_3$) δ 8.42 (d, 1H), 7.75 (d, 1H), 7.13 (s, 1H), 6.81 (s, 1H), 6.76 (m, 2H), 5.94 (s, 2H), 4.41 (s, 2H), 4.22 (q, 1H), 3.63 (m, 2H), 2.97 (m, 2H), 1.71 (d, 3H).

Example 66

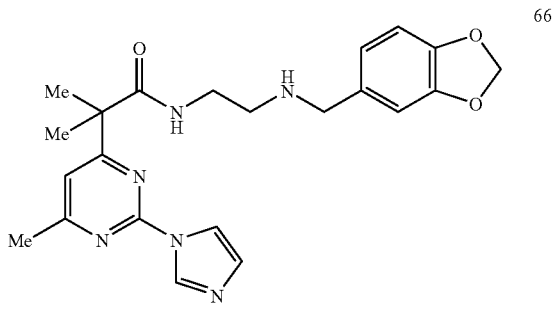

Preparation of compound 66: N-{2-[(Benzo[1,3]dioxol-5-ylmethyl)-amino]-ethyl}-2-(2-imidazol-1-yl-6-methyl-pyrimidin-4-yl)-isobutyramide was prepared following the procedures described in the preparation of Example 56 using 2-(2-imidazol-1-yl-6-methyl-pyrimidin-4-yl)-2-methyl-propionic acid and (2-amino-ethyl)-benzo[1,3]dioxol-5-ylmethyl-carbamic acid tert-butyl ester. [M+H]$^+$ 423.26; $^1$H NMR (400 MHz, CD$_3$OD) δ 8.70 (s, 1H), 8.00 (s, 1H), 7.35 (s, 1H), 7.14 (s, 1H), 6.94-6.80 (m, 3H), 5.98 (s, 2H), 4.10 (s, 2H), 3.53 (t, 2H), 3.13 (t, 2H), 2.58 (s, 3H), 1.63 (s, 6H).

Example 67

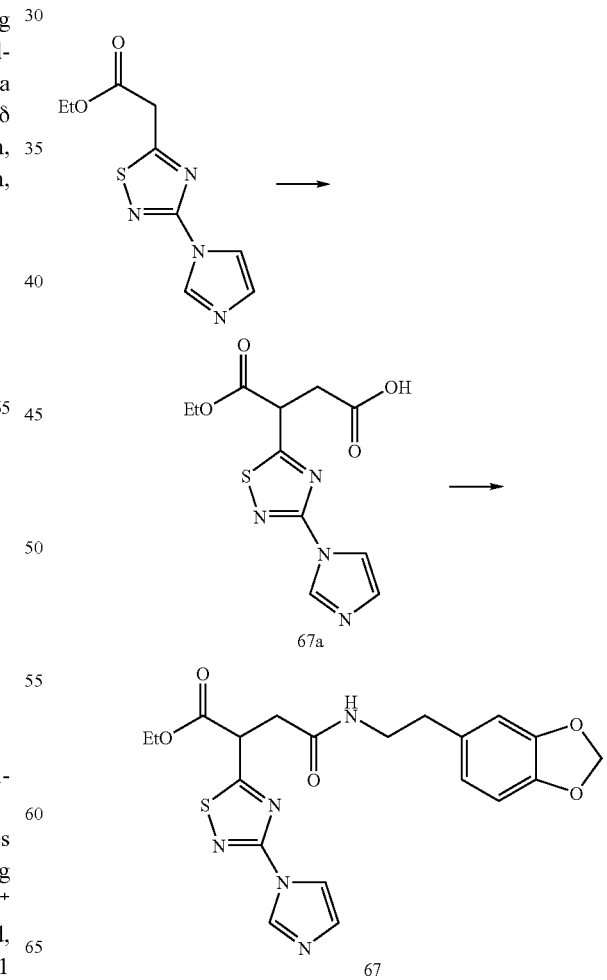

Step 1

Preparation of compound 67a: 2-(3-Imidazol-1-yl-[1,2,4]thiadiazol-5-yl)-succinic acid 1-ethyl ester LiHMDS (4.62 mL of a 1.0M solution in THF, 4.62 mmol) was added dropwise to a −78° C. solution of (3-imidazol-1-yl-[1,2,4]thiadiazol-5-yl)-acetic acid ethyl ester (1.00 g, 4.20 mmol) and THF (42 mL) under a nitrogen atmosphere. The reaction mixture stirred for 30 minutes prior to warming to −40° C. and addition of t-butylbromoacetate (620 μL, 4.20 mmol). The reaction stirred for 15 minutes at −40° C. before slowly warming to r.t. and stirring for an additional 6h. Sat. NH$_4$Cl (100 mL) was added, organic layer was separated, aqueous extracted with EtOAc, the organic layers dried over Na$_2$SO$_4$, filtered and concentrated to a yellow solid. The yellow solid was dissolved in TFA/DCM (1:1, 10 mL) and stirred at room temperature for 45 min. The solvent was evaporated to afford 583 mg (47%) of 2-(3-imidazol-1-yl-[1,2,4]thiadiazol-5-yl)-succinic acid 1-ethyl ester as a white solid. The product was used directly in the subsequent step without further purification.

Step 2

Preparation of compound 67: N-(2-Benzo[1,3]dioxol-5-yl-ethyl)-2-(3-imidazol-1-yl-[2,4]thiadiazol-5-yl)-succinamic acid ethyl ester BOP-Cl (784 mg, 3.08 mmol) was added all at once to a solution 2-(3-imidazol-1-yl-[1,2,4]thiadiazol-5-yl)-succinic acid 1-ethyl ester (389 mg, 1.54 mmol) and DCM (10 mL) and stirred at room temperature for 30 min prior to addition of 2-benzo[1,3]dioxol-5-yl-ethylamine (620 mg, 3.08 mmol) and TEA (859 μL, 6.16 mmol). The reaction mixture stirred at r.t. for an additional 20 h. The solvent was evaporated to afford a white slurry oil, diluted with EtOAc (50 mL), washed with sat. NaHCO$_3$ (50 mL), brine (50 mL), dried over Na$_2$SO$_4$, filtered and concentrated to a white solid. Purification was achieved using column chromatography (CH$_2$Cl$_2$ to 4:1 CH$_2$Cl$_2$/MeOH) to afford 17 mg (3%) of N-(2-benzo[1,3]dioxol-5-yl-ethyl)-2-(3-imidazol-1-yl-[1,2,4]thiadiazol-5-yl)-succinamic acid ethyl ester as a white solid. [M+H]$^+$ 443.90; $^1$H NMR (400 MHz, CDCl$_3$) δ 8.50 (s, 1H), 7.74 (s, 1H), 7.15 (s, 1H), 6.66-6.52 (m, 3H), 6.04 (br s, 1H), 5.86 (s, 2H), 4.31 (q, 2H), 3.78 (t, 1H), 3.63 (t, 2H), 3.16 (t, 2H), 2.83 (d, 2H), 1.32 (t, 3H).

Example 68

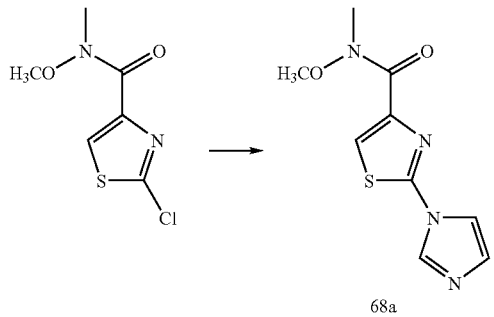

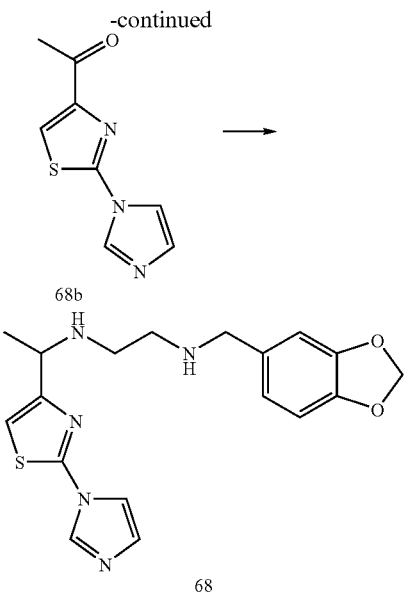

Step 1

Preparation of compound 68a: 2-Imidazol-1-yl-thiazole-4-carboxylic acid methoxy-methyl-amide Cesium(II)carbonate (1.36 g, 4.18 mmol) was added to a solution of 2-bromo-thiazole-4-carboxylic acid methoxy-methyl-amide (500 mg, 1.99 mmol) and imidazole (135 mg, 1.99 mmol) in DMF (5 mL) under a nitrogen atmosphere at r.t. prior to heating at 120° C. for 40 minutes in the microwave reactor. The reaction was then cooled to r.t., diluted with EtOAc (100 mL), washed with 1M NaOH (75 mL), brine (75 mL), dried over Na$_2$SO$_4$, filtered and concentrated to a white solid. Purification was achieved using column chromatography (CH$_2$Cl$_2$ to 9:1 CH$_2$Cl$_2$/MeOH) to afford 435 mg (92%) of 2-imidazol-1-yl-thiazole-4-carboxylic acid methoxy-methyl-amide as a white solid. [M+H]$^+$ 239.02.

Step 2

Preparation of compound 68b: 1-(2-Imidazol-1-yl-thiazol-4-yl)-ethanone

Methyl magnesium(II)chloride (1.12 mL of a 3.0 M solution in THF, 3.36 mmol) was added dropwise to a 0° C. solution of 2-imidazol-1-yl-thiazole-4-carboxylic acid methoxy-methyl-amide obtained from Step 1 (400 mg, 1.68 mmol) in THF (5 mL) under a nitrogen atmosphere. The reaction was then warmed to r.t. over a period of 2 hours, sat. NH$_4$Cl (50 mL) was added and the solution was extracted with methylene chloride (2×70 mL), washed with brine and dried over Na$_2$SO$_4$. Evaporation of the solvent gave 319 mg (98%) of 1-(2-imidazol-1-yl-thiazol-4-yl)-ethanone as a white solid which was which was used without further purification in the subsequent step. [M+H]$^+$ 194.06.

Step 3

Preparation of compound 68: N-Benzo[1,3]dioxol-5-ylmethyl-N'-[1-(2-imidazol-1-yl-thiazol-4-yl)-ethyl]-ethane-1,2-diamine was prepared following the procedures described in the preparation of Example 64 using 1-(2-imidazol-1-ylthiazol-4-yl)-ethanone and (2-amino-ethyl)-benzo[1,3]dioxol-5-ylmethyl-carbamic acid tert-butyl ester. [M+H]+ 372.01; $^1$H NMR (400 MHz, d$_6$-DMSO) δ 8.38 (s, 1H), 7.82 (d, 1H), 7.31 (s, 1H), 7.18 (d, 1H), 6.92 (d, 1H), 6.84 (d, 1H), 6.77 (dd, 1H), 6.00 (s, 2H), 4.14 (br s, 2H), 3.82 (q, 1H), 3.60 (s, 2H), 3.21 (s, 2H), 2.57 (s, 2H), 1.34 (d, 3H).

Example 69

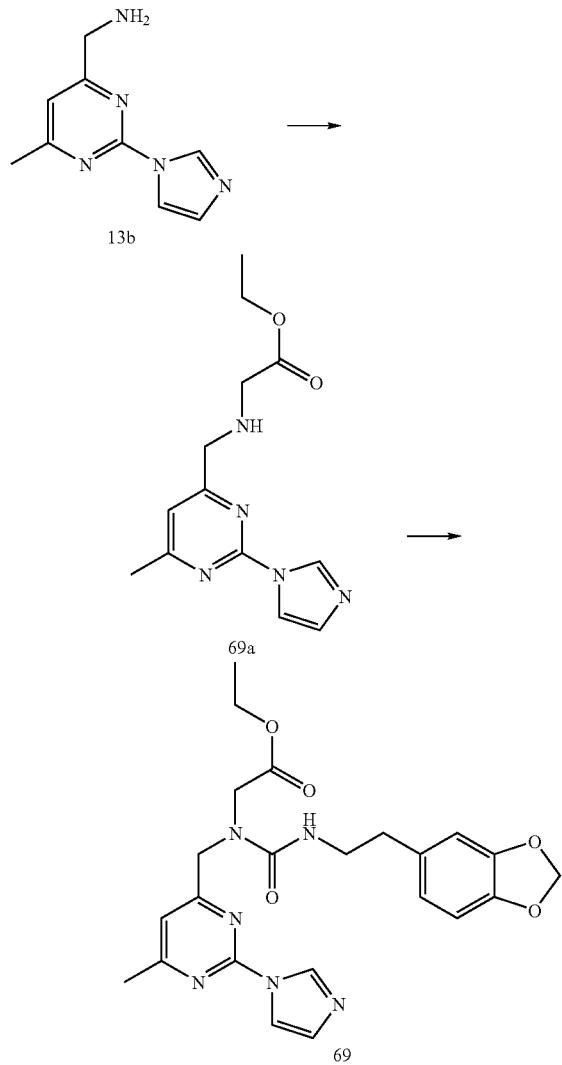

Step 1

Preparation of compound 69a: [(2-Imidazol-1-yl-6-methyl-pyrimidin-4-ylmethyl)-amino]-acetic acid ethyl ester A 25 mL recovery flask was charged with NaH (12 mg, 0.29 mmol, 60% dispersion in mineral oil) and 5:1 mixture of THF:DMF to give ca. 0.05M solution. The flask was cooled down to 0° C. in an ice bath. 13b (50 mg, 0.26 mmol) was then added in one portion and the reaction was allowed to stir for 15-20 min. Then, ethyl bromoacetate (31 □L, 0.29 mmol) was added dropwise. The mixture was warmed to r.t over 6 h. The reaction was quenched by slow addition of water, extracted with EtOAc (5×25 mL), washed with water, brine and dried over Na$_2$SO$_4$. Concentrated in vacuo to give the crude that was purified by column chromatography (DCM to 4:1 DCM/MeOH) to afford 40 mg (55%) of [(2-imidazol-1-yl-6-methyl-pyrimidin-4-ylmethyl)-amino]-acetic acid ethyl ester. This was used without further purification.

Step 2

Preparation of compound 69: [3-(2-Benzo[1,3]dioxol-5-yl-ethyl)-1-(2-imidazol-1-yl-6-methyl-pyrimidin-4-ylmethyl)-ureido]-acetic acid ethyl ester An oven-dried 10-mL recovery flask equipped with a magnetic stir bar, an N$_2$ inlet along with a septum was charged with [(2-imidazol-1-yl-6-methyl-pyrimidin-4-ylmethyl)-amino]-acetic acid ethyl ester (0.20 g, 0.72 mmol) and dissolved in CH$_2$Cl$_2$ to give ca. 0.2 M solution. To this solution, corresponding isocyanide (0.15 g, 0.79 mmol) was added via a syringe at r.t. and allowed to stir at this temperature for about 4 h. Then the mixture was quenched by slow addition of water, extracted with EtOAc (5×25 mL), washed with water, brine and dried over Na$_2$SO$_4$. The solution was concentrated in vacuo to give a crude oil that was purified by column chromatography (EtOAc) to afford 260 mg (77%) of [3-(2-benzo[1,3]dioxol-5-yl-ethyl)-1-(2-imidazol-1-yl-6-methyl-pyrimidin-4-ylmethyl)-ureido]-acetic acid ethyl ester. [M+H]+ 467.00; $^1$H NMR (400 MHz, CDCl$_3$) δ8.53 (s, 1H), 7.79 (s, 1H), 7.14 (s, 1H), 7.07 (s, 1H), 6.61-6.53 (m, 2), 5.88 (s, 2H), 5.00 (br, 1H), 4.46 (s, 2H), 4.18 (q, 2H), 4.12 (s, 2H), 3.44 (q, 2 H), 2.73-2.70 (m, 2H), 2.54 (s, 3H), 1.26 (t, 3H).

Example 70

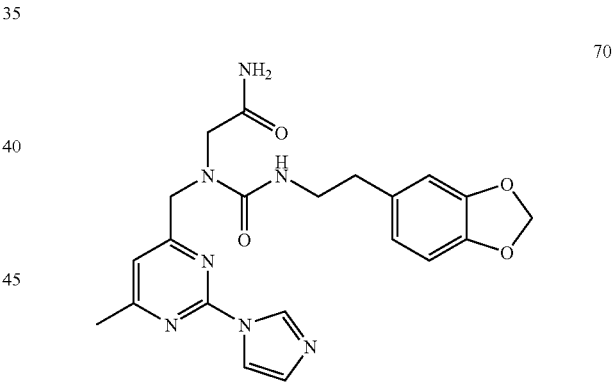

Preparation of compound 70: (2-[3-(2-Benzo[1,3]dioxol-5-yl-ethyl)-1-(2-imidazol-1-yl-6-methyl-pyrimidin-4-ylmethyl)-ureido]-acetamide)

An oven-dried 10-mL recovery flask equipped with a magnetic stir bar, an N$_2$ inlet along with a septum was charged with ester 69 (30 mg, 0.064 mmol) and dissolved in MeOH to give ca. 0.05 M solution. To this, 2M solution of NH$_3$ in MeOH (0.16 mL, 0.32 mmol) was added via a syringe at r.t. and allowed to stir at this temperature for overnight. The mixture was quenched by water, extracted with EtOAc (5×25 mL), washed with water, brine and dried over Na$_2$SO$_4$. The solution was concentrated in vacuo to give a crude oil that was purified by column chromatography, eluting with 100% EtOAc, to afford 28 mg (quant.) of (2-[3-(2-benzo[1,3]dioxol-5-yl-ethyl)-1-(2-imidazol-1-yl-6-methyl-pyrimidin-4- ylmethyl)-ureido]-acetamide). [M+H]+—NH₂ 420.91; ¹H NMR (400 MHz, CDCl₃) δ 8.60 (s, 1H), 7.85 (s, 1H), 7.19 (s, 1H), 7.19 (s, 1H, 7.99 (s, 1H), 6.77-6.72 (m, 2H), 5.95 (s, 2H), 4.65 (br, 1H), 4.06 (s, 2H), 3.79 (t, 2H), 2.92 (t, 2H), 2.60 (s, 3H).

Example 71

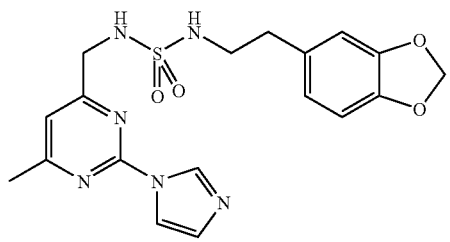

Preparation of compound 71: (2-[3-(2-Benzo[1,3]dioxol-5-yl-ethyl)-1-(2-imidazol-1-yl-6-methyl-pyrimidin-4-ylmethyl)-sulfamide)

13b (100 mg, 0.530 mmol) and 3,4-methylenedioxyphenethylamine hydrochloride (106 mg, 0.530 mmol) were dissolved in CH₂Cl₂ (2.65 mL). The solution was cooled to −78° C. and the 1M solution of sulfuryl chloride (530 μL, 0.530 mmol) was added dropwise via syringe. The reaction was maintained at this temperature for several minutes to facilitate stirring. The reaction was then allowed to return to room temperature over 5 hours. The mixture was quenched with water (25 mL), extracted with EtOAc (5×25 mL), washed with water (25 mL), brine (25 mL) and dried over Na₂SO₄. The solution was concentrated in vacuo to give a crude oil that was purified by preparative TLC to afford 2 mg (1%) of (2-[3-(2-benzo[1,3]dioxol-5-yl-ethyl)-1-(2-imidazol-1-yl-6-methyl-pyrimidin-4-ylmethyl)-sulfamide). ¹H NMR (400 MHz, CDCl₃) □ 8.60 (s, 1H), 7.85 (s, 1H), 7.19 (s, 1H), 6.77-6.72 (m, 2H), 6.64 (s, 1H), 5.95 (s, 2H), 4.01 (s, 2H), 3.5 (t, 2H), 2.65 (t, 2H), 2.45 (s, 3H).

Example 72

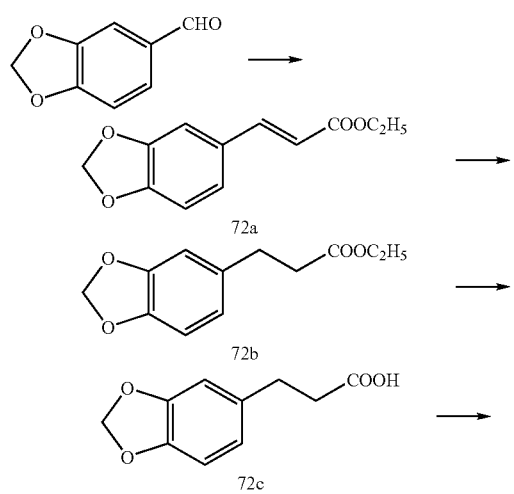

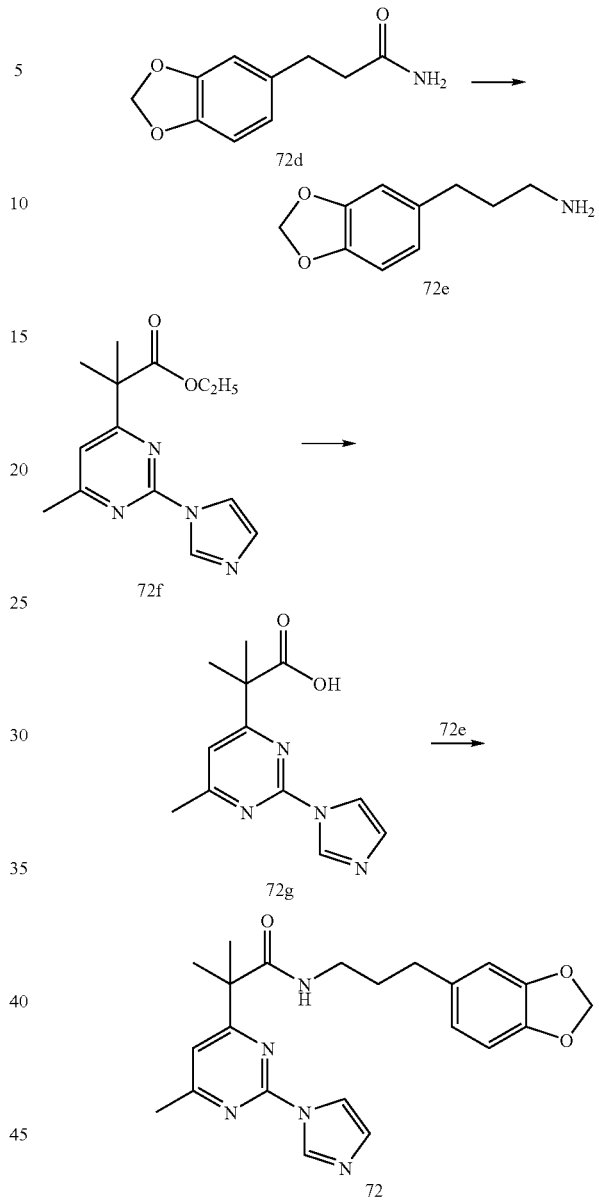

Step 1

Preparation of compound 72a: 3-Benzo[1,3]dioxol-5-yl-acrylic acid ethyl ester

Sodium hydride (60% dispersion in mineral oil, 10.0 g, 250 mmol) was suspended in THF (100 ml) under N₂. Ethyl 2-(diethoxyphosphoryl)acetate (56.0 g, 219 mmol) was added dropwise, while the internal temperature was maintained at 40° C. Piperonylamine (37.5 g, 248 mmol) was then added dropwise over 30 min. The reaction was heated to 65° C. for 1 hour. The solution was warmed to room temperature and then titrated with THF. The filtrate was decanted from the reaction mixture and concentrated under vacuum to afford 43.0 g (57%) of compound 72a, which was used without further purification.

Step 2

Preparation of compound 72b:
3-Benzo[1,3]dioxol-5-yl-propionic acid ethyl ester

Pd/C (725 mg, 6.81 mmol) and 72a (15.0 g, 68.1 mmol) were suspended in methanol (100 mL) and stirred at room temperature under $H_2$ for 3 hours. The mixture was filtered and the filtrate was concentrated down under vacuo to yield 14.3 g (95%) of compound 72b, which was used without further purification.

Step 3

Preparation of compound 72c:
3-Benzo[1,3]dioxol-5-yl-propionic acid 72b (14.3 g, 66.3 mmol) and NaOH (10% w/w, 10 ml) were dissolved in methanol (100 mL) and stirred at room temperature for 2 hours. The solution was washed with EtOAc (2×100 mL) and the organic layer was partitioned from the aqueous layer. The aqueous layer was acidified to pH=5, extracted with EtOAc (2×100 mL), and dried over $Na_2SO_4$. The organic layer was concentrated down under vacuo to yield 13.2 g (100%) of compound 72c, which was used without further purification.

Step 4

Preparation of compound 72d:
3-Benzo[1,3]dioxol-5-yl-propionamide

In a 250 mL one-necked flask fitted with stirrer, the compound 72c (1.4 g) is dissolved into 20 ml $SOCl_2$, and then heated at reflux for 4 h. When the mixture is cooled to room temperature, the solution is removed under vacuum, and the residue treated with 2.0 M $NH_3$ in methanol (200 mL). The mixture was stirred for 30 min then concentrated under vacuum to afford 1.20 g of 72d as a white solid. The product was used directly in the subsequent step.

Step 5

Preparation of compound 72e:
3-(Benzo[d][1,3]dioxol-5-yl)propan-1-amine $LiAlH_4$ (1M in THF, 1.80 g, 47.4 mmol) was added portionwise to a flask of THF (100 mL), while cooling to −5° C. While maintaining the temperature below −5° C., 72d (4.60 g, 23.8 mmol) in THF (10 mL) was added dropwise. The mixture was stirred at room temperature for 30 min. The solvent was removed under vacuo and the residue was dissolved in water (100 mL) and extracted with $CH_2Cl_2$ (3×50 mL). The organic layers were combined, dried over sodium sulfate and concentrated under reduced pressure to afford 3.7 g (88%) of 72e. $[M+H]^+$ 180.01; $^1H$ NMR (400 MHz, $CDCl_3$) δ 6.61 (s, 1H), 6.57 (s, 1H), 6.51 (s, 1H), 5.91 (s, 2H), 2.65 (m, 2H), 2.55 (m, 2H), 2.00 (s, 2H), 1.88 (m, 2H).

Step 6

Preparation of compound 72g: 2-(2-Imidazol-1-yl-6-methyl-pyrimidin-4-yl)-2-methyl-propionic acid 72f (1.2 g, 4.4 mmol) was dissolved in ethanol (20 mL). Sodium hydroxide (200 mg, 5.0 mmol) in water (5 mL) was added to the reaction vessel. The mixture was stirred at room temperature for 16 hours. The reaction was concentrated under vacuo and the residue was dissolved in water (20 mL) and extracted with EtOAc (2×10 mL). The organic layer was discarded and the water layer was acidified to pH=5 with concentrated HCl. The product precipitated as a white solid. It was collected by filtration and dried under vacuo to afford 800 mg (74%) of 72g, which was used without further purification. $[M+H]^+$ 247.10.

Step 7

Preparation of compound 72: 2-(2-(1H-imidazol-1-yl)-6-methylpyrimidin-4-yl)-N-(3-(benzo[d][1,3]dioxol-5-yl)propyl)-2-methylpropanamide 72g (300 mg, 1.22 mmol) and triethylamine (180 mg, 1.78 mmol) were dissolved in THF (40 mL). Upon dissolution, the mixture was cooled to −10° C., ethyl chloroformate (200 mg, 1.84 mmol) was added and the mixture was stirred for 2 h. The solution was maintained at −10° C., while 3-(benzo[d][1,3]dioxol-5-yl)propan-1-amine (330 mg, 1.84 mmol) was added. The mixture was stirred for an additional 2 hours. The reaction mixture was poured into water (20 mL) and extracted with EtOAc (2×20 mL). The organic layer was dried over sodium sulfate and concentrated down to afford the crude product. The crude product was purified by flash chromatography (hexanes to 1:1 hexanes/EtOAc) to afford 320 mg (66%) of 72. $[M+H]^+$ 408.05; $^1H$ NMR (400 MHz, $CDCl_3$) δ 8.64 (s, 1H), 7.92 (s, 1H), 7.12 (d, 1H), 6.99 (s, 1H), 6.80 (m, 3H), 5.94 (s, 2H), 5.84 (d, 1H), 4.14 (t, 1H), 3.34 (d, 2H), 2.66 (s, 3H), 2.13 (s, 3H), 1.89 (m, 2H), 1.69 (s, 6H).

Example 73

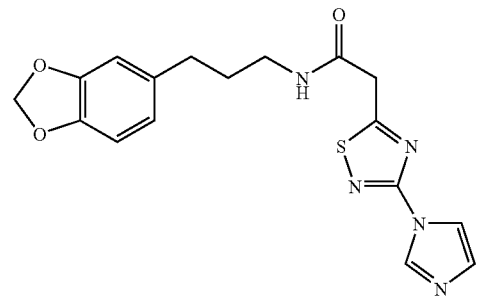

Preparation of compound 73: 2-(3-(1H-Imidazol-1-yl)-1,2,4-thiadiazol-5-yl)-N-(3-(benzo[δ][1,3]dioxol-4-yl)propyl)acetamide Ethyl 2-(3-(1H-imidazol-1-yl)-1,2,4-thiadiazol-5-yl)acetate (320 mg, 1.30 mmol) and 72e (300 mg, 1.60 mmol) were dissolved in p-xylene/1,4-dioxane (v/v 1:1, 30 mL) and refluxed for 24 h. The mixture was concentrated and purified by flash chromatography (DCM to 1:19 MeOH/DCM) to afford 80 mg (13%) of 73. $[M+H]^+$ 372.16.

Example 74

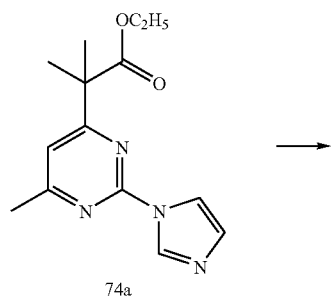
74a

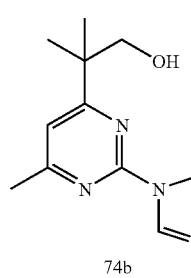
74b

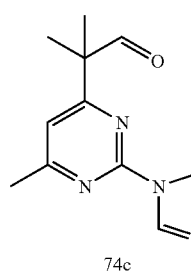
74c

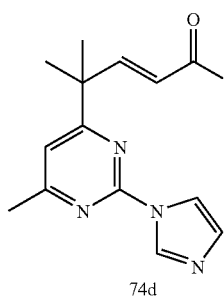
74d

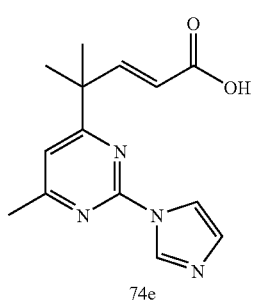
74e

-continued

74

Step 1

Preparation of compound 74b: 2-(2-Imidazol-1-yl-6-methyl-pyrimidin-4-yl)-2-methyl-propan-1-ol Lithium aluminum hydride (100 mg, 2.64 mmol) was dissolved in anhydrous THF (25 mL) and cooled to −20° C. under $N_2$. A solution of 74a (1.0 g, 3.65 mmol) in THF (5 mL) was added dropwise to reaction mixture while maintaining the temperature below −20° C. The reaction was quenched with water and celite. The filtrate was extracted with EtOAc (25 mL) and partitioned from the aqueous layer. The organic layer was dried over sodium sulfate and concentrated down to afford the crude product. The crude material was purified by flash chromatography (hexanes to 4:1 EtOAc/hexanes) to afford 370 mg of 74b. $^1$H NMR (400 MHz, $CDCl_3$) δ 8.60 (s, 1H), 7.86 (s, 1H), 7.14 (s, 1 H), 7.09 (s, 1H), 3.81 (s, 2H), 2.56 (s, 3H), 1.36 (s, 6H).

Step 2

Preparation of compound 74c: 2-(2-Imidazol-1-yl-6-methyl-pyrimidin-4-yl)-2-methyl-propionaldehyde 0.63 g of oxalyl dichloride (630 mg, 4.96 mmol) was dissolved in methylene chloride (10 mL). The reaction vessel was cooled to −50° C. and dimethylsulfoxide (790 mg, 10.11 mmol) in anhydrous methylene chloride (5 mL) was added dropwise to the reaction. The reaction was stirred for 5 minutes. A solution of 74b (370 mg, 1.59 mmol) in methylene chloride (5 mL) was added to the flask while maintaining the temperature below −50° C. The reaction was allowed to continue for 1 h. Triethylamine (665 μL, 4.77 mmol) was added to the reaction, which was then quenched by addition of water (50 mL). The methylene chloride layer was partitioned from the aqueous layer and the aqueous layer was back extracted with methylene chloride (10 mL). The methylene chloride layers were dried over sodium sulfate and concentrated by vacuo to give 74c (280 mg). $^1$H NMR (400 MHz, $CDCl_3$) δ 9.75 (s, 1H), 8.60 (s, 1H), 7.88 (s, 1H), 7.14 (s, 1H), 7.05 (s, 1H), 2.55 (s, 1H), 1.51 (s, 1H).

Preparation of compound 74d: 4-(2-Imidazol-1-yl-6-methyl-pyrimidin-4-yl)-4-methyl-pent-2-enoic acid ethyl ester Sodium hydride (240 mg, 6.0 mmol) was dissolved in dry THF (10 mL). The flask was cooled to 0° C., and ethyl 2-(diethoxyphosphoryl)acetate (1.68 g, 6.56 mmol) was added dropwise. When no more gas evolved, a solution of 74c (1.38 g, 5.99 mmol) in THF (20 mL) was added to the reaction while maintaining the temperature around 0° C. The reaction was allowed to stir for 1 hour. Water (50 mL) was added to quench the reaction. The mixture was extracted with EtOAc (50 mL×3). The organic layers were combined, dried over sodium sulfate and concentrated down to afford the crude product. The crude material was purified by flash chromatography (0-33% hexanes/Ethyl acetate gradient) to afford 1.45 g (81%) of 74d. $^1$H NMR (400 MHz, CDCl$_3$) δ 8.68 (s, 1H), 7.93 (s, 1H), 7.21 (s, 1H), 7.17 (s, 1H), 6.99 (d, 1H), 5.90 (d, 1H), 4.23 (q, 2H), 2.54 (s, 3H), 1.53 (s, 6H), 1.30 (t, 3H).

Preparation of compound 74e: 4-(2-Imidazol-1-yl-6-methyl-pyrimidin-4-yl)-4-methyl-pent-2-enoic acid 74d (1.00 g, 3.33 mmol) was dissolved in ethanol (20 mL). Next, a solution of sodium hydroxide (150 mg, 3.75 mmol) in water (5 mL) was added to the reaction vessel. The reaction mixture was stirred at room temperature for 16 hours. The reaction mixture was concentrated down under vacuo. The residue was dissolved in water (20 mL) and extracted with EtOAc (2×10 mL). The organic layers was discarded and the aqueous layer was acidified to pH=5 with concentrated HCl. The precipitate was collected by filtration and dried under vacuo to yield 800 mg (88%) of 74e, which was used without further purification.

Preparation of compound 74: (E)-4-(2-(1H-Imidazol-1-yl)-6-methylpyrimidin-4-yl)-N-(benzo[d][1,3]dioxol-5-ylmethyl)-4-methylpent-2-enamide 74e (70 mg, 0.26 mmol) was dissolved in THF (20 mL) and cooled to −10° C. Ethyl chloroformate (45 mg, 0.41 mmol) was added to the reaction vessel and it was stirred for 10 min. Triethylamine (60 mg, 0.59 mmol) was added and the mixture was stirred for 1.5 h. To the reaction mixture was maintained at −10° C. and piperonylamine (50 mg, 0.33 mmol) was added. The reaction mixture was stirred for 2 h. Next, the reaction mixture was poured into water (20 mL) and extracted with EtOAc (2×20 mL). The organic layer was dried over sodium sulfate and concentrated to afford the crude product. The crude material was purified by flash chromatography (0-33% Ethyl Acetate/Hexanes gradient) to afford 55 mg (55%) of 74. [M+H]$^+$ 406.05; $^1$H NMR (400 MHz, CDCl$_3$) δ 8.64 (s, 1H), 7.92 (s, 1H), 7.12 (d, 1H), 6.99 (s, 1H), 6.80 (m, 3H), 5.94 (s, 2H), 5.84 (d, 1H), 4.42 (d, 2H), 2.53 (s, 3H), 1.51 (s, 6 H).

Example 75

75

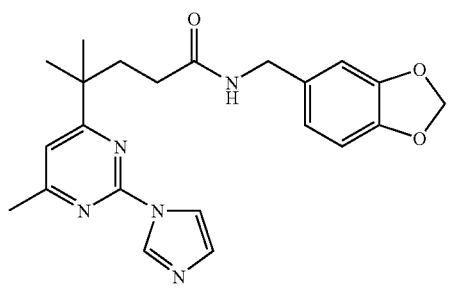

Preparation of compound 75: 4-(2-(1H-Imidazol-1-yl)-6-methylpyrimidin-4-yl)-N-(benzo[d][1,3]dioxol-5-ylmethyl)-4-methylpentanamide 74 (100 mg, 0.25 mmol) was dissolved in glacial acetic acid (10 mL). Under a N$_2$ atmosphere, 10% Pd/C (10 mg, 0.025 mmol) was added to the reaction vessel. The reaction was then placed under a H$_2$ atmosphere and stirred at room temperature for 30 minutes. Water (10 mL) was added to the reaction vessel and the solution was filtered. The filtrate was extracted with dichloromethane (3×10 mL). The combined organic layers were washed with 20% sodium hydroxide (10 mL). The organic layer was dried over sodium sulfate and concentrated to afford to 80 mg (80%) of 75. [M+H]$^+$ 408.05; $^1$H-NMR (400 MHz, CHCl$_3$) δ 8.75 (s, 1H), 7.99 (s, 1H), 7.24 (m, 1H), 7.13 (m, 1H), 6.83 (m, 1H), 6.81 (m, 1H), 6.77 (m, 1H), 6.02 (s, 2H), 5.66 (m, 1H), 4.35 (s, 2H), 2.62 (s, 3H), 2.20 (t, 2H), 2.11 (t, 2H), 1.44 (s, 6H).

Example 76

76

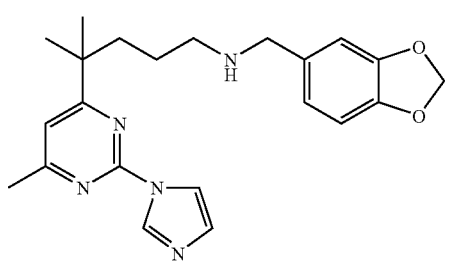

Preparation of compound 76: 4-(2-(1H-Imidazol-1-yl)-6-methylpyrimidin-4-yl)-N-(benzo[d][1,3]dioxol-5-ylmethyl)-4-methylpentan-1-amine 75 (100 mg, 0.30 mmol) was dissolved in anhydrous THF (10 mL). The reaction mixture was cooled to 0° C. and sodium borohydride (1.4 g, 36 mmol) was added to the reaction. Glacial acetic acid (3 g) was added to the reaction mixture, which gas evolution. The reaction mixture was refluxed for 4 hours. Once the reaction mixture returned to room temperature, potassium hydroxide (20% w/w in H$_2$O, 50 mL) was added. The solution was extracted with ethyl acetate (3×20 mL). The organic layer were combined, dried over sodium sulfate and concentrated under vacuum to afford the crude product. The crude material was purified by flash chromatography (0-5% MeOH/DCM gradient) to afford 30 mg (31%) of 76. [M+H]$^+$ 394.29; $^1$H NMR (400 MHz, CHCl$_3$) δ 8.75 (s, 1H), 7.99 (s, 1H), 7.24 (m, 1H), 7.13 (m, 1 H), 6.83 (m, 1H), 6.81 (m, 1H), 6.77 (m, 1H), 6.02 (s, 2H), 5.66 (m, 1H), 4.35 (s, 2H), 2.65 (m, 2H), 2.62 (s, 3H), 2.20 (m, 2H), 2.11 (m, 2H), 1.44 (s, 6H).

Example 77

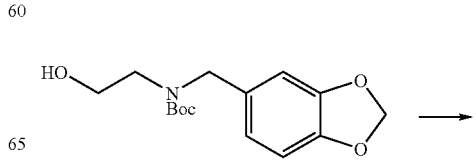

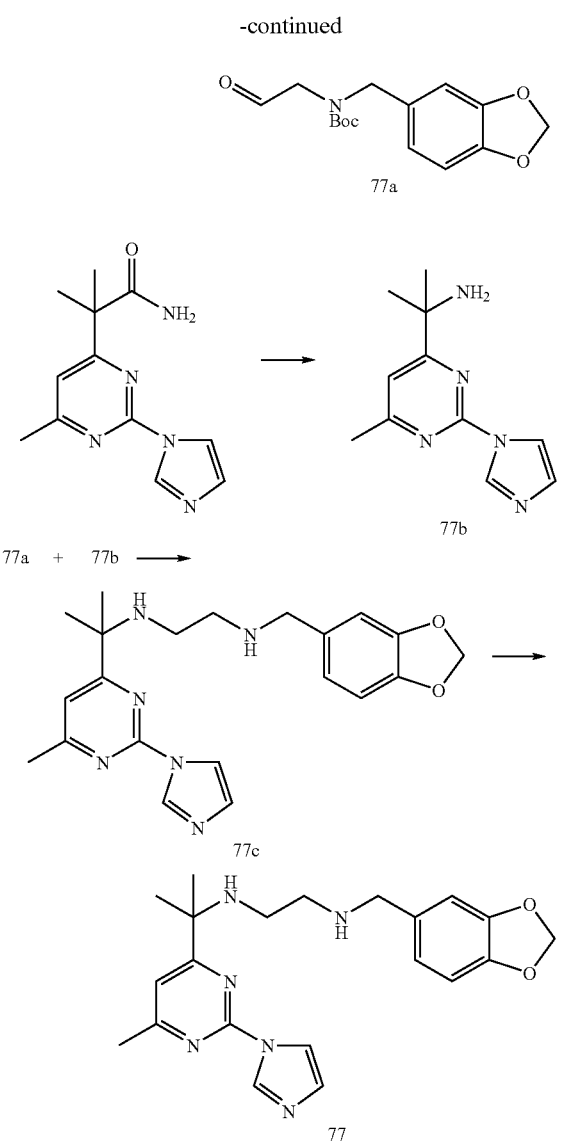

Step 1

Preparation of compound 77a:
Benzo[1,3]dioxol-5-ylmethyl-(2-oxo-ethyl)-carbamic acid tert-butyl ester Oxalyl dichloride (3.80 g, 29.9 mmol) was dissolved in dichloromethane (50 mL) and cooled to −50° C. DMSO (2.50 g, 32.0 mmol) was added dropwise to the reaction and the mixture was stirred for 1 h. Benzo[1,3]dioxol-5-ylmethyl-(2-hydroxy-ethyl)-carbamic acid tert-butyl ester (3.50 g, 11.9 mmol) was then added to the reaction and the temperature was maintained below −50° C. The reaction was stirred for 1 hour. Triethylamine (5.10 g, 50.4 mmol) was added to the reaction and the temperature was raised to −15° C. Water (15 mL) was added and the mixture was stirred for 30 minutes. The organic layer was then partitioned from the aqueous layer and dried over sodium sulfate to afford 3.1 g (81%) of 77a, which was used directly in the subsequent step.

Step 2

Preparation of compound 77b: 1-(2-Imidazol-1-yl-6-methyl-pyrimidin-4-yl)-1-methyl-ethylamine Br$_2$ (1.60 g, 10.0 mmol) was added to a 0° C. solution of sodium hydroxide (2.40 g, 60.0 mmol) in water (10 mL). The 1 ml of the resulting stock solution was added to a reaction vessel. 2-(2-Imidazol-1-yl-6-methyl-pyrimidin-4-yl)-isobutyramide (250 mg, 1.02 mmol) was added to the reaction vessel and the mixture was stirred for 1 h. After this period, the solution was heated and stirred at 50° C. for 1 hour. The solution was transferred to a separatory funnel and extracted with ethyl acetate (3×10 mL). The organic layers were combined, dried over sodium sulfate, concentrated down under vacuo and purified by flash chromatography (0-10% methanol/DCM gradient to afford 80 mg (38%) of 77b.

Step 3

Preparation of compound 77c: Benzo[1,3]dioxol-5-ylmethyl-{2-[1-(2-imidazol-1-yl-6-methyl-pyrimidin-4-yl)-1-methyl-ethylamino]-ethyl}-carbamic acid tert-butyl ester 77b (80 mg, 0.37 mmol) was dissolved in methanol (5 mL), followed by addition of 77a (300 mg, 1.0 mmol). The mixture was stirred for 3 h. Then NaBH$_4$ (240 mg, 6.3 mmol) was added. The mixture was stirred at room temperature for 15 h. The reaction mixture was concentrated under vacuo. The crude residue was dissolved in water (5 mL) and extracted with ethyl acetate (3×10 mL). The organic layer was dried over sodium sulfate and concentrated. The crude product was purified by flash chromatography (0-10% MeOH/DCM gradient) to afford 50 mg (31%) of 77c.

Step 4

Preparation of compound 77: N-1-(2-(2-(1H-Imidazol-1-yl)-6-methylpyrimidin-4-yl)propan-2-yl)-N-2-(benzo[d][1,3]dioxol-5-ylmethyl)ethane-1,2-diamine hydrochloride 3N hydrochloride in ethyl ether (15 mL) was added to 77c (50 mg, 0.10 mmol) while cooling to 0° C. in an ice bath. The mixture was stirred for 6 h and filtered to afford a solid that was washed with anhydrous ethyl ether (2×5 mL). The filtrate was concentrated under vacuum to afford 26 mg of 77. [M+H]$^+$ 395.28; $^1$H NMR (400 MHz, CHCl$_3$) δ 9.50 (s, 1H), 8.30 (s, 1H), 7.55 (m, 1H), 6.87 (m, 1 H), 5.98 (s, 2H), 4.1 (m, 2H), 4.23 (m, 2H), 3.78 (m, 2H), 2.57 (s, 3H), 1.67 (s, 6H).

Example 78

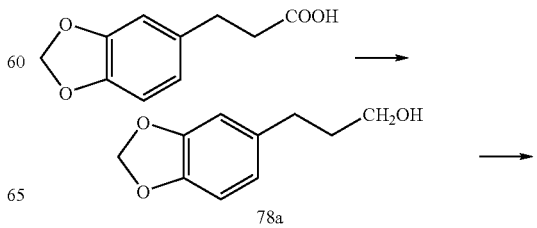

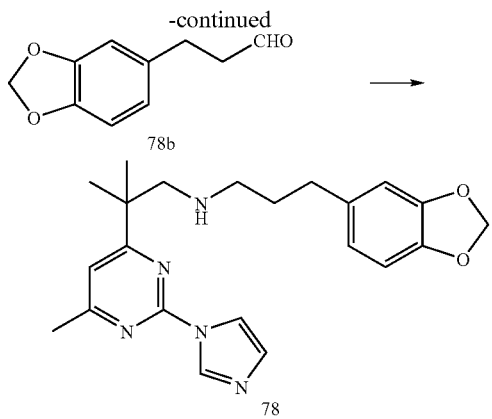

Step 1

Preparation of compound 78a: 3-Benzo[1,3]dioxol-5-yl-propan-1-ol 3-(Benzo[d][1,3]dioxol-5-yl)propanoic acid (3.61 g, 18.6 mmol) was dissolved in anhydrous THF (5 mL and added dropwise to a 0° C. solution of LiAlH$_4$ (710 mg, 18.6 mmol) and anhydrous THF (100 mL). Upon completion of the addition, the reaction mixture was refluxed for 16 hours. The solution was then cooled to 0° C., water (10 mL) was added to the reaction and the solution was allowed to stir for 20 minutes. The solution was then extracted with ethyl acetate (3×20 mL). The organic layer was dried sodium sulfate and concentrated to afford 3.20 g (96%) of 78a.

Step 2

Preparation of compound 78b: 3-Benzo[1,3]dioxol-5-yl-propionaldehyde

Dichloromethane (15 mL) and cooled to −50° C. Oxalyl chloride (18.4 g, 14.5 mmol) in dichloromethane (5 mL) was then added to the reaction. Next, DMSO (2.27 g, 29.0 mmol) in dichloromethane (5 mL) was added dropwise at −50° C. After 5 minutes, 78a (870 mg, 4.83 mmol) in dichloromethane (10 mL) was added dropwise. The reaction mixture stirred for 3 h at −50° C., then triethylamine (5 drops) was added dropwise and the mixture was stirred for 10 min. Water (20 mL) was added to the reaction and the solution was extracted with dichloromethane (3×20 mL). The organic layers were combined, dried over anhydrous sodium sulfate and concentrated under vacuo. The crude product was purified by flash chromatography (0-25% ethyl acetate/hexanes) to afford 700 mg (81.4%) of 78b.

Step 3

Preparation of compound 78: (3-Benzo[1,3]dioxol-5-yl-propyl)-{2-[2-(2H-imidazol-1-yl)-6-methyl-pyrimidin-4-yl]-2-methyl-propyl}-amine hydrochloride 2-[2-(2H-Imidazol-1-yl)-6-methyl-pyrimidin-4-yl]-2-methyl-propylamine (0.15 g, 0.65 mmol) and 78b (0.12 g, 0.65 mmol) were dissolved methanol (10 mL). Glacial acetic acid (2 drops) was added and the mixture was stirred for 3 h at 0° C. in ice bath. NaBH$_3$CN (50 mg, 0.78 mmol) was added in batches and the mixture stirred for 16 h at the room temperature. The resulting solution was concentrated down under vacuo and water (20 mL) was added. The solution was extracted with dichloromethane (3×20 mL), dried over anhydrous sodium sulfate and concentrated to afford the crude product. The crude material was purified by flash chromatography (0-10% MeOH/DCM gradient) to afford the colorless oil. The resulting oil was them dissolved in methanol (10 mL). 1M HCl solution was added to until the pH=2 and the mixture was stirred for 2 hours. The solution was concentrated to afford 30 mg (11%) of 78. [M+H]$^+$ 394.28; NMR (400 MHz, CHCl$_3$) δ 9.58 (s, 1H), 8.25 (s, 1H), 7.54 (d, 2H), 6.69 (d, 1H), 6.57 (d, 1H), 5.87 (s, 1H), 3.47 (s, 2H), 3.24 (s, 6H), 2.90 (m, 2H), 2.56 (s, 2H), 2.47 (m, 2H), 1.82 (m, 2H), 1.32 (s, 3H).

Example 79

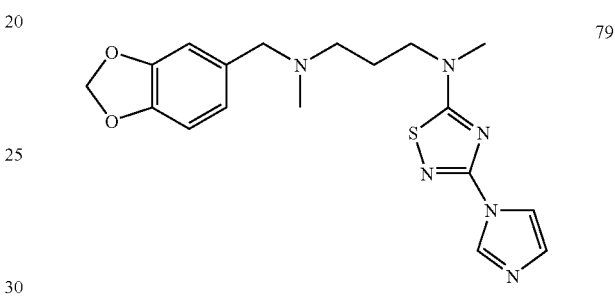

Preparation of compound 79; N-Benzo[1,3]dioxol-5-ylmethyl-N'-(3-imidazol-1-yl-[1,2,4]thiadiazol-5-yl)-N,N'-dimethyl-propane-1,3-diamine was prepared following the procedures described in the preparation of Example 1c using N'-benzo[1,3]dioxol-5-ylmethyl-N-(3-imidazol-1-yl-[1,2,4]thiadiazol-5-yl)-N-methyl-propane-1,3-diamine.

[M+H]$^+$ 387.66; $^1$H NMR (400 MHz, CDCl$_3$) δ 8.29 (s, 1H), 7.64 (t, 1H), 7.07 (t, 1H), 6.81 (s, 1H), 6.72 (m, 2H, 5.93 (s, 2H), 3.60-3.50 (s, 3H), 3.39 (s, 3H), 3.11 (br s, 2H), 2.40 (t, 2H), 2.18 (t, 2H), 1.87 (m, 2H).

Example 80

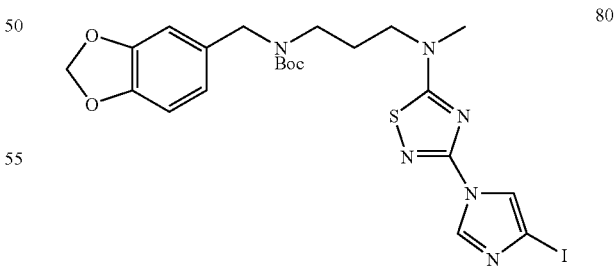

Preparation of compound 80: Benzo[1,3]dioxol-5-ylmethyl-(3-{[3-(4-iodo-imidazol-1-yl)-[1,2,4]thiadiazol-5-yl]-methyl-amino}-propyl-carbamic acid tert-butyl ester was prepared following the procedures described in the preparation of Example 2e using 4-iodo-1H-imidazole. [M+H]$^+$ 598.90.

Example 81

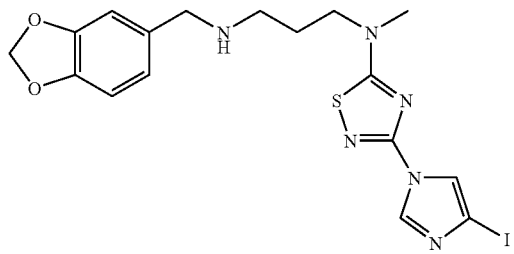

Preparation of compound 81: N'-Benzo[1,3]dioxol-5-ylmethyl-N-[3-(4-iodo-imidazol-1-yl)-[1,2,4]thiadiazol-5-yl]-N-methyl-propane-1,3-diamine was prepared following the procedures described in the preparation of Example 2 using benzo[1,3]dioxol-5-ylmethyl-(3-{[3-(4-iodo-imidazol-1-yl)-[1,2,4]thiadiazol-5-yl]-methyl-amino}-propyl)-carbamic acid tert-butyl ester. [M+H]$^+$ 499.32; $^1$H NMR (400 MHz, CDCl$_3$) δ 8.12 (s, 1H), 7.71 (s, 1H), 6.76 (s, 1H), 6.70 (m, 2H), 5.91 (s, 2H), 3.65 (s, 3H), 3.70-3.50 (br s, 2H), 3.09 (br s, 2H), 2.64 (t, 2H), 1.87 (m, 2H), 1.62 (br s, 1H).

Example 82

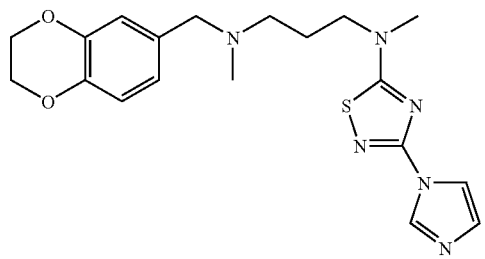

Preparation of compound 82: N-(2,3-Dihydro-benzo[1,4]dioxin-6-ylmethyl)-N'-(3-imidazol-1-yl-[1,2,4]thiadiazol-5-yl)-N,N'-dimethyl-propane-1,3-diamine was prepared following the procedures described in the preparation of Example 1c using N'-(2,3-dihydro-benzo[1,4]dioxin-6-ylmethyl)-N-(3-imidazol-1-yl-[1,2,4]thiadiazol-5-yl)-N-methyl-propane-1,3-diamine. [M+H]$^+$ 401.55; $^1$H NMR (400 MHz, CDCl$_3$) δ 8.30 (s, 1H), 7.64 (s, 1H), 7.10 (s, 1H), 6.80-6.75 (m, 3H), 4.24 (s, 4H), 3.67 (s, 3H), 3.14 (s, 3H), 2.67 (t, 2H), 1.87 (t, 4H).

Example 83

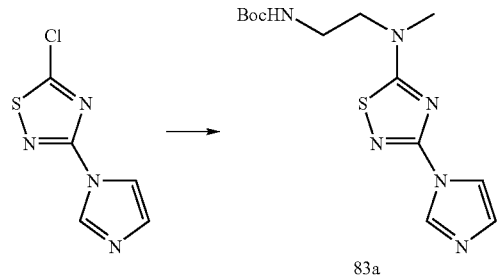

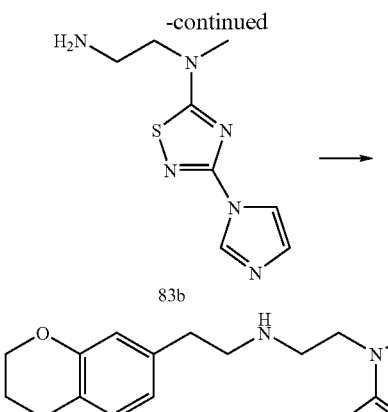

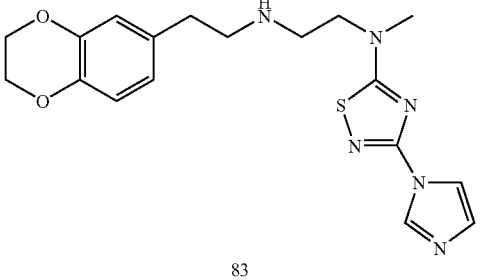

Step 1

Preparation of compound 83a: {2-[(3-Imidazol-1-yl-[1,2,4]thiadiazol-5-yl)-methyl-amino]-ethyl}-carbamic acid tert-butyl ester was prepared following the procedures described in the preparation of Example 23 using (2-methylamino-ethyl)-carbamic acid tert-butyl ester. [M+H]$^+$ 325.12.

Step 2

Preparation of compound 83b: N-1-(3-Imidazol-1-yl-[1,2,4]thiadiazol-5-yl)-N-1-methyl-ethane-1,2-diamine was prepared following was prepared following the procedures described in the preparation of Example 2 using {2-[(3-imidazol-1-yl-[1,2,4]thiadiazol-5-yl)-methyl-amino]-ethyl}-carbamic acid tert-butyl ester. [M+H]$^+$ 225.07.

Step 3

Preparation of compound 83: N'-[2-(2,3-Dihydro-benzo[1,4]dioxin-6-yl)-ethyl]-N-(3-imidazol-1-yl-[1,2,4]thiadiazol-5-yl)-N-methyl-ethane-1,2-diamine was prepared following the procedures described in the preparation of Example 127 using (2,3-dihydro-benzo[1,4]dioxin-6-yl)-acetaldehyde. [M+H]$^+$ 387.74; $^1$H NMR (400 MHz, CDCl$_3$) δ 8.36 (s, 1H), 7.64 (s, 1H), 7.06 (s, 1H), 6.73 (d, 1H), 6.66 (d, 1H), 6.61 (dd, 2H), 4.21 (s, 4H), 3.74 (br s, 2H), 3.13 (s, 3H), 3.06 (t, 2H), 2.98 (t, 2H), 2.78 (t, 2H).

Example 84

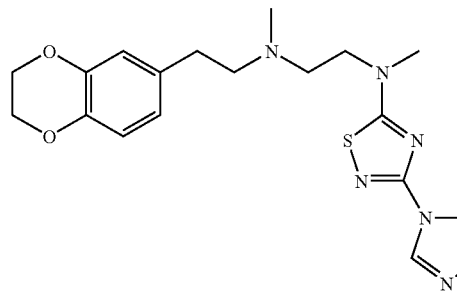

Preparation of compound 84: N-[2-(2,3-Dihydro-benzo[1,4]dioxin-6-yl)-ethyl]-N'-(3-imidazol-1-yl-[1,2,4]thiadiazol-5-yl)-N,N'-dimethyl-ethane-1,2-diamine was prepared fol-

Example 85

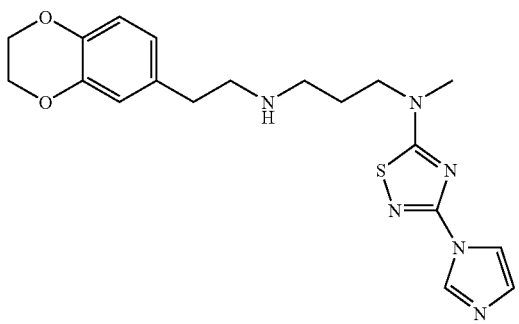

Preparation of compound 85: N'-[2-(2,3-Dihydro-benzo[1,4]dioxin-6-yl)-ethyl]-N-(3-imidazol-1-yl-[1,2,4]thiadiazol-5-yl)-N-methyl-propane-1,3-diamine was prepared following the procedures described in the preparation of Example 127 using 6 and (2,3-dihydro-benzo[1,4]dioxin-6-yl)-acetaldehyde. [M+H]$^+$ 401.29; $^1$H NMR (400 MHz, CDCl$_3$) δ 8.33 (s, 1H), 7.65 (s, 1H), 7.08 (s, 1H), 6.76 (d, 1H), 6.68 (d, 1H), 6.63 (dd, 1H), 4.22 (s, 4H), 3.70-3.50 (br s, 2H), 3.11 (s, 3H), 2.89 (t, 2H), 2.80-2.70 (m, 4H), 1.97 (m, 2H).

Example 86

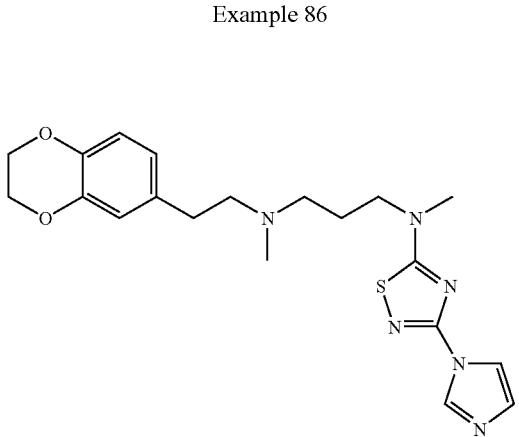

Preparation of compound 86: N-[2-(2,3-Dihydro-benzo[1,4]dioxin-6-yl)-ethyl]-N'-(3-imidazol-1-yl-[1,2,4]thiadiazol-5-yl)-N,N'-dimethyl-propane-1,3-diamine was prepared following the procedures described in the preparation of Example 1c using N'-[2-(2,3-dihydro-benzo[1,4]dioxin-6-yl)-ethyl]-N-(3-imidazol-1-yl-[1,2,4]thiadiazol-5-yl)-N-methyl-ethane-1,2-diamine. [M+H]$^+$ 401.33; $^1$H NMR (400 MHz, CD$_3$OD) δ 8.31 (s, 1H), 7.69 (s, 1H), 7.04 (s, 1H), 6.70-6.50 (m, 3H), 4.13 (s, 4H), 3.74 (br s, 2H), 3.03 (s, 3H), 2.68 (t, 2H), 2.60-2.50 (m, 4H), 2.32 (s, 3H).

Example 87

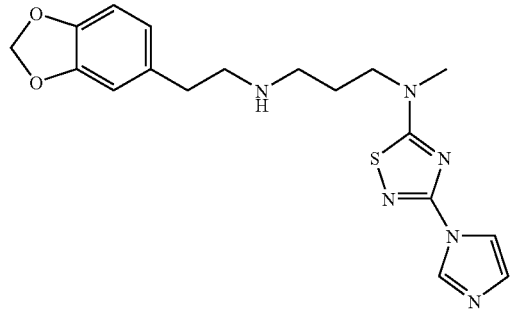

Preparation of compound 87: N'-(2-Benzo[1,3]dioxol-5-ethyl)-N-(3-imidazol-1-yl-[1,2,4]thiadiazol-5-yl)-N-methyl-propane-1,3-diamine was prepared following the procedures described in the preparation of Example 127 using 6 and benzo[1,3]dioxol-5-yl-acetaldehyde. [M+H]$^+$ 387.30; $^1$H NMR (400 MHz, CDCl$_3$) δ 8.31 (s, 1H), 7.65 (s, 1H), 7.08 (s, 1H), 6.70 (d, 1H), 6.67 (d, 1H), 6.62 (dd, 1H), 5.91 (s, 2H), 3.70-3.50 (br s, 2H), 3.11 (s, 3H), 2.85 (t, 2H), 2.76-2.68 (m, 4H), 1.83 (m, 2H).

Example 88

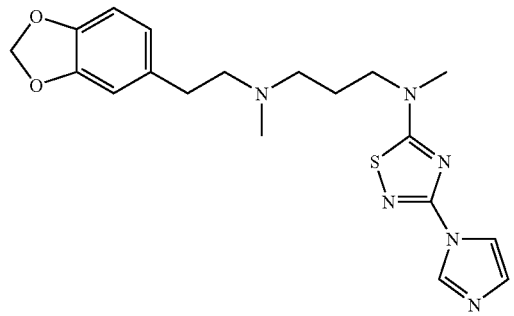

Preparation of compound 88: N-(2-Benzo[1,3]dioxol-5-yl-ethyl)-N'-(3-imidazol-1-yl-[1,2,4]thiadiazol-5-yl)-N,N'-dimethyl-propane-1,3-diamine was prepared following the procedures described in the preparation of Example 1c using N'-(2-benzo[1,3]dioxol-5-yl-ethyl)-N-(3-imidazol-1-yl-[1,2,4]thiadiazol-5-yl)-N-methyl-propane-1,3-diamine. [M+H]$^+$ 401.30; $^1$H NMR (400 MHz, CDCl$_3$) δ 8.28 (s, 1H), 7.63 (s, 1H), 7.06 (s, 1H), 6.69 (d, 1H), 6.65 (d, 1H), 6.60 (dd, 1H), 5.88 (s, 2H), 3.55-3.30 (br s, 2H), 3.08 (s, 3H), 2.66 (t, 2H), 2.55 (t, 2H), 2.42 (t, 2H), 2.27 (s, 3H), 1.81 (m, 2H).

Example 89

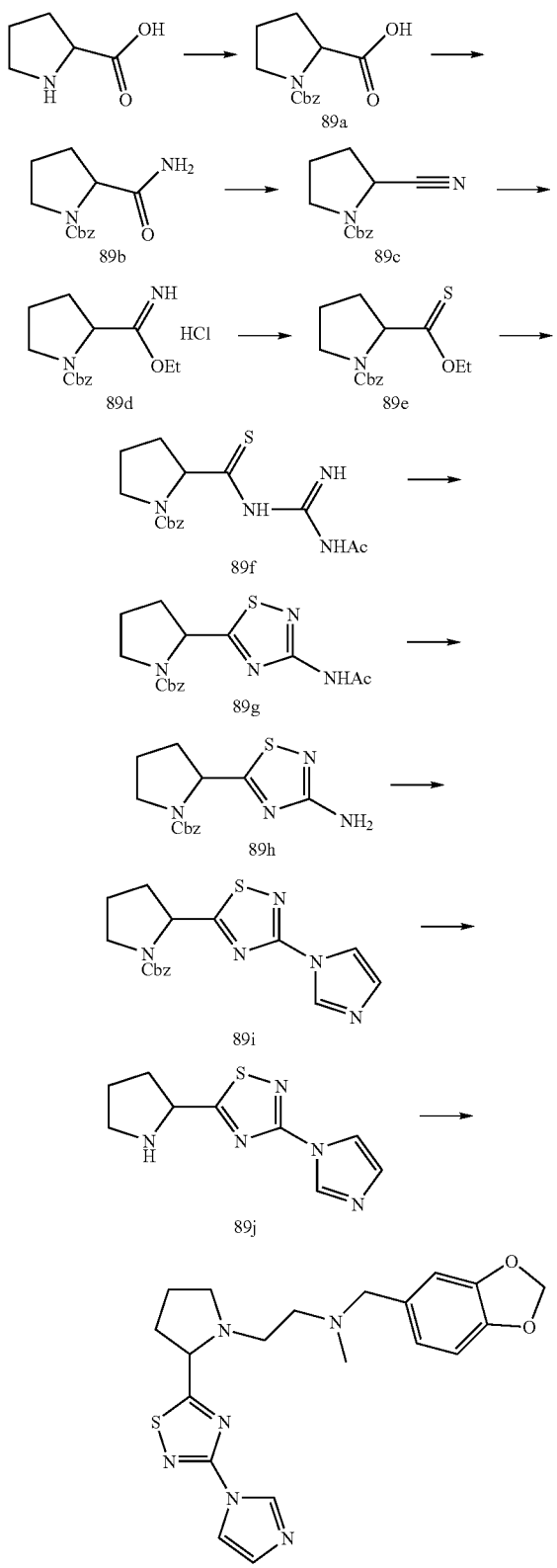

Step 1

Preparation of compound 89a:
Pyrrolidine-1,2-dicarboxylic acid 1-benzyl ester

Benzyl chloroformate (29.7 g, 174 mmol) was added dropwise to a 0° C. solution of Pyrrolidine-2-carboxylic acid (20.0 g, 174 mmol) dissolved in 1N NaOH (350 mL). The solution was stirred at 0° C. for 30 mins. The solution was allowed to equilibrate to room temperature while stirring overnight. The solution was acidified to pH=3 by addition of 1M HCl. The resulting solution was extracted with ethyl acetate (3×300 mL). The organic layers were combined, dried over MgSO₄ and concentrated under vacuo to afford 40.4 g (89%) of the crude product, pyrrolidine-1,2-dicarboxylic acid 1-benzyl ester, as a colorless oil.

Step 2

Preparation of compound 89b:
2-Carbamoyl-pyrrolidine-1-carboxylic acid benzyl ester Pyrrolidine-1,2-dicarboxylic acid 1-benzyl ester (30.0 g, 121 mmol) was dissolved in DCM (180 mL). The solution was cooled to 0° C. and N-methyl-morpholine (12.8 g, 127 mmol) was added over a period of 10 mins. The solution was then cooled to −15° C. and the ethyl chloroformate (13.7 g, 126 mmol) in DCM (30 mL) was added dropwise. The solution was then stirred for 2 hours at −25° C. Next, the solution was placed under NH₃ (g) while maintaining the temperature below −20° C. The reaction mixture was then stirred for 1 hour while allowing the temperature to return to 0° C. The solution was poured in H₂O (120 mL) and the organic layer was partitioned from the aqueous layer. The organic layer was then washed with 1N HCl (2×50 mL), 1N NaHCO₃ (2×50 mL), dried over MgSO₄ and concentrated under vacuo to afford 27.8 g (88%) of 2-carbamoyl-pyrrolidine-1-carboxylic acid benzyl ester, as a colorless oil.

Step 3

Preparation of compound 89c:
2-Cyano-pyrrolidine-1-carboxylic acid benzyl ester

Carbamoyl-pyrrolidine-1-carboxylic acid benzyl ester (25.0 g, 101 mmol) was dissolved in pyridine (125 mL) under an N₂ atmosphere and cooled to −10° C. The phosphorus oxychloride (12.6 mL, 135 mmol) was dissolved in DCM (25 mL) and added dropwise over 40 mins to the pyridine solution. The reaction mixture's temperature was maintained at −10° C. and the solution was allowed to stir for 2 hours. The reaction was quenched by addition of water/ice (100 g) and transferred into a separatory funnel. The solution was extracted with diethyl ether (3×200 mL). The organic layers were combined and washed with saturated cupric sulfate (200 mL). The organic layer was dried over MgSO₄ and concentrated under vacuo to afford 20.0 g (82%) of 2-cyano-pyrrolidine-1-carboxylic acid benzyl ester as a green oil.

Step 4

Preparation of compound 89d:
2-Ethoxycarbonimidoyl-pyrrolidine-1-carboxylic acid benzyl ester 2-Cyano-pyrrolidine-1-carboxylic acid benzyl ester (17.0 g, 73.9 mmol) was dissolved in diethyl ether (100 mL). Ethanol (20.4 g, 444 mmol) was added and gaseous HCl was bubbled through the reaction mixture, while maintaining the temperature at −20° C. The temperature was maintained for 12 hours while stirring. The reaction mixture was concentrated under vacuo to afford 22.0 g (95%) of 2-ethoxycarbonimidoyl-pyrrolidine-1-carboxylic acid benzyl ester as a red oil.

Step 5

Preparation of compound 89e: 2-Ethoxythiocarbonyl-pyrrolidine-1-carboxylic acid benzyl ester 2-Ethoxycarbonimidoyl-pyrrolidine-1-carboxylic acid benzyl ester hydrochloride (42.8 g, 146.0 mmol) was dissolved in THF (150 mL) and cooled to −20° C. Pyridine (80 ml) was added to the reaction and H$_2$S was bubbled through the reaction for 60 min. The reaction's temperature was maintained at −20° C. for 2 hours while stirring. The pH was adjust to pH=4 by addition of 5M HCl. The resulting solution was transferred to a separatory funnel and extracted with diethyl ether (3×100 mL). The organic layers were combined and washed with brine (100 ml). The organic layer was dried over MgSO$_4$ and concentrated under vacuo to afford 20.0 g (47%) of 2-ethoxythiocarbonyl-pyrrolidine-1-carboxylic acid benzyl ester as a yellow oil.

Step 6

Preparation of compound 89f: 2-(N'-Acetyl-guanidinocarbothioyl)-pyrrolidine-1-carboxylic acid benzyl ester 1-Acetylguanidine (7.20 g, 71.0 mmol) was dissolved in THF (100 mL). The solution was cooled to 0° C. and NaH (1.90 g, 80.0 mmol) was added to the reaction in small batches over 5 mins. Next, 2-ethoxythiocarbonyl-pyrrolidine-1-carboxylic acid benzyl ester (19.6 g, 66.9 mmol) in THF (50 mL) was added to the reaction dropwise over 30 minutes while maintaining the temperature between 0-5° C. The reaction was allowed to return to room temperature, while stirring an additional 12 hours. The product was precipitated by addition of petroleum ether. The organic layer was decanted off and the solid was retained and redissolved in water (300 mL). The pH was adjusted to pH=3 by addition of acetic acid. The resulting solution was transferred to a separatory funnel and extracted with DCM (3×250 mL). The organic layers were combined, dried over MgSO$_4$ and concentrated under vacuo to afford 13.0 g (56%) of 2-(N'-acetyl-guanidinocarbothioyl)-pyrrolidine-1-carboxylic acid benzyl ester.

Step 7

Preparation of compound 89g: 2-(3-Acetylamino-[1,2,4]thiadiazol-5-yl)-pyrrolidine-1-carboxylic acid benzyl ester hydrobromide 2-(N'-Acetyl-guanidinocarbothioyl)-pyrrolidine-1-carboxylic acid benzyl ester (13.0 g, 37.4 mmol) was dissolved in ethanol (80 mL). The ethanol solution was cooled to 0° C. and a solution of bromine (6.50 g, 40.6 mmol) in chloroform (30 mL) was added dropwise over 5 minutes. The resulting solution was allowed to return to room temperature while stirring for 3 hours. The reaction mixture was concentrated under vacuo to afford 14.0 g (88%) of 2-(3-acetylamino-[1,2,4]thiadiazol-5-yl)-pyrrolidine-1-carboxylic acid benzyl ester hydrobromide.

Step 8

Preparation of compound 89h: 2-(3-Amino-[1,2,4]thiadiazol-5-yl)-pyrrolidine-1-carboxylic acid benzyl ester 2-(3-Acetylamino-[1,2,4]thiadiazol-5-yl)-pyrrolidine-1-carboxylic acid benzyl ester hydrobromide (14.0 g, 37.8 mmol) was dissolved in ethanol (80 mL). The reaction mixture was cooled to 0° C. and a solution of K$_2$CO$_3$ (15.0 g, 108.7 mmol) in H$_2$O (40 mL) was added. The solution was allowed to return to room temperature while stirring for 30 mins. The solution was concentrated down, redissolved in water (100 mL) and extracted with DCM (3×50 mL). The organic layers were combined and washed with brine (3×50 mL). The organic layer was partitioned from the aqueous layer, dried over MgSO$_4$ and concentrated under vacuo to afford 9.4 g (94%) of 2-(3-amino-[1,2,4]thiadiazol-5-yl)-pyrrolidine-1-carboxylic acid benzyl ester as a yellow oil.

Step 9

Preparation of compound 89i: 2-(3-Imidazol-1-yl-[1,2,4]thiadiazol-5-yl)-pyrrolidine-1-carboxylic acid benzyl ester 2-(3-Amino-[1,2,4]thiadiazol-5-yl)-pyrrolidine-1-carboxylic acid benzyl ester (9.40 g, 30.9 mmol) was dissolved in ethanol (80 mL), glyoxal (40% wt) (19.6 g, 101.4 mmol) was added to the reaction and the solution was refluxed to 3 hours. Ammonium chloride (7.80 g, 146 mmol) and calcium phosphate (11.0 g, 110 mmol) were added followed by subsequent addition of formalin (11.0 g of a 40% aqueous solution, 147 mmol) while the reaction was maintained at reflux for 16 hours. The solution was concentrated under vacuo. The crude residue was dissolved in water (20 mL) and washed with ethyl acetate (15 mL). The aqueous layer was basified to pH=9 with 1N NaOH. The aqueous layer was then extracted with ethyl acetate (2×100 mL). The organic layers were combined and concentrated under vacuo to afford 7.2 g (66%) of 2-(3-imidazol-1-yl-[1,2,4]thiadiazol-5-yl)-pyrrolidine-1-carboxylic acid benzyl ester as red oil.

Step 10

Preparation of compound 89j: 3-Imidazol-1-yl-5-pyrrolidin-2-yl-[1,2,4]thiadiazole 2-(3-Imidazol-1-yl-[1,2,4]thiadiazol-5-yl)-pyrrolidine-1-carboxylic acid tert-butyl ester (359 mg, 1.01 mmol) was dissolved in dioxane (2 mL) and 6M HCl (aq) (2 mL). The reaction vessel was sealed and heated to 100° C. for 1 h. The reaction was allowed to return to room temperature while standing overnight. The reaction mixture was transferred to a separatory funnel and washed with 1M NaOH (30 mL). The aqueous layer was back extracted with DCM (50 mL). The organic layers were combined, dried over Na$_2$SO$_4$ to and concentrated in vacuo to afford 179 mg (80.4%) of 3-imidazol-1-yl-5-pyrrolidin-2-yl-[1,2,4]thiadiazole. [M+H]$^+$ 221.87.

Step 11

Preparation of compound 89: Benzo[1,3]dioxol-5-ylmethyl-{2-[2-(3-imidazol-1-yl-[1,2,4]thiadiazol-5-yl)-pyrrolidin-1-yl]-ethyl}-methyl-amine A solution of benzo[1,3]dioxol-5-ylmethyl-(2-chloroethyl)-methyl-ammonium hydrochloride (130 mg, 492 µmol), 3-imidazol-1-yl-5-pyrrolidin-2-yl-[1,2,4]thiadiazole (110 mg, 497 µmol), potassium iodide (20 mg, 120 µmol), and TEA (200 μL, 1.44 mmol) in DMF (1.8 mL) was heated at 140 C for 7 min. The reaction mixture was cooled to r.t. and poured into 10 mL of 1N K$_2$HPO$_4$(aq)/EtOAc (1:1). The organic layer was isolated and concentrated to crude residue. Purification was achieved using reverse phase HPLC (5% to 100% Acetonitrile/H$_2$O, 0.1% TFA) to afford 10 mg (4%) of benzo[1,3]dioxol-5-ylmethyl-{2-[2-(3-imidazol-1-yl-[1,2,4]thiadiazol-5-yl)-pyrrolidin-1-yl]-ethyl}-methyl-amine as the TFA salt. [M+H]$^+$ 412.85; $^1$H NMR (400 MHz, CDCl$_3$) δ 9.23 (s, 1H), 7.95 (s, 1H), 7.46 (s, 1H), 6.88 (s, 1H), 6.81 (m, 2H), 6.01 (s, 2H), 4.24 (m, 1H), 4.15 (m, 2H), 3.0-3.4 (m, 5H), 2.72 (s, 3H), 2.58 (m, 1H), 2.40 (m, 1H), 1.98 (m, 2H), 1.90 (m, 1H).

Example 90

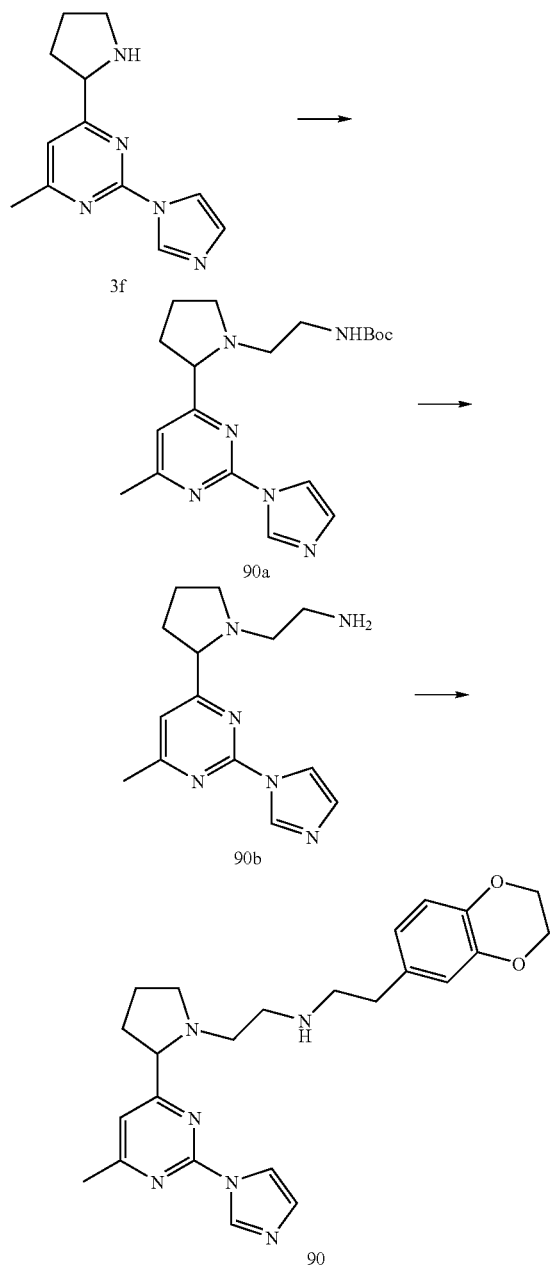

Step 1

Preparation of compound 90a: [2-(2,3-Dihydro-benzo[1,4]dioxin-6-yl)-ethyl]-{2-[2-(2-imidazol-1-yl-6-methyl-pyrimidin-4-yl)-pyrrolidin-1-yl]-ethyl}-amine was prepared following the procedures described in the preparation of Example 3 using (2-bromo-ethyl)-carbamic acid tert-butyl ester and 3f. [M+H]$^+$ 373.47.

Step 2

Preparation of compound 90b: 2-[2-(2-Imidazol-1-yl-6-methyl-pyrimidin-4-yl)-pyrrolidin-1-yl]-ethylamine was prepared following the procedures described in the preparation of Example 2 using {2-[2-(2-imidazol-1-yl-6-methyl-pyrimidin-4-yl)-pyrrolidin-1-yl]-ethyl}-carbamic acid tert-butyl ester. [M+H]$^+$ 273.81.

Step 3

Preparation of compound 90: [2-(2,3-Dihydro-benzo[1,4]dioxin-6-yl)-ethyl]-{2-[2-(2-imidazol-1-yl-6-methyl-pyrimidin-4-yl)-pyrrolidin-1-yl]-ethyl}-amine was prepared following the procedures described in the preparation of Example 127 using (2,3-dihydro-benzo[1,4]dioxin-6-yl)-acetaldehyde and 2-[2-(2-imidazol-1-yl-6-methyl-pyrimidin-4-yl)-pyrrolidin-1-yl]-ethylamine. [M+H]$^+$ 435.54; $^1$H NMR (400 MHz, CDCl$_3$) δ 8.59 (s, 1H), 7.85 (s, 1H), 7.15 (s, 1H), 7.10 (s, 1H), 6.75 (d, 1H), 6.70-6.60 (m, 2H), 4.18 (s, 4H), 3.54 (t, 1H), 3.15 (m, 1H), 2.94-2.74 (m, 5H), 2.52 (s, 3H), 2.40-2.20 (m, 4H), 1.95-1.66 (m, 4H).

Example 91

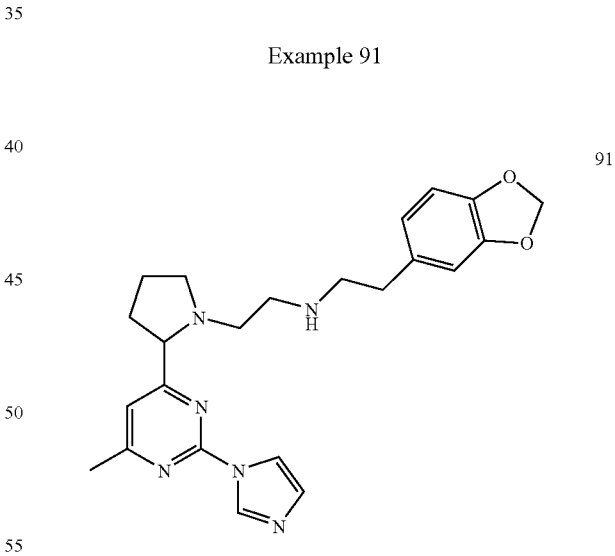

Preparation of compound 91: (2-Benzo[1,3]dioxol-5-yl-ethyl)-{2-[2-(2-imidazol-1-yl-6-methyl-pyrimidin-4-yl)-pyrrolidin-1-yl]-ethyl}-amine was prepared following the procedures described in the preparation of Example 127 using benzo[1,3]dioxol-5-yl-acetaldehyde and 2-[2-(2-imidazol-1-yl-6-methyl-pyrimidin-4-yl)-pyrrolidin-1-yl]-ethylamine. [M+H]$^+$ 421.55; $^1$H NMR (400 MHz, CDCl$_3$) δ 8.57 (s, 1H), 7.86 (s, 1H), 7.17 (s, 1H), 7.10 (s, 1H), 6.90 (d, 1H), 6.65 (d, 1H), 6.60 (dd, 1H), 5.88 (s, 2H), 3.50 (t, 1H), 3.21 (m, 1H), 2.82-2.64 (m, 5H), 2.50 (s, 3H), 2.40-2.20 (m, 4H), 1.95-1.66 (m, 4H).

Example 92

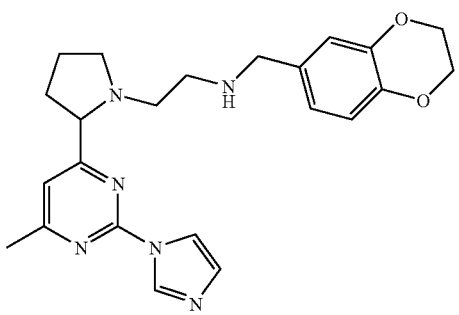

Preparation of compound 92: (2,3-Dihydro-benzo[1,4]dioxin-6-ylmethyl)-{2-[2-(2-imidazol-1-yl-6-methyl-pyrimidin-4-yl)-pyrrolidin-1-yl]-ethyl}-amine A solution of 2-[2-(2-imidazol-1-yl-6-methyl-pyrimidin-4-yl)-pyrrolidin-1-yl]-ethylamine (77 mg, 286 µmol), 2,3-dihydro-benzo[1,4]dioxine-6-carbaldehyde (47 mg, 286 µmol) and p-toluenesulfonic acid monohydrate (5 mg, 26 µmol) in dioxane (3 mL) was heated at 60° C. for 16 h. Sodium triacetoxyborohydride (180 mg, 860 µmol) was then added. The reaction mixture was stirred at r.t. for 1 h. EtOAc (25 mL) and 1N NaOH (25 mL) were then added. The organic layer was isolated, dried (MgSO$_4$), filtered, and concentrated. Silica gel chromatography (0% to 10% MeOH/DCM) afforded 69 mg (57%) of (2,3-dihydro-benzo[1,4]dioxin-6-ylmethyl)-{2-[2-(2-imidazol-1-yl-6-methyl-pyrimidin-4-yl)-pyrrolidin-1-yl]-ethyl}-amine. [M+H]$^+$ 421.23; $^1$H NMR (400 MHz, CDCl$_3$) δ 8.60 (s, 1H), 7.89 (s, 1H), 7.23 (s, 1H), 7.12 (s, 1H), 6.68-6.79 (m, 3H), 4.21 (s, 4H), 3.54 (t, 1H), 3.22 (m, 1H), 2.70-2.82 (m, 2H), 2.20-2.60 (m, 9H), 1.84 (m, 2H), 1.70 (m, 1H).

Example 93

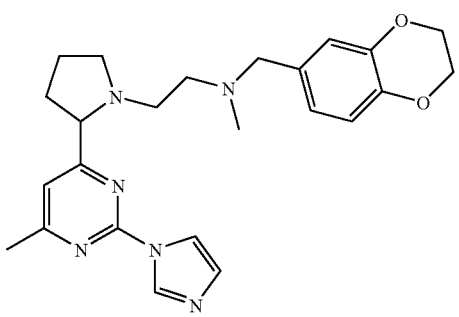

Preparation of compound 93: (2,3-Dihydro-benzo[1,4]dioxin-6-ylmethyl)-{2-[2-(2-imidazol-1-yl-6-methyl-pyrimidin-4-yl)-pyrrolidin-1-yl]-ethyl}-methyl-amine A solution of (2,3-dihydro-benzo[1,4]dioxin-6-ylmethyl)-{2-[2-(2-imidazol-1-yl-6-methyl-pyrimidin-4-yl)-pyrrolidin-1-yl]-ethyl}-amine (65 mg, 156 µmol), formalin (63 µL, 780 µmol), and acetic acid (170 µL, 2.83 mmol) in MeOH (1 mL) was stirred at r.t. for 5 min. Sodium triacetoxyborohydride (99 mg, 470 µmol) was then added. The reaction mixture was stirred at r.t. for 20 min and then concentrated to residue. EtOAc (5 mL) and 1N NaOH (5 mL) were added. The organic layer was isolated, dried (MgSO$_4$), filtered, and concentrated. Silica gel chromatography (0% to 10% MeOH/DCM) afforded 60 mg (89%) of (2,3-dihydro-benzo[1,4]dioxin-6-ylmethyl)-{2-[2-(2-imidazol-1-yl-6-methyl-pyrimidin-4-yl)-pyrrolidin-1-yl]-ethyl}-methyl-amine. [M+H]$^+$ 435.32; $^1$H NMR (400 MHz, CDCl$_3$) δ 8.61 (s, 1H), 7.88 (s, 1H), 7.33 (s, 1H), 7.12 (s, 1H), 6.65-6.79 (m, 3H), 4.21 (s, 4H), 3.54 (t, 1H), 3.24-3.42 (m, 3H), 2.76 (m, 1H), 2.11-2.55 (m, 8H), 2.15 (s, 3H), 1.84 (m, 2H), 1.70 (m, 1H).

Example 94

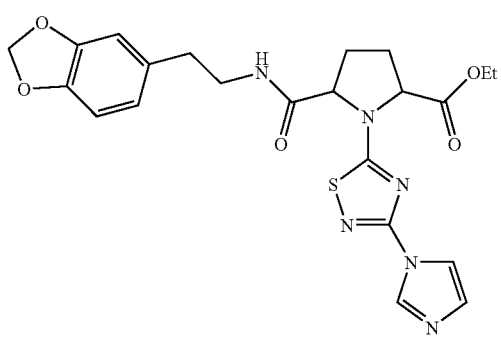

Preparation of compound 94: 5-(2-Benzo[1,3]dioxol-5-yl-ethylcarbamoyl)-1-(3-imidazol-1-yl-[1,2,4]thiadiazol-5-yl)-pyrrolidine-2-carboxylic acid ethyl ester was prepared following the procedures described in the preparation of Example 23 using 5-(2-benzo[1,3]dioxol-5-yl-ethylcarbamoyl)-pyrrolidine-2-carboxylic acid ethyl ester. Isolated as a racemic 3.14:1.00 mixture of rotamers; [M+H]$^+$ 486.15.

Example 95

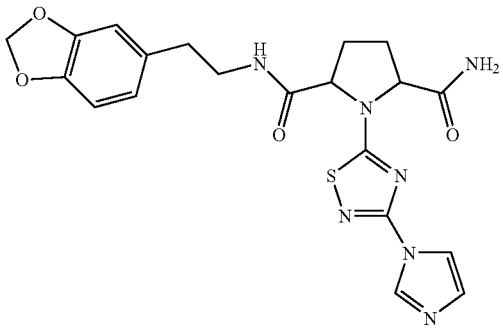

Preparation of compound 95: 1-(3-Imidazol-1-yl-[1,2,4]thiadiazol-5-yl)-pyrrolidine-2,5-dicarboxylic acid 2-amide 5-[(2-benzo[1,3]dioxol-5-yl-ethyl)-amide was prepared following the procedures described in the preparation of Example 54 using 5-(2-benzo[1,3]dioxol-5-yl-ethylcarbamoyl)-1-(3-imidazol-1-yl-[1,2,4]thiadiazol-5-yl)-pyrrolidine-2-carboxylic acid ethyl ester. [M+H]$^+$ 456.56.

Example 96

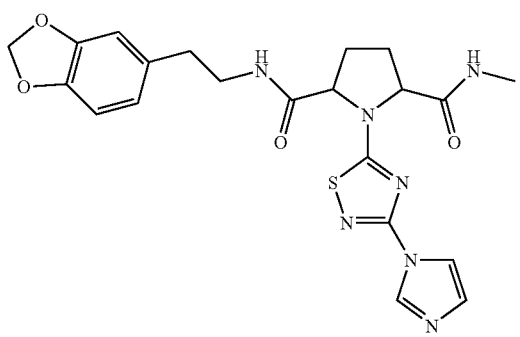

Preparation of compound 96: 1-(3-Imidazol-1-yl-[1,2,4]thiadiazol-5-yl)-pyrrolidine-2,5-dicarboxylic acid 2-[(2-benzo[1,3]dioxol-5-yl-ethyl)-amide] 5-methylamide was prepared following the procedures described in the preparation of Example 54 using 5-(2-benzo[1,3]dioxol-5-yl-ethylcarbamoyl)-1-(3-imidazol-1-yl-[1,2,4]thiadiazol-5-yl)-pyrrolidine-2-carboxylic acid ethyl ester and methylamine. [M+H]$^+$ 470.55.

Example 97

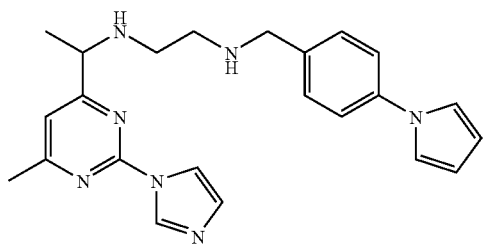

Preparation of compound 97: N-[1-(2-Imidazol-1-yl-6-methyl-pyrimidin-4-yl)-ethyl]-N'-(4-pyrrol-1-yl-benzyl)-ethane-1,2-diamine was prepared following the procedures described in the preparation of Example 44 using 4-pyrrol-1-yl-benzaldehyde. [M+H]$^+$ 402.25.

Example 98

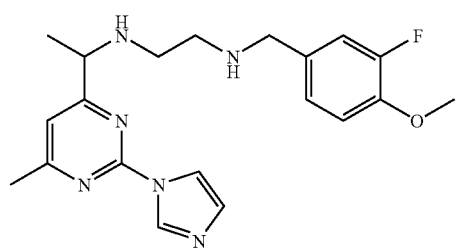

N-(3-Fluoro-4-methoxy-benzyl)-N'-[1-(2-imidazol-1-yl-6-methyl-pyrimidin-4-yl)-ethyl]-ethane-1,2-diamine was prepared following the procedures described in the preparation of Example 44 using 3-fluoro-4-methoxy-benzaldehyde. [M+H]$^+$ 385.05.

Example 99

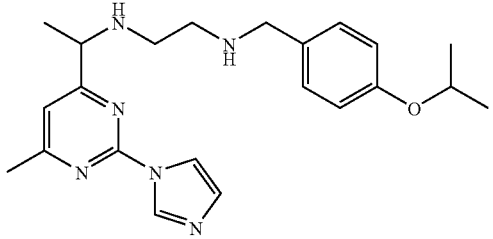

Preparation of compound 99: N-[1-(2-Imidazol-1-yl-6-methyl-pyrimidin-4-yl)-ethyl]-N'-(4-isopropoxy-benzyl)-ethane-1,2-diamine was prepared following the procedures described in the preparation of Example 44 using 4-isopropoxy-benzaldehyde. [M+H]$^+$ 395.40.

Example 100

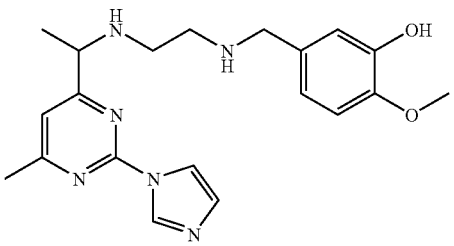

Preparation of compound 100: 5-({2-[1-(2-Imidazol-1-yl-6-methyl-pyrimidin-4-yl)-ethylamino]-ethylamino}-methyl)-2-methoxy-phenol was prepared following the procedures described in the preparation of Example 44 using 3-hydroxy-4-methoxy-benzaldehyde. [M+H]$^+$ 383.06.

Example 101

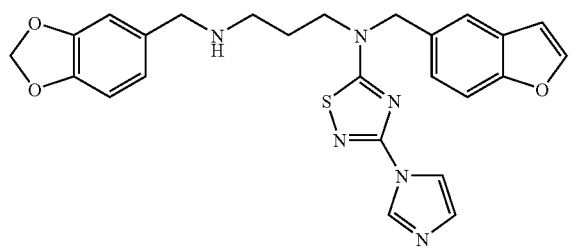

Preparation of compound 101: N'-Benzo[1,3]dioxol-5-ylmethyl-N-benzofuran-5-ylmethyl-N-(3-imidazol-1-yl-[1,2,4]thiadiazol-5-yl)-propane-1,3-diamine was prepared following the procedures described in the preparation of Example 47 using benzo[1,3]dioxol-5-ylmethyl-{3-[(benzofuran-5-ylmethyl)-amino]-propyl}-carbamic acid tert-butyl ester. [M+H]$^+$ 489.39.

Example 102

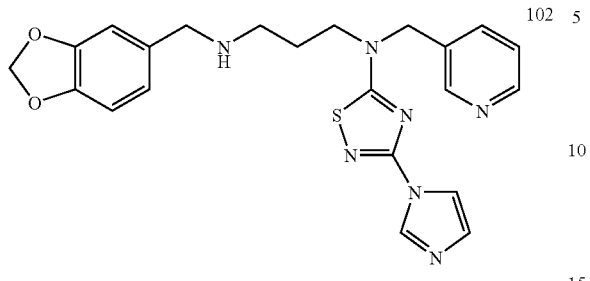

Preparation of compound 102: N'-Benzo[1,3]dioxol-5-ylmethyl-N-(3-imidazol-1-yl-[1,2,4]thiadiazol-5-yl)-N-pyridin-3-ylmethyl-propane-1,3-diamine was prepared following the procedures described in the preparation of Example 47 using benzo[1,3]dioxol-5-ylmethyl-{3-[(pyridin-3-ylmethyl)-amino]-propyl}-carbamic acid tert-butyl ester. [M+H]$^+$ 450.55.

Example 103

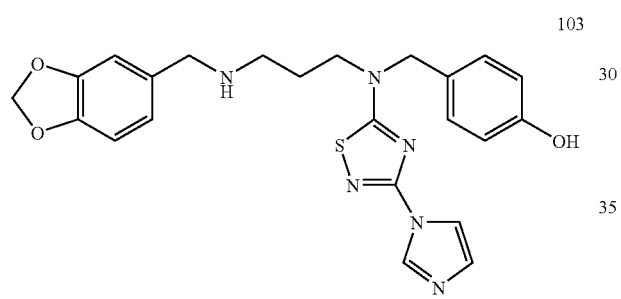

Preparation of compound 103: 4-{[{3-[(Benzo[1,3]dioxol-5-ylmethyl)-amino]-propyl}-(3-imidazol-1-yl-[1,2,4]thiadiazol-5-yl)-amino]-methyl}-phenol was prepared following the procedures described in the preparation of Example 47 using benzo[1,3]dioxol-5-ylmethyl-[3-(4-hydroxy-benzylamino)-propyl]-carbamic acid tert-butyl ester. [M+H]$^+$ 464.96.

Example 104

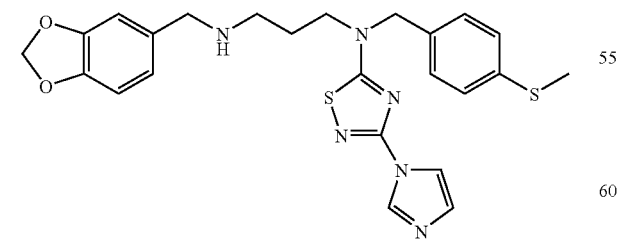

Preparation of compound 104: N'-Benzo[1,3]dioxol-5-ylmethyl-N-(3-imidazol-1-yl-[1,2,4]thiadiazol-5-yl)-N-(4-methylsulfanyl-benzyl)-propane-1,3-diamine was prepared following the procedures described in the preparation of Example 47 using benzo[1,3]dioxol-5-ylmethyl-[3-(4-methylsulfanyl-benzylamino)-propyl]-carbamic acid tert-butyl ester. [M+H]$^+$ 495.59.

Example 105

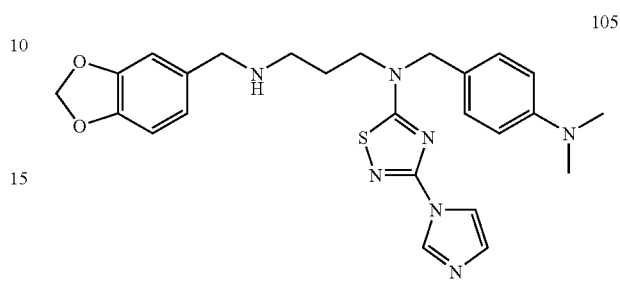

Preparation of compound 105: N-Benzo[1,3]dioxol-5-ylmethyl-N'-(4-dimethylamino-benzyl)-N'-(3-imidazol-1-yl-[1,2,4]thiadiazol-5-yl)-propane-1,3-diamine was prepared following the procedures described in the preparation of Example 47 using benzo[1,3]dioxol-5-ylmethyl-[3-(4-dimethylamino-benzylamino)-propyl]-carbamic acid tert-butyl ester. [M+H]$^+$ 492.64.

Example 106

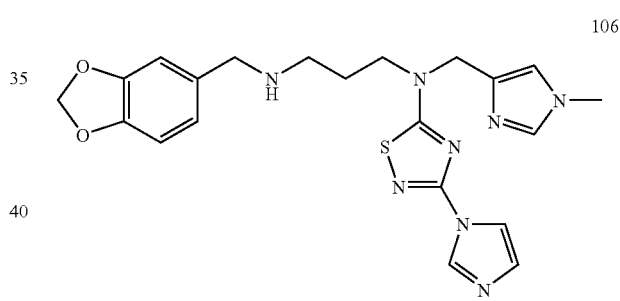

Preparation of compound 106: N'-Benzo[1,3]dioxol-5-ylmethyl-N-(3-imidazol-1-yl-[1,2,4]thiadiazol-5-yl)-N-(1-methyl-1H-imidazol-4-ylmethyl)-propane-1,3-diamine was prepared following the procedures described in the preparation of Example 47 using benzo[1,3]dioxol-5-ylmethyl-{3-[(1-methyl-1 H-imidazol-4-ylmethyl)-amino]-propyl}-carbamic acid tert-butyl ester. [M+H]$^+$ 453.58.

Example 107

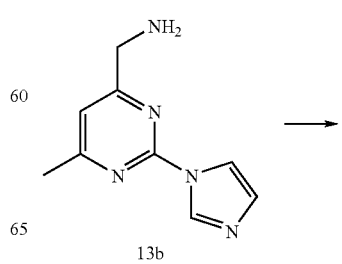

13b

→

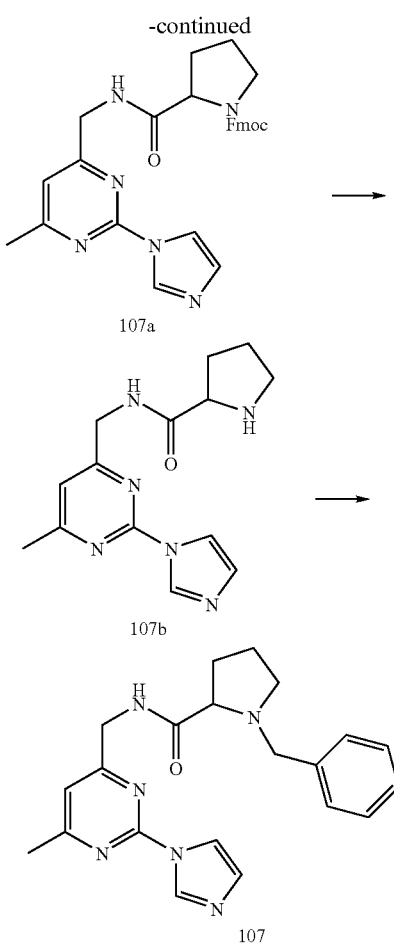

107a

107b

107

Step 1

Preparation of compound 107a: 2-[(2-Imidazol-1-yl-6-methyl-pyrimidin-4-ylmethyl)-carbamoyl]-pyrrolidine-1-carboxylic acid 9H-fluoren-9-ylmethyl ester To a solution of 13b (23 mg, 0.12 mmol) in dimethylformamide (2.0 mL) was added Fmoc-proline-OH (40 mg, 0.12 mmol), followed by 1-ethyl-3-(3-dimethylaminopropyl)carbodiimide hydrochloride (30 mg, 0.16 mmol) at r.t. The solution was stirred for 1 h then the reaction mixture was concentrated under reduced pressure. The residue was diluted with DCM (10 mL), washed with water, and dried over MgSO$_4$. Filtration and concentration gave 44 mg of 2-[(2-imidazol-1-yl-6-methyl-pyrimidin-4-ylmethyl)-carbamoyl]-pyrrolidine-1-carboxylic acid 9H-fluoren-9-ylmethyl ester as a white solid. [M+H]$^+$ 509.38.

Step 2

Preparation of compound 107b: Pyrrolidine-2-carboxylic acid (2-imidazol-1-yl-6-methyl-pyrimidin-4-ylmethyl)-amide To a solution of 2-[(2-imidazol-1-yl-6-methyl-pyrimidin-4-ylmethyl)-carbamoyl]-pyrrolidine-1-carboxylic acid 9H-fluoren-9-ylmethyl ester (435 mg, 0.855 mmol) in dimethylformamide (3.2 mL) was added piperidine (800 µL, 8.09 mmol) at r.t. The solution was stirred for 20 min then concentrated under vacuum to afford 244 mg of pyrrolidine-2-carboxylic acid (2-imidazol-1-yl-6-methyl-pyrimidin-4-ylmethyl)-amide as a brown oil. [M+H]$^+$ 287.28.

Step 3

Preparation of compound 107: 1-(4-Trifluoromethyl-benzyl)-pyrrolidine-2-carboxylic acid (2-imidazol-1-yl-6-methyl-pyrimidin-4-ylmethyl)-amide To a solution of pyrrolidine-2-carboxylic acid (2-imidazol-1-yl-6-methyl-pyrimidin-4-ylmethyl)-amide (43 mg, 0.15 mmol) in dimethylformamide (1.5 mL) was added 4-(trifluoromethyl)benzaldehyde (22 µL, 0.16 mmol) and acetic acid (0.075 mL) at r.t. The solution was allowed to stir for 2 hrs. To the solution was added sodium triacetoxyborohydride (107 mg, 0.50 mmol) at r.t. The solution was stirred for 16 hrs then concentrated under vacuum. The residue was diluted with DCM, washed with NaOH (1N, 30 mL) and water (30 mL), dried over MgSO$_4$, filtered and concentrated. The product was purified using mass-triggered LCMS to afford 5 mg of 1-(4-trifluoromethyl-benzyl)-pyrrolidine-2-carboxylic acid (2-imidazol-1-yl-6-methyl-pyrimidin-4-ylmethyl)-amide as a white solid. [M+H]$^+$ 444.96.

Example 108

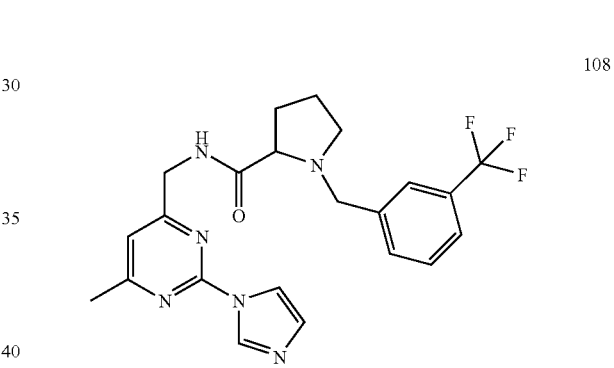

108

Preparation of compound 108: 1-(3-Trifluoromethyl-benzyl)-pyrrolidine-2-carboxylic acid (2-imidazol-1-yl-6-methyl-pyrimidin-4-ylmethyl)-amide was prepared following the procedures described in the preparation of Example 107 using 3-trifluoromethyl-benzaldehyde. [M+H]$^+$ 445.01.

Example 109

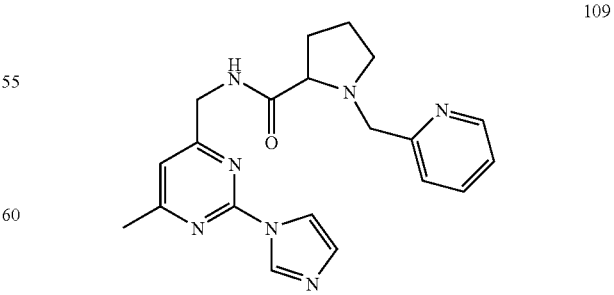

109

Preparation of compound 109: 1-Pyridin-2-ylmethyl-pyrrolidine-2-carboxylic acid (2-imidazol-1-yl-6-methyl-pyrimidin-4-ylmethyl)-amide was prepared following the procedures described in the preparation of Example 107 using pyridine-2-carbaldehyde. [M+H]+ 377.95.

Example 110

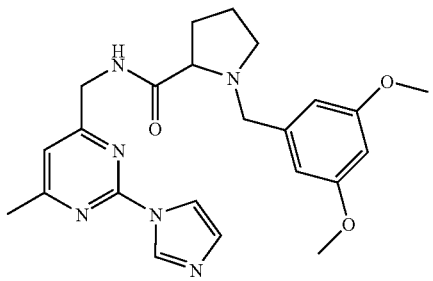

Preparation of compound 110: 1-(3,5-Dimethoxy-benzyl)-pyrrolidine-2-carboxylic acid (2-imidazol-1-yl-6-methyl-pyrimidin-4-ylmethyl)-amide was prepared following the procedures described in the preparation of Example 107 using 3,5-dimethoxy-benzaldehyde. [M+H]+ 437.86.

Example 111

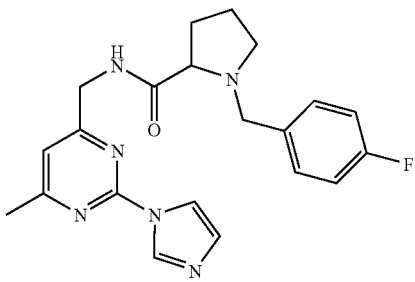

Preparation of compound 111: 1-(4-Fluoro-benzyl)-pyrrolidine-2-carboxylic acid (2-imidazol-1-yl-6-methyl-pyrimidin-4-ylmethyl)-amide was prepared following the procedures described in the preparation of Example 107 using 4-fluoro-benzaldehyde. [M+H]+ 395.52.

Example 112

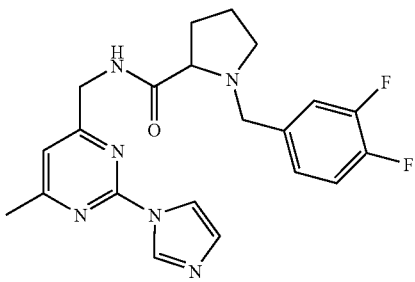

Preparation of compound 112: 1-(3,4-Difluoro-benzyl)-pyrrolidine-2-carboxylic acid (2-imidazol-1-yl-6-methyl-pyrimidin-4-ylmethyl)-amide was prepared following the procedures described in the preparation of Example 107 using 3,4-difluoro-benzaldehyde.
[M+H]+ 413.55.

Example 113

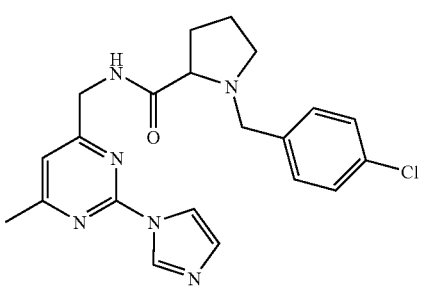

Preparation of compound 113: 1-(4-Chloro-benzyl)-pyrrolidine-2-carboxylic acid (2-imidazol-1-yl-6-methyl-pyrimidin-4-ylmethyl)-amide was prepared following the procedures described in the preparation of Example 107 using 4-chloro-benzaldehyde.
[M+H]+ 412.99.

Example 114

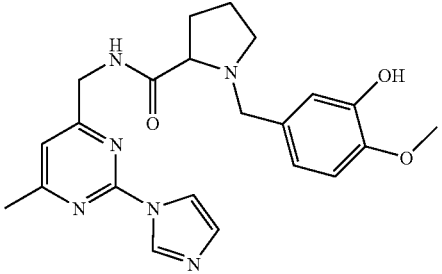

Preparation of compound 114: 1-(3-Hydroxy-4-methoxy-benzyl)-pyrrolidine-2-carboxylic acid (2-imidazol-1-yl-6-methyl-pyrimidin-4-ylmethyl)-amide was prepared following the procedures described in the preparation of Example 107 using 3-hydroxy-4-methoxy-benzaldehyde. [M+H]+ 423.64.

Example 115

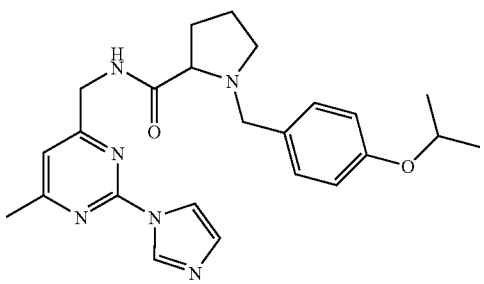

Preparation of compound 115: 1-(4-Isopropoxy-benzyl)-pyrrolidine-2-carboxylic acid (2-imidazol-1-yl-6-methyl-pyrimidin-4-ylmethyl)-amide was prepared following the procedures described in the preparation of Example 107 using 4-isopropoxy-benzaldehyde. [M+H]+ 435.67.

Example 116

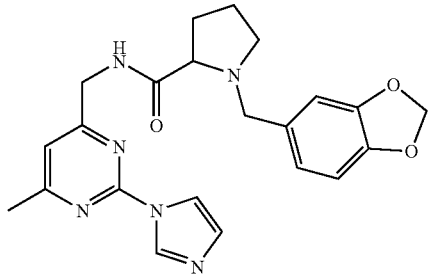

116

Preparation of compound 116: 1-Benzo[1,3]dioxol-5-ylmethyl-pyrrolidine-2-carboxylic acid (2-imidazol-1-yl-6-methyl-pyrimidin-4-ylmethyl)-amide was prepared following the procedures described in the preparation of Example 107 using piperonal. [M+H]+ 421.58.

Example 117

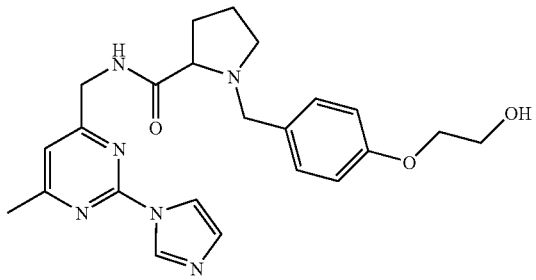

117

Preparation of compound 117: 1-[4-(2-Hydroxy-ethoxy)-benzyl]-pyrrolidine-2-carboxylic acid (2-imidazol-1-yl-6-methyl-pyrimidin-4-ylmethyl)-amide was prepared following the procedures described in the preparation of Example 107 using 4-(2-hydroxy-ethoxy)-benzaldehyde. [M+H]+ 437.62.

Example 118

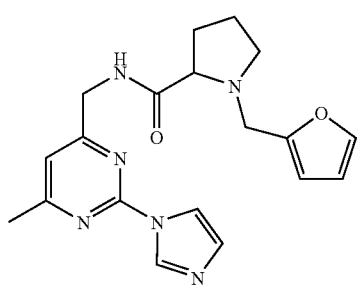

118

Preparation of compound 118: 1-Furan-2-ylmethyl-pyrrolidine-2-carboxylic acid (2-imidazol-1-yl-6-methyl-pyrimidin-4-ylmethyl)-amide was prepared following the procedures described in the preparation of Example 107 using furan-2-carbaldehyde. [M+H]+ 367.57.

Example 119

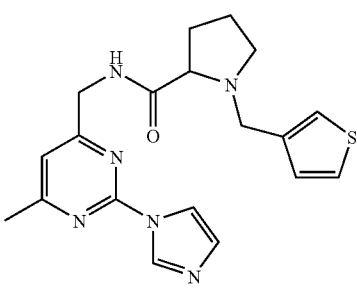

119

Preparation of compound 119: 1-Thiophen-3-ylmethyl-pyrrolidine-2-carboxylic acid (2-imidazol-1-yl-6-methyl-pyrimidin-4-ylmethyl)-amide was prepared following the procedures described in the preparation of Example 107 using thiophene-3-carbaldehyde. [M+H]+ 383.77.

Example 120

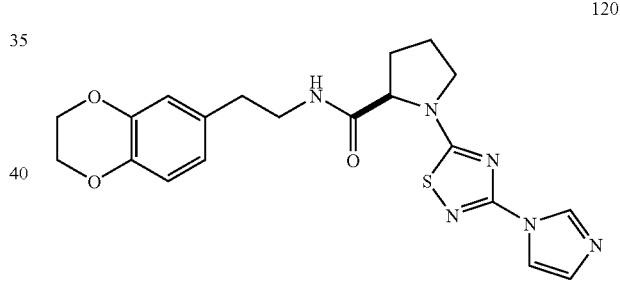

120

Preparation of compound 120: 1-(3-Imidazol-1-yl-[1,2,4]thiadiazol-5-yl)-pyrrolidine-2-carboxylic acid [2-(2,3-dihydro-benzo[1,4]dioxin-6-yl)-ethyl]-amide was prepared following the procedures described in preparation of Example 23 using Boc-D-Pro-OH and 2-(2,3-dihydro-benzo[1,4]dioxin-6-yl)-ethylamine. [M+H]+ 427.31; 1H NMR (400 MHz, CDCl3) δ 8.19 (s, 1H), 7.56 (s, 1H), 7.10 (s, 1H), 6.63-6.49 (m, 3H), 4.18-4.15 (m, 4H), 3.54-3.49 (m, 3H), 3.38-3.28 (m, 2H), 2.5 (m, 2H), 2.15 (m, 2H), 1.85 (m, 2H).

Example 121

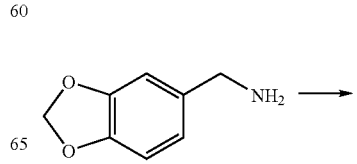

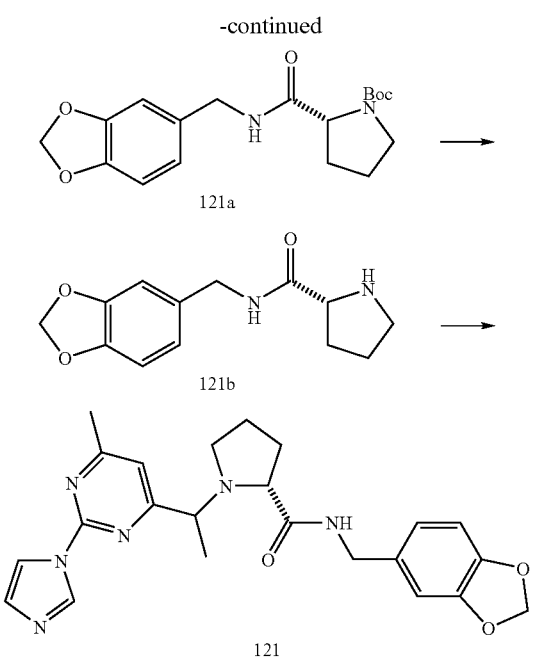

Step 1

Preparation of compound 121a: 2-[(Benzo[1,3]dioxol-5-ylmethyl)-carbamoyl]-pyrrolidine-1-carboxylic acid tert-butyl ester Boc-D-Pro-OH (209 mg, 0.970 mmol) was dissolved in DMF (4 mL), followed by addition of the HBTU (552 mg, 1.46 mmol) and Triethylamine (270 µL). The solution was stirred at room temperature for 30 minutes prior to the addition of piperonylamine (121 µL, 0.970 mmol). The reaction mixture stirred at rt for 16 h then the solution was transferred to a separatory funnel containing DCM (50 mL). The organic layer was washed with NaHCO$_3$ (2×50 mL, sat. aq.) and dried over Na$_2$SO$_4$. The solution was concentrated and purified by prep LCMS to afford 278.0 mg (82.5%) of 2-[(benzo[1,3]dioxol-5-ylmethyl)-carbamoyl]-pyrrolidine-1-carboxylic acid tert-butyl ester. [M+H]$^+$ 349.09.

Step 2

Preparation of compound 121b: Pyrrolidine-2-carboxylic acid (benzo[1,3]dioxol-5-ylmethyl)-amide 2-[(Benzo[1,3]dioxol-5-ylmethyl)-carbamoyl]-pyrrolidine-1-carboxylic acid tert-butyl ester (278 mg, 0.80 mmol) was dissolved in DCM:TFA (1:1, 6 mL) and stirred at room temperature for 3 hours. After this period, the solution was concentrated down under vacuum. The crude material was diluted in DCM (50 mL) and washed with 1M NaOH (aq) (50 mL) to afford the crude residue. The crude product was purified by Flash chromatography (0-10% methanol/DCM gradient) to afford 85.1 mg (43%) of pyrrolidine-2-carboxylic acid (benzo[1,3]dioxol-5-ylmethyl)-amide. [M+H]$^+$ 249.08.

Step 3

Preparation of compound 121: 1-[1-(2-Imidazol-1-yl-6-methyl-pyrimidin-4-yl)-ethyl]-pyrrolidine-2-carboxylic acid (benzo[1,3]dioxol-5-ylmethyl)-amide Pyrrolidine-2-carboxylic acid (benzo[1,3]dioxol-5-ylmethyl)-amide (85 mg, 0.34 mmol) was dissolved in dioxane (2.5 mL). Next, TsOH monohydrate (30 mg) and the 1-(2-imidazol-1-yl-6-methyl-pyrimidin-4-yl)-ethanone (69 mg, 0.34 mmol) were added and the reaction mixture was microwaved for 20 mins at 130° C. Upon completion of heating, the solution was allowed to return to room temperature and the sodium triacetoxyborohydride (145 mg, 0.68 mmol) was added to the reaction vessel and it was allowed to stir at room temperature for an additional 16 hours. After this period, the solution was concentrated under vacuum, diluted in ethyl acetate (50 mL) and transferred to a separatory funnel. The organic layer was washed with 1M NaOH (50 mL), dried over Na$_2$SO$_4$ and concentrated down by vacuum to afford the crude product. This material was purified by Flash Chromatography (0-40% ACN/DCM gradient) to afford 12 mg (8%) of 1-[1-(2-imidazol-1-yl-6-methyl-pyrimidin-4-yl)-ethyl]-pyrrolidine-2-carboxylic acid (benzo[1,3]dioxol-5-ylmethyl)-amide. Product isolated as a mixture of diasteromers; [M+H]$^+$ 435.03.

Example 122

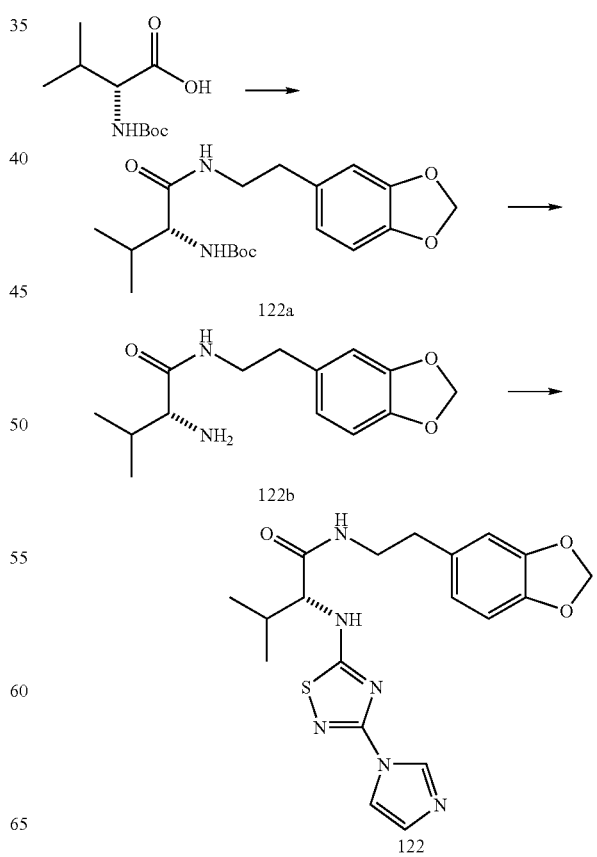

Step 1

Preparation of compound 122a: (R)—[1-(2-Benzo[1,3]dioxol-5-yl-ethylcarbamoyl)-2-methyl-propyl]-carbamic acid tert-butyl ester Boc-D-Val-OH (282 mg, 1.30 mmol) was dissolved in DCE (5 mL), followed by addition of CDI (253 mg, 1.56 mmol). The reaction solution was stirred for 30 mins to activate the acid. After this period, 3,4-Methylenedioxyphenethylamine HCl (263 mg, 1.30 mmol) and triethylamine (363 µL) were added to the reaction vessel and it was stirred at room temperature for 16 hours. Next, the reaction mixture was concentrated under vacuum. The crude material was dissolved in DCM (50 mL), transferred to a separatory funnel, washed with sat. NaHCO$_3$ (aq) (50 mL), dried over Na$_2$SO$_4$ and concentrated down to yield 447.1 mg (94.6%) of crude product, [1-(2-benzo[1,3]dioxol-5-yl-ethylcarbamoyl)-2-methyl-propyl]-carbamic acid tert-butyl ester, which was taken on crude. [M+H]$^+$ 365.00.

Step 2

Preparation of compound 122b: (R)-2-Amino-N-(2-benzo[1,3]dioxol-5-yl-ethyl)-3-methyl-butyramide

[1-(2-Benzo[1,3]dioxol-5-yl-ethylcarbamoyl)-2-methyl-propyl]-carbamic acid tert-butyl ester (447.1 mg, 1.23 mmol) was dissolved in 1:1 TFA:DCM (6 mL) and stirred at room temperature for 3 hours. After this time, the solvent was removed by vacuum. The crude material was dissolved in DCM (75 mL) and washed with 1M NaOH (aq) (75 mL) to afford the crude product as the freebase. The product was purified by Flash Chromatography (0-10% methanol/DCM gradient) to afford 270.7 mg (83.5%) of the pure product, 2-amino-N-(2-benzo[1,3]dioxol-5-yl-ethyl)-3-methyl-butyramide. [M+H]$^+$ 265.1

Step 3

Preparation of compound 122: (R)—N-(2-Benzo[1,3]dioxol-5-yl-ethyl)-2-(3-imidazol-1-yl-[1,2,4]thiadiazol-5-ylamino)-3-methyl-butyramide 2-Amino-N-(2-benzo[1,3]dioxol-5-yl-ethyl)-3-methyl-butyramide (135 mg, 0.51 mmol) was dissolved in DMSO (2 mL) and triethylamine (150 µL). Next, the 5-chloro-3-imidazol-1-yl-[1,2,4]thiadiazole (95.1 mg, 0.51 mmol) was added to the reaction vessel and it was stirred at room temperature for 16 hours. After this period, a portion of brine (50 mL) was added and the mixture was transferred to a separatory funnel and extracted with ethyl acetate (75 mL). The organic layer was dried over Na$_2$SO$_4$ and concentrated under vacuum. The crude material was purified by Flash Chromatography (0-50% ACN/DCM gradient) to afford 20.4 mg of pure product, N-(2-benzo[1,3]dioxol-5-yl-ethyl)-2-(3-imidazol-1-yl-[1,2,4]thiadiazol-5-ylamino)-3-methyl-butyramide. [M+H]$^+$ 414.84; $^1$H NMR (400 MHz, CDCl$_3$) δ 8.52 (s, 1H), 7.71 (s, 1H), 6.99 (s, 1H), 6.62-6.52 (m, 3H), 5.82-5.80 (m, 2H), 4.0 (Br s, 1H), 3.64-3.47 (m, 3H), 2.76-2.72 (m, 2H), 2.30-2.29 (m, 1H), 1.03-1.01 (m, 6H).

Example 123

Preparation of compound 123: (2R,4R)-4-Hydroxy-1-(3-imidazol-1-yl-[1,2,4]thiadiazol-5-yl)-pyrrolidine-2-carboxylic acid [2-(2,3-dihydro-benzo[1,4]dioxin-6-yl)-ethyl]-amide (2R,4R)-4-Hydroxy-1-(3-imidazol-1-yl-[1,2,4]thiadiazol-5-yl)-pyrrolidine-2-carboxylic acid [2-(2,3-dihydro-benzo[1,4]dioxin-6-yl)-ethyl]-amide was prepared from the procedures described in preparation of Example 23 using cis-D-4-hydroxy-pyrrolidine-1,2-dicarboxylic acid 1-tert-butyl ester and 2-(2,3-dihydro-benzo[1,4]dioxin-6-yl)-ethylamine. [M+H]$^+$ 443.27; $^1$H NMR (400 MHz, CDCl$_3$) δ 8.17 (s, 1H), 7.53 (s, 1H), 7.46 (Br m, 1H) 7.09 (s, 1H), 6.65-6.51 (m, 3H), 4.61 (m, 1H), 4.19-4.14 (m, 4H), 3.61-3.46 (m, 4H), 2.74-2.36 (m, 6H).

Example 124

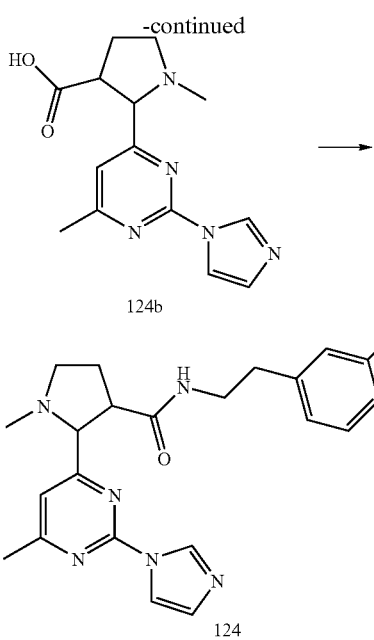

124b

124

Step 1

Preparation of compound 124a: 2-(2-Imidazol-1-yl-6-methyl-pyrimidin-4-yl)-1-methyl-pyrrolidine-3-carboxylic acid ethyl ester 2-(2-Imidazol-1-yl-6-methyl-pyrimidin-4-yl)-pyrrolidine-3-carboxylic acid ethyl ester (300 mg, 0.996 mmol), formaldehyde, 37 wt % in H$_2$O (500 µL), methanol (8 mL) and acetic acid (550 µL) were all combined in a reaction vessel and stirred for 30 mins. Next, sodium triacetoxyborohydride (530 mg, 2.49 mmol) was added and the solution was allowed to stir at room temperature for an additional 30 mins. After this period of time, the reaction mixture was concentrated under vacuum, dissolved in ethyl acetate (75 mL) and poured into ice (25 mL). The pH was adjusted to pH=8 with 1M NaOH. The organic layer was partitioned from the aqueous layer, dried over Na$_2$SO$_4$ and concentrated down to afford the crude product. The product was purified by Flash Chromatography (0-10% methanol/DCM gradient) to afford 130 mg (42%) 2-(2-imidazol-1-yl-6-methyl-pyrimidin-4-yl)-1-methyl-pyrrolidine-3-carboxylic acid ethyl ester. [M+H]$^+$ 316.56.

Step 2

Preparation of compound 124b: 2-(2-Imidazol-1-yl-6-methyl-pyrimidin-4-yl)-1-methyl-pyrrolidine-3-carboxylic acid 2-(2-Imidazol-1-yl-6-methyl-pyrimidin-4-yl)-1-methyl-pyrrolidine-3-carboxylic acid ethyl ester (130 mg, 0.41 mmol) was transferred to a 20 mL scintillation vial and dissolved in THF (550 µL) and methanol (550 µL). Next, a 1M solution of LiOH (620 µL) was added to the vial. The mixture was allowed to stir at room temperature for 1 hour. Reaction was not complete after this time, so it was allowed to continue to stir over night. After this period, the reaction was concentrated to afford 97 mg of the lithium salt of 2-(2-imidazol-1-yl-6-methyl-pyrimidin-4-yl)-1-methyl-pyrrolidine-3-carboxylic acid which was used directly in the subsequent step. [M+H]$^+$ 288.54.

Step 3

Preparation of compound 124: 2-(2-Imidazol-1-yl-6-methyl-pyrimidin-4-yl)-1-methyl-pyrrolidine-3-carboxylic acid [2-(2,3-dihydro-benzo[1,4]dioxin-6-yl)-ethyl]-amide 2-(2-Imidazol-1-yl-6-methyl-pyrimidin-4-yl)-1-methyl-pyrrolidine-3-carboxylic acid (27.0 mg, 0.094 mmol) was dissolved in DMF (1 mL). Next, the HBTU (54.0 mg, 0.141 mmol) was added. The reaction was stirred at room temperature for 30 minutes prior to addition of 2-(2,3-dihydro-benzo[1,4]dioxin-6-yl)-ethylamine (17.0 mg, 0.094 mmol) and the triethylamine (50 µL). The reaction was stirred at rt for 12 h then heated to 60° C. for 16 h. After this period, the reaction mixture was transferred to a separatory funnel with ethyl acetate (20 mL). The organic layer was washed with saturated NaHCO$_3$ (aq) (30 mL) and H$_2$O (30 mL), respectively. The aqueous layers were back extracted with ethyl acetate and all of the organic portions were combined, dried over Na$_2$SO$_4$ and concentrated under vacuum. The material was purified by Flash Chromatography (10 g, 0-10% methanol/DCM gradient) to afford 3.3 mg of 2-(2-imidazol-1-yl-6-methyl-pyrimidin-4-yl)-1-methyl-pyrrolidine-3-carboxylic acid [2-(2,3-dihydro-benzo[1,4]dioxin-6-yl)-ethyl]-amide. Product isolated as a mixture of diasteromers; [M+H]$^+$ 449.84.

Example 125

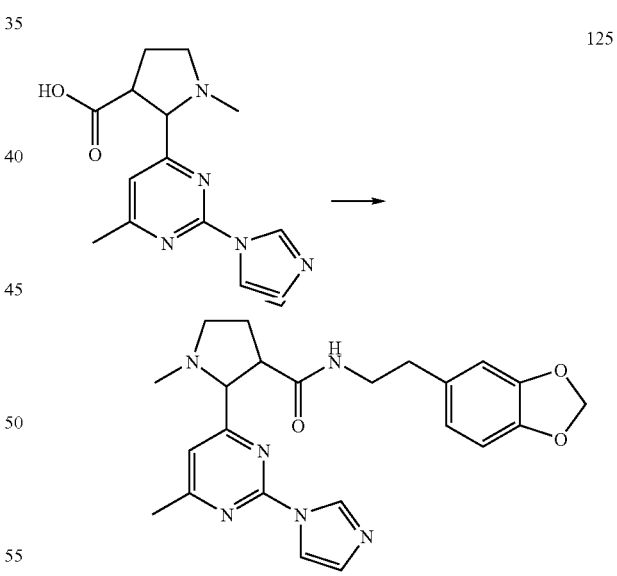

125

Preparation of compound 125: 2-(2-Imidazol-1-yl-6-methyl-pyrimidin-4-yl)-1-methyl-pyrrolidine-3-carboxylic acid (2-benzo[1,3]dioxol-5-yl-ethyl)-amide 2-(2-Imidazol-1-yl-6-methyl-pyrimidin-4-yl)-1-methyl-pyrrolidine-3-carboxylic acid (31.9 mg, 0.111 mmol) was dissolved in DMF (1 mL). Next, the HBTU (64.0 mg, 0.167 mmol) was added. The reaction was stirred at room temperature for 30 minutes prior to addition of 3,4-methylenedioxyphenethyl amine hydrochloride (22.4 mg, 0.111 mmol) and triethylamine (50 μL). The reaction was stirred at rt for 12 h then heated to 60° C. for 16 h. After this period, the reaction mixture was transferred to a separatory funnel with ethyl acetate (20 mL). The organic layer was washed with sat. NaHCO$_3$ (aq) (30 mL) and H$_2$O (30 mL). The aqueous layers were back extracted with ethyl acetate (25 mL) and all of the organic portions were combined, dried over Na$_2$SO$_4$ and concentrated down under vacuum. The material was purified by Flash Chromatography (10 g, 0-10% methanol/DCM gradient) to afford 2-(2-imidazol-1-yl-6-methyl-pyrimidin-4-yl)-1-methyl-pyrrolidine-3-carboxylic acid (2-benzo[1,3]dioxol-5-yl-ethyl)-amide. Product isolated as a mixture of diasteromers; [M+H]$^+$ 435.63.

Example 126

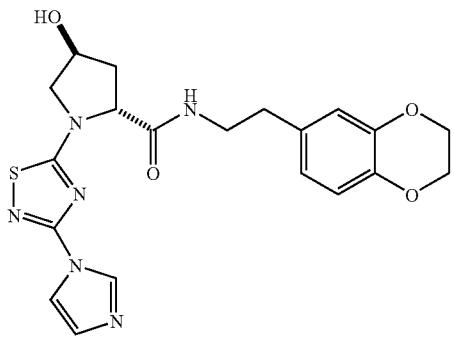

Preparation of compound 126: (2R,4S)-4-Hydroxy-1-(3-imidazol-1-yl-[1,2,4]thiadiazol-5-yl)-pyrrolidine-2-carboxylic acid [2-(2,3-dihydro-benzo[1,4]dioxin-6-yl)-ethyl]-amide (2R,4S)-4-Hydroxy-1-(3-imidazol-1-yl-[1,2,4]thiadiazol-5-yl)-pyrrolidine-2-carboxylic acid [2-(2,3-dihydro-benzo[1,4]dioxin-6-yl)-ethyl]-amide was prepared from the procedures described in preparation of Example 23. [M+H]$^+$ 443.79; $^1$H NMR (400 MHz, CD$_3$OD) δ 8.31 (s, 1H), 7.73 (s, 1H), 7.07 (s, 1H), 6.65-6.62 (m, 3H), 4.57 (m, 1H), 4.17 (m, 4H), 3.86-3.82 (m, 1H), 3.45-3.40 (m, 3H), 2.72-2.69 (m, 2H), 2.38-3.32 (m, 2H), 2.19-2.17 (m, 2H).

Example 127

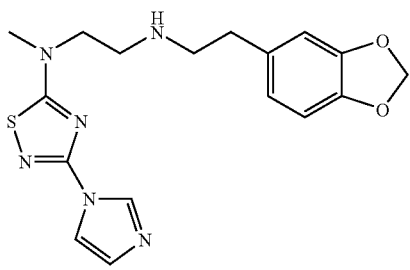

Preparation of compound 127: N'-(2-Benzo[1,3]dioxol-5-yl-ethyl)-N-(3-imidazol-1-yl-[1,2,4]thiadiazol-5-yl)-N-methyl-ethane-1,2-diamine N-1-(3-Imidazol-1-yl-[1,2,4]thiadiazol-5-yl)-N-1-methyl-ethane-1,2-diamine (1.94 g, 8.64 mmol) was dissolved in DCM (36 mL) and a minimal amount of methanol. Benzo[1,3]dioxol-5-yl-acetaldehyde (709 mg, 0.930 mmol) was then added and the solution was stirred at room temperature for 10 minutes. After this period, sodium triacetoxyborohydride (2.75 g, 12.9 mmol) was added and the reaction was allowed to stir at room temperature for 1 hour. The reaction mixture was concentrated under vacuum, dissolved in DCM (75 mL) and transferred to a separatory funnel. The organic layer was then washed with 1M NaOH (aq) (100 mL) and brine (100 mL), dried over Na$_2$SO$_4$, filtered and concentrated. The crude material was purified by Flash Chromatography (0-10% methanol/ethyl acetate to 0-10% methanol/DCM gradient) to afford 875 mg (55%) of product, N'-(2-benzo[1,3]dioxol-5-yl-ethyl)-N-(3-imidazol-1-yl-[1,2,4]thiadiazol-5-yl)-N-methyl-ethane-1,2-diamine. [M+H]$^+$ 373.23; $^1$H NMR (400 MHz, CDCl$_3$) δ 8.30 (s, 1H), 7.62 (s, 1H), 7.04 (s, 1H), 6.65-6.56 (m, 3H), 5.90 (s, 2H), 3.60 (Br s, 2H), 3.12 (m, 3H), 2.93 (m, 2H), 2.87 (m, 2H), 2.69 (m, 2H).

Example 128

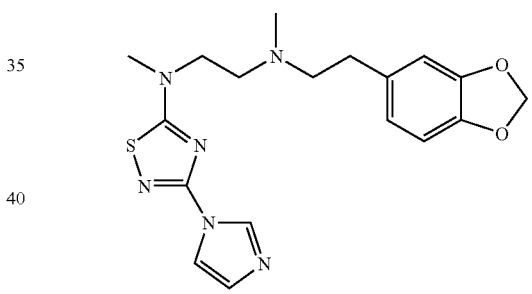

Preparation of compound 128: N-(2-Benzo[1,3]dioxol-5-yl-ethyl)-N'-(3-imidazol-1-yl-[1,2,4]thiadiazol-5-yl)-N,N'-dimethyl-ethane-1,2-diamine N'-(2-Benzo[1,3]dioxol-5-yl-ethyl)-N-(3-imidazol-1-yl-[1,2,4]thiadiazol-5-yl)-N-methyl-ethane-1,2-diamine (438 mg, 1.20 mmol) was dissolved in methanol (8 mL) and acetic acid (1.0 mL) and stirred at room temperature for 15 minutes. After this period, the sodium triacetoxyborohydride (750 mg, 3.60 mmol) was added and the reaction was allowed to stir at room temperature After this period, the reaction mixture was concentrated down under vacuum. The crude material was purified by Prep LCMS and the fractions were concentrated down. This material was then neutralized with 1M NaOH and extracted with DCM to afford 303 mg of N-(2-benzo[1,3]dioxol-5-yl-ethyl)-N'-(3-imidazol-1-yl-[1,2,4]thiadiazol-5-yl)-N,N'-dimethyl-ethane-1,2-diamine. [M+H]$^+$ 387.31; $^1$H NMR (400 MHz, CDCl$_3$) δ 8.26 (s, 1H), 7.62 (s, 1H), 7.05 (s, 1H), 6.66-6.53 (m, 3H), 5.85 (s, 1H), 3.12 (m, 3H), 2.68-2.60 (m, 6H), 2.31 (s, 3H).

Example 129

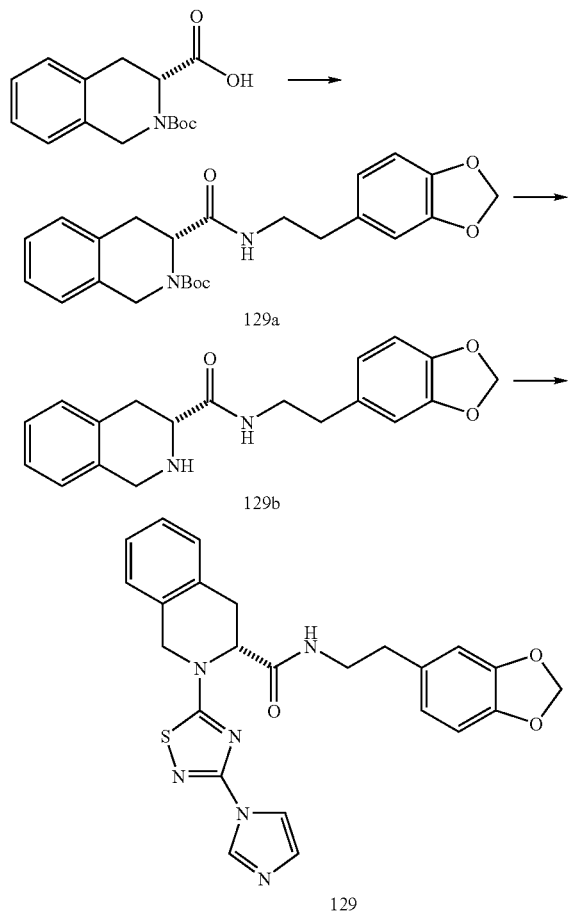

Step 1

Preparation of compound 129a: (R)-3-(2-Benzo[1,3]dioxol-5-yl-ethylcarbamoyl)-3,4-dihydro-1H-isoquinoline-2-carboxylic acid tert-butyl ester A mixture of Boc-[3R]-1,2,3,4-tetrahydroisoquinoline-3-carboxylic acid (277 mg, 1.00 mmol), 2-benzo[1,3]dioxol-5-yl-ethylamine hydrochloride (202 mg, 1.00 mmol), HBTU (450 mg, 1.19 mmol) and triethylamine (0.5 mL) in DMF (3 mL) was stirred at room temperature for 2 h. Water was added and the solution was extracted with ethyl acetate (2×30 mL), washed with brine and dried over sodium sulfate. Evaporation of the solvent and purification by column chromatography gave the desired product 129a (520 mg). [M+H]+ 425.00.

Step 2

Preparation of compound 129b: (R)-1,2,3,4-Tetrahydro-isoquinoline-3-carboxylic acid (2-benzo[1,3]dioxol-5-ylethyl)-amide A solution of 129a in TFA/DCM (50%, 5 mL) was stirred at r.t. for 20 min. The solvent was evaporated and purified by column chromatography to give 289 mg of 1,2,3,4-tetrahydro-isoquinoline-3-carboxylic acid (2-benzo[1,3]dioxol-5-ylethyl)-amide as a clear oil. [M+H]+ 325.40.

Step 3

Preparation of compound 129: (R)-2-(3-Imidazol-1-yl-[1,2,4]thiadiazol-5-yl)-1,2,3,4-tetrahydro-isoquinoline-3-carboxylic acid (2-benzo[1,3]dioxol-5-yl-ethyl)-amide was prepared following the procedures described in the preparation of Example 23 using 1,2,3,4-tetrahydro-isoquinoline-3-carboxylic acid (2-benzo[1,3]dioxol-5-ylethyl)-amide. [M+H]+ 475.54.

Example 130

Preparation of compound 130: N-Benzo[1,3]dioxol-5-yl-methyl-N'-[1-(2-imidazol-1-yl-6-methyl-pyrimidin-4-yl)-ethyl]-N-methyl-ethane-1,2-diamine was prepared following the procedures described in preparation of Example 1. A single enantiomer of Example 1 was obtained by chiral HPLC (chiralcel ODH, 4.6×150 mm, Hex/IPA 96:4 (v/v), flow rate 1.0 mL/min) separation. Analytical data are identical to Example 1.

Example 131

Preparation of compound 131: N-Benzo[1,3]dioxol-5-yl-methyl-N-[1-(2-imidazol-1-yl-6-methyl-pyrimidin-4-yl)-ethyl]-N-methyl-ethane-1,2-diamine was prepared following the procedures described in preparation of Example 1. A single enantiomer of Example 1 was obtained by chiral HPLC (chiralcel ODH, 4.6×150 mm, Hex/IPA 96:4 (v/v), flow rate 1.0 mL/min) separation. Analytical data are identical to Example 1.

Example 132

Preparation of compound 132: Benzo[1,3]dioxol-5-ylm-ethyl-{2-[2-(2-imidazol-1-yl-6-methyl-pyrimidin-4-yl)-pyrrolidin-1-yl]-ethyl}-amine was prepared following the procedures described in preparation of Example 3. A single enantiomer of Example 3 was obtained by chiral HPLC (chiralpak ADRH, 4.6×150 mm, 10 mM NH4OAc/EtOH 4:6 (v/v), flow rate 0.5 mL/min) separation. Analytical data are identical to Example 3.

Example 133

Preparation of compound 133: Benzo[1,3]dioxol-5-ylm-ethyl-{2-[2-(2-imidazol-1-yl-6-methyl-pyrimidin-4-yl)-pyrrolidin-1-yl]-ethyl}-amine was prepared following the procedures described in preparation of Example 3. A single enantiomer of Example 3 was obtained by chiral HPLC (chiralpak ADRH, 4.6×150 mm, 10 mM NH4OAc/EtOH 4:6 (v/v), flow rate 0.5 mL/min) separation. Analytical data are identical to Example 3.

Example 134

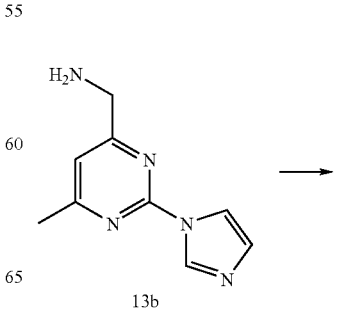

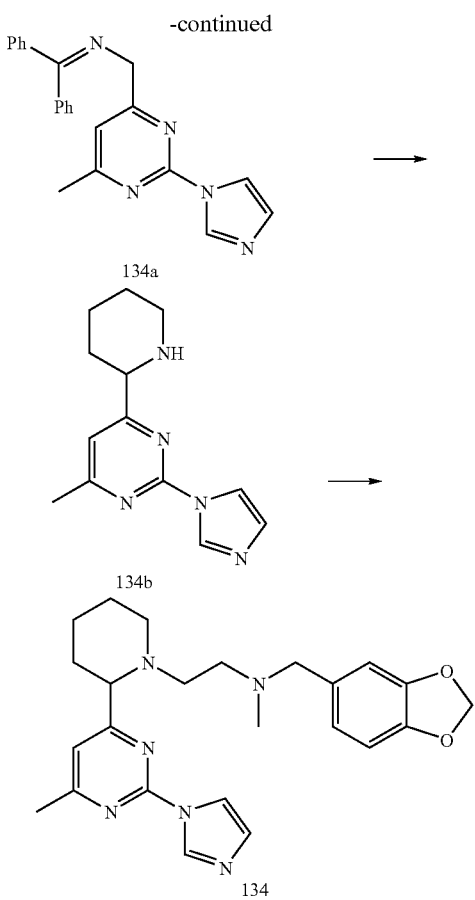

Step 1

Preparation of compound 134a: Benzhydrylidene-(2-imidazol-1-yl-6-methyl-pyrimidin-4-ylmethyl)-amine A mixture of (2-(1H-imidazol-1-yl)-6-methylpyrimidin-4-yl)methanamine hydrochloride (20.4 g, 90.3 mmol) and triethylamine (60.0 mL, 452 mmol) in dichloromethane (300 mL) was stirred at room temperature for 30 min then the mixture was concentrated under vacuum. The residue was dissolved in toluene (500 mL) then benzophenone (57.5 g, 316 mmol) and p-toluenesulfonic acid monohydrate (4.50 g, 23.7 mmol) were added to the solution. The mixture was heated to 110° C. for 12 h then concentrated under vacuum. The residue was extracted with ethyl acetate (2×500mL), washed with water (2×100 mL), dried over anhydrous sodium sulfate and concentrated. The product was purified using column chromatography (1:10 EtOAc/hexanes to EtOAc) to afford benzhydrylidene-(2-imidazol-1-yl-6-methyl-pyrimidin-4-ylmethyl)-amine as a yellow solid (14.0 g, 42.6%).

Step 2

Preparation of compound 134b: 2-imidazol-1-yl-4-methyl-6-piperidin-2-yl-pyrimidine nButyllithium (7.00 mL of a 2.82 M solution in cyclohexane, 19.8 mmol) was added dropwise over a 10 minute period to a solution of diisopropylamine (2.8 mL, 19.8 mmol) in anhydrous THF (20 mL) at 0° C. under nitrogen. The solution was transferred to a −78° C. mixture of 134a (5.00 g, 14.2 mmol) and anhydrous THF (200 mL) under nitrogen. The mixture warmed to −45° C. then stirred for 30 min prior to dropwise addition of 1,4-diiodobutane (6.60 g, 21.3 mmol) over 15 minutes. The reaction mixture was warmed to 0° C. and stirred for 4 hours. Aqueous HCl (200 mL of a 10% v/v solution) was added and the mixture stirred at room temperature for 20 min. The mixture was extracted with ethyl acetate (2×100 mL) and the aqueous layer was adjusted to pH=10 with NaOH (2N aqueous). The solution was extracted with dichloromethane (3×100 mL) and the combined organic layer was dried over anhydrous sodium sulfate. Concentration and purification using column chromatography gave 1.38 g of 2-imidazol-1-yl-4-methyl-6-piperidin-2-yl-pyrimidine. [M+H]$^+$ 244.00.

Step 3

Preparation of compound 134: Benzo[1,3]dioxol-5-ylmethyl-{2-[2-(2-imidazol-1-yl-6-methyl-pyrimidin-4-yl)-piperidin-1-yl]-ethyl}-amine To a solution of 2-(benzo[1,3]dioxol-5-ylmethyl-methylamino)-ethanol (720 mg, 3.4 mmol) in DCM (15 mL) and pyridine (3 mL) at 0° C. was added methanesulfonyl chloride (470 mg, 4.10 mmol) dropwise over 10 minutes. The ice water bath was removed and the solution was reacted at room temperature for 20 min. The reaction was concentrated under vacuum and acetonitrile (30 mL), triethylamine (2 mL) and 134b (830 mg, 2.43 mmol) were added. The solution was heated at 65° C. for 2 h then cooled to rt and stirred for 12 h. Water was added and solution was extracted with ethyl acetate (2×100 mL), washed with brine and dried over Na$_2$SO$_4$. Concentration and purification by column chromatography gave 293 mg of benzo[1,3]dioxol-5-ylmethyl-{2-[2-(2-imidazol-1-yl-6-methyl-pyrimidin-4-yl)-piperidin-1-yl]-ethyl}-amine as a yellow oil. [M+H]$^+$ 435.65. $^1$HNMR (400 MHz, CDCl$_3$) δ 8.58 (s, 1H), 7.86 (s, 1H), 7.20 (s, 1H), 7.09 (s, 1H), 6.68 (s, 1H), 6.62 (m, 2H), 5.86 (s, 2H), 3.59 (t, 1H), 3.40 (s, 1H), 3.00-3.30 (m, 3H), 2.30-2.60 (m, 6H), 2.00-2.20 (m, 6H), 1.30-1.80 (m, 4H). $^{13}$C-NMR (100 MHz, CDCl$_3$) δ 175.7, 169.6, 154.3, 147.8, 146.6, 136.4, 133.1, 130.4, 122.0, 116.8, 115.8, 109.3, 107.9, 101.0, 69.5, 62.6, 58.4, 54.4, 53.4, 42.8, 41.7, 34.8, 25.8, 24.3.

Example 135

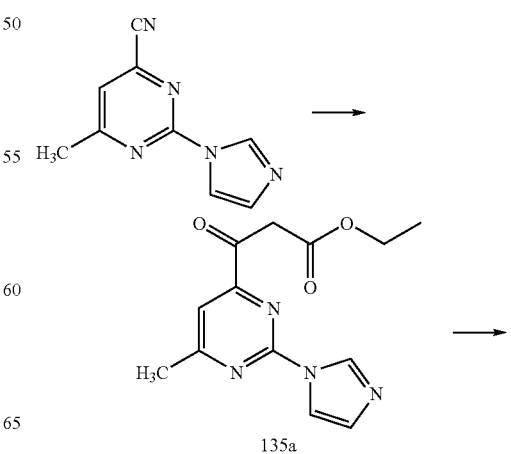

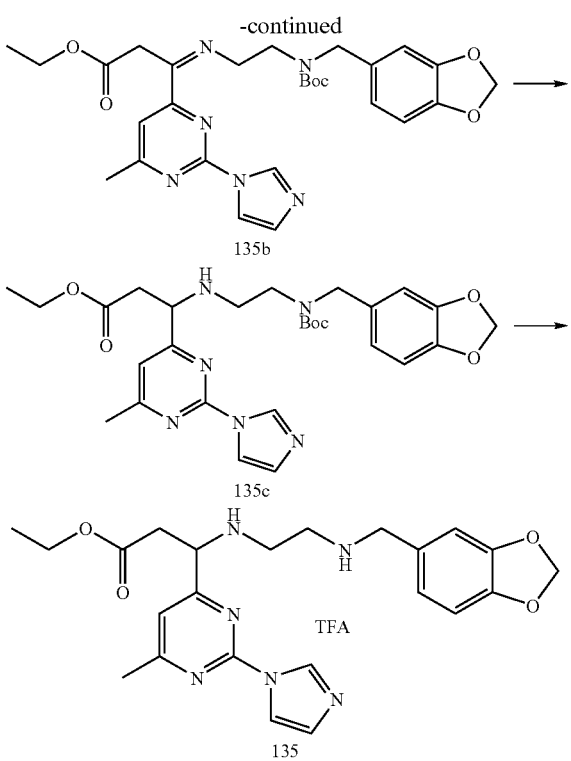

Step 1

Preparation of compound 135a: Ethyl 3-(2-(1H-imidazol-1-yl)-6-methylpyrimidin-4-yl)-3-oxopropanoate Methanesulfonic acid (200 µL, 3.08 mmol) was added dropwise to a suspension of zinc powder (70.4 g, 1.08 mol) in anhydrous THF (228 mL) and the mixture was heated to 67° C. After 1 hour, a solution of 2-(1H-imidazol-1-yl)-6-methylpyrimidine-4-carbonitrile (20.0 g, 108 mmol) in THF (120 mL) was added followed by subsequent dropwise addition of ethyl 2-bromoacetate (90.8 g, 540 mmol) over a period of 1.5 h. The mixture was stirred for an additional 30 minutes at 67° C. then cooled to rt. The inorganic solids were removed by vacuum filtration, washed with THF (200 mL), and the filtrate was brought to pH=1 with 3 M hydrochloric acid (200 mL). The solution was stirred for 30 minutes at rt prior to removal of the solvent under vacuum. Ethyl 3-(2-(1H-imidazol-1-yl)-6-methylpyrimidin-4-yl)-3-oxopropanoate (14.3 g) was obtained as yellow solid and was used directly in the next step.

Step 2

Preparation of compound 135b: (Z)-Ethyl 3-(2-(1H-imidazol-1-yl)-6-methylpyrimidin-4-yl)-3-(2-(tert-butoxycarbonyl)ethylimino)propanoate tert-Butyl 2-aminoethyl(benzo[d][1,3]dioxol-5-ylmethyl) carbamate (2.17 g, 7.37 mmol) was added all at once to mixture of ethyl 3-(2-(1H-imidazol-1-yl)-6-methylpyrimidin-4-yl)-3-oxopropanoate (2.00 g, 7.29 mmol), ethanol (50 mL), methylene chloride (50 mL) and 4 Å molecular sieves type (5 g). Acetic acid (417 µL, 7.29 mmol) was added prior to heating to 58° C. for a period of 12 h. The reaction mixture was cooled to rt, solids were removed via filtration and the filtrate was concentrated under vacuum to afford (Z)-ethyl 3-(2-(1H-imidazol-1-yl)-6-methylpyrimidin-4-yl)-3-(2-(tert-butoxycarbonyl)ethylimino)propanoate (1.00 g) as a light yellow solid.

Step 3

Preparation of compound 135c: 3-[2-(Benzo[1,3]dioxol-5-ylmethyl-tert-butoxycarbonyl-amino)-ethylamino]-3-(2-imidazol-1-yl-6-methyl-pyrimidin-4-yl)-propionic acid ethyl ester 10% Pd/C (80 mg) was added all at once to a vacuum purged solution of (Z)-ethyl 3-(2-(1H-imidazol-1-yl)-6-methylpyrimidin-4-yl)-3-(2-(tert-butoxycarbonyl)ethylimino)propanoate (0.79 g, 1.4 mmol) and ethanol (15 ml) at rt. The reaction mixture was stirred under an atmosphere of hydrogen for 16 h then filtered through celite. The filtrate was concentrated under vacuum and purified using column chromatography (DCM to 9:1 DCM/MeOH) to afford 350 mg (44%) of 3-[2-(benzo[1,3]dioxol-5-ylmethyl-tert-butoxycarbonyl-amino)-ethylamino]-3-(2-imidazol-1-yl-6-methyl-pyrimidin-4-yl)-propionic acid ethyl ester as a yellow oil.

Step 4

Preparation of compound 135: Benzo[1,3]dioxol-5-ylmethyl-{2-[2-ethoxycarbonyl-1-(2-imidazol-1-yl-6-methyl-pyrimidin-4-yl)-ethylamino]-ethyl}-ammonium trifluoroacetate was prepared following the procedures described in the preparation of Example 2 using 3-[2-(benzo[1,3]dioxol-5-ylmethyl-tert-butoxycarbonyl-amino)-ethylamino]-3-(2-imidazol-1-yl-6-methyl-pyrimidin-4-yl)-propionic acid ethyl ester. [M+H]+ 453.42.

Example 136

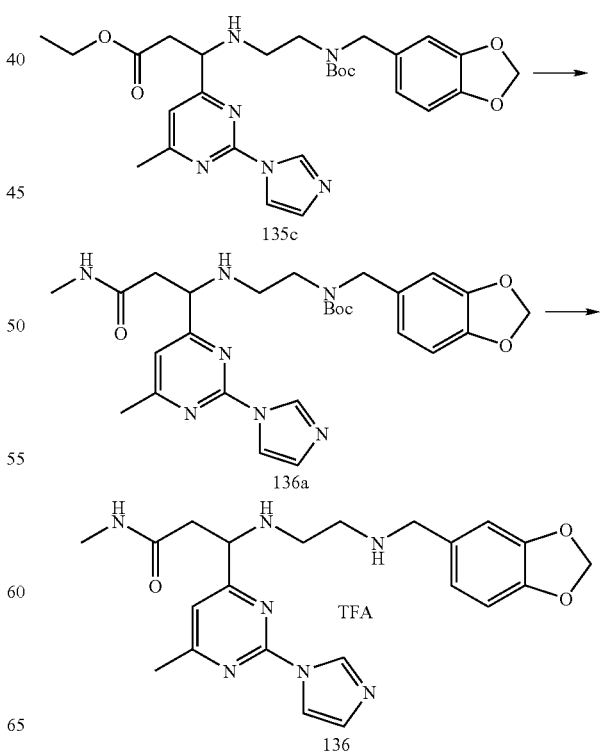

Step 1

Preparation of compound 136a: Benzo[1,3]dioxol-5-ylmethyl-{2-[1-(2-imidazol-1-yl-6-methyl-pyrimidin-4-yl)-2-methylcarbamoyl-ethylamino]-ethyl}-carbamic acid tert-butyl ester Methylamine (800 μL, 40 wt % aqueous) was added to a solution of 3-[2-(benzo[1,3]dioxol-5-ylmethyl-tert-butoxycarbonyl-amino)-ethylamino]-3-(2-imidazol-1-yl-6-methyl-pyrimidin-4-yl)-propionic acid ethyl ester (15 mg, 0.027 mmol) in THF (0.8 mL). The reaction mixture stirred at room temperature for 16 h then was concentrated under reduced pressure. The residue was purified using column chromatography (DCM to 9:1 DCM/MeOH) to afford 14 mg (96%) of benzo[1,3]dioxol-5-ylmethyl-{2-[1-(2-imidazol-1-yl-6-methyl-pyrimidin-4-yl)-2-methylcarbamoyl-ethylamino]-ethyl}-carbamic acid tert-butyl ester as a clear oil.

Step 2

Preparation of compound 136: Benzo[1,3]dioxol-5-ylmethyl-{2-[1-(2-imidazol-1-yl-6-methyl-pyrimidin-4-yl)-2-methylcarbamoyl-ethylamino]-ethyl}-ammonium trifluoroacetate was prepared following the procedures described in the preparation of Example 2 using benzo[1,3]dioxol-5-ylmethyl-{2-[1-(2-imidazol-1-yl-6-methyl-pyrimidin-4-yl)-2-methylcarbamoyl-ethylamino]-ethyl}-carbamic acid tert-butyl ester. [M+H]$^+$ 438.57.

Example 137

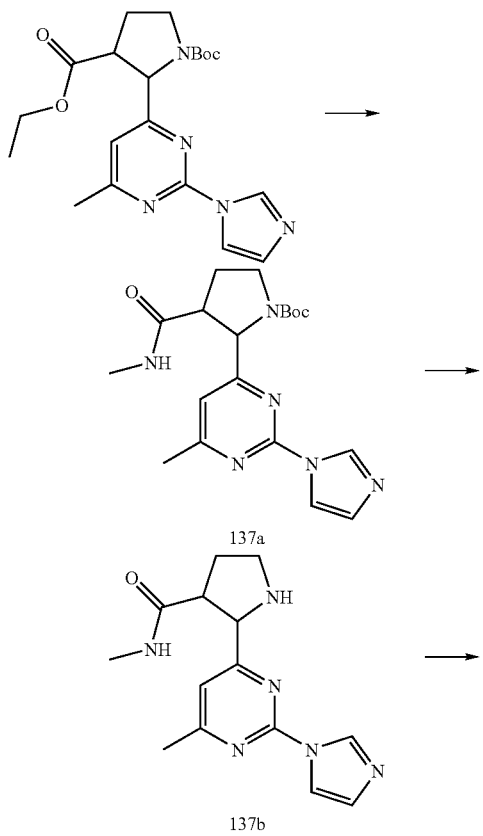

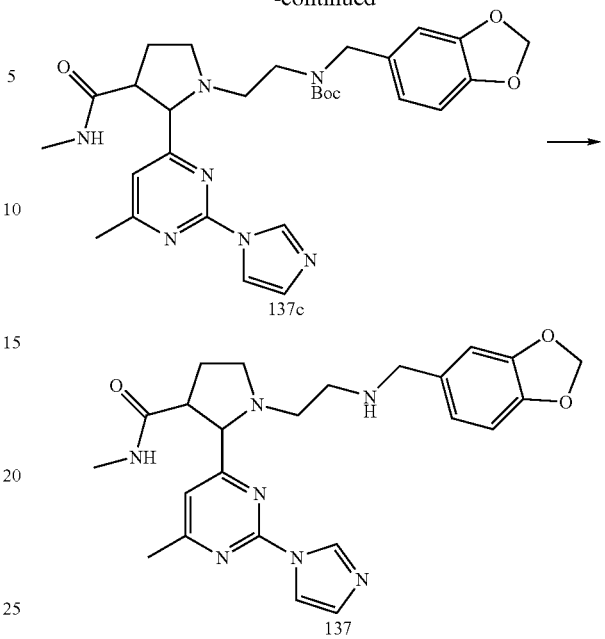

Step 1

Preparation of compound 137a: tert-Butyl 2-(2-(1H-imidazol-1-yl)-6-methylpyrimidin-4-yl)-3-(methylcarbamoyl)pyrrolidine-1-carboxylate Methylamine (35 mL of a 25 wt % solution in THF) was added all at once to a solution of 1-tert-butyl 3-ethyl 2-(2-(1H-imidazol-1-yl)-6-methylpyrimidin-4-yl)pyrrolidine-1,3-dicarboxylate (650 mg, 1.6 mmol) in THF (30 mL). The reaction mixture was heated to 60° C. for a period 12 h then cooled to rt. Water (50 mL) was added and the resulting solution was extracted with EtOAc (3×10 mL). The combined organic layers were dried over Na$_2$SO$_4$, filtered and concentrated under vacuum to afford tert-butyl 2-(2-(1H-imidazol-1-yl)-6-methylpyrimidin-4-yl)-3-(methylcarbamoyl)pyrrolidine-1-carboxylate (620 mg) as yellow oil.

Step 2

Preparation of compound 137b: 2-(2-(1H-imidazol-1-yl)-6-methylpyrimidin-4-yl)-N-methylpyrrolidine-3-carboxamide 2,2,2-Trifluoroacetic acid (20.0 mL, 269 mmol) was added dropwise over 5 minutes to a 0° C. solution of tert-butyl 2-(2-(1H-imidazol-1-yl)-6-methylpyrimidin-4-yl)-3-(methylcarbamoyl)pyrrolidine-1-carboxylate (720 mg, 1.86 mmol) in CH$_2$Cl$_2$ (20 mL). The reaction mixture was warmed to rt over 30 minutes then brought to pH=8 with Na$_2$CO$_3$ (400 mL, sat. aqueous solution). The mixture was extracted with CH$_2$Cl$_2$ (5×30 mL), the combined organic layers were dried over Na$_2$SO$_4$, filtered and concentrated under vacuum to afford 2-(2-(1H-imidazol-1-yl)-6-methylpyrimidin-4-yl)-N-methylpyrrolidine-3-carboxamide (230 mg, 43%) as a yellow oil.

Step 3

Preparation of compound 137c: tert-Butyl 2-(2-(2-(1H-imidazol-1-yl)-6-methylpyrimidin-4-yl)-3-(methylcarbamoyl)pyrrolidin-1-yl)ethyl(benzo[d][1,3]dioxol-5-ylmethyl)carbamate NaBH$_3$CN (76 mg, 1.2 mmol) was added all at once to a stirred solution of 2-(2-(1H-imidazol-1-yl)-6-methylpyrimidin-4-yl)-N-methylpyrrolidine-3-carboxamide (230 mg, 0.80 mmol), tert-butyl benzo[d][1,3]dioxol-5-ylmethyl(2-oxoethyl)carbamate (280 mg, 0.95 mmol), acetic acid (100 µL, 1.59 µmol) and trimethyl orthoformate (20 ml). The reaction mixture stirred at rt for 16 h then water (20 mL) was added. The solution was extracted with EtOAc (2×20 mL), the combined organic layers were dried over Na$_2$SO$_4$, filtered and concentrated under vacuum. The residue was purified using column chromatography (20:1 CHCl$_3$/MeOH) to afford 100 mg (22%) of tert-butyl 2-(2-(2-(1H-imidazol-1-yl)-6-methylpyrimidin-4-yl)-3-(methylcarbamoyl)pyrrolidin-1-yl)ethyl(benzo[d][1,3]dioxol-5-ylmethyl)carbamate as a colorless oil.

Step 4

Preparation of compound 137: 2-(2-(1H-Imidazol-1-yl)-6-methylpyrimidin-4-yl)-1-(2-(benzo[d][1,3]dioxol-5-ylmethylamino)ethyl)-N-methylpyrrolidine-3-carboxamide 2,2,2-Trifluoroacetic acid (5.00 mL, 67.3 mmol) was added dropwise over 5 minutes to a 0° C. solution of tert-butyl 2-(2-(2-(1H-imidazol-1-yl)-6-methylpyrimidin-4-yl)-3-(methylcarbamoyl)pyrrolidin-1-yl)ethyl(benzo[d][1,3]dioxol-5-ylmethyl)carbamate (100 mg, 0.18 mmol) in CH$_2$Cl$_2$ (5 mL). The reaction mixture was warmed to rt over 30 minutes then water (20 mL) was added. The solution was brought to pH=9 with ammonium hydroxide (100 mL), extracted with CH$_2$Cl$_2$ (3×10 mL), the combined organic layers were dried over Na$_2$SO$_4$, filtered and concentrated under vacuum to afford 50 mg (61%) of 2-(2-(1 H-imidazol-1-yl)-6-methylpyrimidin-4-yl)-1-(2-(benzo[d][1,3]dioxol-5-ylmethylamino)ethyl)-N-methylpyrrolidine-3-carboxamide as yellow oil. [M–H]$^+$ 462.00.

Example 138

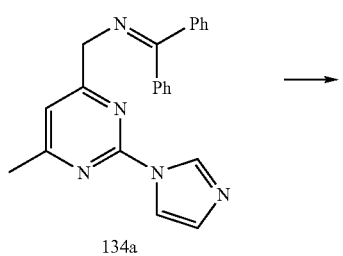

134a

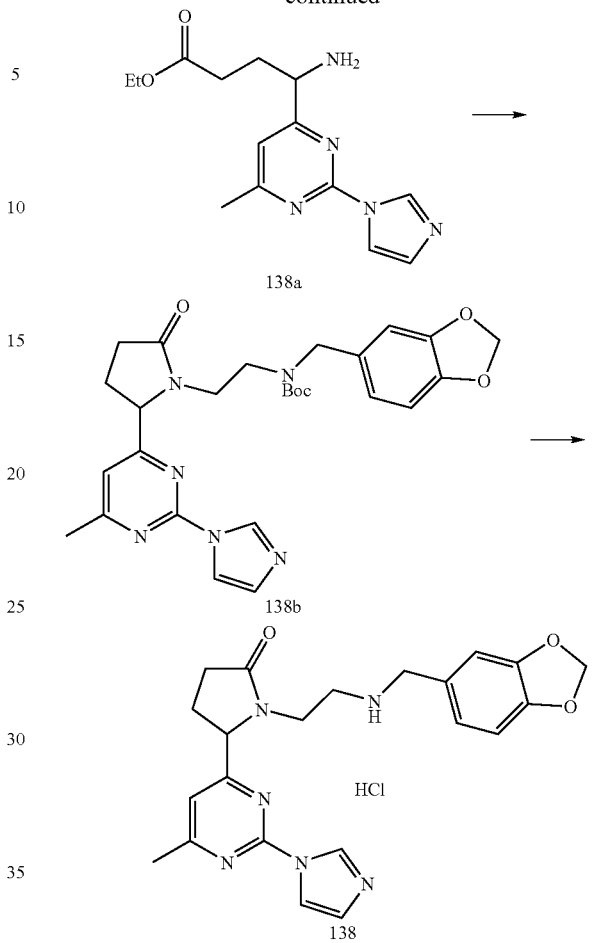

Step 1

Preparation of compound 138a: Amino-4-(2-imidazol-1-yl-6-methyl-pyrimidin-4-yl)-butyric acid ethyl ester nButyllithium (1.50 mL of a 2.82 M solution in hexanes, 4.23 mmol) was added dropwise over 10 minutes to a solution of diisopropylamine (370 mg, 3.66 mmol) and anhydrous THF (10 mL) at 0° C. under an atmosphere of N$_2$. The mixture was stirred for 10 minutes then cannulated into a −45° C. solution of (2-(1H-imidazol-1-yl)-6-methylpyrimidin-4-yl)-N-(diphenylmethylene)methanamine (1.00 g, 2.83 mmol) and anhydrous THF (10 mL) under a N$_2$ atmosphere. The reaction mixture was stirred for 30 minutes then ethyl acrylate (341 mg, 3.41 mmol) was added dropwise over 10 minutes. The reaction mixture was warmed to rt then stirred for 12 h. The mixture was cooled to 0° C. then HCl (50 ml, 10% v/v aqueous) was added dropwise over 15 minutes. The solution was warmed to rt, extracted with ethyl ether (3×30 mL), and the aqueous layer was adjusted to pH=8.5 with solid K$_2$CO$_3$. The resulting solution was extracted with DCM (3×30 mL), combined organic layers were dried over Na$_2$SO$_4$, filtered and concentrated under vacuum to afford 1.10 g of amino-4-(2-imidazol-1-yl-6-methyl-pyrimidin-4-yl)-butyric acid ethyl ester as a brown solid.

Step 2

Preparation of compound 138b: Benzo[1,3]dioxol-5-ylmethyl-{2-[2-(2-imidazol-1-yl-6-methyl-pyrimidin-4-yl)-5-oxo-pyrrolidin-1-yl]-ethyl}-carbamic acid tert-butyl ester was prepared following the procedures described in the preparation of Example 77c using amino-4-(2-imidazol-1-yl-6-methyl-pyrimidin-4-yl)-butyric acid ethyl ester and 77a.

$^1$H NMR (400 MHz, CDCl$_3$) δ 8.60 (s, 1H), 7.90 (s, 1H), 7.18 (s, 1H), 6.93 (s, 1H), 6.72 (s, 2H), 6.68 (s, 1H), 5.94 (s, 2H), 4.97 (m, 1H), 4.60 (m, 1H), 4.30 (m, 1H), 4.07 (m, 2H), 2.90 (m, 1H), 2.59 (s, 3H), 2.48 (m, 2H), 2.04 (m, 1H), 1.50 (s, 9H).

Step 3

Preparation of compound 138: 1-{2-[(Benzo[1,3]dioxol-5-ylmethyl)-amino]-ethyl}-5-(2-imidazol-1-yl-6-methyl-pyrimidin-4-yl)-pyrrolidin-2-one hydrochloride was prepared following the procedures described in the preparation of Example 2 using benzo[1,3]dioxol-5-ylmethyl-{2-[2-(2-imidazol-1-yl-6-methyl-pyrimidin-4-yl)-5-oxo-pyrrolidin-1-yl]-ethyl}-carbamic acid tert-butyl ester. [M+H]$^+$ 420.95.
$^1$H NMR (400 MHz, CDCl$_3$) δ 9.52 (s, 1H), 8.18 (s, 1H), 7.59 (s, 1H), 7.40 (s, 1 H), 6.75 (m, 3H), 5.93 (s, 2H), 4.91 (m, 1H), 4.29 (m, 1H), 4.05 (m, 2H), 3.10 (m, 1H), 2.99 (m, 2H), 2.60 (m, 1H), 2.58 (s, 3H), 2.44 (m, 1H), 2.00 (m, 1H).

Example 139

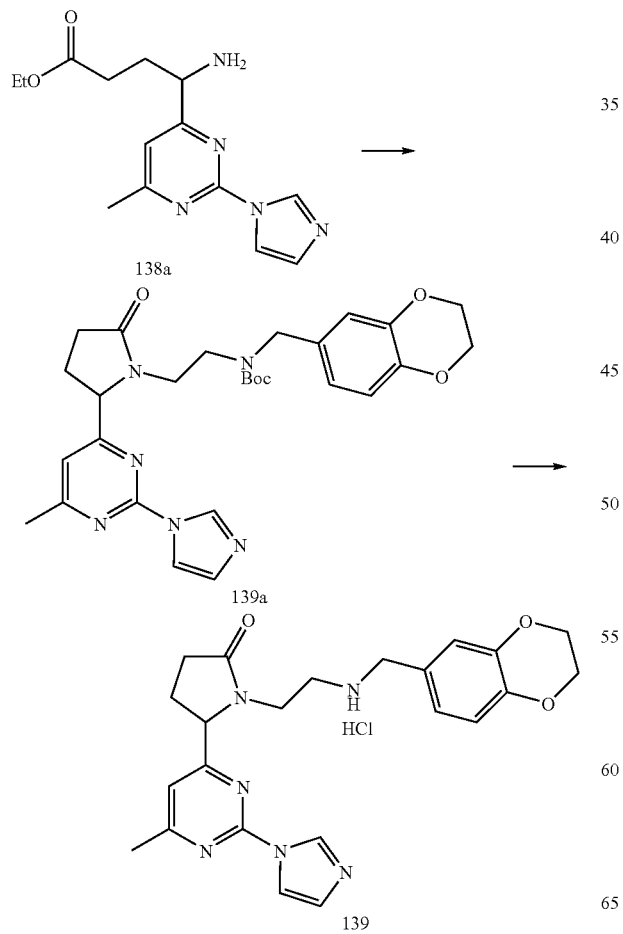

Example 140

Step 1

Preparation of compound 139a: (2,3-Dihydro-benzo[1,4]dioxin-6-ylmethyl)-{2-[2-(2-imidazol-1-yl-6-methyl-pyrimidin-4-yl)-5-oxo-pyrrolidin-1-yl]-ethyl}-carbamic acid tert-butyl ester was prepared following the procedures described in the preparation of Example 77c using 4-amino-4-(2-imidazol-1-yl-6-methyl-pyrimidin-4-yl)-butyric acid ethyl ester and (2,3-dihydro-benzo[1,4]dioxin-6-ylmethyl)-(2-oxo-ethyl)-carbamic acid tert-butyl ester.

Step 2

Preparation of compound 139: 1-{2-[(2,3-Dihydro-benzo[1,4]dioxin-6-ylmethyl)-amino]-ethyl}-5-(2-imidazol-1-yl-6-methyl-pyrimidin-4-yl)-pyrrolidin-2-one hydrochloride was prepared following the procedures described in the preparation of Example 2 using (2,3-dihydro-benzo[1,4]dioxin-6-ylmethyl)-{2-[2-(2-imidazol-1-yl-6-methyl-pyrimidin-4-yl)-5-oxo-pyrrolidin-1-yl]-ethyl}-carbamic acid tert-butyl ester. [M+H]$^+$ 435.48.

Example 140

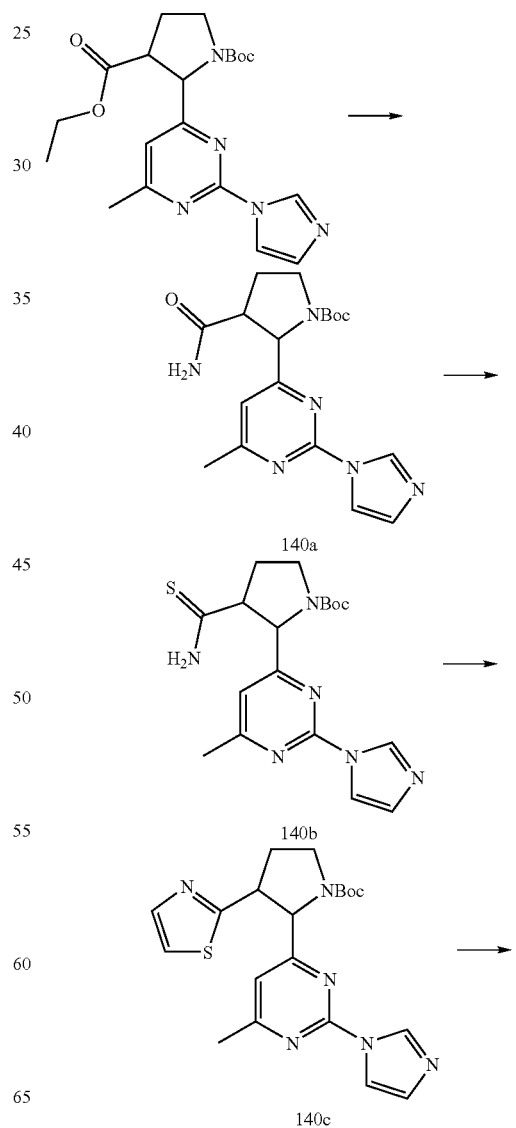

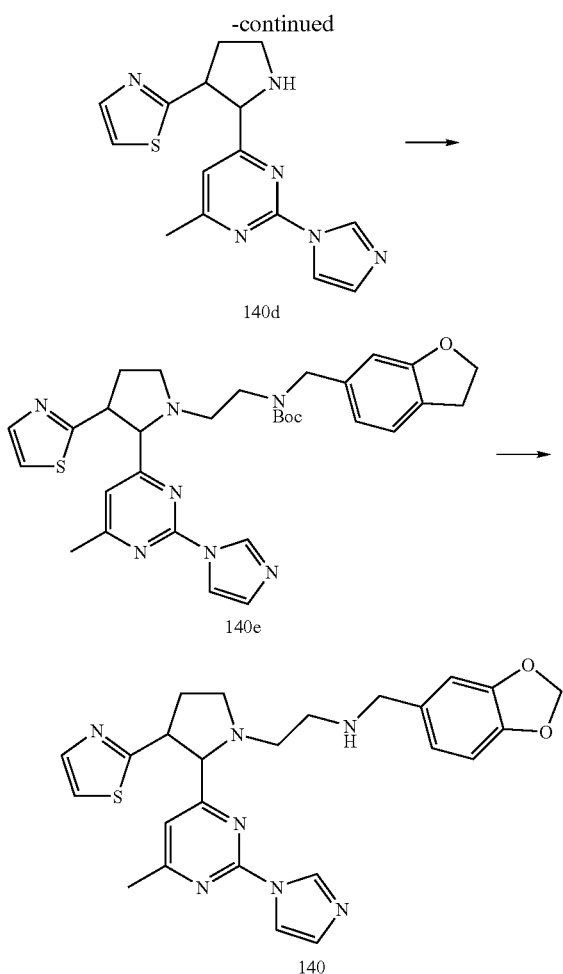

Step 1

Preparation of compound 140a: 3-Carbamoyl-2-(2-imidazol-1-yl-6-methyl-pyrimidin-4-yl)-pyrrolidine-1-carboxylic acid tert-butyl ester was prepared following the procedures described in the preparation of Example 54 using 2-(2-imidazol-1-yl-6-methyl-pyrimidin-4-yl)-pyrrolidine-1,3-dicarboxylic acid 1-tert-butyl ester 3-ethyl ester.

Step 2

Preparation of compound 140b: 2-(2-Imidazol-1-yl-6-methyl-pyrimidin-4-yl)-3-thiocarbamoyl-pyrrolidine-1-carboxylic acid tert-butyl ester $P_2S_5$ (60 mg, 0.27 mmol) was added to a solution of 3-carbamoyl-2-(2-imidazol-1-yl-6-methyl-pyrimidin-4-yl)-pyrrolidine-1-carboxylic acid tert-butyl ester (10 mg, 0.30 mmol) in dimethoxyethane (10 mL) at rt under an atmosphere of $N_2$. The reaction mixture was heated to 100° C. for 2 h then cooled to rt. Water (20 mL) was added and the solution was extracted with DCM (3×30 mL). The combined organics were dried over $Na_2SO_4$, filtered and concentrated under vacuum to afford 100 mg (86%) of 2-(2-imidazol-1-yl-6-methyl-pyrimidin-4-yl)-3-thiocarbamoyl-pyrrolidine-1-carboxylic acid tert-butyl ester as a yellow oil.

Step 3

Preparation of compound 140c: 2-(2-Imidazol-1-yl-6-methyl-pyrimidin-4-yl)-3-thiazol-2-yl-pyrrolidine-1-carboxylic acid tert-butyl ester Potassium carbonate (700 mg, 5.20 mmol) and 2-chloroacetaldehyde (400 mg, 5.20 mmol) were added sequentially to a solution of 2-(2-imidazol-1-yl-6-methyl-pyrimidin-4-yl)-3-thiocarbamoyl-pyrrolidine-1-carboxylic acid tert-butyl ester (400 mg, 1.04 mmol) in DME (10 mL) at rt under an atmosphere of $N_2$. The reaction mixture was stirred at room temperature for 16 h then filtered under vacuum. The filtrate was concentrated and the residue dissolved in DME (10 mL) prior to cooling to 0° C. Trifluoroacetic anhydride (655 mg, 3.12 mmol) and pyridine (575 mg, 7.28 mmol) were added and reaction mixture was stirred at rt for 4 h. The mixture was concentrated and the residue was diluted with DCM (20 mL). The solution was washed with water (2×30 mL), dried over $Na_2SO_4$, filtered and concentrated. The crude product was purified using column chromatography (DCM to 9:1 DCM/MeOH) to afford 2-(2-imidazol-1-yl-6-methyl-pyrimidin-4-yl)-3-thiazol-2-yl-pyrrolidine-1-carboxylic acid tert-butyl ester as a yellow oil (200 mg, 50%).

Step 4

Preparation of compound 140d: 2-Imidazol-1-yl-4-methyl-6-(3-thiazol-2-yl-pyrrolidin-2-yl)-pyrimidine was prepared following the procedures described in the preparation of Example 2 using 2-(2-imidazol-1-yl-6-methyl-pyrimidin-4-yl)-3-thiazol-2-yl-pyrrolidine-1-carboxylic acid tert-butyl ester.

Step 5

Preparation of compound 140e: Benzo[1,3]dioxol-5-ylmethyl-{2-[2-(2-imidazol-1-yl-6-methyl-pyrimidin-4-yl)-3-thiazol-2-yl-pyrrolidin-1-yl]-ethyl}-carbamic acid tert-butyl ester was prepared following the procedures described in the preparation of Example 77c using 2-imidazol-1-yl-4-methyl-6-(3-thiazol-2-yl-pyrrolidin-2-yl)-pyrimidine and 77a.

Step 6

Preparation of compound 140: Benzo[1,3]dioxol-5-ylmethyl-{2-[2-(2-imidazol-1-yl-6-methyl-pyrimidin-4-yl)-3-thiazol-2-yl-pyrrolidin-1-yl]-ethyl}-amine was prepared following the procedures described in the preparation of Example 2 using benzo[1,3]dioxol-5-ylmethyl-{2-[2-(2-imidazol-1-yl-6-methyl-pyrimidin-4-yl)-3-thiazol-2-yl-pyrrolidin-1-yl]-ethyl}-carbamic acid tert-butyl ester. $^1$H NMR (400 MHz, $CDCl_3$) δ 8.03 (s, 1H), 7.74 (d, 1H), 7.46 (s, 1H), 7.27 (s, 1H), 7.12 (d, 1H), 7.10 (s, 1H), 6.54-6.46 (m, 3H), 5.90 (s, 2H), 3.91 (m, 1H), 3.81 (s, 2H), 3.25 (m, 1H), 2.65 (t, 2H), 2.48 (t, 2H), 2.35 (s, 3H), 2.30-2.20 (m, 2H), 2.00 (m, 1H), 1.75 (m, 1H).

Example 141

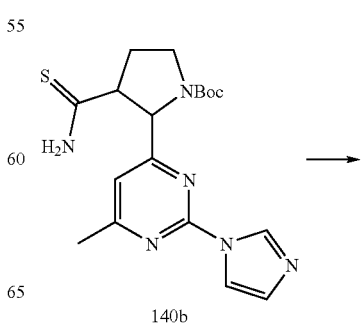

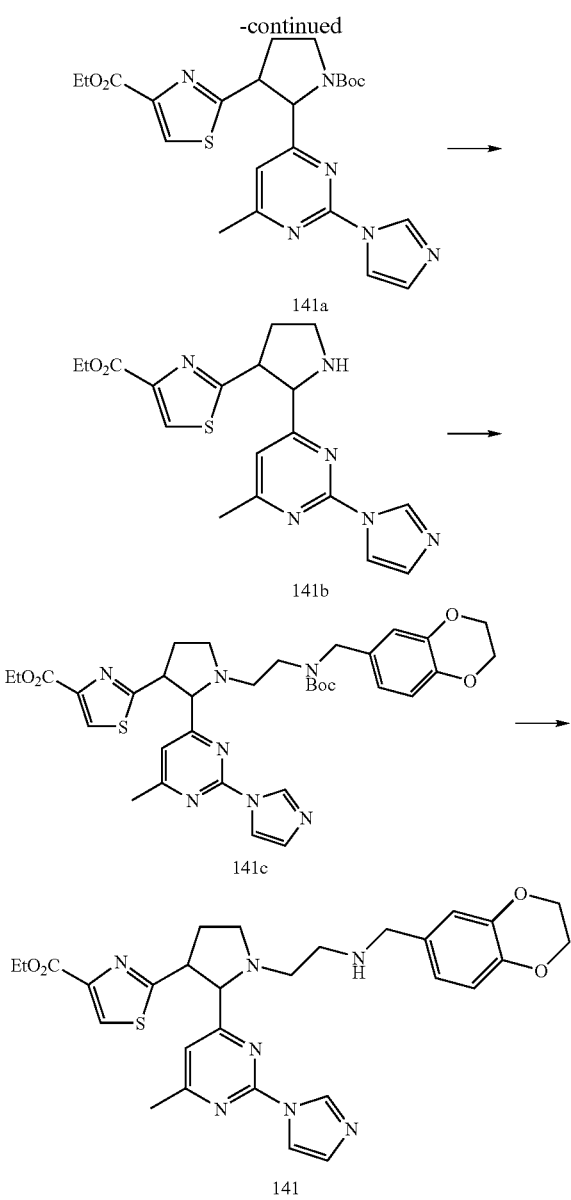

Step 2

Preparation of compound 141b: 2-[2-(2-Imidazol-1-yl-6-methyl-pyrimidin-4-yl)-pyrrolidin-3-yl]-thiazole-4-carboxylic acid ethyl ester was prepared following the procedures described in the preparation of Example 2 using 2-[1-tert-butoxycarbonyl-2-(2-imidazol-1-yl-6-methyl-pyrimidin-4-yl)-pyrrolidin-3-yl]-thiazole-4-carboxylic acid ethyl ester.

Step 3

Preparation of compound 141c: 2-[1-[2-(Benzo[1,3]dioxol-5-ylmethyl-tert-butoxycarbonyl-amino)-ethyl]-2-(2-imidazol-1-yl-6-methyl-pyrimidin-4-yl)-pyrrolidin-3-yl]-thiazole-4-carboxylic acid ethyl ester was prepared following the procedures described in the preparation of Example 77c using 2-[2-(2-imidazol-1-yl-6-methyl-pyrimidin-4-yl)-pyrrolidin-3-yl]-thiazole-4-carboxylic acid ethyl ester and 77a.

Step 4

Preparation of compound 141: 2-[1-{2-[(Benzo[1,3]dioxol-5-ylmethyl)-amino]-ethyl}-2-(2-imidazol-1-yl-6-methyl-pyrimidin-4-yl)-pyrrolidin-3-yl]-thiazole-4-carboxylic acid ethyl ester was prepared following the procedures described in the preparation of Example 2 using 2-[1-[2-(benzo[1,3]dioxol-5-ylmethyl-tert-butoxycarbonyl-amino)-ethyl]-2-(2-imidazol-1-yl-6-methyl-pyrimidin-4-yl)-pyrrolidin-3-yl]-thiazole-4-carboxylic acid ethyl ester. $[M+H]^+$ 562.45; $^1$H NMR (400 MHz, CDCl$_3$) δ 8.03 (s, 1H), 7.90 (s, 1H), 7.46 (s, 1H), 7.27 (s, 1H), 7.10 (s, 1H), 6.54-6.46 (m, 3H), 5.90 (s, 2H), 4.29 (q, 2H), 3.91 (m, 1H), 3.81 (s, 2H), 3.25 (m, 1H), 2.65 (t, 2H), 2.48 (t, 2H), 2.35 (s, 3H), 2.30-2.20 (m, 2H), 2.00 (m, 1H), 1.75 (m, 1H), 1.30 (t, 3H).

Example 142

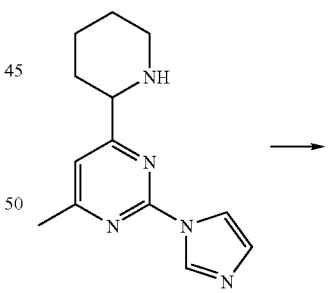

Preparation of compound 141a: 2-[1-tert-Butoxycarbonyl-2-(2-imidazol-1-yl-6-methyl-pyrimidin-4-yl)-pyrrolidin-3-yl]-thiazole-4-carboxylic acid ethyl ester Ethyl 3-bromo-2-oxopropanoate (350 mg, 1.79 mmol) was added to a solution of tert-butyl 2-(2-(1 H-imidazol-1-yl)-6-methylpyrimidin-4-yl)-3-carbamothioylpyrrolidine-1-carboxylate (700 mg, 1.80 mmol) in DCM (20 mL) at rt under an atmosphere of N$_2$. The reaction mixture was heated to 100° C. for 2 h then cooled to rt. Sodium bicarbonate (20 mL, sat. aq.) was added and the mixture extracted with DCM (2×20 mL). The combined organic layers were dried over Na$_2$SO$_4$, filtered and concentrated. The residue was then purified using column chromatography (DCM to 9:1 DCM/MeOH) to afford 500 mg (80%) of 2-[1-tert-butoxycarbonyl-2-(2-imidazol-1-yl-6-methyl-pyrimidin-4-yl)-pyrrolidin-3-yl]-thiazole-4-carboxylic acid ethyl ester as a yellow oil.

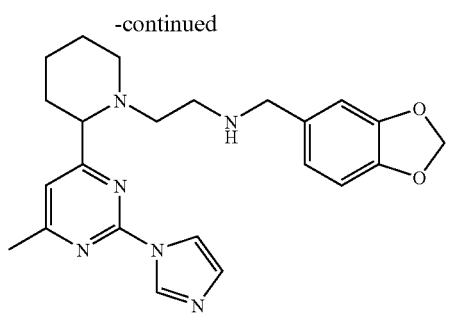

142

Step 1

Preparation of compound 142a: Benzo[1,3]dioxol-5-ylmethyl-{2-[2-(2-imidazol-1-yl-6-methyl-pyrimidin-4-yl)-piperidin-1-yl]-ethyl}-carbamic acid tert-butyl ester was prepared following the procedures described in the preparation of Example 77c using 2-imidazol-1-yl-4-methyl-6-piperidin-2-yl-pyrimidine and 77a.

Step 2

Preparation of compound 142: Benzo[1,3]dioxol-5-ylmethyl-{2-[2-(2-imidazol-1-yl-6-methyl-pyrimidin-4-yl)-piperidin-1-yl]-ethyl}-amine was prepared following the procedures described in the preparation of Example 2 using benzo[1,3]dioxol-5-ylmethyl-{2-[2-(2-imidazol-1-yl-6-methyl-pyrimidin-4-yl)-piperidin-1-yl]-ethyl}-carbamic acid tert-butyl ester. [M+H]$^+$ 421.39.

Example 143

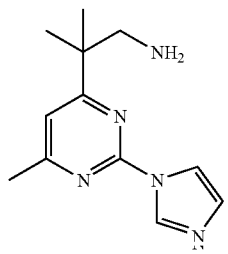

143

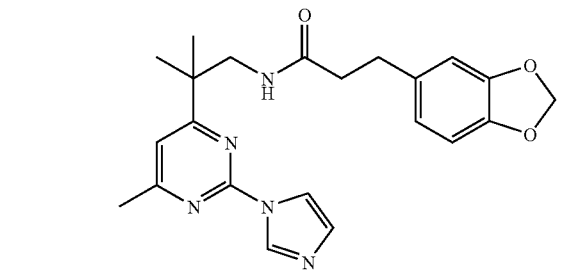

Preparation of compound 143: 3-Benzo[1,3]dioxol-5-yl-N-[2-(2-imidazol-1-yl-6-methyl-pyrimidin-4-yl)-2-methyl-propyl]-propionamide 3-Benzo[1,3]dioxol-5-yl-propionic acid (2.50 g, 12.9 mmol) and thionyl chloride (20 mL, 274 mmol) were heated to 79° C. for 4 h then concentrated to afford 3-(benzo[d][1,3]dioxol-5-yl)propanoyl chloride as a brown oil. 2-(2-Imidazol-1-yl-6-methyl-pyrimidin-4-yl)-2-methyl-propylamine (100 mg, 0.432 mmol) and methylene chloride (20 mL) were added and the reaction mixture stirred at rt for about 2 h. The reaction mixture was filtered, filtrate washed with K$_2$CO$_3$ (100 mL, sat. aq.), and the organic layer was dried over Na$_2$SO$_4$. Filtration, concentration and purification using column chromatography gave 40 mg of 3-benzo[1,3]dioxol-5-yl-N-[2-(2-imidazol-1-yl-6-methyl-pyrimidin-4-yl)-2-methyl-propyl]-propionamide as a white solid. $^1$H NMR (400 MHz, CDCl$_3$) δ 8.90 (s, 1H), 7.92 (s, 1H), 7.05 (s, 1H), 6.90 (s, 1H), 6.70 (m, 3H), 5.90 (s, 2H), 3.59 (d, 2H), 2.94 (t, 2H), 2.57 (s, 3H), 2.40 (t, 2H), 1.28 (s, 6H).

Example 144

144

Preparation of compound 144: 1-Benzo[1,3]dioxol-5-ylmethyl-3-[2-(2-imidazol-1-yl-6-methyl-pyrimidin-4-yl)-2-methyl-propyl]-urea was prepared following the procedures described in the preparation of Example 13 using 2-(2-imidazol-1-yl-6-methyl-pyrimidin-4-yl)-2-methyl-propylamine. [M+H]$^+$ 409.04.

Example 145

145

Preparation of compound 145: N'-Benzo[1,3]dioxol-5-ylmethyl-N-methyl-N-(3-[1,2,4]triazol-1-yl-[1,2,4]thiadiazol-5-yl)-propane-1,3-diamine was prepared following the procedures described in the preparation of Example 2 using sodium 1,2,4-triazole. [M+H]$^+$ 374.12; $^1$H-NMR (400 MHz, CDCl$_3$) δ 8.91 (s, 1H), 8.06 (s, 1H), 6.84 (s, 1H), 6.74 (d, 1H), 6.69 (d, 1H), 5.91 (s, 2 H), 3.85 (s, 3H), 3.64 (br s, 1H), 3.09 (br s, 2H), 2.82 (t, 2H), 2.05 (m, 2H), 1.99 (s, 2H).
The following compounds can generally be made using the methods described above. It is expected that these compounds when made will have activity similar to those that have been made in the examples above.
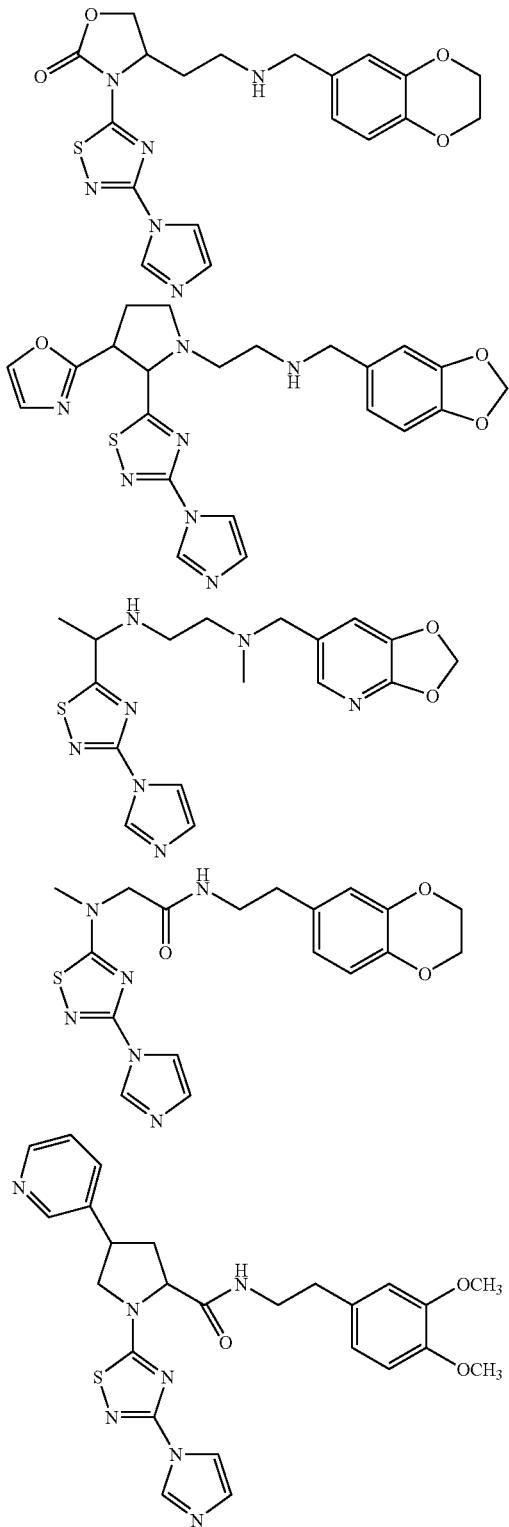
-continued
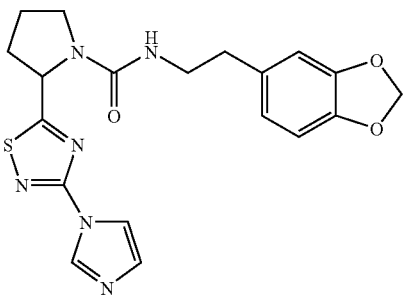
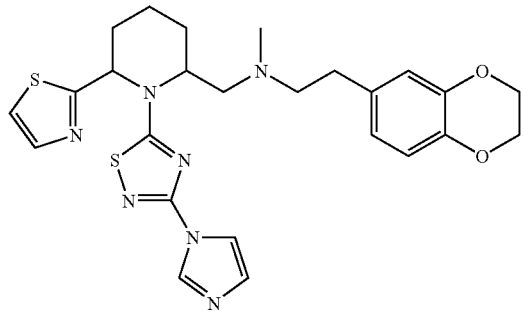
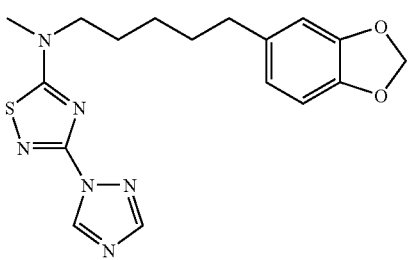
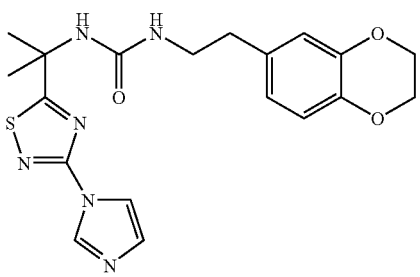
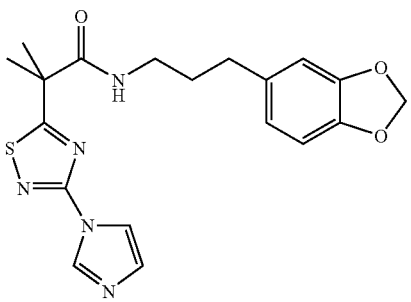

-continued
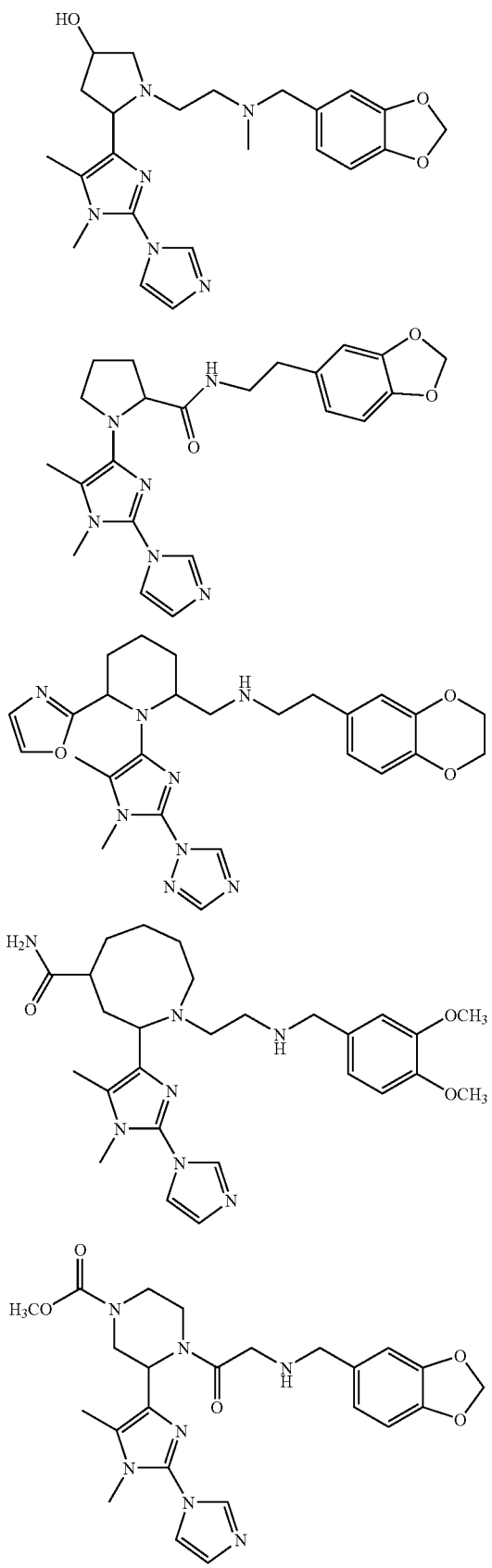

171
-continued
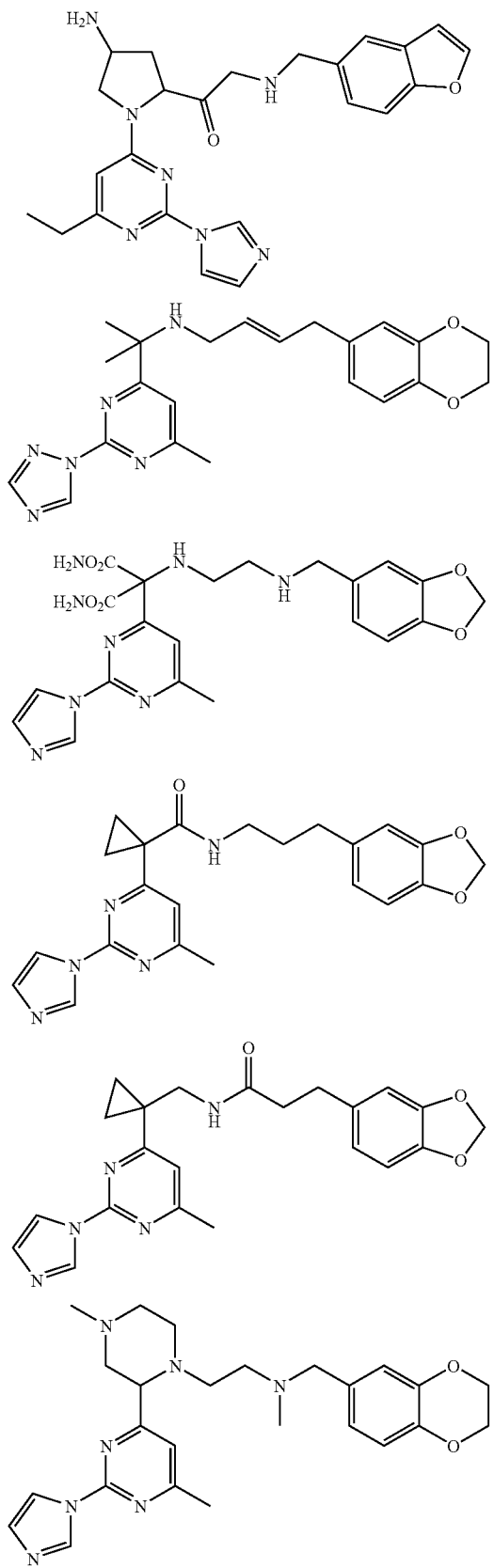
172
-continued
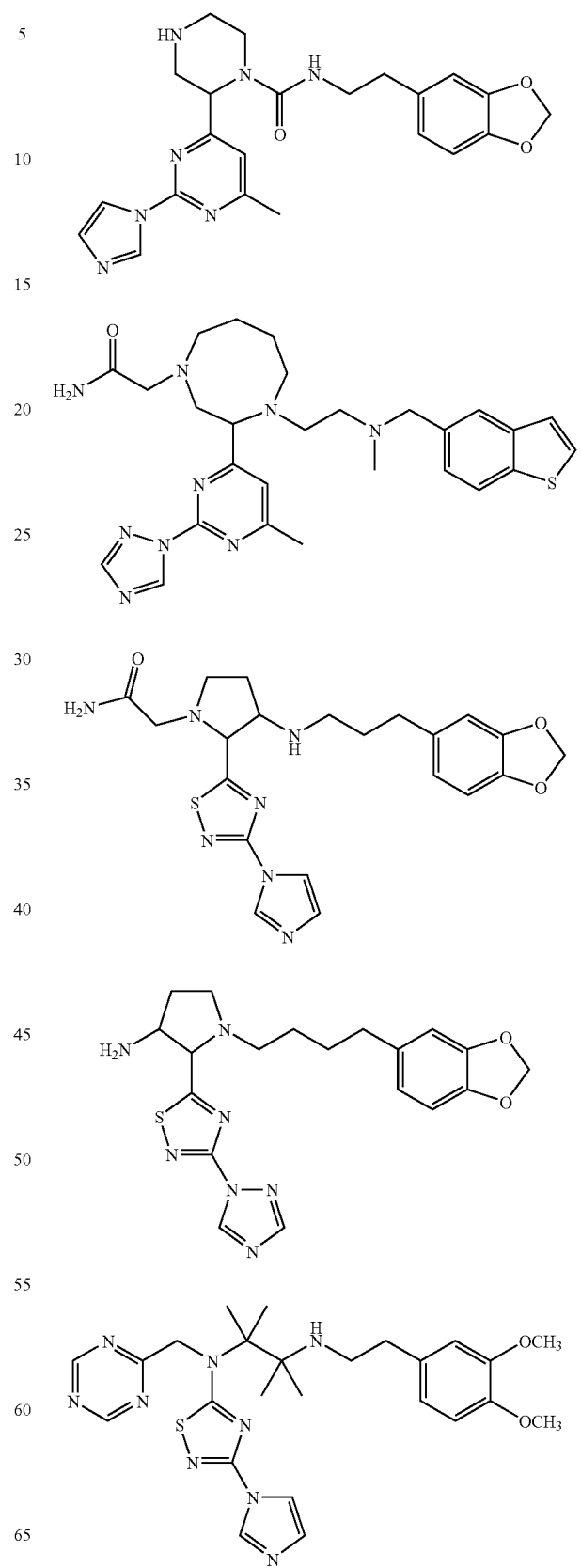

-continued
173
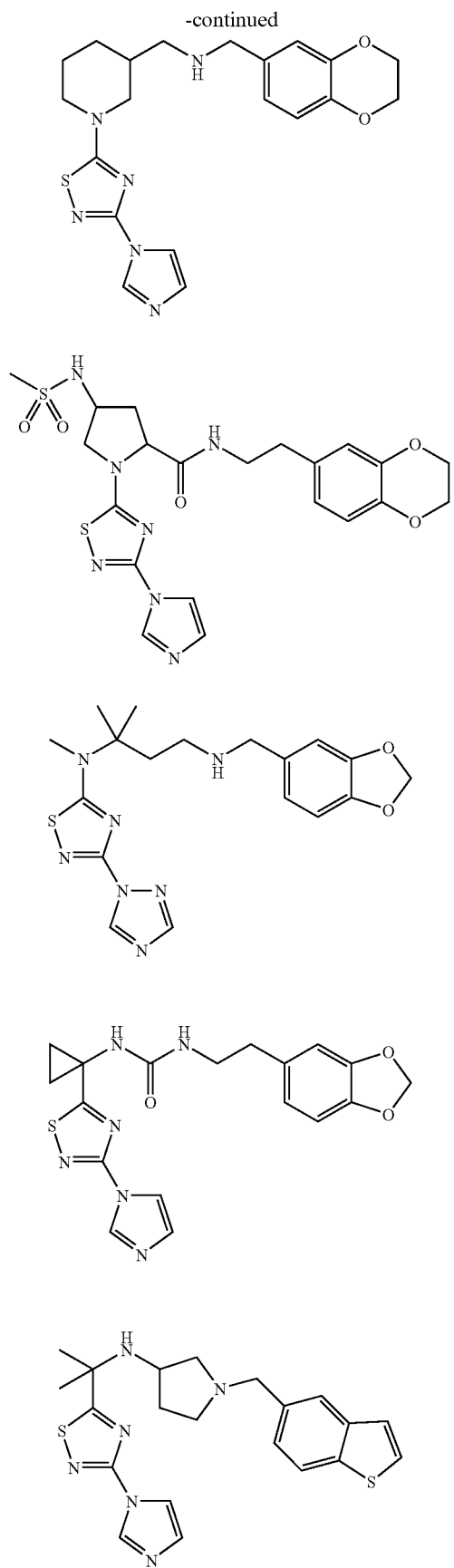
174
-continued
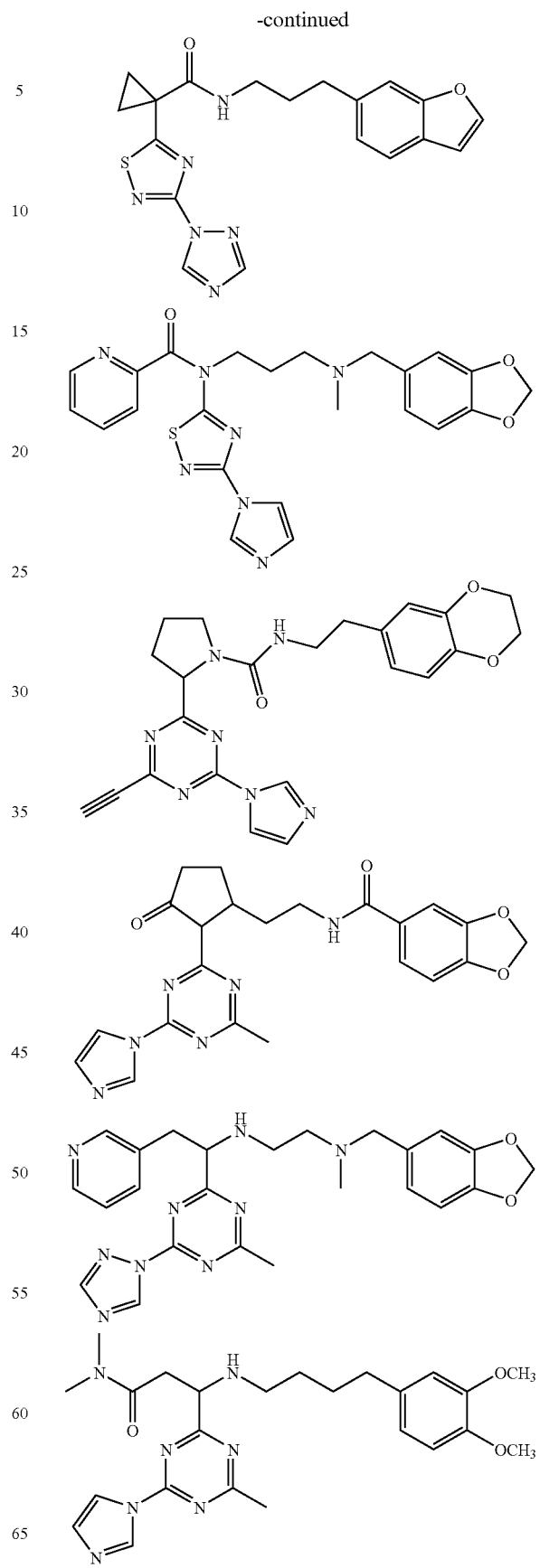

-continued
175
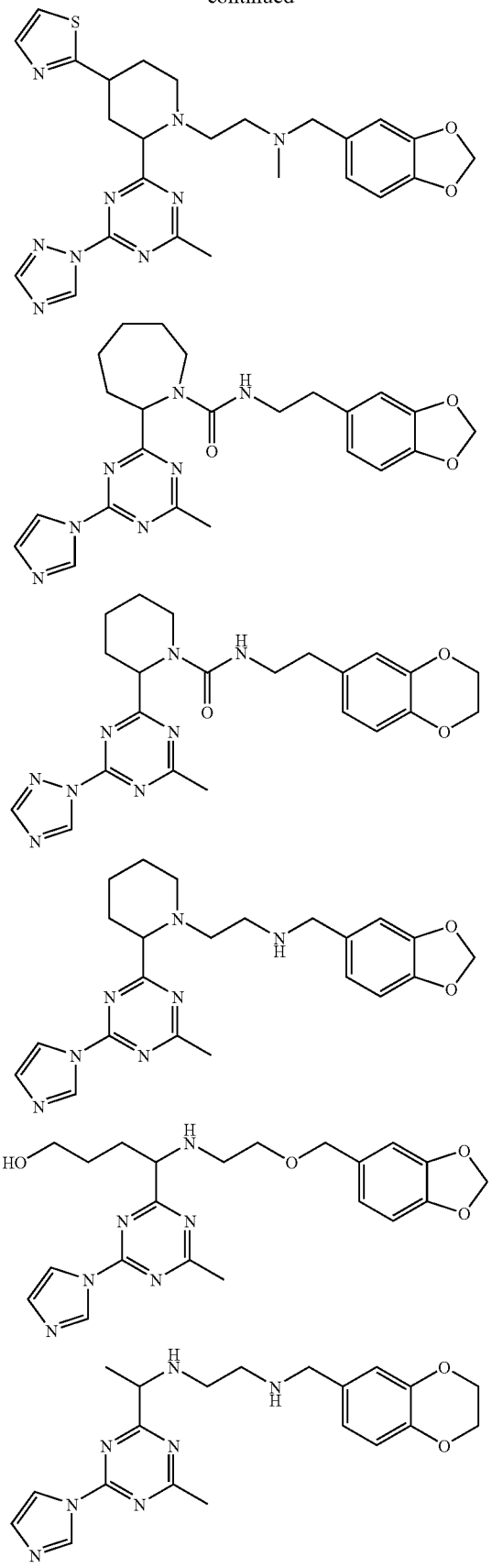
176
-continued
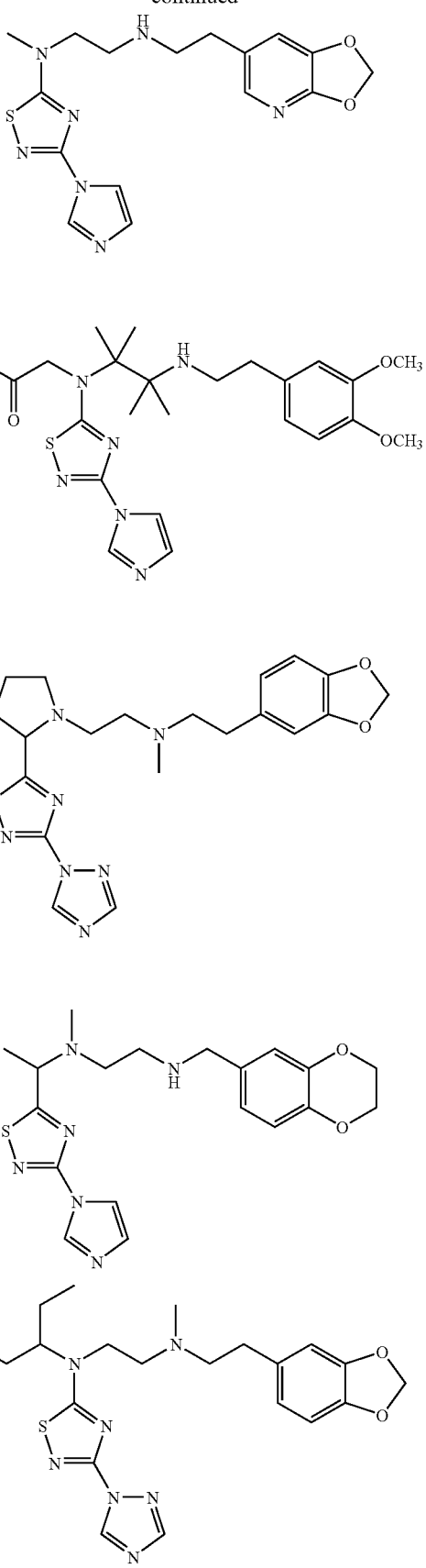

-continued
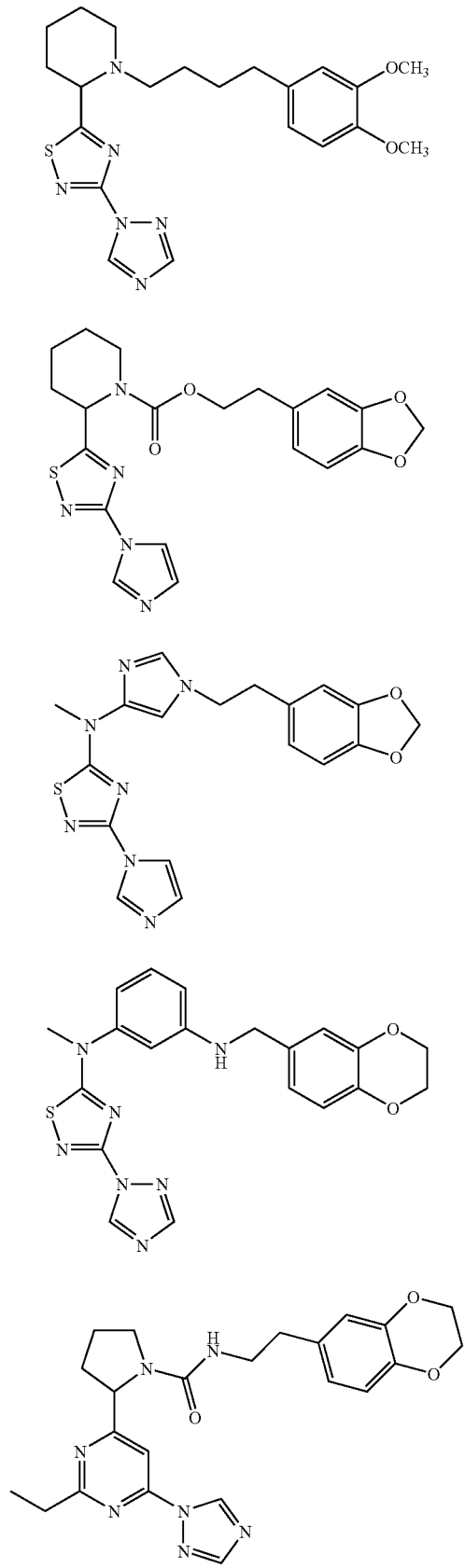
-continued
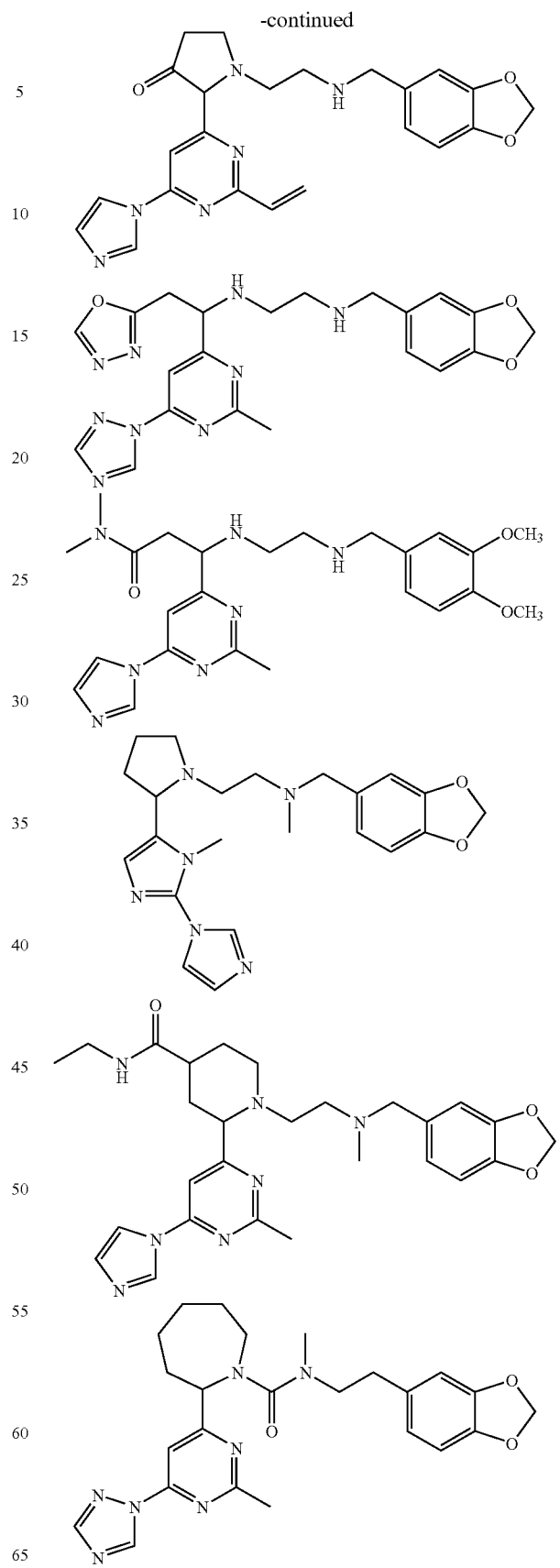

-continued
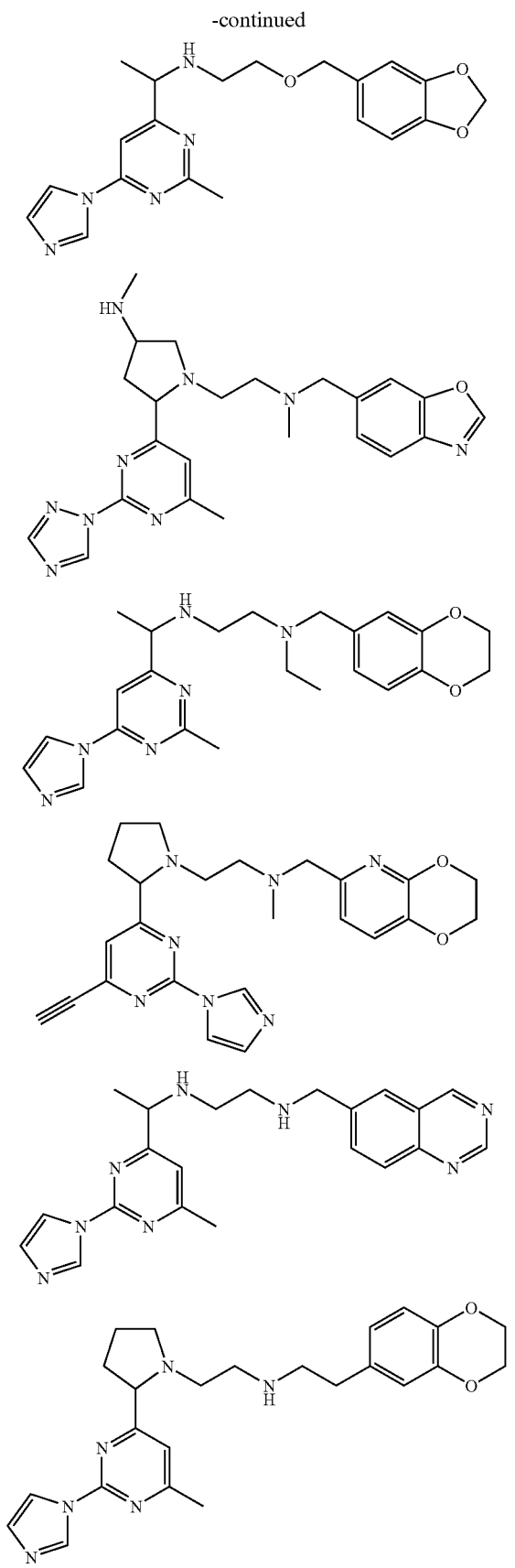
-continued
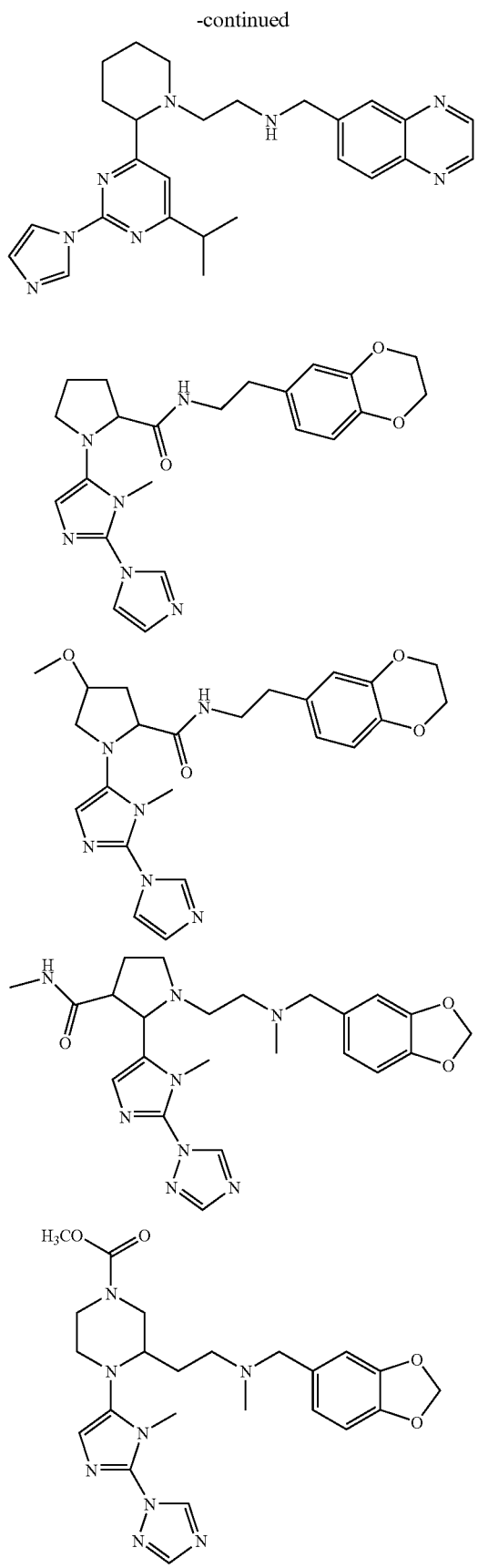

-continued
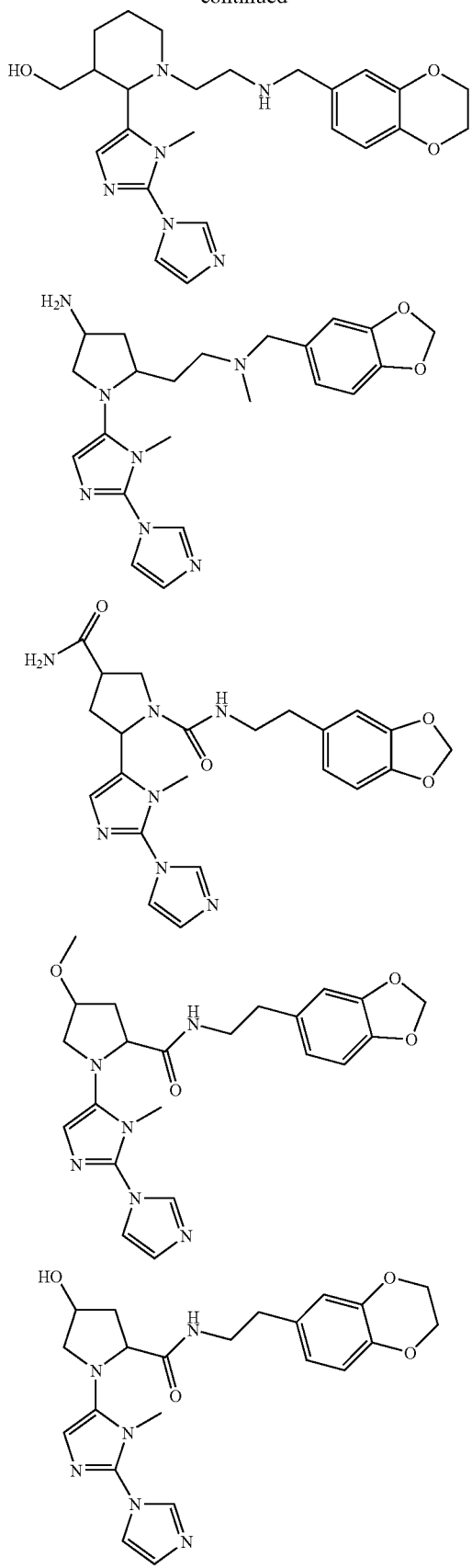 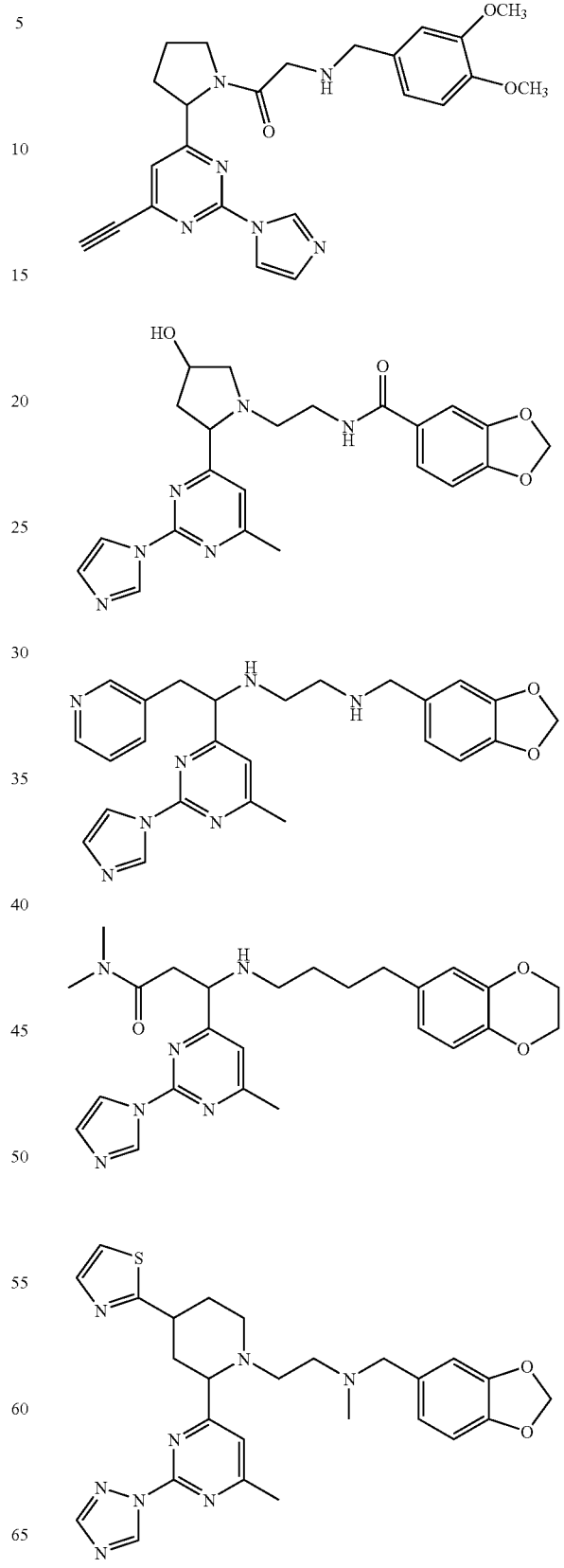

-continued

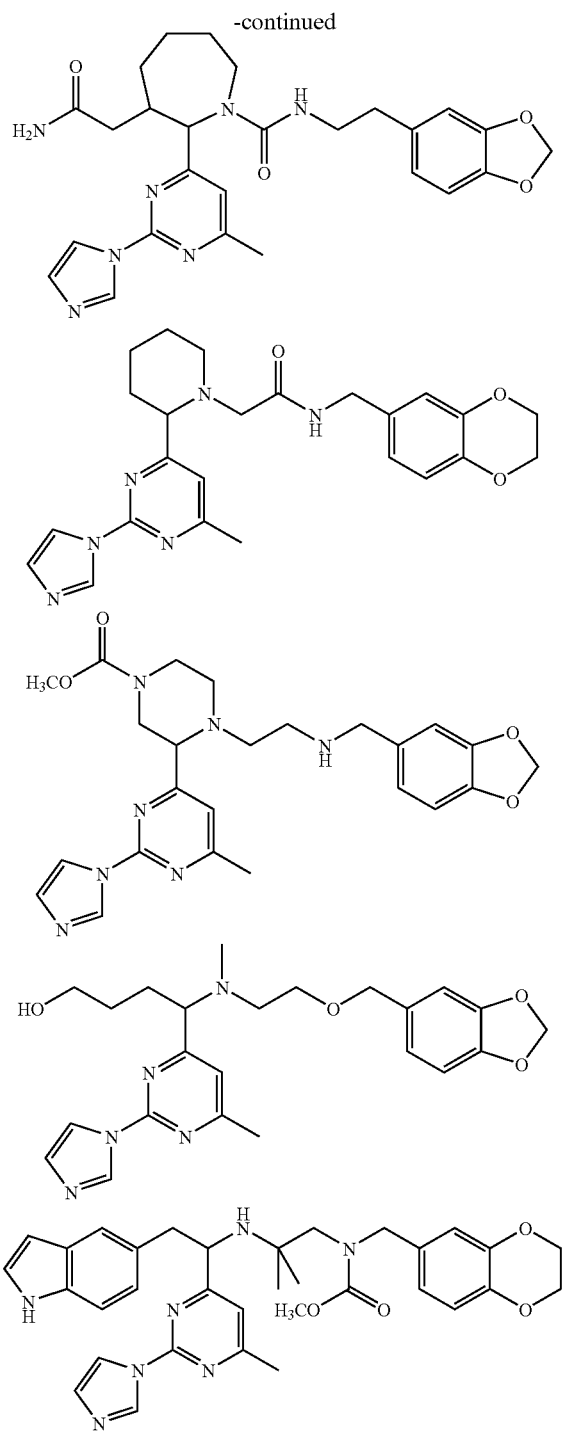

The activity of the compounds as NO synthase inhibitors in examples 1-145 has been shown by the following assays. The other compounds listed above, which have not yet been made, are predicted to have activity in these assays as well.

Biological Activity Assay

Enzyme Source

The source of nitric oxide synthase (NOS) enzyme can be generated in several ways including induction of endogenous iNOS using cytokines and/or lipopolysaccharide (LPS) in various cell types known in the art. Alternatively, the gene encoding the enzyme can be cloned and the enzyme can be generated in cells via heterologous expression from a transient or stable expression plasmid with suitable features for protein expression as are known in the art. Enzymatic activity (nitric oxide production) is calcium independent for iNOS, while the constitutive NOS isoforms, nNOS and eNOS, become active with the addition of various cofactors added to cellular media or extract as are well known in the art. Enzymes specified in Table 1 were expressed in HEK293 cells transiently transfected with the indicated NOS isoform.

DAN Assay

A major metabolic pathway for nitric oxide is to nitrate and nitrite, which are stable metabolites within tissue culture, tissue, plasma, and urine (S Moncada, A Higgs, N Eng J Med 329, 2002 (1993)). Tracer studies in humans have demonstrated that perhaps 50% of the total body nitrate/nitrite originates from the substrate for NO synthesis, L-arginine (P M Rhodes, A M Leone, P L Francis, A D Struthers, S Moncada, Biomed Biophys Res. Commun. 209, 590 (1995); L. Castillo et al., Proc Natl Acad Sci USA 90, 193 (1993). Although nitrate and nitrite are not measures of biologically active NO, plasma and urine samples obtained from subjects after a suitable period of fasting, and optionally after administration of a controlled diet (low nitrate/low arginine), allow the use of nitrate and nitrite as an index of NO activity (C Baylis, P Vallance, Curr Opin Nephrol Hypertens 7, 59 (1998)).

The level of nitrate or nitrite in the specimen can be quantified by any method known in the art which provides adequate sensitivity and reproducibility. A variety of protocols have also been described for detecting and quantifying nitrite and nitrate levels in biological fluids by ion chromatography (e.g., S A Everett et al., J. Chromatogr. 706, 437 (1995); J M Monaghan et al., J. Chromatogr. 770, 143 (1997)), high-performance liquid chromatography (e.g., M Kelm et al., Cardiovasc. Res. 41, 765 (1999)), and capillary electrophoresis (M A Friedberg et al., J. Chromatogr. 781, 491 (1997)). For example, 2,3-diaminonaphthalene reacts with the nitrosonium cation that forms spontaneously from NO to form the fluorescent product 1H-naphthothiazole. Using 2,3-diaminonaphthalene ("DAN"), researchers have developed a rapid, quantitative fluorometric assay that can detect from 10 nM to 10 µM nitrite and is compatible with a multi-well microplate format. DAN is a highly selective photometric and fluorometric reagent for Se and nitrite ion. DAN reacts with nitrite ion and gives fluorescent naphthothiazole (M C Carré et al., Analysis 27, 835-838 (1999)). Table 1 provides the test results of various compounds of the subject invention using the DAN assay.

A specimen can be processed prior to determination of nitrate or nitrite as required by the quantification method, or in order to improve the results, or for the convenience of the investigator. For example, processing can involve centrifuging, filtering, or homogenizing the sample. If the sample is whole blood, the blood can be centrifuged to remove cells and the nitrate or nitrite assay performed on the plasma or serum fraction. If the sample is tissue, the tissue can be dispersed or homogenized by any method known in the art prior to determination of nitrate or nitrite. It may be preferable to remove cells and other debris by centrifugation or another method and to determine the nitrate or nitrite level using only the fluid portion of the sample, or the extracellular fluid fraction of the sample. The sample can also be preserved for later determination, for example by freezing of urine or plasma samples.

When appropriate, additives may be introduced into the specimen to preserve or improve its characteristics for use in the nitrate or nitrite assay.

The "level" of nitrate, nitrite, or other NO-related product usually refers to the concentration (in moles per liter, micromoles per liter, or other suitable units) of nitrate or nitrite in the specimen, or in the fluid portion of the specimen. However, other units of measure can also be used to express the level of nitrate or nitrite. For example, an absolute amount (in micrograms, milligrams, nanomoles, moles, or other suitable units) can be used, particularly if the amount refers back to a constant amount (e.g., grams, kilograms, milliliters, liters, or other suitable units) of the specimens under consideration. A number of commercially available kits can be used.

TABLE 1

| Compound ID | EC50 hiNOS | EC50 heNOS | EC50 hnNOS |
|---|---|---|---|
| Example 1 | <1 μM | >10 μM | >1 μM |
| Example 2 | <1 μM | >10 μM | >1 μM |
| Example 3 | <1 μM | >10 μM | >1 μM |
| Example 4 | <1 μM | >10 μM | 0.7 μM |
| Example 5 | <1 μM | >10 μM | >1 μM |
| Example 6 | >50 μM | Not Tested | Not Tested |
| Example 7 | <50 μM | Not Tested | Not Tested |
| Example 8 | <1 μM | Not Tested | Not Tested |
| Example 9 | >50 μM | Not Tested | Not Tested |
| Example 10 | >50 μM | Not Tested | Not Tested |
| Example 11 | >50 μM | Not Tested | Not Tested |
| Example 12 | >50 μM | Not Tested | Not Tested |
| Example 13 | <1 μM | Not Tested | Not Tested |
| Example 14 | <1 μM | Not Tested | Not Tested |
| Example 15 | >50 μM | Not Tested | Not Tested |
| Example 16 | <1 μM | Not Tested | Not Tested |
| Example 17 | <1 μM | Not Tested | Not Tested |
| Example 18 | >50 μM | Not Tested | Not Tested |
| Example 19 | >50 μM | Not Tested | Not Tested |
| Example 20 | >50 μM | Not Tested | Not Tested |
| Example 21 | >50 μM | Not Tested | Not Tested |
| Example 22 | >50 μM | Not Tested | Not Tested |
| Example 23 | <1 μM | Not Tested | Not Testedμ |
| Example 24 | <1 μM | Not Tested | Not Tested |
| Example 25 | >50 μM | Not Tested | Not Tested |
| Example 26 | <1 μM | Not Tested | Not Tested |
| Example 27 | <1 μM | Not Tested | Not Tested |
| Example 28 | <1 μM | Not Tested | Not Tested |
| Example 29 | <1 μM | Not Tested | Not Tested |
| Example 30 | <1 μM | Not Tested | Not Tested |
| Example 31 | <1 μM | Not Tested | Not Tested |
| Example 32 | <1 μM | Not Tested | Not Tested |
| Example 33 | <50 μM | Not Tested | Not Tested |
| Example 34 | >50 μM | Not Tested | Not Tested |
| Example 35 | <1 μM | Not Tested | Not Tested |
| Example 36 | <1 μM | Not Tested | Not Tested |
| Example 37 | <1 μM | Not Tested | Not Tested |
| Example 38 | <1 μM | Not Tested | Not Tested |
| Example 39 | <1 μM | Not Tested | Not Tested |
| Example 40 | <1 μM | Not Tested | Not Tested |
| Example 41 | <1 μM | Not Tested | Not Tested |
| Example 42 | <1 μM | Not Tested | Not Tested |
| Example 43 | <1 μM | Not Tested | Not Tested |
| Example 44 | <1 μM | Not Tested | Not Tested |
| Example 45 | <1 μM | Not Tested | Not Tested |
| Example 46 | <1 μM | Not Tested | Not Tested |
| Example 47 | <1 μM | Not Tested | Not Tested |
| Example 48 | <1 μM | Not Tested | Not Tested |
| Example 49 | <1 μM | Not Tested | Not Tested |
| Example 50 | — | Not Tested | Not Tested |
| Example 51 | — | Not Tested | Not Tested |
| Example 52 | <1 μM | Not Tested | Not Tested |
| Example 53 | <1 μM | Not Tested | Not Tested |
| Example 54 | <1 μM | Not Tested | Not Tested |
| Example 55 | <50 μM | Not Tested | Not Tested |
| Example 56 | <1 μM | Not Tested | Not Tested |
| Example 57 | <1 μM | Not Tested | Not Tested |
| Example 58 | <1 μM | Not Tested | Not Tested |
| Example 59 | <1 μM | Not Tested | Not Tested |

TABLE 1-continued

| Compound ID | EC50 hiNOS | EC50 heNOS | EC50 hnNOS |
|---|---|---|---|
| Example 60 | <1 μM | Not Tested | Not Tested |
| Example 61 | <1 μM | Not Tested | Not Tested |
| Example 62 | <1 μM | Not Tested | Not Tested |
| Example 63 | <1 μM | Not Tested | Not Tested |
| Example 64 | <1 μM | Not Tested | Not Tested |
| Example 65 | <1 μM | Not Tested | Not Tested |
| Example 66 | <1 μM | Not Tested | Not Tested |
| Example 67 | <1 μM | Not Tested | Not Tested |
| Example 68 | <1 μM | Not Tested | Not Tested |
| Example 69 | <1 μM | Not Tested | Not Tested |
| Example 70 | <1 μM | Not Tested | Not Tested |
| Example 71 | <50 μM | Not Tested | Not Tested |
| Example 72 | <50 μM | Not Tested | Not Tested |
| Example 73 | <50 μM | Not Tested | Not Tested |
| Example 74 | <50 μM | Not Tested | Not Tested |
| Example 75 | <1 μM | Not Tested | Not Tested |
| Example 76 | <1 μM | Not Tested | Not Tested |
| Example 77 | <1 μM | Not Tested | Not Tested |
| Example 78 | <1 μM | Not Tested | Not Tested |
| Example 79 | <1 μM | Not Tested | Not Tested |
| Example 80 | >50 μM | Not Tested | Not Tested |
| Example 81 | >50 μM | Not Tested | Not Tested |
| Example 82 | <1 μM | Not Tested | Not Tested |
| Example 83 | <1 μM | Not Tested | Not Tested |
| Example 84 | <1 μM | Not Tested | Not Tested |
| Example 85 | <1 μM | Not Tested | Not Tested |
| Example 86 | <1 μM | Not Tested | Not Tested |
| Example 87 | <1 μM | Not Tested | Not Tested |
| Example 88 | <1 μM | Not Tested | Not Tested |
| Example 89 | <1 μM | Not Tested | Not Tested |
| Example 90 | Not Tested | Not Tested | Not Tested |
| Example 91 | Not Tested | Not Tested | Not Tested |
| Example 92 | <1 μM | Not Tested | Not Tested |
| Example 93 | <1 μM | Not Tested | Not Tested |
| Example 94 | <1 μM | Not Tested | Not Tested |
| Example 95 | <1 μM | Not Tested | Not Tested |
| Example 96 | <50 μM | Not Tested | Not Tested |
| Example 97 | <50 μM | Not Tested | Not Tested |
| Example 98 | <1 μM | Not Tested | Not Tested |
| Example 99 | Not Tested | Not Tested | Not Tested |
| Example 100 | <50 μM | Not Tested | Not Tested |
| Example 101 | <1 μM | Not Tested | Not Tested |
| Example 102 | <1 μM | Not Tested | Not Tested |
| Example 103 | <1 μM | Not Tested | Not Tested |
| Example 104 | <1 μM | Not Tested | Not Tested |
| Example 105 | <1 μM | Not Tested | Not Tested |
| Example 106 | <1 μM | Not Tested | Not Tested |
| Example 107 | >50 μM | Not Tested | Not Tested |
| Example 108 | >50 μM | Not Tested | Not Tested |
| Example 109 | >50 μM | Not Tested | Not Tested |
| Example 110 | >50 μM | Not Tested | Not Tested |
| Example 111 | >50 μM | Not Tested | Not Tested |
| Example 112 | >50 μM | Not Tested | Not Tested |
| Example 113 | <50 μM | Not Tested | Not Tested |
| Example 114 | >50 μM | Not Tested | Not Tested |
| Example 115 | >50 μM | Not Tested | Not Tested |
| Example 116 | >50 μM | Not Tested | Not Tested |
| Example 117 | >50 μM | Not Tested | Not Tested |
| Example 118 | >50 μM | Not Tested | Not Tested |
| Example 119 | >50 μM | Not Tested | Not Tested |
| Example 120 | <1 μM | Not Tested | Not Tested |
| Example 121 | <1 μM | Not Tested | Not Tested |
| Example 122 | <1 μM | Not Tested | Not Tested |
| Example 123 | <1 μM | Not Tested | Not Tested |
| Example 124 | <1 μM | Not Tested | Not Tested |
| Example 125 | <1 μM | Not Tested | Not Tested |
| Example 126 | <1 μM | Not Tested | Not Tested |
| Example 127 | <1 μM | Not Tested | Not Tested |
| Example 128 | <1 μM | Not Tested | Not Tested |
| Example 129 | <1 μM | Not Tested | Not Tested |
| Example 130 | <1 μM | Not Tested | Not Tested |
| Example 131 | <1 μM | Not Tested | Not Tested |
| Example 132 | <1 μM | Not Tested | Not Tested |
| Example 133 | <1 μM | Not Tested | Not Tested |
| Example 134 | <1 μM | Not Tested | Not Tested |
| Example 135 | <1 μM | Not Tested | Not Tested |
| Example 136 | <1 μM | Not Tested | Not Tested |

TABLE 1-continued

| Compound ID | EC50 hiNOS | EC50 heNOS | EC50 hnNOS |
|---|---|---|---|
| Example 137 | <1 µM | Not Tested | Not Tested |
| Example 138 | <1 µM | Not Tested | Not Tested |
| Example 139 | <1 µM | Not Tested | Not Tested |
| Example 140 | <1 µM | Not Tested | Not Tested |
| Example 141 | <1 µM | Not Tested | Not Tested |
| Example 142 | <1 µM | Not Tested | Not Tested |
| Example 143 | <1 µM | Not Tested | Not Tested |
| Example 144 | <1 µM | Not Tested | Not Tested |
| Example 145 | >50 µM | Not Tested | Not Tested |

Carrageenan Test

Injection of carrageenan subcutaneously into the hind foot (paw) of a rat induces robust inflammation and pain. The inflammatory response begins 1-2 hrs post-carrageenan injection and persists for at least five hours following inoculation. In addition, the rat's inflamed hind paw is sensitive to noxious (hyperalgesia) or innocuous (allodynia) stimuli, compared to the contralateral hind paw. Compounds can be evaluated in this model for anti-hyperalgesia and anti-inflammatory activity. A general increase in threshold or time to respond following drug administration suggests analgesic efficacy. A general decrease in paw swelling following drug administration suggests anti-inflammatory efficacy. It is possible that some compounds will affect the inflamed paw and not affect the responses of the contralateral paw.

Embodiments of the carrageenan foot edema test are performed with materials, reagents and procedures essentially as described by Winter, et al., (Proc. Soc. Exp. Biol. Med., 111, 544 (1962)). Male Sprague-Dawley rats were selected in each group so that the average body weight was as close as possible (175-200 g). The rats are evaluated for their responsiveness to noxious (paw pinch, plantar test) or innocuous (cold plate, von Frey filaments) stimuli.

In a prophylactic embodiment, following determination of "Pre-carrageenan" responses, a subplantar injection of the test compound or a placebo are administered. Following determination of "Pre-carrageenan" responses, the left hind paw of the rat is wrapped in a towel so that its right hind paw is sticking out. One hour thereafter, a subplantar injection of 100 µL of a 1% solution of carrageenan/sterile saline is injected subcutaneously into the plantar right hind paw, similar. Three hours (and optionally five hours) after carrageenan injection, the rats are evaluated for their responsiveness to noxious or innocuous stimuli and the paw volume was again measured. The paw withdrawal thresholds and average foot swelling in a group of drug-treated animals are compared with those of the group of placebo-treated animals and the percentage inhibition of pain and/or edema is determined (Otterness and Bliven, Laboratory Models for Testing NSAIDs, in Non-steroidal Anti-Inflammatory Drugs, (J. Lombardino, ed. 1985)).

In a therapeutic embodiment, following determination of "Pre-carrageenan" responses a subplantar injection of 100 µL of a 1% solution of carrageenan/sterile saline is administered. Two hours after carrageenan injection, the rats are evaluated for their responsiveness to noxious or innocuous stimuli and the paw volume is measured. Immediately following this testing, a subplantar injection of the test compound or a placebo was administered. Three hours and five hours after carrageenan injection (one and three hours after compound/placebo injection), the rats are evaluated for their responsiveness to noxious or innocuous stimuli and the paw volume is again measured. The paw withdrawal thresholds and average foot swelling in a group of drug-treated animals are compared with those of the group of placebo-treated animals and the percentage inhibition of pain and/or edema is determined.

Formalin Test

Subcutaneous injection of dilute formalin into the hind paw of a rat induces chronic pain. To test the efficacy of prophylactic and therapeutic agents, pain-related behaviors are observed over a period of time after introduction thereof. Biting, scratching, and flinching of the hind paw is measured to determine a response to the test compound. Typically, numerous biting and flinching behaviors are observed following formalin injection ("acute phase"), followed by a period of non-activity (10-15 minutes, "interphase"), followed by reemergence of pain behavior for the remainder of the test (15-60 minutes, "chronic phase"). Compared to saline-treated rats, rats treated with a typical analgesic such as morphine display fewer of these pain related behaviors.

Rats must weigh between 250-300 g and if naïve should be handled once before running. Scrap rats may be used if they have had at least 5 days recovery, have no residual effects from previous procedures, and are within this weight range. Run subjects between 8:00-2:00 to minimize time of day effects in testing.

In a prophylactic embodiment, a subplantar injection of the test compound or a placebo was administered. One hour thereafter, a subcutaneous injection of 50 µL of a 5% formalin/sterile saline was administered. Pain related behaviors were then evaluated as described above.

In a therapeutic embodiment, a subcutaneous injection of 50 µL of a 5% formalin/sterile saline was administered. Fifteen minutes thereafter (i.e., during the "interphase"), a subplantar injection of the test compound or a placebo was administered. Pain related behaviors were then evaluated as described above.

Capsaicin Test

Subcutaneous injection of dilute capsaicin into the rat hind paw produces transient but pronounced hyperalgesia, allodynia and pain. This effect may be mitigated by pretreatment with a suitable agent, such as a topical anaesthetic or analgesic, and the extent of this mitigation quantified by evaluation of pain-related behaviors in response to noxious or innocuous stimuli as described above; rats pretreated with a known analgesic display fewer pain and allodynia related behaviors than controls. Compounds may be evaluated for their efficacy as potential analgesics in this manner as well.

Male Lewis rats weighing between 180 and 250 grams are used. The right hind paw is dipped into vehicle (100% acetone) or compound in vehicle for 30 seconds and then allowed to air-dry for 30 sec. To prevent the animal from licking the compound off the paw, the paw is wiped twice with a wet paper towel. At 15 min after application of vehicle or compound, 0.1 mg in 10 µL capsaicin is injected into right hind paw. Measurement of allodynia is performed 0.5 to 1 hour after capsaicin injection.

One procedure for quantifying allodynia measures the rat behavioral response to presentation of von Frey filaments of increasing diameter. Each rat is placed in a small, clear cage on an elevated screen. Beginning with 4.31, the von Frey hair is presented perpendicularly to the right mid-plantar hind paw with sufficient force to cause slight buckling, for 6-8 seconds. If presentation lifts the hind paw it is disregarded, as it changes the nature of the stimulus. A positive response is noted if the paw is sharply withdrawn upon onset or offset of stimulus. Ambulation is considered an ambiguous response and the presentation is repeated. Stimuli are presented in a consecutive fashion. A positive response would call for the presentation of the immediately weaker weight filament next; likewise, no response would call for the immediately stronger. Presentations continue until a series of six consecutive responses from the first change is logged. The next rat is then tested. This procedure is standard in the art for the measurement of allodynia, but any other method known in the art which provides adequate sensitivity and reproducibility may be substituted.

Spinal Nerve Ligation Surgery

Neuropathy of dorsal spinal nerve roots L5 and L6 may be induced in rats. Kim S. H., and Chung J. M., *An experimental model for peripheral neuropathy produced by segmental spinal nerve ligation in the rat*. Pain 50: 355-363 (1992). Tight ligation of these nerve roots produces chronic neuropathic pain symptoms characterized by allodynia and hyperalgesia. The efficacy of potential analgesics on allodynia and hyperalgesia may be assessed in rats in a protocol and procedure described and adapted by T. Yaksh. Yaksh T. et al., Physiology and Pharmacology of Neuropathic Pain, Anesthesiology Clinics of North America, Vol. 14, Number 2 (1997) at pages 334 through 352.

Measuring Paw Volume (Edema)

Inflammation or edema may be quantified by measurement of paw volume (in ml), as injection of irritants such as CFA i.pl. results in an increase in paw volume as compared to an uninjected paw. Therefore, measurement of paw volume is a useful method for quantifying the ability of treatments to reduce inflammation in rats after administration of inflammatory agents.

This procedure is performed utilizing the UGO Basile Plethysmometer, which measures paw volume in ml. Setup involves filling the apparatus with solution, and then calibrating of the instrument. Solution should be changed every 2 to 3 days, and the calibration should be confirmed each time a test session is to be conducted. Detailed instructions regarding operation of the instrument are also included in the manual and will not be described here.

The procedure of paw volume measurement is simple. For each animal, the instrument should first be zeroed. Then the animal's irritated paw is placed into the measurement receptacle such that the entire paw up to the ankle is submerged. When the paw is submerged correctly and is restrained from movement, the foot pedal is pressed. This pedal serves as a signal to the instrument to measure change in volume in the measurement chamber (and therefore paw volume) at that moment. The animal is returned to its home cage, and the next animal is tested.

Occasionally, the measurement receptacle must be refilled to the top line, as repeated tests of animals gradually depletes the amount of solution in the instrument due to solution leaving the receptacle on animals' paws. The instrument may now be zeroed and is ready for more use.

Paw volume measurements generally are obtained before inflammatory introduction (baseline) and at several time points post-inflammation. Agents such as CFA, carrageenan, and capsaicin may be used, however, inflammation caused by these agents occur at different times.

LPS Challenge

Inhibition of induction of iNOS can be quantified via the LPS challenge. Inflammation, edema, and the onset of sepsis can be observed following an injection of lipopolysaccharide (LPS), a substance produced by Gram-negative bacteria. Injection of LPS has been shown to induce iNOS transcription, leading to measurable increases in both iNOS and NO. (Iuvone T et al., Evidence that inducible nitric oxide synthase is involved in LPS-mediated plasma leakage in rat skin through the activation of nuclear factor-κB, Br J Pharm 1998: 123 1325-1330.) As described above, the level of nitric oxide in the specimen can be quantified by correlation with plasma nitrate or nitrite levels via chemiluminescence, fluorescence, spectrophotometric assays, or by any method known in the art which provides adequate sensitivity and reproducibility, including those described above.

Male Lewis rats weighing 150-250 g are used in the studies. Rats may be fasted for up to 16 hours prior to the administration of LPS. Free access to water is maintained. Test compounds are administered with LPS or alone. Compounds are dissolved in the vehicle of 0.5% methycele/0.025% Tween 20 or 20% encapsin for oral administration. For the intravenous dosing, compounds are dissolved in saline or 0.5-3% DMSO/20% encapsin. The dosing volumes are 1-2 ml for oral and 0.3-1 ml for intravenous administration.

LPS is injected intravenously (under anesthesia) or intraperitoneally in sterile saline at a dose between 0.1-10 mg/kg in a volume not excess to 1 ml. The needle is 26-30 gauge. Following LPS injection, rats usually exhibit flu-like symptoms, principally involving lack of activity and diarrhea. In routine screening experiments, rats are sacrificed 1.5-6 hr after LPS injection and a terminal bleeding is performed under anesthesia to collect 1-3 ml blood samples and then animals are then euthanized by $CO_2$.

The following Table 2 lists compounds of the subject invention that were tested according to the above mentioned assays.

TABLE 2

|  | Formalin-Induced Pain | Chung-Neuropathic Pain | Carrageenan Inflamed Pain at 30 mg/kg, (+) = >40% inhibition (−) = <40% inhibition | LPS Induced iNOS In Vivo (+) = ED50 < 10 (−) = ED50 > 10 | Topical Capsaicin Allodynia (+) = >15% inhibition (−) = <15% inhibition |
|---|---|---|---|---|---|
| Example 1 | P < 0.01 at 50 mg/kg | P < 0.01 at 50 mg/kg | + | − | Not Tested |
| Example 2 | P < 0.001 at 50 mg/kg | P < 0.001 at 25 mg/kg | − | + | + at 0.5 hr<br>+ at 1 hr |
| Example 3 | P < 0.01 at 25 mg/kg | P < 0.001 at 25 mg/kg | + | + | + at 0.5 hr<br>+ at 1 hr |
| Example 4 | Not Tested | Not Tested | Not Tested | + | − at 0.5 hr<br>+ at 1 hr |
| Example 5 | Not Tested | Not Tested | Not Tested | 64% inhibition at 16 mg/kg | + at 0.5 hr<br>− at 1 hr |

TABLE 2-continued

|  | Formalin-Induced Pain | Chung-Neuropathic Pain | Carrageenan Inflamed Pain at 30 mg/kg, (+) = >40% inhibition (−) = <40% inhibition | LPS Induced iNOS In Vivo (+) = ED50 < 10 (−) = ED50 > 10 | Topical Capsaicin Allodynia (+) = >15% inhibition (−) = <15% inhibition |
|---|---|---|---|---|---|
| Example 12 | Not Tested | Not Tested | Not Tested | Not Tested | − at 0.5 hr − at 1 hr |
| Example 13 | Not Tested | Not Tested | Not Tested | Not Tested | − at 0.5 hr + at 1 hr |
| Example 28 | Not Tested | Not Tested | Not Tested | Not Tested | + at 0.5 hr + at 1 hr |
| Example 29 | Not Tested | Not Tested | Not Tested | Not Tested | − at 0.5 hr + at 1 hr |
| Example 38 | Not Tested | Not Tested | Not Tested | Not Tested | + at 0.5 hr + at 1 hr |
| Example 49 | Not Tested | Not Tested | Not Tested | Not Tested | + at 0.5 hr + at 1 hr |
| Example 50 | Not Tested | Not Tested | Not Tested | Not Tested | + at 0.5 hr + at 1 hr |
| Example 59 | Not Tested | Not Tested | Not Tested | Not Tested | + at 0.5 hr + at 1 hr |

From the foregoing description, one skilled in the art can easily ascertain the essential characteristics of this invention, and without departing from the spirit and scope thereof, can make various changes and modifications of the invention to adapt it to various usages and conditions.

We claim:

1. A compound of the Formula IV:

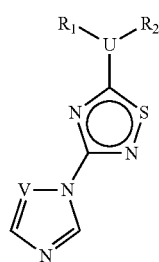

or a salt thereof, wherein:

U is $CR^{10}$ or N;

V is $CR^4$ or N;

$R^1$ and $R^2$ are independently selected from the group consisting of hydrogen, halogen, optionally substituted alkyl, optionally substituted alkoxy, haloalkyl, haloalkoxy, optionally substituted aralkyl, optionally substituted aryl, optionally substituted heteroaryl, optionally substituted heteroaralkyl, optionally substituted alkene, optionally substituted alkyne, —C(O)N($R^{11}$)$R^{12}$, —P(O)[N($R^{11}$)$R^{12}$]$_2$, —SO$_2$NHC(O)$R^{11}$, —N($R^{11}$)SO$_2$$R^{12}$, —SO$_2$N($R^{11}$)$R^{12}$, —NSO$_2$N($R^{11}$)$R^{12}$, —C(O)NHSO$_2$$R^{11}$, —CH=NOR$^{11}$, —OR$^{11}$, —S(O)$_t$—$R^{11}$, —N($R^{11}$)$R^{12}$, —N($R^{11}$)C(O)N($R^{12}$)$R^{13}$, —N($R^{11}$)C(O)OR$^{12}$, —N($R^{11}$)C(O)$R^{12}$, —[C($R^{14}$)$R^{15}$]$_r$—$R^{12}$, —[C($R^{14}$)$R^{15}$]$_r$—C(O)OR$^{11}$, —[C($R^{14}$)$R^{15}$]$_r$—[C(O)OR$^{11}$]$_2$, —[C($R^{14}$)$R^{15}$]$_r$—C(O)N($R^{11}$)$R^{12}$, —[C($R^{14}$)$R^{15}$]$_r$—N($R^{11}$)$R^{12}$, —[C($R^{14}$)$R^{15}$]$_r$—N($R^{11}$)—[C($R^{14}$)$R^{15}$]$_r$—$R^{12}$, —[C($R^{14}$)$R^{15}$]$_r$—N($R^{13}$)—C(O)N($R^{11}$)$R^{12}$, —[C($R^{14}$)$R^{15}$]$_r$—N($R^{13}$)S(O)$_t$—C(O)N($R^{11}$)$R^{12}$, —[C($R^{14}$)$R^{15}$]$_r$—OR$^{11}$, —N($R^{11}$)—[C($R^{14}$)$R^{15}$]$_r$—$R^{12}$, —N($R^{11}$)C(O)N($R^{13}$)—[C($R^{14}$)$R^{15}$]$_r$—$R^{12}$, —C(O)—[C($R^{14}$)$R^{15}$]$_r$—N($R^{11}$)$R^{12}$, —N($R^{13}$)C(O)-L-($R^{11}$)$R^{12}$, —N($R^{11}$)—[C($R^{14}$)$R^{15}$]$_r$-L-$R^{12}$, —N($R^{11}$)C(O)N($R^{11}$)—[C($R^{14}$)$R^{15}$]$_r$-L-$R^{12}$, —[C($R^{14}$)$R^{15}$]$_r$-L-$R^{12}$, and -L-C(O)N($R^{11}$)$R^{12}$;

t is an integer from 0 to 2;

r is an integer from 0 to 5;

L is selected from the group consisting of an optionally substituted 3- to 7-membered carbocyclic group, an optionally substituted 3- to 7-membered heterocyclic group, an optionally substituted 6-membered aryl group, and an optionally substituted 6-membered heteroaryl group;

$R^4$, $R^{10}$, $R^{14}$, $R^{15}$, $R^{16}$, $R^{17}$, and $R^{18}$ are independently selected from the group consisting of hydrogen, halogen, optionally substituted alkyl, optionally substituted haloalkyl, haloalkoxy, optionally substituted aralkyl, optionally substituted aryl, optionally substituted heteroaryl, optionally substituted heteroaralkyl, optionally substituted alkene, optionally substituted alkyne; or $R^{14}$ and $R^{15}$ may together form a carbonyl, optionally substituted carbocycle or optionally substituted heterocycle; or $R^{14}$ and $R^{15}$ together may be null, forming an additional bond;

$R^{11}$, $R^{12}$, and $R^{13}$ are independently selected from the group consisting of hydrogen, halogen, optionally substituted alkyl, haloalkyl, haloalkoxy, optionally substituted aralkyl, optionally substituted aryl, optionally substituted heteroaryl, optionally substituted heteroaralkyl, optionally substituted alkene, optionally substituted alkyne, OR$^{17}$, —S(O)$_t$—$R^{17}$, —[C($R^{14}$)$R^{15}$]$_r$—C(O)OR$^{17}$, —[C($R^{14}$)$R^{15}$]$_r$—N($R^{17}$)$R^{18}$, —[C($R^{14}$)$R^{15}$]$_r$—N($R^{16}$)C(O)N($R^{17}$)$R^{18}$, —[C($R^{14}$)$R^{15}$]$_r$—N($R^{17}$)C(O)OR$^{18}$, —[C($R^{14}$)$R^{15}$]$_r$—$R^{17}$, and —[C($R^{14}$)$R^{15}$]$_r$—N($R^{17}$)C(O)$R^{18}$; or $R^{11}$ or $R^{12}$ may be defined by a structure selected from the group consisting of

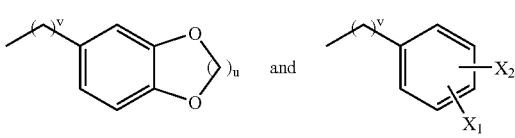

wherein:

u and v are independently an integer from 0 to 3; and $X^1$ and $X^2$ are independently selected from the group consisting of hydrogen, halogen, hydroxy, lower acyloxy, optionally substituted lower alkyl, optionally substituted lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl;

provided that:

when U is $CR^{10}$, then none of $R^1$, $R^2$, nor $R^4$ is OH.

2. The compound as recited in claim 1 wherein V is $CR^4$.

3. The compound as recited in claim 2 wherein:

$R^1$ and $R^2$ are independently selected from the group consisting of hydrogen, halogen, lower alkyl, haloalkyl, optionally substituted aralkyl, optionally substituted aryl, optionally substituted heteroaryl, lower alkene, lower alkyne, —(O)N($R^{11}$)$R^{12}$, —P(O)[N($R^{11}$)$R^{12}$]$_2$, —SO$_2$NHC(O)$R^{11}$, —N($R^{11}$)SO$_2$$R^{12}$, —SO$_2$N($R^{11}$)H, —C(O)NHSO$_2$$R^{11}$, —CH=NO$R^{11}$, —S(O)$_t$—$R^{11}$, —N($R^{11}$)$R^{12}$, —N($R^{11}$)C(O)N($R^{12}$)$R^{13}$, —N($R^{11}$)C(O)O$R^{12}$, —N($R^{11}$)C(O)$R^{12}$, —[C($R^{14}$)$R^{15}$]$_r$—C(O)O$R^{11}$, [C($R^{14}$)$R^{15}$]$_r$—[C(O)O$R^{11}$]$_2$, —[C($R^{14}$)$R^{15}$]$_r$—N($R^{11}$)$R^{12}$, —[C($R^{14}$)$R^{15}$]$_r$—C(O)N($R^{11}$)$R^{12}$, —N($R^{11}$)—[C($R^{14}$)$R^{15}$]$_r$—$R^{12}$, —N($R^{11}$)C(O)N($R^{12}$)—[C($R^{14}$)$R^{15}$]$_r$—$R^{12}$, —[C($R^{14}$)$R^{15}$]$_r$—$R^{12}$, —[C($R^{14}$)$R^{15}$]$_r$—N($R^{13}$)—C(O)N($R^{11}$)$R^{12}$, —[C($R^{14}$)$R^{15}$]$_r$—N($R^{13}$)S(O)$_t$—C(O)N($R^{11}$)$R^{12}$, —N($R^{11}$)—[C($R^{14}$)$R^{15}$]$_r$-L-$R^{12}$, —[C($R^{14}$)$R^{15}$]$_r$-L-$R^{12}$ and —N($R^{11}$)C(O)N($R^{12}$)$R^{13}$—[C($R^{14}$)$R^{15}$]$_r$-L-$R^{12}$; or $R^5$ and $R^6$ together may form an optionally substituted aryl, optionally substituted heteroaryl, optionally substituted cycloalkyl, or optionally substituted heterocycloalkyl;

$R^4$, $R^{10}$, $R^{11}$, $R^{15}$, $R^{16}$, $R^{17}$ and $R^{18}$ are independently selected from the group consisting of hydrogen, halogen, lower alkyl, haloalkyl, optionally substituted aralkyl, optionally substituted aryl, optionally substituted heteroaryl, lower alkene, and lower alkyne; or $R^{14}$ and $R^{15}$ may together form a carbonyl, optionally substituted carbocycle or optionally substituted heterocycle; and $R^{11}$, $R^{12}$, and $R^{13}$ are independently selected from the group consisting of hydrogen, halo, lower alkyl, haloalkyl, optionally substituted aralkyl, optionally substituted aryl, optionally substituted heteroaralkyl, optionally substituted heteroaryl, lower alkene, and lower alkyne; or $R^{11}$ or $R^{12}$ may be defined by a structure selected from the group consisting of wherein:

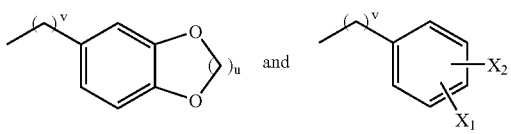

u and v are independently an integer from 0 to 3; and $X^1$ and $X^2$ are independently selected from the group consisting of hydrogen, halogen, hydroxy, lower acyloxy, lower alkyl, lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

4. The compound as recited in claim 3 wherein:

$R^1$ is selected from the group consisting of hydrogen, halogen, lower alkyl, haloalkyl, optionally substituted aralkyl, optionally substituted aryl, optionally substituted heteroaryl, lower alkene, lower alkyne, —N($R^{11}$)SO$_2$$R^{12}$, —SO$_2$N($R^{11}$)H, —O$R^{11}$, —S(O)$_t$—$R^{11}$, —N($R^{11}$)$R^{12}$, —N($R^{11}$)C(O)N($R^{12}$)$R^{13}$, —N($R^{11}$)C(O)$R^{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, —N($R^{11}$)—[C($R^{14}$)$R^{15}$]$_r$—$R^{12}$, —N($R^{11}$)—[C($R^{14}$)$R^{15}$]$_r$-L-$R^{12}$, —[C($R^{14}$)$R^{15}$]$_r$-L-$R^{12}$, —N($R^{11}$)C(O)N($R^{12}$)$R^{13}$—[C($R^{14}$)$R^{15}$]$_r$-L-$R^{12}$, —[C($R^{14}$)$R^{15}$]$_r$—N($R^{13}$)—C(O)N($R^{11}$)$R^{12}$, and —[C($R^{14}$)$R^{15}$]$_r$—N($R^{13}$)S(O)$_t$—C(O)N($R^{11}$)$R^{12}$; and $R^2$ is selected from the group consisting of hydrogen, halo, lower alkyl, haloalkyl, optionally substituted aralkyl, optionally substituted aryl, optionally substituted heteroaryl, lower alkene, lower alkyne, —N($R^{11}$)C(O)$R^{12}$, —[C($R^{14}$)$R^{15}$]$_r$—C(O)O$R^{11}$, —[C($R^{14}$)$R^{15}$]$_r$—N($R^{11}$)$R^{12}$, —[C($R^{14}$)$R^{15}$]$_r$—C(O)N($R^{11}$)$R^{12}$, and —N($R^{11}$)—[C($R^{14}$)$R^{15}$]$_r$—$R^{12}$.

5. The compound as recited in claim 4 wherein $R^1$ is selected from the group consisting of hydrogen, halogen, lower alkyl, haloalkyl, optionally substituted aralkyl, optionally substituted aryl, optionally substituted heteroaryl, lower alkene, lower alkyne, —N($R^{11}$)SO$_2$$R^{12}$, —SO$_2$N($R^{11}$)H, —O$R^{11}$, —S(O)$_t$—$R^{11}$, —N($R^{11}$)$R^{12}$, —N($R^{11}$)C(O)N($R^{12}$)$R^{13}$, —N($R^{11}$)C(O)$R^{12}$, —[C($R^{14}$)$R^{15}$]$_r$—N($R^{11}$)$R^{12}$, —[C($R^{14}$)$R^{15}$]$_r$—C(O)N($R^{11}$)$R^{12}$, —N($R^{11}$)—[C($R^{14}$)$R^{15}$]$_r$—$R^{12}$, —[C($R^{14}$)$R^{15}$]$_r$—N($R^{13}$)—C(O)N($R^{11}$)$R^{12}$, and —[C($R^{14}$)$R^{15}$]$_r$—N($R^{13}$)S(O)$_t$—C(O)N($R^{11}$)$R^{12}$.

6. The compound as recited in claim 5 wherein U is N.

7. The compound as recited in claim 6 wherein $R^1$ is selected form the group consisting of —[C($R^{14}$)$R^{15}$]$_r$—N($R^{11}$)$R^{12}$, —[C($R^{14}$)$R^{15}$]$_r$—C(O)N($R^{11}$)$R^{12}$, —[C($R^{14}$)$R^{15}$]$_r$—N($R^{13}$)—C(O)N($R^{11}$)$R^{12}$, and —[C($R^{14}$)$R^{15}$]$_r$—N($R^{13}$)S(O)$_t$—C(O)N($R^{11}$)$R^{12}$.

8. The compound as recited in claim 6 wherein $R^{12}$ is selected from the group consisting of NH$_2$ and heteroaryl, or is defined by one of the following structural formulae:

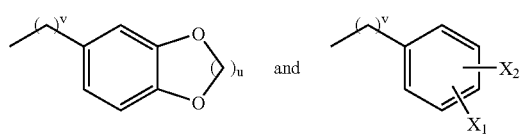

wherein:

u and v are independently an integer from 0 to 3; and $X^1$ and $X^2$ are independently selected from the group consisting of hydrogen, halogen, hydroxy, lower acyloxy, lower alkyl, lower alkoxy, lower haloalkyl, lower haloalkoxy, and lower perhaloalkyl; or $X^1$ and $X^2$ together may form an optionally substituted aryl, optionally substituted heteroaryl, optionally substituted cycloalkyl, or optionally substituted heterocycloalkyl.

9. The compound as recited in claim 8 wherein $X_1$ and $X_2$ are independently selected from the group consisting of hydrogen, halogen, hydroxy, lower alkyl, lower alkoxy, lower haloalkyl, lower haloalkoxy, and lower perhaloalkyl.

10. The compound as recited in claim 8 wherein $R^9$ is —[C($R^{14}$)$R^{15}$]$_r$—N($R^{11}$)$R^{12}$.

11. The compound as recited in claim 9 wherein $R^{12}$ is defined by the following structural formula:

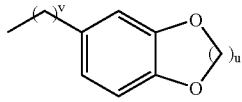

and u and v are independently 1 or 2.

12. The compound as recited in claim 11 wherein $R^{14}$ and $R^{15}$ are both hydrogen.

13. The compound as recited in claim 12 wherein $R^2$ is selected from the group consisting of hydrogen and lower alkyl.

14. The compound as recited in claim 13 wherein $R^{11}$ is hydrogen or methyl.

15. The compound as recited in claim 14 wherein $R^2$ is methyl.

16. The compound as recited in claim 15 wherein $R^{10}$, $R^{11}$ and $R^4$ are hydrogen, and u and v are 1.

17. The compound as recited in claim 16 wherein Y and X are N, T is S, and V is $CR^4$.

18. A pharmaceutical composition comprising a compound as recited in claim 1, together with a pharmaceutically acceptable carrier.

19. The pharmaceutical composition as recited in claim 18 formulated for topical administration.

20. A compound selected from the group consisting of

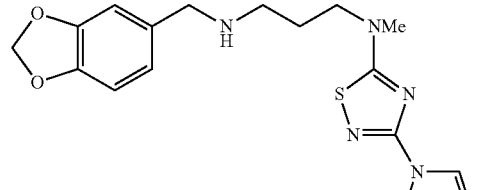

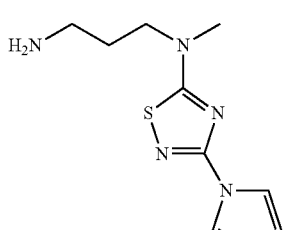

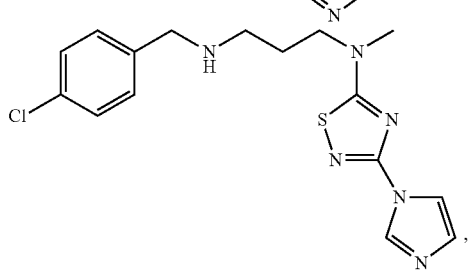

-continued

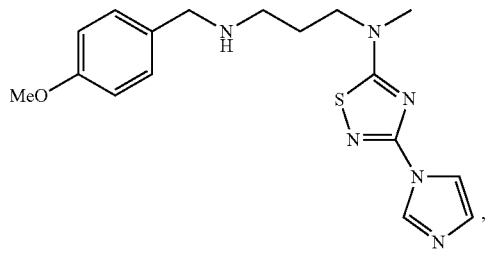

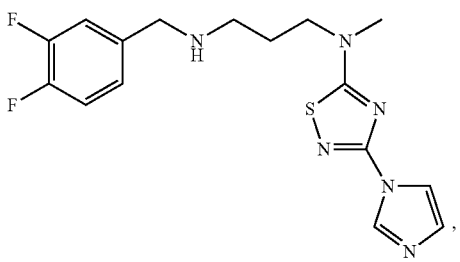

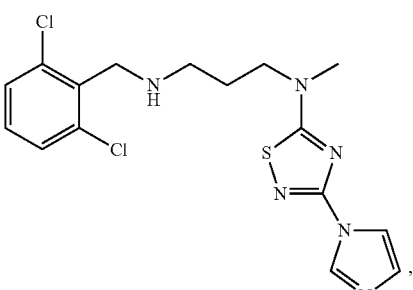

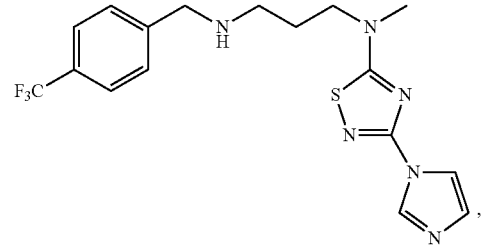

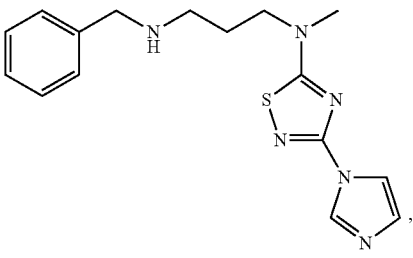

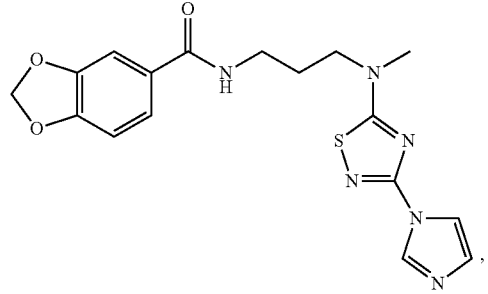

197
-continued
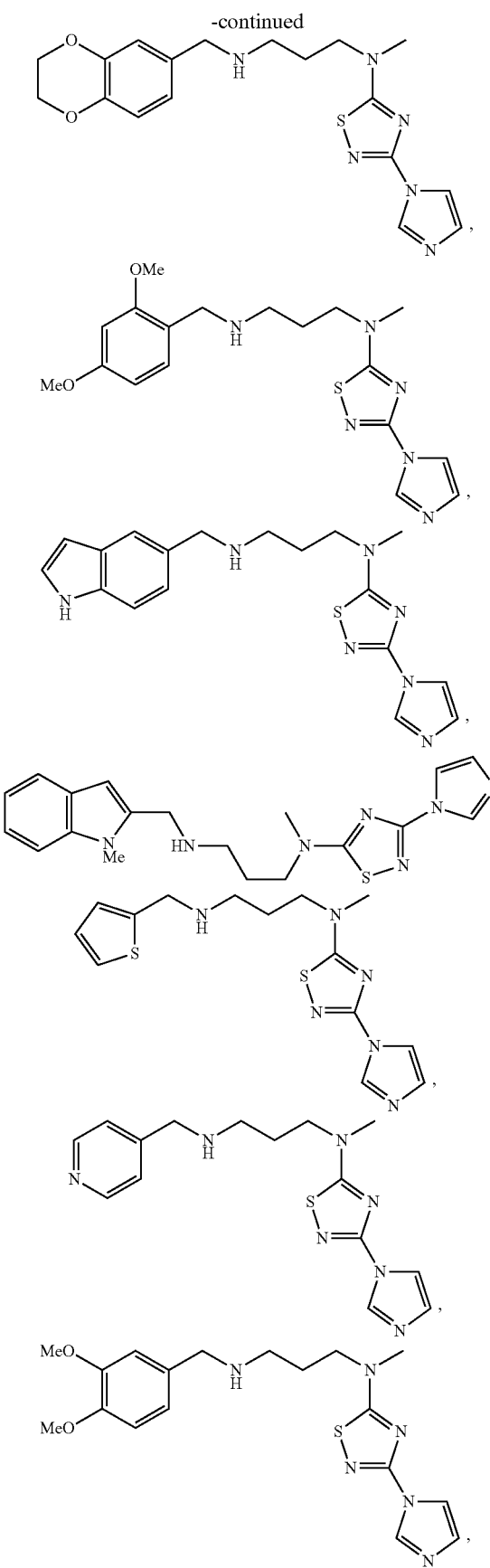
198
-continued
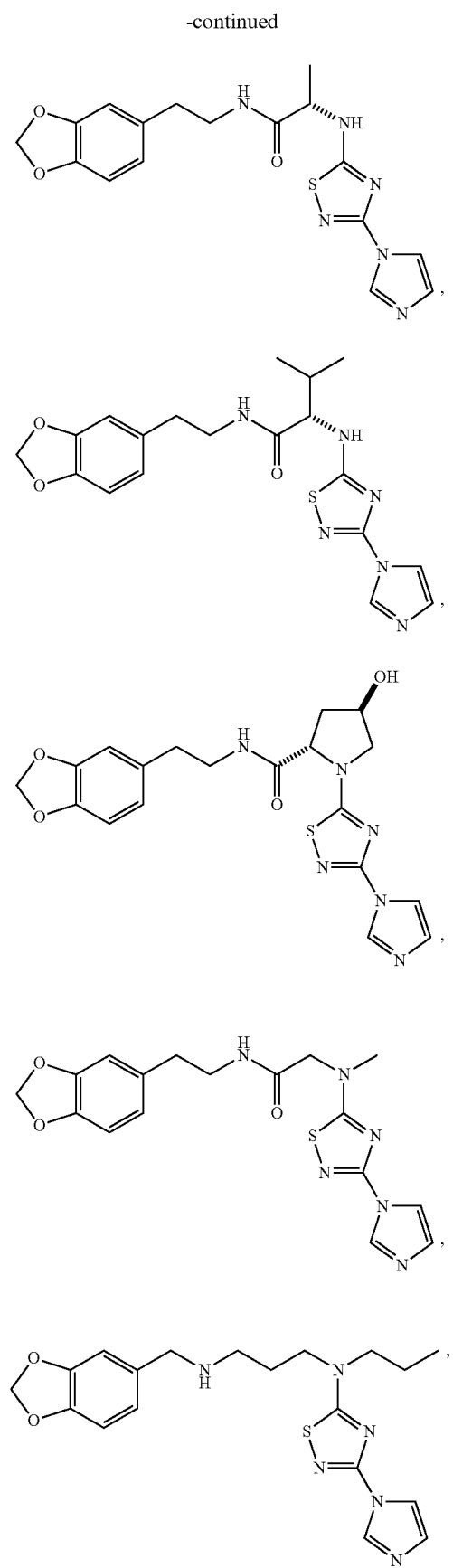

199
-continued
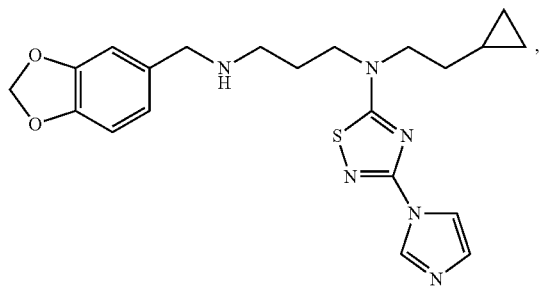
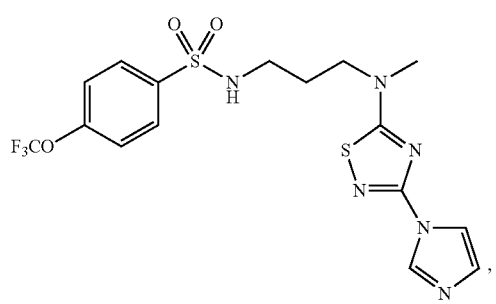
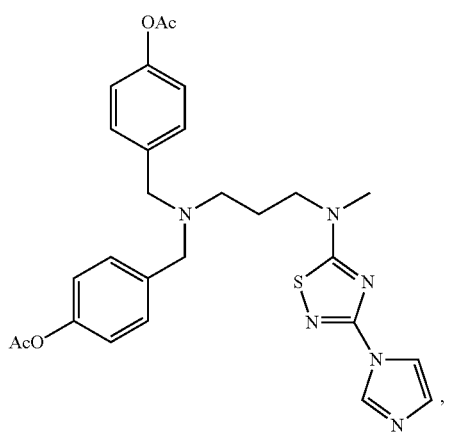
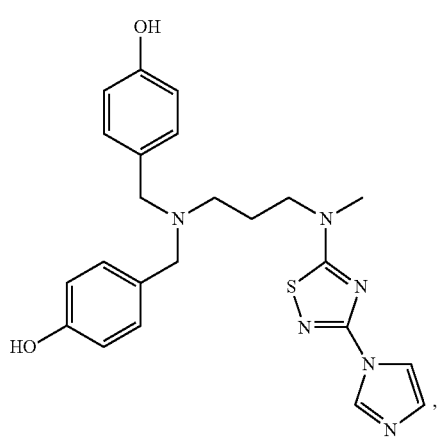
200
-continued
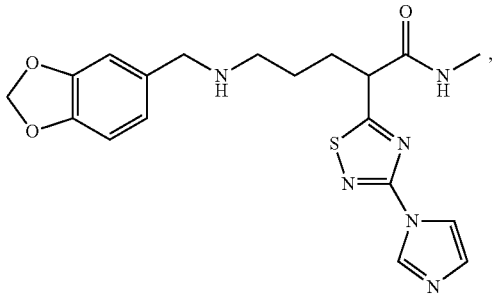
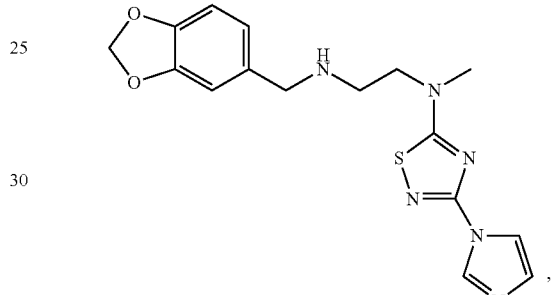
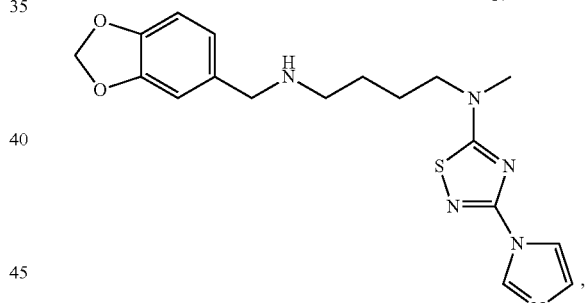
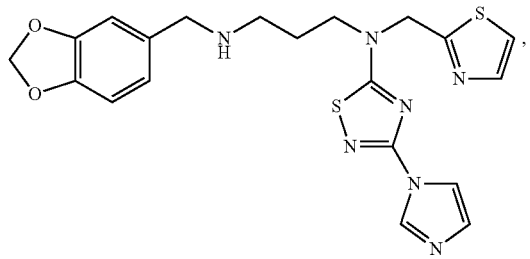
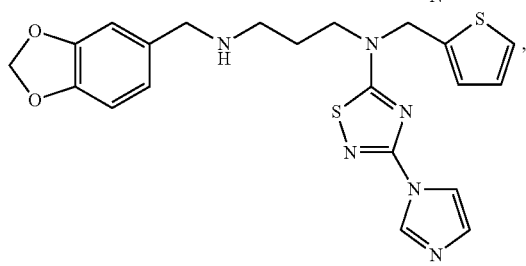

201
-continued
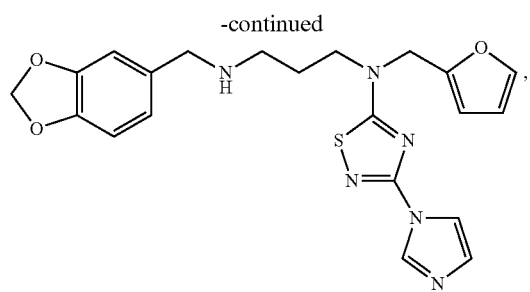
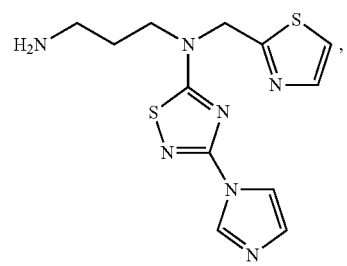
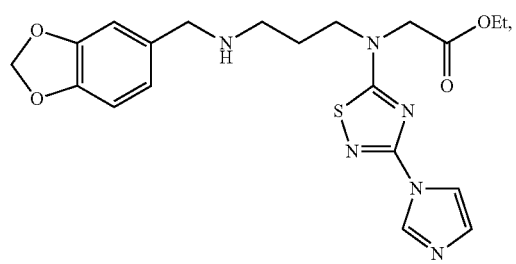
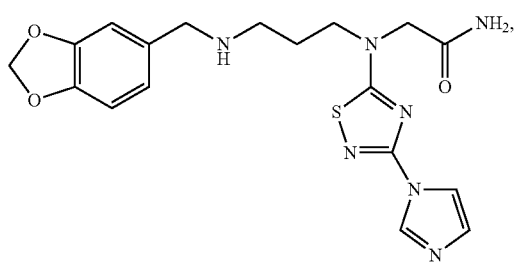
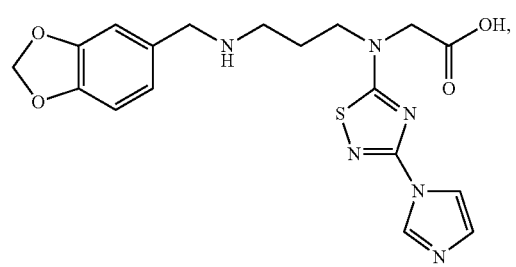
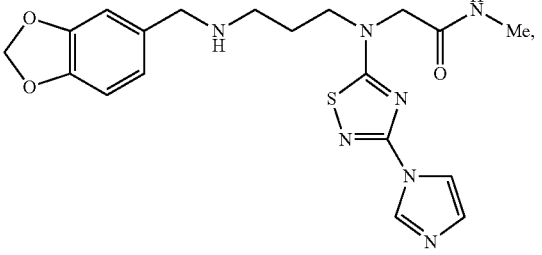
202
-continued
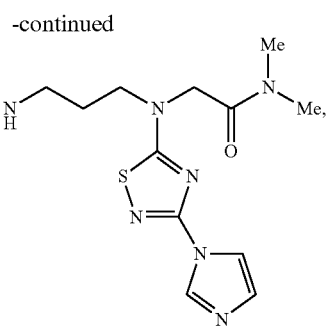
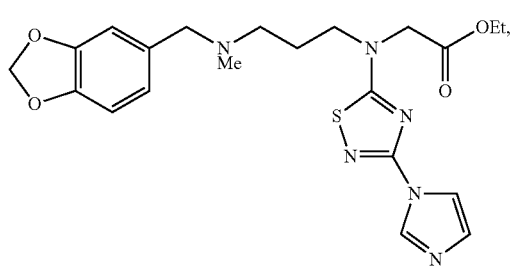
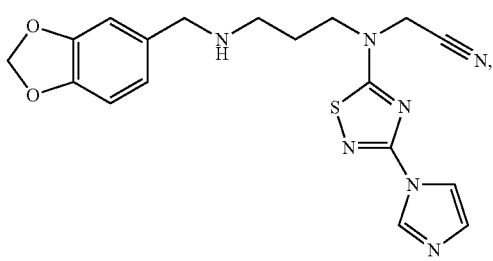
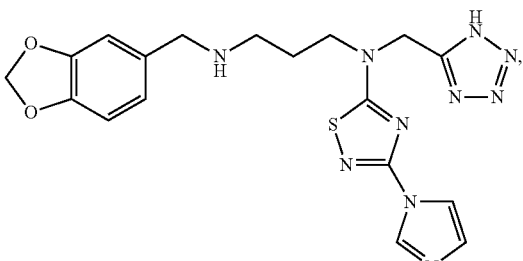
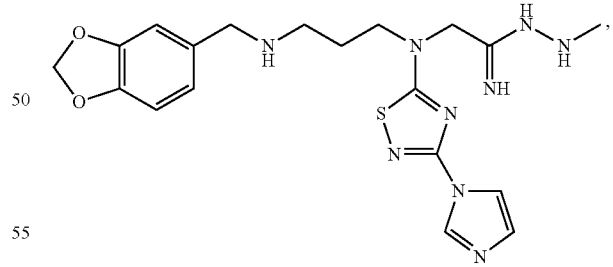
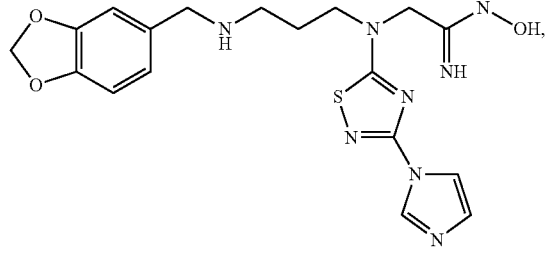

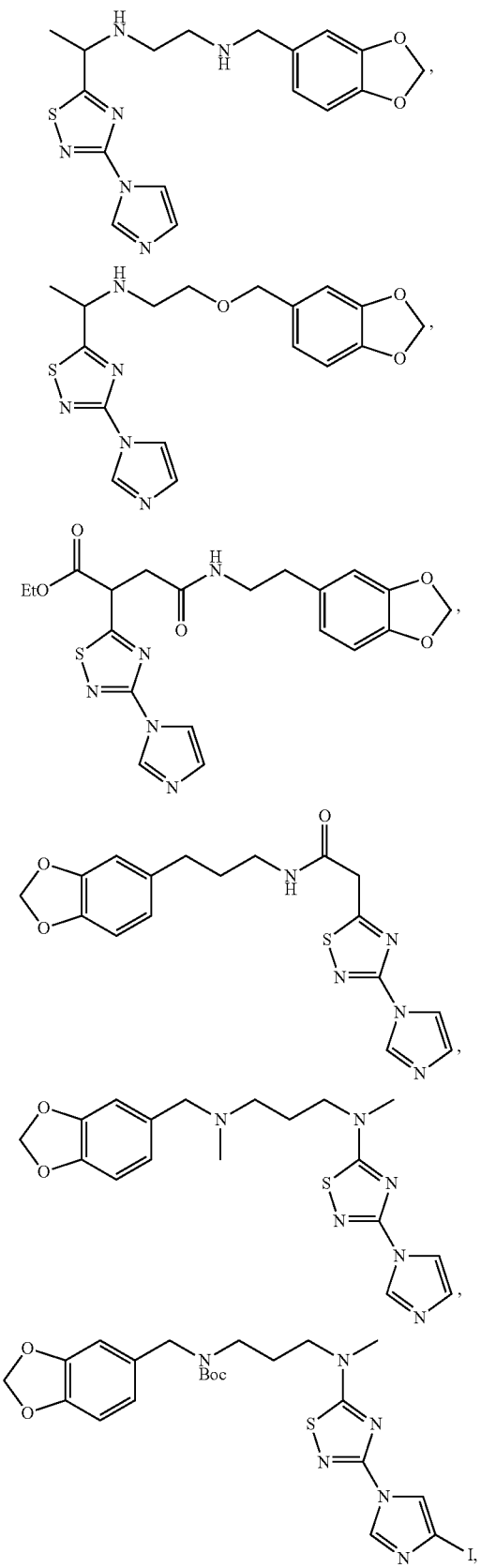
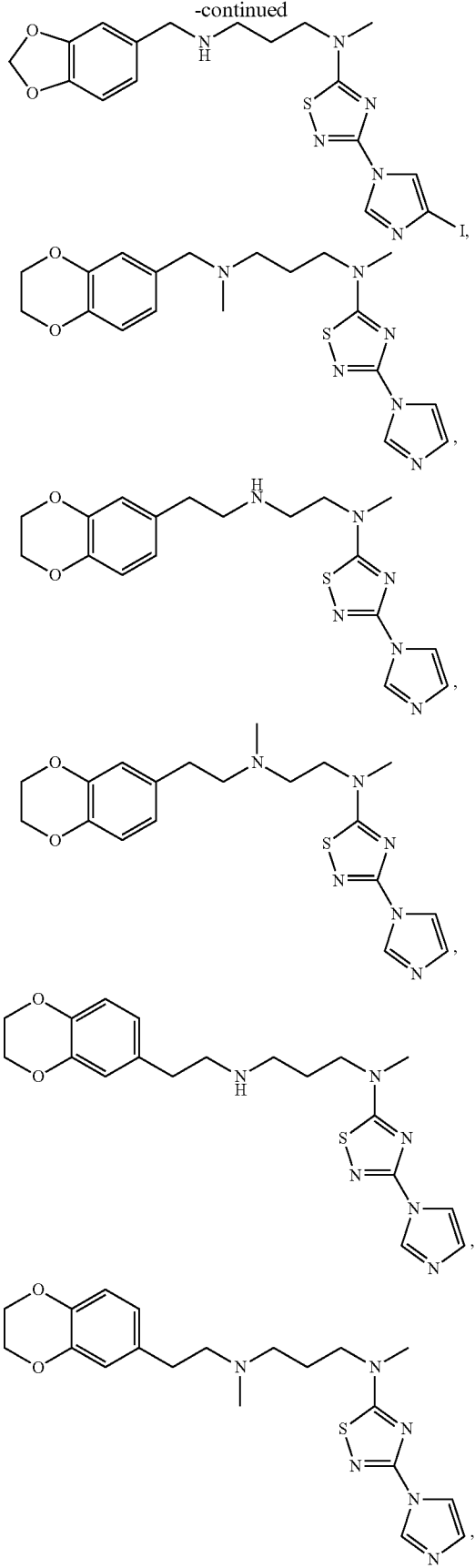

-continued
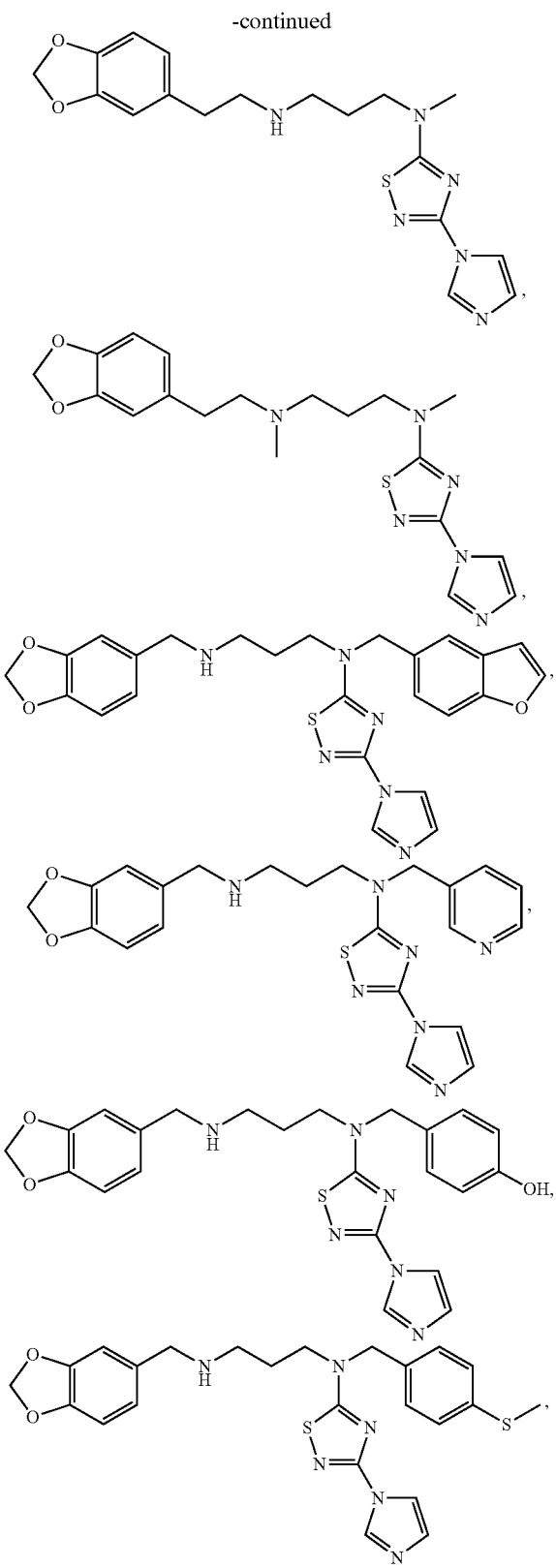
-continued
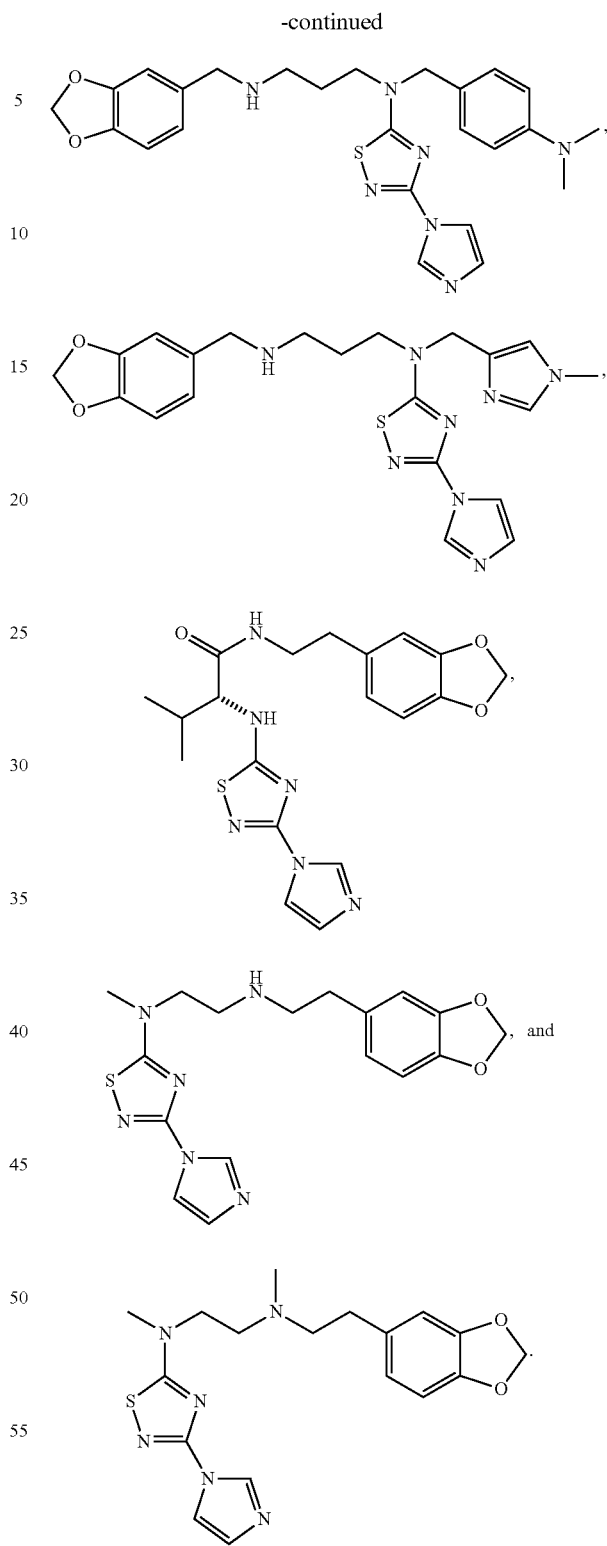
* * * * *